United States Patent
Ohler et al.

(10) Patent No.: US 9,862,906 B2
(45) Date of Patent: Jan. 9, 2018

(54) BASE OILS AND METHODS FOR MAKING THE SAME

(75) Inventors: Nicholas Ohler, Emeryville, CA (US);
Karl Fisher, Emeryville, CA (US);
Shakeel Tirmizi, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 1004 days.

(21) Appl. No.: 14/112,238

(22) PCT Filed: Feb. 13, 2012

(86) PCT No.: PCT/US2012/024926
§ 371 (c)(1),
(2), (4) Date: Mar. 28, 2014

(87) PCT Pub. No.: WO2012/141784
PCT Pub. Date: Oct. 18, 2012

(65) Prior Publication Data
US 2014/0221258 A1    Aug. 7, 2014

Related U.S. Application Data

(60) Provisional application No. 61/475,217, filed on Apr. 13, 2011, provisional application No. 61/475,221, (Continued)

(51) Int. Cl.
*C10M 169/04*    (2006.01)
*C07C 9/00*    (2006.01)
(Continued)

(52) U.S. Cl.
CPC ............. *C10M 105/02* (2013.01); *C07C 5/03* (2013.01); *C07C 5/05* (2013.01); *C10L 1/04* (2013.01); *C10M 105/04* (2013.01); *C10M 107/14* (2013.01); *C07C 2521/04* (2013.01); *C07C 2523/44* (2013.01); *C07C 2523/75* (2013.01); *C10M 2203/003* (2013.01); *C10M 2203/022* (2013.01); *C10M 2203/024* (2013.01);
(Continued)

(58) Field of Classification Search
CPC ......... C10N 2220/022; C10M 2205/00; C07C 2527/173
USPC .................... 508/110; 585/18, 255
See application file for complete search history.

(56) References Cited

U.S. PATENT DOCUMENTS 2,674,634 A    4/1954    Greensfelder
3,398,168 A    8/1968    Medema
(Continued)

FOREIGN PATENT DOCUMENTS

WO    WO 2007/139924    12/2007
WO    WO 2010/027464    3/2010
(Continued)

OTHER PUBLICATIONS

U.S. Appl. No. 61/475,217, filed Apr. 13, 2011, Ohler et al.
(Continued)

*Primary Examiner* — Vishal Vasisth
(74) *Attorney, Agent, or Firm* — Squire Patton Boggs (US) LLP

(57) ABSTRACT

Provided herein are isoparaffins derived from hydrocarbon terpenes such as myrcene, ocimene and farnesene, and methods for making the same. In certain variations, the isoparaffins have utility as lubricant base stocks.

33 Claims, 32 Drawing Sheets

Related U.S. Application Data filed on Apr. 13, 2011, provisional application No. 61/482,122, filed on May 3, 2011, provisional application No. 61/493,316, filed on Jun. 3, 2011, provisional application No. 61/502,252, filed on Jun. 28, 2011, provisional application No. 61/524,143, filed on Aug. 16, 2011.

(51) Int. Cl.

| | |
|---|---|
| *C07C 11/00* | (2006.01) |
| *C07C 2/74* | (2006.01) |
| *C10M 105/02* | (2006.01) |
| *C07C 5/05* | (2006.01) |
| *C10L 1/04* | (2006.01) |
| *C10M 105/04* | (2006.01) |
| *C10M 107/14* | (2006.01) |
| *C07C 5/03* | (2006.01) |

(52) U.S. Cl.
CPC ............... *C10M 2203/0206* (2013.01); *C10M 2205/083* (2013.01); *Y02P 20/582* (2015.11)

(56) References Cited

U.S. PATENT DOCUMENTS

| | | | |
|---|---|---|---|
| 3,475,509 | A | 10/1969 | Go Hata et al. |
| 3,702,348 | A | 11/1972 | Nehring et al. |
| 4,546,110 | A | 10/1985 | Dawson et al. |
| 4,590,319 | A | 5/1986 | Imaki et al. |
| 5,151,172 | A | 9/1992 | Kukes et al. |
| 5,153,157 | A | 10/1992 | Hlatky et al. |
| 5,198,401 | A | 3/1993 | Turner et al. |
| 5,241,025 | A | 8/1993 | Hlatky et al. |
| 5,378,767 | A | 1/1995 | Massie |
| 6,239,324 | B1 | 5/2001 | Fujiwhara et al. |
| 6,403,844 | B1 | 6/2002 | Zhang et al. |
| 7,399,323 | B2 | 7/2008 | Renninger et al. |
| 7,592,295 | B1 | 9/2009 | Fisher et al. |
| 7,659,097 | B2 | 2/2010 | Renninger et al. |
| 8,257,957 | B2 | 9/2012 | Keasling et al. |
| 8,586,814 | B2 | 11/2013 | Fisher et al. |
| 2008/0146469 | A1 | 6/2008 | Sato et al. |
| 2008/0274523 | A1 | 11/2008 | Renninger et al. |
| 2009/0137014 | A1 | 5/2009 | Tsuruta et al. |
| 2010/0056743 | A1 | 3/2010 | Mcphee |
| 2013/0123379 | A1 | 5/2013 | Mcphee |
| 2013/0252295 | A1 | 9/2013 | Renninger et al. |

FOREIGN PATENT DOCUMENTS

| | | | | |
|---|---|---|---|---|
| WO | WO 2010115097 A2 | * | 10/2010 | ............... C07C 5/03 |
| WO | WO 2012/141783 | | 10/2012 | |
| WO | WO 2013/028307 | | 2/2013 | |

OTHER PUBLICATIONS

U.S. Appl. No. 61/475,221, filed Apr. 13, 2011, Tirmizi et al.
U.S. Appl. No. 61/482,122, filed May 3, 2011, Ohler.
U.S. Appl. No. 61/493,316, filed Jun. 3, 2011, Ohler et al.
U.S. Appl. No. 61/502,252, filed Jun. 28, 2011, Fisher et al.
U.S. Appl. No. 61/524,143, filed Aug. 16, 2011, Fisher et al.
Anet E.F.L.J., "Synthesis of (E,Z)-α-, and (Z)-β-farnesene", Aust. J. Chem. 23, pp. 2101-2108 (1970).
Dieguez et al., "Weakening C—O Bonds: Ti(I11), a New Regent for Alcohol Deoxygenation and Carbonyl Coupling Olefination," J. Am. Chem. Soc., vol. 132, pp. 254-259 (2010).
Frolov et al., "Highly active supported palladium catalysts for selective hydrogenation of conjugated dienes into olefins," Reaction Kinetics and Catalysis Letters, vol. 25, Nos. 3-4, pp. 319-322 (1984) book 4 pgs attached.
Hilt et al., Synthesis J. of Synthetic Organic Chemistry No. 5, pp. 609-618 (2002).
Jong Tae Lee et al, "Regioselective hydrogenation of conjugated dienes catalyzed by hydridopentacyanocobaltate anion using β-cyclodextrin as the phase transfer agent and lanthanide halides as promoters," J. Org. Chem. 55 (6), pp. 1854-1856 (1990).
Malcolm P. Stevens, "Polymer Chemistry, an Introduction," Third Edition, Oxford University Press, pp. 236-245 and p. 251 (1999).
Moreau et al., Iron-Catalyzed 1,4-Addition of α-Olefins to Dienes, Organic Letters, 11, 337-339 (2009).
Scheirs et al., "Metallocene-Based Polyolefins: Preparation, Properties, and Technology," vol. 1, Wiley (2000).
Sharma et al., "Asymmetric Hydrovinylation of Unactivated Linear 1, 3-Dienes", J. Am. Chem. Soc. 132, pp. 3295-3297 (2010).
Smith, J. Am. Chem. Soc. 65, pp. 745-750 (1943).
Tae Oan Ahn et al., "Modification of a Ziegler-Natta catalyst with a metallocene catalyst and its olefin polymerization behavior," Polymer Engineering and Science, 39(7), p. 1257 (1999).
Tungler et al., "Reduction of Dienes and Polyenes," in *The Chemistry of Dienes and Polyenes*, vol. 2 (ed. Z. Rappoport), John Wiley & Sons, Ltd, Chichester, UK . (2000).
International Search Report for PCT/US2012/024926, dated Jul. 12, 2012, 3 pgs. (2012).

* cited by examiner

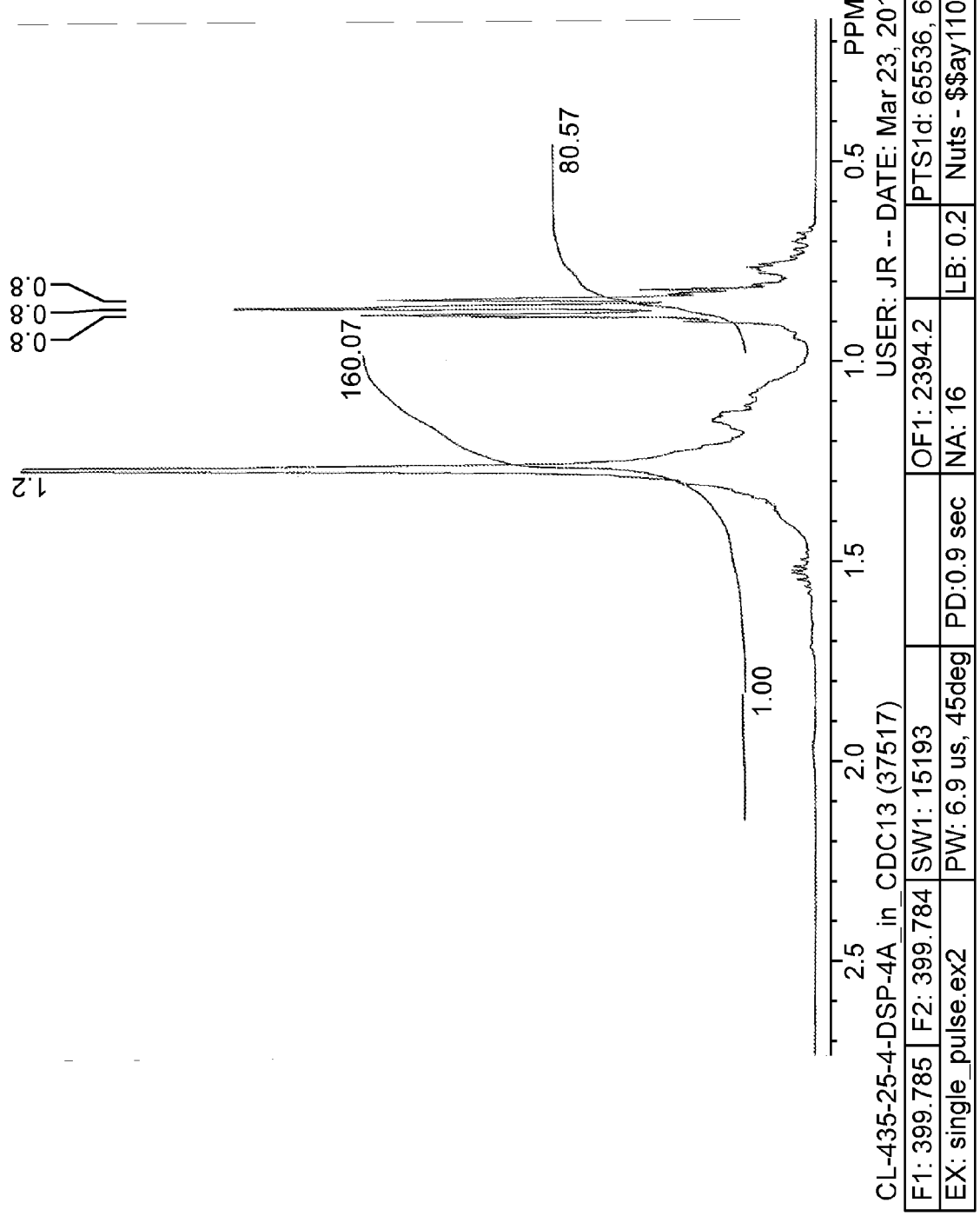

Retention Time Calibration
ASTM D6417
*FID(1) Channel*

| Component | Time | BP(C) | Skewness |
|---|---|---|---|
| n-C10 | 0.097 | 174.1 | |
| n-C12 | 0.253 | 216.3 | |
| n-C14 | 0.817 | 253.9 | |
| n-C16 | 1.872 | 287.2 | |
| n-C18 | 3.058 | 316.1 | |
| n-C20 | 4.202 | 343.9 | |
| n-C22 | 5.258 | 368.3 | |
| n-C24 | 6.245 | 391.1 | |
| n-C26 | 7.165 | 412.2 | |
| n-C28 | 8.018 | 431.1 | |
| n-C30 | 8.818 | 449.7 | |
| n-C32 | 9.573 | 466.1 | |
| n-C34 | 10.292 | 481.1 | |
| n-C36 | 10.973 | 496.1 | |
| n-C38 | 11.630 | 508.9 | |
| n-C40 | 12.293 | 522.2 | |
| n-C42 | 12.863 | 533.9 | |
| n-C44 | 13.428 | 545.0 | |
| n-C46 | 13.977 | 556.1 | |
| n-C48 | 14.515 | 566.1 | |
| n-C50 | 15.028 | 575.0 | |
| n-C52 | 15.513 | 583.9 | |
| n-C54 | 15.972 | 592.2 | |
| n-C56 | 16.422 | 600.0 | |
| n-C58 | 16.865 | 607.8 | |
| n-C60 | 17.280 | 615.0 | |
| n-C62 | 17.677 | 622.2 | |
| n-C64 | 18.055 | 628.9 | |
| n-C66 | 18.423 | 635.0 | |
| n-C68 | 18.782 | 641.1 | |
| n-C70 | 19.127 | 647.2 | |
| n-C72 | 19.463 | 652.8 | |
| n-C74 | 19.787 | 657.8 | |
| n-C76 | 20.095 | 663.9 | |
| n-C78 | 20.393 | 670.0 | |
| n-C80 | 20.690 | 675.0 | |
| n-C82 | 20.978 | 681.1 | |

BASE OILS AND METHODS FOR MAKING THE SAME

CROSS-REFERENCE TO RELATED APPLICATIONS

This application is a 371 of PCT/US2012/024926, filed Feb. 13, 2012.

This application claims the benefit of and priority to U.S. provisional patent application 61/475,217 filed Apr. 13, 2011, U.S. provisional patent application 61/475,221 filed Apr. 13, 2011, U.S. provisional patent application 61/482,122 filed May 3, 2011, U.S. provisional patent application 61/493,316 filed Jun. 3, 2011, U.S. provisional patent application 61/502,252 filed Jun. 28, 2011, and U.S. provisional patent application 61/524,143 filed Aug. 16, 2011, each of which is incorporated by reference herein in its entirety as if put forth fully below.

STATEMENT REGARDING FEDERALLY FUNDED RESEARCH

Some of the work described herein was funded by Award No. DE-EE0002869 awarded by the U.S. Department of Energy. Accordingly, the Government may have rights to some embodiments of this invention.

FIELD

Described herein are isoparaffins derived from hydrocarbon terpenes. The isoparaffinic hydrocarbons have use as lubricant base oils.

BACKGROUND

Polyalpha-olefins (PAOs) make up an important class of hydrocarbon lubricating oils. PAOs are typically produced by the polymerization of alpha-olefins in the presence of a catalyst such as $AlCl_3$, $BF_3$, or a $BF_3$ complex. For example, ethylene, propylene, 1-octene, 1-decene, 1-dodecene, and 1-tetradecene have been used to manufacture PAOs. Oligomerization of the alpha-olefins is typically followed by fractionation and hydrogenation to remove any remaining unsaturated moieties.

It is known to carry out alkylation reactions between isobutane and $C_3$-$C_5$ olefins using $H_2SO_4$ or HF as a catalyst to obtain a mixture of alkylates. The mixture of alkylates can have a high octane number, and is a preferred blendstock for reformulated gasolines.

PAOs are commonly categorized by kinematic viscosity (KV) in centistokes (cSt), measured at 100° C. according to ASTM D445. For example, 2 cSt, 2.5 cSt, 4 cSt, 5 cSt, 6 cSt, 7 cSt, 8 cSt, and 9 cSt PAOs comprising various combinations of oligomers and homopolymers of 1-decene and 1-dodecene are known. PAOs are being developed as high performance functional lubricating oils that have improved performance, e.g., over a wide operational temperature range.

Large quantities of PAOs are used in a variety of lubricating applications. However, PAOs existing in the market today are derived from fossil fuels, and hence are not renewable.

There is a continuing need for improved base oils, e.g. base oils that have a wide operational temperature range, and a continuing need for base oils derived from renewable feedstock.

SUMMARY

Provided herein are base oils and lubricant compositions derived from terpene feedstocks and one or more olefin co-monomers. The base oils can display wide operational temperature ranges. For example, certain base oils have a kinematic viscosity at 100° C. of about 4-5 cSt, a viscosity index (VI) of about 120 or greater, about 122 or greater, or about 124 or greater, and a Cold Cranking Simulator viscosity at −30° C. of about 1800 cP or less, about 1500 cP or less, about 1200 cP or less, about 1100 cP or less, about 1000 cP or less, or about 900 cP or less. Certain base oils have a kinematic viscosity at 100° C. of about 6 cSt, a viscosity index of about 120 or greater, about 125 or greater, about 130 or greater, or about 132 or greater, and a CCS viscosity at −30° C. of about 3000 cP or less, about 2900 cP or less, or about 2800 cP or less or a CCS viscosity at −35° C. of about 7000 cP or less or about 6500 cP or less. Certain base oils have a kinematic viscosity at 100° C. of about 10 cSt and a viscosity index of about 120 or greater, about 125 or greater, about 128 or greater, or about 130 or greater. Certain base oils have a kinematic viscosity at about 100° C. of about 12 cSt, a viscosity index of about 120 or greater, about 125 or greater, about 128 or greater, or about 130 or greater.

In advantageous embodiments, the base oils are derived from one or more renewable feedstocks. Certain base oils comprise at least about 30%, at least about 40%, at least about 50%, at least about 60%, at least about 70%, at least about 80%, at least about 90%, or about 100% carbon content from renewable carbon sources, and have performance comparable to Group III base oils or Group IV PAOs. Accordingly, the present invention provides, in certain embodiments, renewable sources for base oils and lubricant compositions that can have useful, wide temperature ranges as described herein.

In one aspect, provided herein are methods for making isoparaffins. In the methods, a hydrocarbon terpene feedstock is coupled with one or more olefin co-monomers in the presence of a catalyst to form one or more branched alkenes comprising one or more hydrocarbon terpene:olefin co-monomer adducts. In certain embodiments, the one or more branched alkenes are hydrogenated to form one or more isoparaffins. In certain embodiments, the one or more olefin co-monomers are not terpenes. In certain embodiments, a non-terpene co-monomer is linear or only lightly branched, e.g., containing one or two branches. In the instances in which a hydrocarbon terpene and a linear or only lightly branched non-terpene olefin co-monomer are coupled together, the resulting adducts comprises one or more sections with regularly spaced methyl branching originating from the one or more terpenes and one or more sections with little or no branching originating from the one or more olefin co-monomers. The one or more isoparaffins can be used for any purpose apparent to one of skill in the art. For instance, in certain embodiments, they can be used to make a base oil or a lubricant composition as described herein.

The properties of the isoparaffins are determined by any one of the group consisting of the hydrocarbon terpene feedstock, the one or more olefin co-monomers, the catalyst, and the coupling reaction conditions as described herein. For example, it is possible to build a family of base oils having a range of kinematic viscosities by systematically varying the olefin co-monomers. Furthermore, it is possible to choose the catalyst and coupling reaction to control the degree of branching in the resulting base oil. The hydrocarbon terpene feedstock contributes methyl branching to the resulting base oils, and the overall branching in a product can be varied by introducing more or less branching through the olefin co-monomer and/or the coupling mechanism. Depending on coupling reaction, the hydrocarbon terpene feedstock may contribute a controlled or fixed degree of methyl branching to the resulting base oils.

In those variations in which the isoparaffins are used as a base oil, it may be desired to vary the hydrocarbon terpene feedstock, the olefin co-monomers and coupling reaction to provide isoparaffins exhibiting a desired combination of viscosity index and cold temperature properties (e.g., pour point as measured by ASTM D97 and/or cold cranking simulator viscosity as measured by ASTM D5293, each of which is incorporated by reference herein in its entirety). For example, it may be desired to vary the hydrocarbon terpene feedstock, the olefin co-monomers, and the coupling reaction to produce a base oil having a viscosity index of at least about 120 and a cold cranking simulator viscosity at −30° C. of about 1800 cP or less and/or a pour point temperature of less than about −50° C.

The hydrocarbon terpene feedstock can be derived from any terpene known to those of skill in the art. In certain embodiments, the terpene is an acyclic terpene. In certain embodiments, the terpene is selected from acyclic $C_{10}$-$C_{30}$ terpenes. In certain embodiments, the terpene is an acyclic $C_{10}$ terpene, an acyclic $C_{15}$ terpene, or an acyclic $C_{20}$ terpene. In certain embodiments, the terpene is selected from the group consisting of myrcene, ocimene and farnesene. In certain embodiments, the terpene is β-farnesene.

In certain variations, the hydrocarbon terpene feedstock comprises a partially hydrogenated hydrocarbon terpene. The terpene feedstock can be partially hydrogenated according to any method apparent to skill in the art. In certain embodiments, the terpene feedstock is mono-olefinc. In certain embodiments, the terpene feedstock comprises at least about 50% mono-olefin and less than about 25% alkane. In certain embodiments, the terpene feedstock comprises at least about 50% mono-olefin and about 10% or less di-olefin. In certain embodiments, the terpene feedstock comprises at least about 50% mono-olefin and about 5% or less di-olefin.

In advantageous embodiments, the terpene is produced by a microorganism, such as a bioengineered microorganism, for example from a renewable carbon source.

The olefin co-monomer can be any olefin co-monomer deemed useful to one of skill in the art. Useful olefin co-monomers are described herein. The type, molecular weight, and degree of branching in the olefin co-monomer may be selected to produce isoparaffins having desired properties. In some variations, the olefin co-monomer is not a terpene. In some variations, a non-terpene olefin co-monomer is linear or lightly branched (e.g., containing 1 or 2 branches). In other variations, the olefin co-monomer is a terpene. In certain embodiments, the olefin co-monomer comprises one or more alpha-olefins. In certain non-limiting variations, the olefin co-monomer comprises one or more $C_6$-$C_{20}$ alpha-olefins, e.g., one or more $C_6$-$C_{20}$ linear alpha-olefins.

The catalyst used in the coupling reaction can be any catalyst deemed useful for oligomerization by one of skill in the art. Useful catalysts are described in the sections below. In certain embodiments, the catalyst is a hydrovinylation catalyst. In certain embodiments the catalyst is a cationic initiator such as a protic acid or a Lewis acid, which may in some variations be used in combination with a co-catalyst. In certain embodiments, the catalyst comprises $BF_3$ and one or more co-catalysts. Useful co-catalysts are described in the sections below. In certain embodiments, the catalyst is a Ziegler-Natta catalyst. In certain embodiments, the catalyst is a metallocene catalyst.

In certain embodiments, provided herein are methods for making a base oil, comprising coupling a partially hydrogenated hydrocarbon terpene feedstock with one or more olefin co-monomers in the presence of a catalyst to form an unsaturated reaction product, hydrogenating the unsaturated reaction product to form a mixture of isoparaffins, and making a base oil from at least a portion of the isoparaffins. Useful partially hydrogenated hydrocarbon terpene feedstocks, catalysts, and olefin co-monomers are described in the sections below.

In certain embodiments, provided herein are methods for making a base oil, comprising coupling a hydrocarbon terpene feedstock comprising a conjugated diene moiety with one or more alpha-olefins in the presence of a catalyst to form an unsaturated reaction product, hydrogenating the unsaturated reaction product to form a mixture of isoparaffins, and making a base oil from at least a portion of the isoparaffins. Useful hydrocarbon terpene feedstocks, catalysts, and olefin co-monomers are described in the sections below.

In certain embodiments, provided herein are methods for making a base oil, comprising coupling a partially hydrogenated β-farnesene feedstock with one or more olefin co-monomers in the presence of a catalyst to form an unsaturated reaction product, hydrogenating the unsaturated reaction product to form a mixture of isoparaffins, and making a base oil from at least a portion of the isoparaffins.

In certain embodiments, provided herein are methods for making a base oil, comprising coupling β-farnesene with one or more alpha-olefins in the presence of a catalyst to form an unsaturated reaction product, hydrogenating the unsaturated reaction product to form a mixture of isoparaffins, and making a base oil from at least a portion of the isoparaffins. In certain embodiments, provided herein are methods for making a base oil, comprising coupling partially hydrogenated β-farnesene with one or more alpha-olefins in the presence of a catalyst to form an unsaturated reaction product, hydrogenating the unsaturated reaction product to form a mixture of isoparaffins, and making a base oil from at least a portion of the isoparaffins.

Non-limiting examples of useful olefin co-monomers include linear alpha-olefins selected from the group consisting of 1-hexene, 1-octene, 1-decene, 1-dodecene, 1-tetradecene, 1-hexadecene, 1-octadecene, 1-eicosene, and any combination of two or more thereof. For example, a useful co-monomer may comprise a mixture of 1-decene and 1-dodecene, a mixture of 1-dodecene and 1-tetradecene, a mixture of 1-tetradecene and 1-hexadecene, a mixture of 1-hexadecene and 1-octadecene, or a mixture of 1-octadecene and 1-eicosene.

In another aspect, provided herein are isoparaffinic compositions produced by any of the methods described herein.

In another aspect, provided herein are isoparaffinic base oils produced by any of the methods described herein. The methods described herein allow tuning of the viscometric and cold temperature flow properties of the resulting base oils. In some variations, the methods produce base oils having kinematic viscosity at 100° C. of about 2-3 cSt, 4-5 cSt, 6 cSt, 8 cSt, 9 cSt, 10 cSt, 11 cSt, 12 cSt, or greater than 12 cSt. In some variations, the methods produce base oils having viscosity index of at least about 120, e.g., at least about 120, at least about 130, or at least about 140. In some variations, the methods produce a base oil having a kinematic viscosity of about 4 cSt or 5 cSt at 100° C. and a viscosity index of at least about 120, at least about 122, or at least about 124, wherein at least about 40%, least about 50%, at least about 60%, at least about 70%, at least about 80%, at least about 90%, or about 100% of the carbon atoms in the base oil originate from a renewable carbon source. In one variation, the methods produce a base oil having a kinematic viscosity of about 6 cSt at 100° C. and a viscosity index of at least about 120, at least about 125, at least about 128, at least about 130, or at least about 132, wherein at least about 30%, at least about 40%, at least about 50%, at least about 60%, at least about 70%, at least about 80%, at least about 90%, or about 100% of the carbon atoms in the base oil originate from a renewable carbon source. In some variations, the methods produce a base oil having a kinematic viscosity of about 10 cSt at 100° C. and a viscosity index of at least about 120, at least about 125, at least about 128, or at least about 130, wherein at least about 25%, at least about 30%, at least about 40%, at least about 50%, at least about 60%, at least about 70%, at least about 80%, at least about 90%, or about 100% of the carbon atoms in the base oil originate from renewable carbon sources. In some variations, the methods produce a base oil having a kinematic viscosity of about 12 cSt at 100° C. and a viscosity index of at least about 120, at least about 125, at least about 128, or at least about 130, wherein at least about 25%, at least about 30%, at least about 40%, at least about 50%, at least about 60%, at least about 70%, at least about 80%, at least about 90% or about 100% of the carbon atoms originate from renewable carbon sources. In one variation, the methods produce a base oil having a kinematic viscosity of about 4 cSt or 5 cSt at 100° C., a viscosity index of at least about 120, and a cold cranking simulator viscosity at −30° C. of about 1500 cP or less, wherein at least about 40% or at least about 50% of the carbon atoms in the base oil originate from renewable carbon sources.

In some variations, described herein are base oils comprising hydrocarbon terpene feedstock:olefin adducts, hydrogenated. In certain variations, the adducts may be 1:1 hydrocarbon terpene feedstock:olefin adducts, 1:2 hydrocarbon terpene feedstock:olefin adducts, 2:1 hydrocarbon terpene feedstock:olefin adducts, or combinations of two or more of the foregoing. The hydrocarbon terpene feedstock may comprise a partially hydrogenated hydrocarbon terpene in some variations. In some variations, the hydrocarbon terpene feedstock comprises β-farnesene or partially hydrogenated β-farnesene. In some variations, the olefin comprises one or more alpha-olefins selected from the group consisting of 1-decene, 1-dodecene, 1-tetradecene, 1hexadecene, 1-octadecene or a mixture of two or more of the foregoing. In some variations, the hydrocarbon terpene feedstock comprises partially hydrogenated β-farnesene and the olefin comprises 1-tetradecene, 1-hexadecene or a mixture of 1-tetradecene and 1-hexadecene.

In another aspect, provided herein are lubricant compositions comprising an isoparaffinic base oil described herein.

BRIEF DESCRIPTION OF THE DRAWINGS

In FIG. 3C, β-farnesene is shown as a model hydrocarbon terpene.

FIG. 8B provides a proton NMR spectrum of the mixture of isoparaffins as in FIG. 8A, on an expanded scale of about 0.2 ppm-2.7 ppm.

FIG. 9E provides retention time calibration data for n-alkanes for the simulated distillation apparatus used to generate FIG. 9A.

FIG. 16A shows % mono-olefin vs. % di-olefin. FIG. 16B shows % di-olefin vs. % farnesane. FIG. 16C shows % mono-olefin vs. % farnesane. FIG. 16D shows % mono-olefin vs. second stage hydrogenation temperature (° C.). FIG. 16E shows % farnesane vs. second stage hydrogenation temperature (° C.). FIG. 16F shows % di-olefin vs. second stage hydrogenation temperature (° C.).

DETAILED DESCRIPTION

Figure 1:
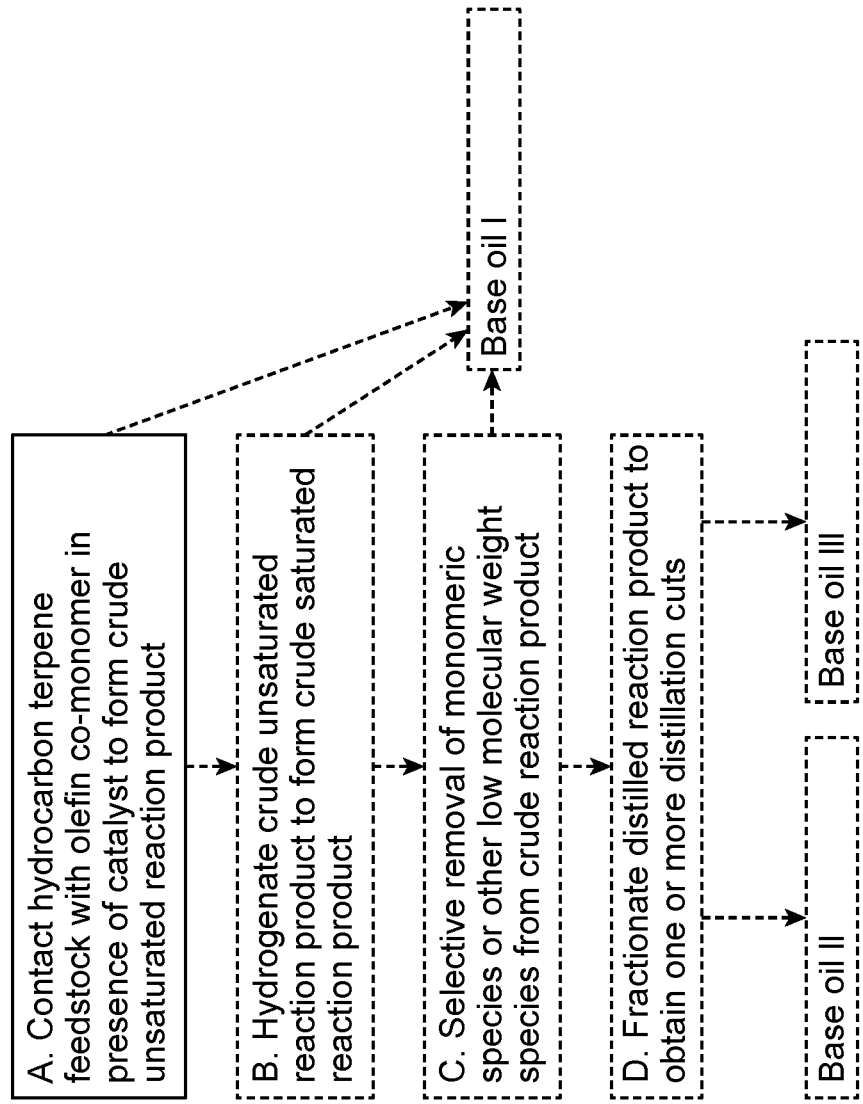
FIG. 1 provides a non-limiting example of a flow chart for a process of coupling a hydrocarbon terpene feedstock with one or more olefin co-monomers to produce one or more base oils.

"Terpene" as used herein is a compound that is capable of being derived from isopentyl pyrophosphate (IPP) or dimethylallyl pyrophosphate (DMAPP), and the term terpene encompasses hemiterpenes, monoterpenes, sesquiterpenes, diterpenes, sesterterpenes, triterpenes, tetraterpenes and polyterpenes. A hydrocarbon terpene contains only hydrogen and carbon atoms and no heteroatoms such as oxygen, and in some embodiments has the general formula $(C_5H_8)_n$, where n is 1 or greater. A "conjugated terpene" or "conjugated hydrocarbon terpene" as used herein refers to a terpene comprising at least one conjugated diene moiety. It should be noted that the conjugated diene moiety of a conjugated terpene may have any stereochemistry (e.g., cis or trans) and may be part of a longer conjugated segment of a terpene, e.g., the conjugated diene moiety may be part of a conjugated triene moiety. It should be understood that hydrocarbon terpenes as used herein also encompasses monoterpenoids, sesquiterpenoids, diterpenoids, triterpenoids, tetraterpenoids and polyterpenoids that exhibit the same carbon skeleton as the corresponding terpene but have either fewer or additional hydrogen atoms than the corresponding terpene, e.g., terpenoids having 2 fewer, 4 fewer, or 6 fewer hydrogen atoms than the corresponding terpene, or terpenoids having 2 additional, 4 additional or 6 additional hydrogen atoms than the corresponding terpene. Some non-limiting examples of conjugated hydrocarbon terpenes include isoprene, myrcene, α-ocimene, β-ocimene, α-farnesene, β-farnesene, β-springene, geranylfarnesene, neophytadiene, cis-phyta-1,3-diene, trans-phyta-1,3-diene, isodehydrosqualene, isosqualane precursor I, and isosqualane precursor II.

The terms terpene and isoprenoids are used interchangeably herein, and are a large and varied class of organic molecules that can be produced by a wide variety of plants and some insects. Some terpenes or isoprenoid compounds can also be made from organic compounds such as sugars by microorganisms, including bioengineered microorganisms. Because terpenes or isoprenoid compounds can be obtained from various renewable sources, they are useful monomers for making eco-friendly and renewable base oils. In certain embodiments, the conjugated hydrocarbon terpenes as described herein are derived from microorganisms using a renewable carbon source, such as a sugar.

The terms terpene and isoprenoids are used interchangeably herein, and are a large and varied class of organic molecules that can be produced by a wide variety of plants and some insects. Some terpenes or isoprenoid compounds can also be made from organic compounds such as sugars by microorganisms, including bioengineered microorganisms. Because terpenes or isoprenoid compounds can be obtained from various renewable sources, they are useful monomers for making eco-friendly and renewable base oils. In certain embodiments, the conjugated hydrocarbon terpenes as described herein are derived from microorganisms using a renewable carbon source, such as a sugar.

"Isoprene" refers to a compound having the following structure:

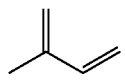

or a stereoisomer thereof.

"Myrcene" refers to a compound having the following structure:

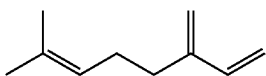

or a stereoisomer thereof.

"Ocimene" refers to α-ocimene, β-ocimene or a mixture thereof.

"α-ocimene" refers to a compound having the following formula:

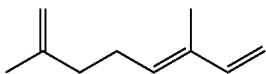

or a stereoisomer thereof.

"β-ocimene" refers to a compound having the following formula:

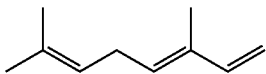

or a stereoisomer thereof.

"Farnesene" as used herein refers to α-farnesene, β-farnesene or a mixture thereof.

"α-Farnesene" refers to a compound having the following structure:

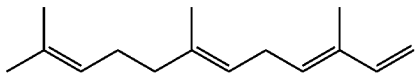

or a stereoisomer (e.g., s-cis isomer) thereof. In some embodiments, α-farnesene comprises a substantially pure stereoisomer of α-farnesene. In some embodiments, α-farnesene comprises a mixture of stereoisomers, such as s-cis and s-trans isomers. In some embodiments, the amount of each of the stereoisomers in an α-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. % or from about 20 wt. % to about 80 wt. %, based on the total weight of the α-farnesene mixture of stereoisomers.

"β-farnesene" refers to a compound having the following structure:

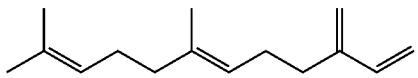

or a stereoisomer (e.g., s-cis isomer) thereof. In some embodiments, β-farnesene comprises a substantially pure stereoisomer of β-farnesene. Substantially pure β-farnesene refers to compositions comprising at least 80%, at least 90%, at least 95%, at least 97%, at least 98% or at least 99% β-farnesene by weight, based on total weight of the farnesene. In other embodiments, β-farnesene comprises a mixture of stereoisomers, such as s-cis and s-trans isomers. In some embodiments, the amount of each of the stereoisomers in a β-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, or from about 20 wt. % to about 80 wt. %, based on the total weight of the β-farnesene mixture of stereoisomers.

"Farnesane" refers to a compound having the following structure:

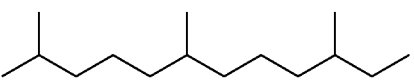

or a stereoisomer thereof.

β-springene (or springene) refers to a compound having the following structure:

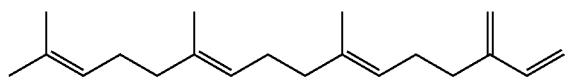 [SMILES: C=CC(=C)CC/C=C(\C)CC/C=C(\C)CCC=C(C)C]

or a stereoisomer thereof.

Neophytadiene refers to a compound having the following structure:

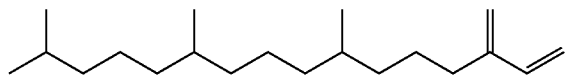 [SMILES: C=CC(=C)CCCC(C)CCCC(C)CCCC(C)C]

or a stereoisomer thereof.

Trans-phyta-1,3-diene refers to a compound having the following structure:

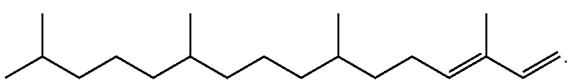 [SMILES: C=C/C(C)=C/CCC(C)CCCC(C)CCCC(C)C]

or a stereoisomer thereof.

Cis-phyta-1,3-diene refers to a compound having the following structure:

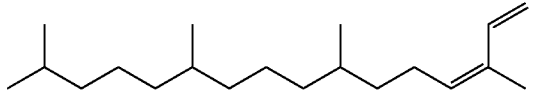 [SMILES: C=C/C(C)=C\CCC(C)CCCC(C)CCCC(C)C]

or a stereoisomer thereof.

"Squalene" refers to a compound having the following structure:

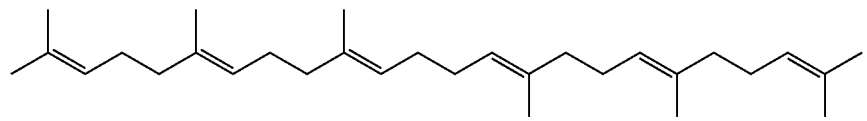 [SMILES: CC(C)=CCC/C(C)=C/CC/C(C)=C/CC/C=C(\C)CC/C=C(\C)CCC=C(C)C]

or a stereoisomer thereof.

As used herein, "isodehydrosqualene" refers to a compound having the following structure:

or a stereoisomer thereof.

As used herein, "isosqualane precursor I" or 2,6,18,22-tetramethyl-10-methylene-14-vinyltricosa-2,6,11,17,21-pentaene refers to a compound having the following structure:

or a stereoisomer thereof.

As used herein, "isosqualane precursor II" or 2,6,14,18,22-pentamethyl-10-vinyltricosa-2,6,10,14,17,21-pentaene refers to a compound having the following structure:

or a stereoisomer thereof.

Geranylfarnesene refers to a compound having the following structure:

or a stereoisomer thereof.

"Hydrogenated hydrocarbon terpene" refers to a hydrocarbon terpene having at least one carbon-carbon double bond, wherein at least one carbon-carbon double bond is hydrogenated. Partially hydrogenated hydrocarbon terpene refers to a hydrocarbon terpene molecule in which not all of the carbon-carbon double bonds have been hydrogenated, and also refers to a hydrogenated hydrocarbon terpene sample in which at least about 5% of the carbon-carbon double bonds remain unsaturated.

"Hydrogenated myrcene" refers to a myrcene molecule in which at least one carbon-carbon double bond is hydrogenated. Hydrogenated myrcene encompasses myrcene in which one, two, or three double bonds are hydrogenated, and any mixtures thereof. Partially hydrogenated myrcene is an example of a partially hydrogenated hydrocarbon terpene, and refers to a myrcene molecule in which only one or two double bonds have been hydrogenated, and also refers to a hydrogenated myrcene sample in which at least about 5% of the carbon-carbon double bonds remain unsaturated. A sample of partially hydrogenated myrcene may comprise dihydromyrcene, tetrahydromyrcene, hexahydromyrcene, or any combination thereof. In some cases, a partially hydrogenated myrcene sample comprises myrcene in addition to one or more of dihydromyrcene, tetrahydromyrcene, and hexahydromyrcene.

"Hydrogenated farnesene" refers to farnesene (e.g. β-farnesene or α-farnesene) wherein at least one carbon-carbon double bond is hydrogenated. Hydrogenated farnesene encompasses β-farnesene or α-farnesene in which one, two, three or four double bonds are hydrogenated, and any mixtures thereof. Hydrogenated farnesene is obtained by complete or partial hydrogenation of farnesene, and encompasses farnesane. Partially hydrogenated farnesene refers to farnesene (e.g. β-farnesene or α-farnesene) in which one, two, or three double bonds are hydrogenated, and any mixture thereof. Partially hydrogenated farnesene refers to a farnesene molecule in which only one, two or three double bonds have been hydrogenated, and also refers to a hydrogenated farnesene sample in which at least about 5% of the carbon-carbon double bonds remain unsaturated. A sample of partially hydrogenated farnesene may include farnesene in addition to one or more of dihydrofarnesene, tetrahydrofarnesene, hexahydrofarnesene, and farnesane.

"Olefin co-monomer" refers to any olefin containing at least one carbon-carbon double bond. "Olefin co-monomer(s)" means one or more olefin co-monomers, where it is understood that two olefin co-monomers refers to two olefin co-monomers that are different from each other, etc.

"Alpha-olefin" as used herein refers to any olefin having at least one terminal unconjugated carbon-carbon double bond. "Alpha-olefin" encompasses linear alpha-olefins (LAOS) and branched alpha-olefins. Alpha-olefins may contain one or more carbon-carbon double bonds in addition to the terminal olefinic bond, e.g., α,ω-dienes. LIOs refers to linear internal olefins, which are linear olefins containing one or more carbon-carbon double bonds, none of which are located at a terminal position. Branched internal olefins refers to branched olefins containing one or more carbon-carbon double bonds, none of which are located at a terminal position.

"Oligomer" as used herein refers to a molecule having 2-100 monomer units, and encompasses dimers, trimers, tetramers, pentamers, and hexamers. An oligomer may comprise one type of monomer unit or more than one type of monomer unit, e.g. two types of monomer units, or three types of monomer units. "Oligomerization" refers to the formation of a molecule having 2-100 monomer units from one or more monomers, and encompasses dimerization, trimerization, etc. of one type of monomer, and also encompasses the formation of adducts between more than one type of monomer.

"Polymer" as used herein refers to a polymeric compound prepared by polymerizing monomers, whether of the same or a different type, and having more than 100 monomeric units. The generic term "polymer" embraces the terms "homopolymer," "copolymer," "terpolymer" as well as "interpolymer." The generic term "interpolymer" encompasses the term "copolymer" (which generally refers to a polymer prepared from two different monomers) as well as the term "terpolymer" (which generally refers to a polymer prepared from three different types of monomers), and polymers made by polymerizing four or more types of polymers.

"Dimer" or "dimeric species" as used herein refers to any type of adducts formed between two molecules, and encompasses 1:1 adducts of same type of molecules or 1:1 adducts of different type of molecules unless specifically stated otherwise. "Trimer" or "trimeric species" refers to any type of adducts formed between three molecules, and encompasses 1:1:1 of same type of molecules or three different types of molecules, and 1:2 or 2:1 adducts of two different types of molecules. "Tetramer" or "tetrameric species" refers to any type of adducts formed between four molecules. "Pentamer" or "pentameric species" refers to any type of adducts formed between five molecules. "Hexamer" or "hexameric species" refers to any type of adducts formed between six molecules.

"Viscosity index" as used herein refers to viscosity index as measured according to ASTM D2270 "Standard Practice for Calculating Viscosity Index From Kinematic Viscosity at 40 and 100° C.," published by ASTM International, which is incorporated herein by reference in its entirety.

Kinematic viscosities at 40° C. and at 100° C. are measured according to ASTM D445 "Standard Test Method for Kinematic Viscosity of Transparent and Opaque Liquids (and Calculation of Dynamic Viscosity)," published by ASTM International, which is incorporated herein by reference in its entirety.

"Pour point" is measured according to ASTM D97 "Standard Test Method for Pour Point of Petroleum Products," published by ASTM International, which is incorporated herein by reference in its entirety.

"Cold cranking simulator viscosity" as used herein refers to cold cranking simulator viscosity as measured according to ASTM D5293 "Standard Test Method for Apparent Viscosity of Engine Oils Between −5 and −35° C. Using the Cold-Cranking Simulator," published by ASTM International, which is incorporated herein by reference in its entirety.

"Boiling point" refers to the natural boiling point of a substance at atmospheric pressure, unless indicated otherwise.

Simulated Distillation may be carried out according to ASTM D 6352-02 "Standard Test Method for Boiling Range Distribution of Petroleum Distillates in Boiling Range from 174 to 700° C. by Gas Chromatography," ASTM D2887 "Test Method for Boiling Range Distribution of Petroleum Fractions by Gas Chromatography," or ASTM D 6417 "Standard Test Method for Estimation of Engine Oil Volatility by Capillary Gas Chromatography," each published by ASTM International, and each of which is incorporated herein by reference in its entirety.

Evaporative weight loss may be carried out according to ASTM D5800 "Standard Test Method for Evaporation Loss of Lubricating Oils by the Noack Method," or ASTM D6375 "Standard Test Method for Evaporation Loss of Lubricating Oils by Thermogravimetric Analyzer (TGA) Noack Method" (TGA-Noack method), each published by ASTM International, and each of which is incorporated herein by reference in its entirety.

In the following description, all numbers disclosed herein are approximate values, regardless of whether the word "about" or "approximate" is used in connection therewith. Numbers may vary by 1%, 2%, 5%, or sometime, 10 to 20%. Whenever a numerical range with a lower limit $R^L$ and an upper limit $R^U$ is disclosed, any number falling within the range is specifically disclosed. In particular, the following numbers $R_k$ within the range are specifically disclosed: $R_k=R^L+k*(R^U-R^L)$, wherein k is a variable ranging from 1% to 100% with a 1% increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Further, any numerical range defined by any two numbers $R_k$ as defined above is also specifically disclosed herein.

As used herein and unless otherwise indicated, a reaction that is "substantially complete" means that the reaction contains more than about 80% desired product by percent yield, more than about 90% desired product by percent yield, more than about 95% desired product by percent yield, or more than about 97% desired product by percent yield. As used herein, a reactant that is "substantially consumed" means that more than about 85%, more than about 90%, more than about 95%, more than about 97% of the reactant has been consumed, by weight %, or by mol %.

As used herein, % refers to % measured as wt. % or as area % by GC-MS or GC-FID, unless specifically indicated otherwise.

As used herein and unless otherwise indicated, a composition that is made up "predominantly" of a particular component includes at least about 60% of that component. A composition that "consists essentially of" a component refers to a composition comprising 80% or more of that component, unless indicated otherwise.

In some embodiments, described herein are isoparaffinic compositions that have utility as base oils. Also described herein are methods for oligomerizing a hydrocarbon terpene feedstock to make isoparaffins, and also methods for oligomerizing a hydrocarbon terpene feedstock with one or more olefinic co-monomers to make isoparaffins. In some variations of the methods, partially hydrogenated terpene is oligomerized to make isoparaffins. In some embodiments, partially hydrogenated terpene is coupled with one or more olefins in an oligomerization reaction in which adducts between the hydrocarbon terpene feedstock and the one or more olefins are formed, e.g. 1:1 terpene:olefin adducts, 1:2 terpene:olefin adducts, 2:1 terpene:olefin adducts, etc.

Advantageously, in some embodiments, the terpene from which the isoparaffins are derived is made from a renewable resource. In some variations, a conjugated terpene is obtained using genetically modified organisms that are grown using renewable carbon sources (e.g., sugar cane). In some variations, a conjugated terpene is prepared by contacting a cell capable of making a conjugated terpene with a suitable carbon source under conditions suitable for making a conjugated terpene. Nonlimiting examples conjugated terpenes (e.g., myrcene, ocimene, farnesene, isodehydrosqualene, isosqualane precursor I, and isosqualane precursor II) obtained using genetically modified microbial cells are provided in U.S. Pat. No. 7,399,323, U.S. Pat. Publ. 2008/0274523, International Patent Publication WO 2007/140339, International Patent Publication WO 2007/139924, U.S. Pat. No. 7,659,097, International Patent Publication WO 2010/042208 and U.S. patent application Ser. No. 13/112,991, each of which is incorporated herein by reference in its entirety as if put forth fully below.

Any carbon source that can be converted into one or more isoprenoid compounds can be used herein. In some variations, the carbon source is a sugar or a nonfermentable carbon source. The sugar can be any sugar known to one of skill in the art. For example, in some variations, the sugar is a monosaccharide, disaccharide, polysaccharide, or a combination of two or more of the foregoing. In some cases, the sugar is a simple sugar (a monosaccharide or a disaccharide). Some non-limiting examples of suitable monosaccharides include glucose, galactose, mannose, fructose, ribose, and combinations of two or more of the foregoing. Some non-limiting examples of suitable disaccharides include sucrose, lactose, maltose, trehalose, cellobiose, and combinations of two or more of the foregoing. In some cases, the sugar is sucrose. In some cases, a conjugated terpene can be obtained from a polysaccharide. Non-limiting examples of suitable polysaccharides include starch, glycogen, cellulose, chitin, and combinations of two or more of the foregoing.

As used herein, a "renewable carbon" source refers to a carbon source that is made from modern carbon that can be regenerated within a several months, years or decades rather than a carbon source derived from fossil fuels (e.g., petroleum) that takes typically a million years or more to regenerate. The terms "renewable carbon" and "biobased carbon" are used interchangeably herein. "Atmospheric carbon" refers to carbon atoms from carbon dioxide molecules that have been free in earth's atmosphere recently, e.g., in the most recent few decades. For example, conjugated hydrocarbon terpenes used in any one of the embodiments described herein can be made from microorganisms, including bioengineered microorganisms, using a renewable carbon source.

Renewable carbon content can be measured using any suitable method. For example, renewable carbon content can be measured according to ASTM D6866-11, "Standard Test Methods for Determining the Biobased Content of Solid, Liquid, and Gaseous Samples Using Radiocarbon Analysis," published by ASTM International, which is incorporated herein by reference in its entirety. Some carbon in atmospheric carbon dioxide is the radioactive $^{14}C$ isotope, having a half-life of about 5730 years. Atmospheric carbon dioxide is utilized by plants to make organic molecules. The atmospheric $^{14}C$ becomes part of biologically produced substances. As the biologically produced organic molecules degrade to produce carbon dioxide into the atmosphere, no net increase of carbon in the atmosphere is produced as a result, which may control or diminish undesired climate effects that may result when molecules produced from fossil fuels degrade to produce carbon dioxide to increase carbon in the atmosphere.

Isotope fractionation occurs during physical processes and chemical reactions, and is accounted for during radiocarbon measurements. Isotope fractionation results in enrichment of one isotope over another isotope. Exemplary processes that can affect isotope fractionation include diffusion (e.g., thermal diffusion), evaporation, and condensation. In some chemical reactions, certain isotopes may exhibit different equilibrium behaviors than others. In some chemical reactions, kinetic effects may affect isotope ratios. In the carbon cycle of plants, isotope fractionation occurs. During photosynthesis, the relative amounts of different carbon isotopes that are consumed are $^{12}C > ^{13}C > ^{14}C$, due to slower processing of heavier isotopes. Plants species exhibit different isotope fractionation due to isotopic discrimination of photosynthetic enzymes and diffusion effects of their stomata. For example $C_3$ plants exhibit different isotope fractionation than $C_4$ plants. The international reference standard for isotope fractionation between $^{13}C$ and $^{12}C$ is PDB (Pee Dee Belemnite standard) or VPDB (Vienna Pee Dee Belemnite standard, replacement for depleted PDB standard). For a given sample, isotope fractionation can be expressed as $\delta^{13}C$ (per mil)=$\{[R(sample)/R(VPDB\ standard)]-1\} \times 1000‰$, where $R(sample)=^{13}C/^{12}C$ and $R(VPDB\ standard)=^{13}C/^{12}C$ for the VPDB standard. Instead of a $^{13}C/^{12}C$ ratio, $\delta^{13}C$ is the relative change of the $^{13}C/^{12}C$ ratio for a given sample from that of the VPDB standard. Carbon isotopic ratios are reported on a scale defined by adopting a $\delta^{13}C$ value of +0.00195 for NBS-19 limestone (RM 8544) relative to VPDB. "New IUPAC guidelines for the reporting of stable hydrogen, carbon, and oxygen isotope-ratio data," Letter to the Editor, J. Res. Natl. Stand. Technol. 100, 285 (1995). Most naturally occurring materials exhibit negative $\delta^{13}$ values. In general, for atmospheric $CO_2$ $\delta^{13}$ ranges between −11 to −6 ‰, for $C_3$ plants, $\delta^{13}C$ varies between −22 and −32 ‰, and for $C_4$ plants $\delta^{13}C$ varies between −8 to −18 ‰. The $^{14}C$ fractionation factor can be approximated as the square of the $^{13}C$ fractionation factor. See, e.g., M. Stuiver and S. W. Robinson, Earth and Planetary Science Letters, vol. 23, 87-90.

$^{14}C$ content of a sample can be measured using any suitable method. For example, $^{14}C$ content can be measured using Accelerator Mass Spectrometry (AMS), Isotope Ratio Mass Spectrometry (IRMS), Liquid Scintillation Counting (LSC), or a combination of two or more of the foregoing, using known instruments. Activity refers to the number of decays measured per unit time and per unit mass units. To compare activity of a sample with that of a known reference material, isotope fractionation effects can be normalized. If an activity of a sample is measured to be $A_S$, the sample activity normalized to the reference is $A_{SN}$ and can be expressed as: $A_{SN}=A_S\{[(^{13}C/^{12}C)reference]/[(^{13}C/^{12}C)sample]\}^2$.

Radiocarbon measurements are performed relative to a standard having known radioactivitiy. SRM 4990B is an oxalic acid dehydrate Standard Reference Material provided by the U.S. National Bureau of Standards (now National Institute of Standards and Technology, NIST) in the late 1950s having $\delta^{13}C=-19‰$ (PDB). SRM 4990B has been depleted so another standard is used, such as SRM 4990C, a second oxalic acid standard from NIST having $\delta^{13}C=-17.8‰$ (VPDB). Modern carbon, referenced to AD 1950, is 0.95 times $^{14}C$ concentration of SRM 4990B, normalized to $\delta^{13}C=-19‰$ (PDB). The factor 0.95 is used to correct the value to 1950 because by the late 1950s, $^{14}C$ in the atmosphere had artificially risen about 5% above natural values due to testing of thermonuclear weapons. Fraction of modern ($f_M$) refers to a radiocarbon measured compared to modern carbon, referenced to AD1950. Modern carbon as defined above has $f_M=1$. For current living plant material not more than a few years old (such as corn), $f_M$ is approximately 1.1. Percent modern carbon (pMC) is $f_M \times 100\%$. The AD 1950 standard had 100 pMC. Fresh plant material may exhibit a pMC value of about 107.5. Biobased carbon content is determined by setting 100% biobased carbon equal to the pMC value of freshly grown plant material (such as corn), and pMC value of zero corresponds to a sample in which all of the carbon is derived from fossil fuel (e.g., petroleum). A sample containing both modern carbon and carbon from fossil fuels will exhibit a biobased carbon content between 0 and 100%. In some cases, a sample that is more than several years old but containing all biobased carbon (such as wood from a mature tree trunk) will exhibit a pMC value to yield a biobased carbon content>100%.

Renewable carbon content or biobased carbon content as used herein refers to fraction or percent modern carbon determined by measuring $^{14}C$ content, e.g., by any of Method A, Method B, or Method C as described in ASTM D6866-11 "Standard Test Methods for Determining the Biobased Content of Solid, Liquid, and Gaseous Samples Using Radiocarbon Analysis." Counts from $^{14}C$ in a sample can be compared directly or through secondary standards to SRM 4990C. A measurement of 0% $^{14}C$ relative to the appropriate standard indicates carbon originating entirely from fossils (e.g., petroleum based). A measurement of 100% $^{14}C$ indicates carbon originating entirely from modern sources. A measurement of >100% $^{14}C$ indicates the source of carbon has an age of more than several years.

In some variations, about 100% of the carbon atoms in the hydrocarbon terpene feedstocks described herein originate from renewable carbon sources. In some variations, about 100% of the carbon atoms in the olefin co-monomer originate from renewable carbon sources. For example, an alpha-olefin co-monomer may be produced by oligomerization of ethylene derived from dehydration of ethanol produced from a renewable carbon source. In some variations, an alpha-olefin co-monomer may be produced by dehydration of a primary alcohol other than ethanol that is produced from a renewable carbon source. Advantageously, in some embodiments, hydrocarbon terpene feedstocks derived from renewable resources are coupled with one or more olefins that are derived from renewable resources. In some variations, the terpene feedstocks or base oils have a $\delta^{13}C$ of from about −11 to about −6‰, from about −15 to about −10‰, from about −22 to about −15‰, from about −22 to about −32‰, from −8 to about −18‰, from about −14 to about −12‰, or from about −13 to about −11‰. In some variations, the terpene feedstocks or base oils have a $f_M$ greater than about 0.3, greater than about 0.4, greater than about 0.5, greater than about 0.6, greater than about 0.7, greater than about 0.8, greater than about 0.9, or greater than about 1.0. In some variations, the terpene feedstocks or base oils have a $f_M$ of about 1.0 to about 1.05, about 1.0 to about 1.1, or about 1.1 to about 1.2. In some variations, the terpene feedstocks or base oils have a $\delta^{13}C$ from about −15 to about −10‰ and a $f_M$ greater than about 0.5, greater than about 0.7, or greater than about 1.0. In some variations, the terpene feedstocks or base oils have a $\delta^{13}C$ from about −8 to about −18‰ and a $f_M$ greater than about 0.5, greater than about 0.7, or greater than about 1.0. In some variations, the conjugated hydrocarbon terpene (e.g., myrcene, β-farnesene, or α-farnesene) is made by genetically modified microorganisms using renewable carbon sources such as a sugar (e.g., sugar cane). In some variations, the base oils described herein have a renewable carbon content of at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%. The renewable carbon content of the olefinic feedstocks may be measured using any suitable method, e.g., using radiocarbon analysis as described herein, such as according to ASTM D6866.

In some variations, the base oils described herein comprise virtually no sulfur. In some variations, the base oils described herein comprise virtually no aromatic compounds. In some variations, the base oils described herein comprise virtually no sulfur and virtually no aromatic compounds. Reduction or elimination of sulfur and/or aromatic compounds makes them environmentally preferable over conventional olefins derived from fossil fuels, which in many cases contain sulfur and aromatics, such as naphthalenes. In certain embodiments, the base oils comprise less than about 10 ppm sulfur, less than about 1 ppm sulfur, less than about 100 ppb sulfur, less than about 10 ppb sulfur or less than about 1 ppb sulfur. In certain embodiments, the base oils comprise less than about 10 ppm aromatics, less than about 1 ppm aromatics, less than about 100 ppb aromatics, less than about 10 ppb aromatics or less than about 1 ppb aromatics. In certain embodiments, the base oils comprise less than about 10 ppm sulfur and less than about 10 ppm aromatics, less than about 1 ppm sulfur and less than about 1 ppm aromatics, less than about 100 ppb sulfur and less than about 100 ppb aromatics, less than about 10 ppb sulfur and less than about 10 ppb aromatics, or less than about 1 ppb sulfur and less than about 1 ppb aromatics.

I. Methods

In certain embodiments, provided herein are methods for making one or more branched alkenes, comprising catalytically coupling a hydrocarbon terpene feedstock with one or more olefin co-monomers to form branched alkenes. In some instances, the methods further comprise hydrogenating the branched alkenes to form isoparaffins. At least a portion of the branched alkenes or isoparaffins so formed may be used as a base oil, or as a component of a base oil. In those base oil applications in which thermo-oxidative stability is important, it may be desired to use hydrogenated isoparaffins to make base oils. Unsaturated bonds, especially in low molecular weight oligomers, may be susceptible to oxidation. If higher molecular weight oligomers or polymers are formed, it may not be necessary to hydrogenate the reaction product for use in certain base oil applications, especially if the concentration of unsaturated bonds is relatively low, e.g., so that the bromine index is about 500 or less, about 200 or less, or about 100 or less (units of mg Br/100 g substance).

The reaction product (branched alkenes if not hydrogenated, or isoparaffins if hydrogenated) made by the methods may in certain variations comprise 1:1 adducts between the hydrocarbon terpene feedstock and the one or more olefin co-monomers. As described herein, the terms hydrocarbon terpene feedstock and terpene feedstock encompass hydrocarbon terpenes and partially hydrogenated hydrocarbon terpenes. In certain variations, the reaction product made by the methods may comprise adducts selected from the group consisting of 1:1 terpene feedstock:olefin adducts, 1:2 terpene feedstock:olefin adducts, 2:1 terpene feedstock:olefin adducts, 1:3 terpene feedstock:olefin adducts, 3:1 terpene feedstock:olefin adducts, 2:2 terpene feedstock:olefin adducts, and mixtures comprising two or more of the foregoing. In certain variations, the reaction product made by the methods may comprise pentamers or higher oligomers. In some embodiments, the reaction product comprises 1:1, 2:1 and 1:2 terpene feedstock:olefin adducts. In some embodiments, the reaction product comprises 1:1 and 1:2 terpene feedstock:olefin adducts. In some embodiments, the reaction product comprises 1:1 and 2:1 terpene feedstock:olefin adducts.

In some embodiments, the reaction product (one or more branched alkenes if not hydrogenated, or isoparaffins if hydrogenated) made by the methods described herein comprises dimers and/or trimers of a terpene feedstock. In some embodiments, the reaction product comprises dimers, trimers, and tetramers of a terpene feedstock. In some embodiments, the reaction product comprises tetramers and/or pentamers of a terpene feedstock. In certain embodiments, the reaction products may comprise hexamers or higher oligomers or polymers of the hydrocarbon terpene feedstock.

In certain variations, the reaction product (one or more branched alkenes if not hydrogenated, or isoparaffins if hydrogenated) prepared by the methods described herein may be used as-is as a base oil or as a component of a base oil, without the need for a separation process other than routine removal of catalyst, solvent and monomeric species.

In certain variations, the reaction product prepared by the methods described herein may be fractionated prior to further use, e.g., as a base oil or as a component of a base oil. For instance, the reaction product may comprise a broad carbon number distribution, so that it may be desired to select for use certain fractions of the reaction product. Accordingly, provided herein are methods that comprise one or more distillation steps to isolate desired distillation cuts from the reaction product. The one or more such distillation cuts can be used as or in a base oil. For example, a distillation cut that consists predominantly of 1:1 terpene feedstock:olefin adducts may be collected, and/or a distillation cut that consists predominantly of 1:2 terpene feedstock:olefin and/or 2:1 terpene feedstock:olefin may be collected. One or more distillation cuts isolated from the adducts may be used to form one or more base oils. For example, from a single reaction product, a lower boiling distillation cut (e.g., a cut composed predominantly of 1:1 terpene feedstock:olefin adducts) may be used as a low viscosity base oil, and a higher boiling distillation cut (e.g., a cut composed predominantly of 1:2 and/or 2:1 terpene feedstock:olefin adducts or higher oligomers) may be used as a higher viscosity base oil. As used herein, a distillation cut may refer to a lower boiling portion that is vaporized and subsequently condensed. The term distillation cut is meant to also encompass the residue or bottoms, a higher boiling portion that remains in the pot following vaporization of lower boiling components.

In some variations, the methods result in reaction products in which adducts derived only from olefin co-monomers (e.g. dimers, trimers, tetramers, or pentamers of olefin co-monomers) make up about 50% or less, 45% or less, 40% or less, 35% or less, 30% or less, 25% or less, 20% or less, 15% or less, 10% or less, 5% or less, or 1% or less of the branched alkenes or isoparaffinic reaction product. In some variations, the reaction products contain less than 1% adducts derived only from olefin co-monomers. In some variations, the reaction products contain less than 5% adducts derived only from olefin co-monomers.

Advantageously, in certain variations, the methods result in reaction products in which at least about 20%, at least about 30%, at least about 40%, at least about 50%, at least about 60%, at least about 70%, at least about 80%, or at least about 90% of the carbon atoms in the adducts originate from renewable carbon sources. In some variations, the methods result in reaction products in which at least about 95%, at least about 97%, at least about 99%, or about 100% of the carbon atoms originate from renewable carbon sources. The origin of carbon atoms in the reaction product adducts may be determined by any suitable method, including but not limited to reaction mechanism combined with analytical results that demonstrate structure and/or molecular weight of adducts, or by carbon dating (e.g., according to ASTM D6866 "Standard Test Methods for Determining the Biobased Content of Solid, Liquid, and Gaseous Samples Using Radiocarbon Analysis," which is incorporated herein by reference in its entirety). For example, using ASTM D6866 or another suitable technique, a ratio of carbon 14 isotope to carbon 12 isotope can be measured by liquid scintillation counting and/or isotope ratio mass spectroscopy to determine the amount of modern carbon content in the sample. A measurement of no modern carbon content indicates all carbon is derived from fossil fuels. A sample derived from renewable carbon sources will indicate a concomitant amount of modern carbon content, up to 100%.

Provided herein are methods of making a base oil. In the methods, one or more reaction products, produced by the methods described herein, is used to make a base oil. In certain embodiments, the reaction product or products can be used directly as a base oil. In certain embodiments, the reaction product or products can undergo one or more steps before being used as a base oil. For instance, in certain embodiments, unreacted hydrogenated or unhydrogenated monomeric species can be removed from the one or more reaction products. In certain embodiments, low molecular weight species can be removed from the one or more reaction products. In certain embodiments, the one or more reaction products can be fractionated, for example, by distillation. Any distillation cut or any combination of distillation cuts can provide a base oil or can be used to make a base oil. In some cases, a distillation cut comprising predominantly unsaturated monomeric species may be recycled for reuse. In some cases, a distillation cut comprising predominantly saturated monomeric species (e.g., hydrogenated hydrocarbon terpene, alkanes derived from olefin comonomers, or a mixture of the two) may be used as a solvent in a lubricant additive, or may be suitable for use as a fuel, e.g., as a diesel fuel.

In certain embodiments, the methods described herein may include one or more pre-reaction processes and/or one or more post-reaction processes (where reaction refers to the coupling between the hydrocarbon terpene feedstock and one or more olefin co-monomers). For example, the methods may comprise any one of or any combination of the following non-limiting examples of pre-reaction processes: filtration, distillation, or other pre-treatment of the hydrocarbon terpene feedstock and/or the olefin co-monomer (e.g., to remove oxygenates such as alcohols, acids, epoxides, or glycerides, or low boiling components); blending of multiple components within the hydrocarbon terpene feedstock; blending of multiple components within the olefin comonomer feedstock; or blending of hydrocarbon terpene feedstock with olefin co-monomer(s). Non-limiting examples of pre-treatments to remove oxygenates from hydrocarbon terpene feedstock include distillation, filtration using silica or basic alumina, treatment using molecular sieves (e.g. 13× molecular sieves), or caustic washing (e.g., using 5-30% caustic) followed by centrifuge and separation of aqueous content. In some variations, a combination of two or more of caustic wash, filtration using alumina, and distillation is used to pre-treat hydrocarbon terpene feedstock. It should be noted that such pretreatment may occur prior to and/or following a partial hydrogenation step for the hydrocarbon terpene. In some variations, a hydrocarbon terpene feedstock is treated to remove oxygenates prior to partial hydrogenation (e.g., using silica or basic alumina), and is filtered using diatomaceous earth following partial hydrogenation. In some cases, the hydrocarbon terpene feedstock is stored under inert atmosphere (e.g., dry nitrogen). In some variations, a hydrocarbon terpene feedstock has a purity of greater than 97%, a farnesene dimer content of less than 3%, a water content measured by Karl Fischer titration of less than 400 ppm, and total acid number (TAN) of less than 0.1%. In some variations, a hydrocarbon terpene feedstock may include an antioxidant (e.g, TBC (4-tert-butyl catechol) of about 50-125 ppm. It should be noted that in the case of a partially hydrogenated feedstock, the hydrocarbon terpene may be pretreated prior to the selective hydrogenation process using any one of or any combination of the pre-treatments described herein or known in the art. The presence of oxygenates or other contaminants may cause poisoning of catalyst or slow or unpredictable hydrogenation rates, so in some variations it may be desired to pre-treat a hydrocarbon terpene prior to the selective hydrogenation process. In some variations, the hydrocarbon terpene is not pre-treated to remove oxygenates or other contaminants prior to a selective hydrogenation process. In some variations, the hydrocarbon terpene is pre-treated both prior to and after selective hydrogenation. The methods may comprise any one of or any combination of the following non-limiting examples of post-reaction processes in a useful sequence: distillation to remove unreacted monomer, hydrogenation, filtration, purification, distillation to remove low boiling components, distillation to prepare desired distillation cuts, or blending together of one or more distillation cuts.

FIG. 1 provides one non-limiting example of a process for making a base oil by methods described herein that includes a number of optional post-reaction processes. As shown in Step A, the hydrocarbon terpene feedstock is contacted with the olefin co-monomer in the presence of a catalyst to form a crude unsaturated reaction product. The catalyst is removed from the crude unsaturated reaction product using any suitable method. Optionally, as shown in Step B, the crude unsaturated reaction product may be hydrogenated. Optionally, as shown in Step C, the monomeric or other low molecular weight species that may be present are selectively removed from the reaction product (hydrogenated in some cases), for example, by distillation. Note that if the reaction has gone essentially to completion such that the amount of unreacted monomeric species is suitably small, Step C may be omitted. As shown, a base oil (illustrated schematically as Base oil I) may be made from the crude reaction product, a hydrogenated crude reaction product, or a reaction product (hydrogenated or not hydrogenated) from which monomeric or other low molecular weight species have been selectively removed. Optionally, the reaction product (hydrogenated or not hydrogenated) undergoes one or more distillation steps (Step D) through which one or more distillation cuts are obtained. Optionally, more than one base oil (schematically illustrated as Base oil II and Base oil III in FIG. 1) can be made from multiple distillation cuts, either with each distillation cut be used to make a separate base oil, or by combining multiple distillation cuts to make a base oil. It should be noted that the number of different base oils that can be made from distillation cuts is not limited to two, e.g., three, four, or more different base oils can be made from distillation cuts. In some variations, heavier molecular weight residue remaining after fractionation step D is a distillation cut used in the making of one or more base oils.

Figure 2:
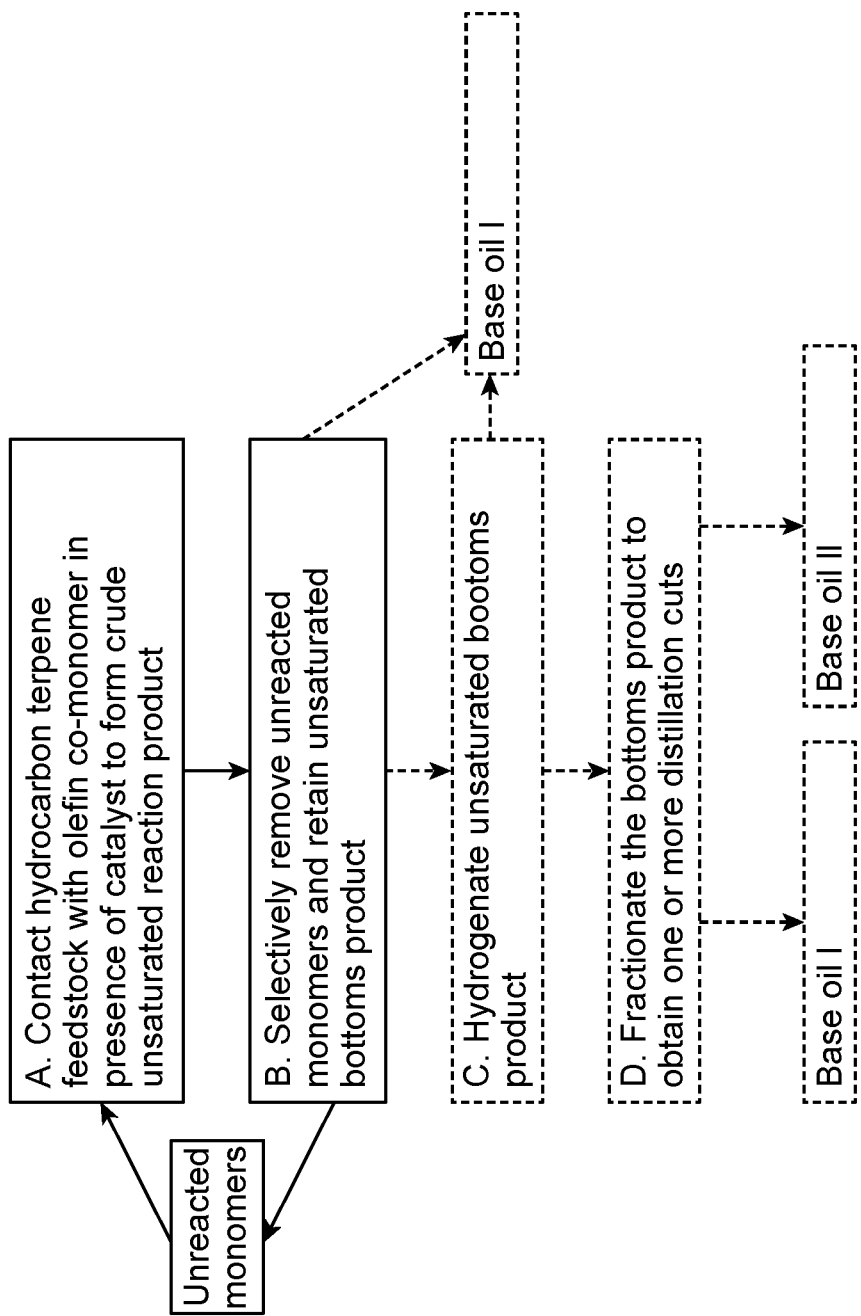
FIG. 2 provides another non-limiting example of a flow chart for a process of coupling a hydrocarbon terpene feedstock with one or more olefin co-monomers to produce one or more base oils.

In some variations of the methods, unreacted monomers may be recycled. A non-limiting example of such as process is shown in FIG. 2. For FIG. 2, Step A is as in FIG. 1. Catalyst is removed from the reaction product using any suitable method. In Step B, unreacted monomers (unreacted hydrocarbon terpene feedstock and/or unreacted olefin co-monomer) are selectively removed from the crude, nonhydrogenated reaction product and collected, e.g., by a distillation procedure, and fed back into the coupling reaction. (Note that any applicable treatment steps are performed on the recycled monomer prior to reuse in the coupling reaction, e.g., filtration, washing, distillation, or the like). Optionally, the crude nonhydrogenated reaction product is hydrogenated (Step C). Optionally, a base oil can be made from the crude hydrogenated or nonhydrogenated bottoms product (illustrated schematically as Base oil I). Optionally, the bottoms product (hydrogenated or not hydrogenated) undergeoes one or more distillation steps (Step D) by which one or more distillation cuts are obtained. Optionally, more than one base oil (schematically illustrated as Base oils II and Base oil III in FIG. 2) can be made from multiple distillation cuts, either with each distillation cut be used to make a separate base oil, or by combining multiple distillation cuts to make a base oil. It should be noted that the number of different base oils that can be made from distillation cuts is not limited to two, e.g., three, four, or more different base oils can be made from distillation cuts. In some variations, heavier molecular weight residue remaining after fractionation step D is a distillation cut used in the making of one or more base oils.

As illustrated in FIG. 1 and FIG. 2, the methods may optionally comprise fractionating a mixture of branched alkenes or a mixture isoparaffins to collect one or more cuts, each cut characterized by a pre-selected boiling point range, which may be correlated to a desired hydrocarbon molecular weight range. As discussed, a residue remaining in a pot after distillation may also be characterized by a pre-selected boiling point lower limit (meaning the boiling point of the residue in the pot is greater than a pre-selected boiling point limit), which may be correlated to a desired hydrocarbon molecular weight range.

In certain variations of the methods, catalysis conditions are selected that result in formation of a new carbon-carbon bond between a hydrocarbon terpene and an olefin co-monomer (e.g., an alpha-olefin co-monomer) using stoichiometric amounts of reagents to activate the starting materials. In other variations of the methods, catalysis conditions are selected that do not require stoichiometric amounts of reagents to activate the starting materials.

For the methods described herein, any suitable coupling mechanism or reaction may be used to couple the hydrocarbon terpene to the one or more olefin co-monomers. Certain coupling mechanisms may involve reaction of a conjugated diene moiety on the hydrocarbon terpene feedstock with a terminal olefin. One non-limiting example of such a reaction is a hydrovinylation reaction. Other coupling mechanisms may utilize a hydrocarbon terpene feedstock that is substantially free of conjugated diene functionality, so that the hydrocarbon terpene feedstock in such instances may be partially hydrogenated, or may comprise one or more selected species of partially hydrogenated hydrocarbon terpene. One non-limiting example of such a reaction involves a cationic initiator that catalyzes the coupling reaction of a partially hydrogenated hydrocarbon terpene feedstock and one or more olefin co-monomers (e.g., one or more alpha-olefin co-monomers).

Certain methods may comprise controlling the nature and/or degree of branching and/or a molecular weight range or distribution of the reaction product (one or more branched alkenes or isoparaffins) to tune viscometric and/or cold temperature properties of a base oil made from the reaction product. The nature and/or degree of branching may be measured by any known technique, e.g., by a methyl-methylene carbon branch ratio as measured by NMR, by average branching number (ABN), and the like. For example, the type and composition of the olefin co-monomer may be varied to modulate the properties of a base oil made by the methods described herein. In some variations, a linear alpha-olefin may be selected to couple with a hydrocarbon terpene to result in a base oil wherein branching originates predominantly from branching existing on the hydrocarbon terpene. A branched alpha-olefin may be selected to couple with a hydrocarbon terpene to result in a base oil having an increased degree of branching relative to the hydrocarbon terpene. In some variations, a point of attachment between the hydrocarbon terpene and the alpha-olefin may be used to modulate branching and/or viscosity index in the resulting base oil. In some variations, an olefin co-monomer comprises a blend of two or more olefins, and relative amounts of the two or more olefins in the olefin co-monomers are varied to tune the properties of a resulting base oil. For example, if an olefin co-monomer comprises a higher molecular weight LAO and a lower molecular weight LAO, the amount of the lower molecular weight LAO in the olefin co-monomer may be increased to improve low temperature properties of the base oil, and the amount of higher molecular weight LAO may be increased to improve viscosity index of the base oil. The relative amounts of the lower molecular weight LAO and the higher molecular weight LAO may be tuned to produce a base oil with a desired balance between viscosity index and cold temperature flow properties.

In some variations, a catalyst and/or catalyst conditions that are likely to isomerize the hydrocarbon terpene:olefin adducts may be used to modulate branching and/or viscosity index in the resulting base oil. In some variations, hydrocarbon terpene:olefin adducts prepared by the methods described herein may be dewaxed to remove waxy paraffins. In some variations, hydrocarbon terpene:olefin adducts prepared by the methods described herein may be alkylated or hydroisomerized to increase branching using methods known in the art. In some variations, hydrocarbon terpene:olefin adducts prepared by the methods described herein may be dewaxed and hydroisomerized, or dewaxed and alkylated.

Any reaction parameter may be used to tune viscometric and/or cold temperature properties of a base oil made by the methods described herein. For example, one of or any combination of the group consisting of molecular weight of hydrocarbon terpene feedstock, branching in the hydrocarbon terpene feedstock, composition of a partially hydrogenated hydrocarbon terpene feedstock, composition of a hydrocarbon terpene feedstock that comprises a mixture of terpenes, olefin co-monomer molecular weight, composition of olefin co-monomer (e.g., percentage that is alpha-olefin and/or relative amounts of constituents of a mixture of olefins that is used as a co-monomer), branching in an olefin co-monomer, relative concentrations of hydrocarbon terpene feedstock and olefin co-monomers, feed rate of hydrocarbon terpene feedstock and olefin co-monomers, feed rate of catalyst, type of catalyst, catalyst loading, temperature, presence or absence of moisture, pressure, solvent, reaction quenching (if any), chain termination (if any), and reaction time may be used to tune viscometric and/or cold temperature properties of a base oil made from the reaction product. For example, any one of or any combination of the foregoing may be selected to control regioselectivity of new carbon-carbon bonds formed between the hydrocarbon terpene feedstock and the olefin co-monomers, degree of isomerization, and/or nature and degree of oligomerization (e.g., types and relative amounts of dimers, trimers, tetramers, pentamers, etc.).

Any relative amount of hydrocarbon terpene feedstock to olefin co-monomer may be used to form adducts having desired properties. For example, a molar ratio of hydrocarbon terpene feedstock to olefin co-monomer may be about 10:1, 9:1, 8:1, 7:1, 6:1, 5:1, 4:1, 3:1, 2:1, 1:2, 1:3, 1:4, 1:5, 1:6, 1:7, 1:8, 1:9, or 1:10. In some variations, the molar ratio of hydrocarbon terpene feedstock:olefin is about 1:1. The ratio may be adjusted to tune any desired property of the resulting adducts, including but not limited to renewable carbon content of adducts, to suppress formation of olefin:olefin adducts, to favor formation of certain trimers or tetramers, and the like.

In certain variations, the reaction conditions for the coupling reaction are selected to avoid formation of cyclic adducts, e.g., Diels-Alder adducts. In certain variations, the reaction conditions are selected to limit the formation of adducts between olefin co-monomers, and instead to favor formation of adducts between the hydrocarbon terpene and the olefin co-monomer. In certain variations, the reaction conditions are selected to control the molecular weight of the adducts formed, e.g., to favor formation of dimers and/or trimers, without formation of polymers. In certain variations, reaction conditions are selected to form copolymers having a desired molecular weight range from the hydrocarbon terpene feedstock and the olefin co-monomers. The methods described herein may be used to build a family of base oils by systematic coupling of a hydrocarbon terpene feedstock with selected olefin co-monomers. For example, the hydrocarbon terpene feedstock may be used as a basis for a family of base oils, where the properties of the base oils in the family may be varied as the olefin co-monomer is varied. For example, hydrocarbon terpene-derived base oils having kinematic viscosities at 100° C. of about 2 cSt, about 3 cSt, about 4 cSt, about 5 cSt, about 6 cSt, about 7 cSt, about 8 cSt, about 9 cSt, about 10 cSt, about 11 cSt, 12 cSt, and greater than about 12 cSt are described herein. In some variations, the viscosity index of the hydrocarbon terpene-derived base oils is at least about 120, at least about 122, at least about 124, at least about 126, at least 128, at least about 130, at least 132, at least about 134, at least about 136, at least about 138, or at least about 140. In one variation, a family of base oils is built using the methods described herein from β-farnesene, wherein farnesane is the lowest viscosity member of the family (having a kinematic viscosity at 100° C. of about 1 cSt), and other higher viscosity base oils are derived by systematic coupling a hydrocarbon terpene feedstock based derived from β-farnesene with olefin co-monomer(s) according to the methods described herein. For example, farnesene-derived base oils having kinematic viscosities at 100° C. of about 2 cSt, about 3 cSt, about 4 cSt, about 5 cSt, about 6 cSt, about 7 cSt, about 8 cSt, about 9 cSt, about 10 cSt, about 11 cSt, about 12 cSt, and greater than about 12 cSt are described herein. In some variations, the viscosity index of the farnesene-derived base oils is at least about 120, at least about 122, at least about 124, at least about 126, at least about 128, at least about 130, at least about 132, at least about 134, at least about 136, at least about 138, or at least about 140.

For the methods described herein comprising catalyzing formation of hydrocarbon terpene:olefin adducts, any one of or any combination of the following may be independently varied, each of which is described in more detail below: A) hydrocarbon terpene feedstock; B) olefin co-monomer; and C) catalyst. It should be understood that unless stated otherwise, the methods for making branched alkenes or isoparaffins may employ any combination of: i) any variation of the hydrocarbon terpene feedstock described herein or otherwise known, ii) any variation of olefin co-monomer described herein or otherwise known; and iii) any variation of catalyst described herein or otherwise known.

A. Hydrocarbon Terpene Feedstock

As used herein, "hydrocarbon terpene feedstock" or "terpene feedstock" refers to a hydrocarbon terpene, a hydrocarbon terpene that has been partially hydrogenated, or a saturated hydrocarbon terpene. Non-limiting examples hydrocarbon terpene feedstocks include, but are not limited to, acyclic $C_{10}$-$C_{30}$ or $C_{10}$-$C_{20}$ hydrocarbon terpenes, e.g., myrcene, α-farnesene, β-farnesene, farnesane, β-springene, geranylfarnesene, squalene, isodehydrosqualene, isosqualane precursor I, isosqualane precursor II, neophytadiene, trans-phyta-1,3-diene, cis-phyta-1,3-diene, or any of the foregoing that have been partially hydrogenated. Non-limiting examples of hydrocarbon terpene feedstocks are described in U.S. provisional patent application 61/475,217 filed 13 Apr. 2011, U.S. provisional patent application 61/493,316 filed 3 Jun. 2011, U.S. provisional patent application 61/502,252 filed 28 Jun. 2011, U.S. provisional patent application 61/524,143 filed 16 Aug. 2011, and PCT International Application No. PCT/US2012/024922 entitled "OLEFINS AND METHODS FOR MAKING THE SAME" filed concurrently herewith on 13 Feb. 2012 (which claims priority from U.S. provisional applications 61/475,217, 61/475,221, 61/482,122, 61/493,316, 61/502,252, and 61/524,143), each of which is incorporated herein by reference in its entirety.

The conjugated terpenes disclosed herein may be obtained from any suitable source. In some embodiments, the conjugated terpene is obtained from naturally occurring plants or marine species. For example, farnesene can be obtained or derived from naturally occurring terpenes that can be produced by a variety of plants, such as *Copaifera langsdorfii*, conifers, and Spurges; or by insects, such as swallowtail butterflies, leaf beetles, termites, or pine sawflies; and marine organisms, such as algae, sponges, corals, mollusks, and fish. Terpene oils can also be obtained from conifers and Spurges. Conifers belong to the plant division Pinophya or Coniferae and are generally cone-bearing seed plants with vascular tissue. Conifers may be trees or shrubs. Non-limiting examples of suitable conifers include cedar, cypress, douglas fir, fir, juniper, kauris, larch, pine, redwood, spruce and yew. Spurges, also known as *Euphorbia*, are a diverse worldwide genus of plants belonging to the Spurge family (euphorbiaceae). Farnesene is a sesquiterpene, a member of the terpene family, and can be derived or isolated from terpene oils for use as described herein. In some embodiments, a conjugated terpene is derived from a fossil fuel (petroleum or coal), for example, by fractional distillation of petroleum or coal tar. In some embodiments, a conjugated terpene is made by chemical synthesis. For example, one non-limiting example of suitable chemical synthesis of farnesene includes dehydrating nerolidol with phosphoryl chloride in pyridine as described in the article by Anet E. F. L. J., "Synthesis of (E,Z)-α-, and (Z)-β-farnesene, Aust. J. Chem. 23(10), 2101-2108, which is incorporated herein by reference in its entirety. U.S. Pat. No. 4,546,110, which is incorporated herein by reference in its entirety, describes synthesis of a mixture of (E)-β-farnesene and (Z)-β-farnesene from nerolidol. Farnesol or nerolidol may be converted into α-farnesene or β-farnesene, or a combination thereof by dehydration with a dehydrating agent or an acid catalyst. Any suitable dehydrating agent or acid catalyst that can convert an alcohol into an alkene may be used. Non-limiting examples of suitable dehydrating agents or acid catalysts include phosphoryl chloride, anhydrous zinc chloride, phosphoric acid, and sulfuric acid.

In some embodiments, a conjugated terpene is obtained using genetically modified organisms that are grown using renewable carbon sources (e.g., sugar cane). In certain embodiments, a conjugated terpene is prepared by contacting a cell capable of making a conjugated terpene with a suitable carbon source under conditions suitable for making a conjugated terpene. Non-limiting examples conjugated terpenes obtained using genetically modified organisms are provided in U.S. Pat. No. 7,399,323, U.S. Pat. Publ. Nos. 2008/0274523 and 2009/0137014, and International Patent Publication WO 2007/140339, and International Patent Publication WO 2007/139924, each of which is incorporated herein by reference in its entirety. Any carbon source that can be converted into one or more isoprenoid compounds can be used herein. In some embodiments, the carbon source is a fermentable carbon source (e.g., sugars), a nonfermentable carbon source or a combination thereof. A non-fermentable carbon source is a carbon source that cannot be converted by an organism into ethanol. Non-limiting examples of suitable non-fermentable carbon sources include acetate, glycerol, lactate and ethanol.

The sugar can be any sugar known to one of skill in the art. For example, in some embodiments, the sugar is a monosaccharide, disaccharide, polysaccharide or a combination thereof. In certain embodiments, the sugar is a simple sugar (a monosaccharide or a disaccharide). Some non-limiting examples of suitable monosaccharides include glucose, galactose, mannose, fructose, ribose and combinations thereof. Some non-limiting examples of suitable disaccharides include sucrose, lactose, maltose, trehalose, cellobiose, and combinations thereof. In some embodiments, the sugar is sucrose. In certain embodiments, the carbon source is a polysaccharide. Non-limiting examples of suitable polysaccharides include starch, glycogen, cellulose, chitin, and combinations thereof.

The sugar suitable for making a conjugated terpene can be obtained from a variety of crops or sources. Non-limiting examples of suitable crops or sources include sugar cane, bagasse, miscanthus, sugar beet, sorghum, grain sorghum, switchgrass, barley, hemp, kenaf, potato, sweet potato, cassava, sunflower, fruit, molasses, whey, skim milk, corn, stover, grain, wheat, wood, paper, straw, cotton, cellulose waste, and other biomass. In certain embodiments, suitable crops or sources include sugar cane, sugar beet and corn. In some embodiments, the sugar source is cane juice or molasses.

In certain embodiments, a conjugated terpene can be prepared in a facility capable of biological manufacture of isoprenoids. For example, for making a $C_{15}$ isoprenoid, the facility may comprise any structure useful for preparing $C_{15}$ isoprenoids (e.g., α-farnesene, β-farnesene, nerolidol or farnesol) using a microorganism capable of making the $C_{15}$ isoprenoids with a suitable carbon source under conditions suitable for making the $C_{15}$ isoprenoids. In some embodiments, the biological facility comprises a cell culture comprising a desired isoprenoid (e.g., a $C_5$, $C_{10}$, a $C_{15}$, a $C_{20}$, or a $C_{25}$ isoprenoid) in an amount of at least about 1 wt. %, at least about 5 wt. %, at least about 10 wt. %, at least about 20 wt. %, or at least about 30 wt. %, based on the total weight of the cell culture. In certain embodiments, the biological facility comprises a fermentor comprising one or more cells capable of generating a desired isoprenoid. Any fermentor that can provide for cells or bacteria a stable and optimal environment in which they can grow or reproduce may be used herein. In some embodiments, the fermentor comprises a culture comprising one or more cells capable of generating a desired isoprenoid (e.g., a $C_{10}$, a $C_{15}$, a $C_{20}$, or a $C_{25}$ isoprenoid). In some embodiments, the fermentor comprises a cell culture capable of biologically manufacturing farnesyl pyrophosphate (FPP). In certain embodiments, the fermentor comprises a cell culture capable of biologically manufacturing isopentenyl diphosphate (IPP). In some embodiments, the fermentor comprises a cell culture comprising a desired isoprenoid (e.g., a $C_{10}$, a $C_{15}$, a $C_{20}$, or a $C_{25}$ isoprenoid) in an amount of at least about 1 wt. %, at least about 5 wt. %, at least about 10 wt. %, at least about 20 wt. %, or at least about 30 wt. %, based on the total weight of the cell culture.

The facility may further comprise any structure capable of manufacturing a chemical derivative from the desired isoprenoid (e.g., a $C_5$, $C_{10}$, a $C_{15}$, a $C_{20}$, or a $C_{25}$ isoprenoid). In some embodiments, a facility comprises a reactor for dehydrating nerolidol or farnesol to α-farnesene or β-farnesene or a combination thereof. In certain embodiments, a facility comprises a reactor for dehydrating linalool to myrcene or ocimene or a combination thereof. Any reactor that can be used to convert an alcohol into an alkene under conditions known to skilled artisans may be used. In some embodiments, the reactor comprises a dehydrating catalyst.

In certain variations, the hydrocarbon terpene feedstock comprises a terpene produced by a microorganism, such as a bioengineered microorganism, for example from a renewable carbon source (e.g., a sugar, such as sugar cane or any other suitable sugar source as described herein or otherwise known in the art).

In certain embodiments, the hydrocarbon terpene feedstock comprises a hydrocarbon terpene containing a conjugated diene moiety, which may or may not be positioned as a 1,3-conjugated diene. In certain variations, molecules containing a conjugated diene moiety may make up at least about 50%, at least about 60%, at least about 70%, at least about 80%, at least about 90%, or at least about 95% of the hydrocarbon terpene feedstock.

In other embodiments, the hydrocarbon terpene feedstock comprises predominantly hydrocarbon terpenes in which few or none of the olefinic bonds are conjugated with another olefinic bond. A hydrocarbon terpene containing few or no conjugated olefinic bonds can be obtained from any source or by using any suitable method. In some cases, a suitable feedstock is derived from a hydrocarbon terpene comprising a conjugated diene moiety by selectively hydrogenating at least one of the olefinic bonds in the conjugated diene moiety to produce a partially hydrogenated hydrocarbon terpene feedstock. Examples of suitable partially hydrogenated hydrocarbon terpene feedstocks and methods for making the same are described in U.S. provisional patent application 61/475,217 filed 13 Apr. 2011, U.S. provisional patent application 61/493,316 filed 3 Jun. 2011, U.S. provisional patent application 61/502,252 filed 28 Jun. 2011, U.S. provisional patent application 61/524,143 filed 16 Aug. 2011, and PCT International Application No. PCT/US2012/024922 entitled "OLEFINS AND METHODS FOR MAKING THE SAME" filed concurrently herewith on 13 Feb. 2012 (which claims priority from U.S. provisional applications 61/475,217, 61/475,221, 61/482,122, 61/493,316, 61/502,252, and 61/524,143), each of which is incorporated by reference herein. In some variations, a suitable hydrocarbon terpene feedstock may comprise about 10% or less, about 5% or less, about 1% or less, about 0.5% or less, about 0.3% or less, or about 0.1% or less conjugated olefinic bonds. In some variations, a suitable hydrocarbon terpene feedstock comprises about 1% or less conjugated olefinic bonds.

In some variations, about 100% of the carbon atoms in the olefinic feedstocks described herein originate from renewable carbon sources. In some variations, the olefinic feedstocks have a $\delta^{13}C$ of from about −11 to about −6‰, from about −15 to about −10‰, from about −22 to about −15‰, from about −22 to about −32‰, from −8 to about −18‰, from about −14 to about −12‰, or from about −13 to about −11‰. In some variations, the olefinic feedstocks have a $f_M$ greater than about 0.3, greater than about 0.4, greater than about 0.5, greater than about 0.6, greater than 0.7, greater than about 0.8, greater than about 0.9, or greater than about 1.0. In some variations, the olefinic feedstocks have a $f_M$ of about 1.0 to about 1.05, about 1.0 to about 1.1, or about 1.1 to about 1.2. In some variations, the olefinic feedstocks have a $\delta^{13}C$ from about −15 to about −10‰ and a $f_M$ greater than about 0.5, greater than about 0.7, or greater than about 1.0. In some variations, the olefinic feedstocks have a $\delta^{13}C$ from about −8 to about −18‰ and a $f_M$ greater than about 0.5, greater than about 0.7, or greater than about 1.0. In some variations, the conjugated hydrocarbon terpene (e.g., myrcene, β-farnesene, or α-farnesene) is made by genetically modified microorganisms using renewable carbon sources such as a sugar (e.g., sugar cane). The renewable carbon content of the olefinic feedstocks may be measured using any suitable method, e.g., using radiocarbon analysis as described herein.

The olefinic feedstocks described herein comprise virtually no sulfur and no aromatic compounds, making them environmentally preferable over conventional olefins derived from fossil fuels, which in many cases contain sulfur and aromatics, such as naphthalenes. In certain embodiments, the olefinic feedstocks comprise less than about 10 ppm sulfur, less than about 1 ppm sulfur, less than about 100 ppb sulfur, less than about 10 ppb sulfur or less than about 1 ppb sulfur. In certain embodiments, the olefinic feedstocks comprise less than about 10 ppm aromatics, less than about 1 ppm aromatics, less than about 100 ppb aromatics, less than about 10 ppb aromatics or less than about 1 ppb aromatics. In certain embodiments, the olefinic feedstocks comprise less than about 10 ppm sulfur and less than about 10 ppm aromatics, less than about 1 ppm sulfur and less than about 1 ppm aromatics, less than about 100 ppb sulfur and less than about 100 ppb aromatics, less than about 10 ppb sulfur and less than about 10 ppb aromatics, or less than about 1 ppb sulfur and less than about 1 ppb aromatics.

In those variations in which the olefinic feedstocks are derived from an acyclic conjugated hydrocarbon alkene, the olefinic feedstocks described herein may comprise less than about 5%, less than about 2%, less than about 1%, less than about 0.1%, or less than about 0.01% cyclic compounds.

In certain embodiments, the olefinic feedstocks described herein comprise one or more methylated alkenes, e.g., one or more methylated mono-alkenes, methylated di-alkenes, methylated tri-alkenes, or methylated tetra-alkenes, where the number of carbon atoms in the base alkene for any of the above corresponds to the number of carbon atoms in the main chain of a conjugated alkene (which may be a hydrocarbon terpene in some variations) used to make the feedstock, and the number of methyl substituents corresponds to the number of methyl substituents (or in some cases, methyl and methylene substituents) on the conjugated alkene (which may be a hydrocarbon terpene in some variations) used to make the feedstock. In some variations, the olefinic feedstocks are derived from a $C_{10}$-$C_{30}$ conjugated alkene comprising 1-10 methyl or methylene substituents, e.g., 1, 2, 3, 4, 5, 6, 7, 8, 9, or 10 methyl or methylene substituents. In some variations, the olefinic feedstocks are derived from a $C_{10}$-$C_{30}$ conjugated alkene comprising at least one ethyl or vinyl substituent. In some variations, the olefinic feedstocks are derived from a $C_{10}$-$C_{30}$ conjugated alkene comprising 1-10 methyl or methylene substituents and at least one ethyl or vinyl substituent.

The olefinic feedstocks described herein can comprise a well-defined distribution of methylated alkenes and (in some cases methylated alkanes) within a very narrow molecular weight range (e.g. a distribution spanning a range from about 2-10 amu, or from about 2-20 amu) as molecules within the distribution have the same number of carbon atoms. Thus, a feedstock comprising a very narrow molecular weight range can be produced directly, without the need for cracking or a separation process such as distilling from a crude mixture, as is commonly employed in the production of $C_{10}$-$C_{30}$ olefinic feedstocks from petroleum products. An olefinic feedstock described herein that is derived from more than one partially hydrocarbon terpene species can exhibit a broader but predictable molecular weight distribution as produced, again without the need for a separation process.

The feedstocks described herein can provide unique methylated olefinic feedstocks that do not require an extra alkylation step to incorporate short chain branching, or any separation step to isolate. Furthermore, the degree of branching, the type of branching, and the branching position in the olefins in feedstocks described herein are predetermined by the source hydrocarbon terpene or terpenes, unlike other feedstocks comprising branched olefins, wherein the branched olefins comprise a complex mixture of isomers wherein the degree of branching, the type of branching and the branching position are all varied.

Provided herein are methods for making olefinic feedstocks from a conjugated alkene (e.g., a $C_{10}$-$C_{30}$ conjugated hydrocarbon terpene) comprising at least one conjugated diene and at least one additional carbon-carbon double bond by controlled partial hydrogenation. In certain variations, an olefinic feedstock is made by controlled partial hydrogenation of myrcene, ocimene, farnesene, springene, geranylfarnesene, isodehydrosqualene, isosqualane precursor I, or isosqualane precursor II.

The controlled partial hydrogenation process may in some variations be staged, so as to comprise two or more stages, with each stage designed to tune the resulting olefin composition of the olefinic feedstock. For example, a multi-stage hydrogenation process may be used to produce an olefinic feedstock that is rich in mono-olefinic species (e.g., comprises at least about 60% mono-olefins). In one variation of a staged hydrogenation process, a first hydrogenation stage may comprise selectively hydrogenating at least one olefinic bond in the conjugated diene to produce an intermediate partially hydrogenated product, and a second hydrogenation stage may comprise selectively hydrogenating the intermediate product in a second hydrogenation stage to produce a desired olefinic composition, e.g., an olefinic composition rich in mono-olefins, and/or an olefinic composition in which alkane formation has been minimized.

Also provided herein are examples of specific compositions for olefinic feedstocks derived by partial hydrogenation of conjugated hydrocarbon terpenes. For example, the following classes of olefinic feedstock compositions are disclosed herein: i) olefinic feedstocks compositions that have very low amounts of conjugated dienes (e.g., less than about 10% conjugated diene, less than about 5% conjugated diene, or less than about 1% conjugated diene); ii) olefinic feedstocks comprised predominantly of mono-olefins and di-olefins (e.g., at least about 80%, or at least about 90%, or at least about 95% mono-olefins and di-olefins); iii) olefinic feedstock compositions comprised predominantly of mono-olefinic species (e.g., at least about 60%, at least about 65%, at least about 70%, at least about 75%, or at least about 80% mono-olefins); v) olefinic feedstock compositions that have limited amounts of alkanes (e.g., less than about 25%, less than about 20%, less than about 15%, less than about 10%, or less than about 5%); vi) olefinic feedstock compositions that have limited amounts of conjugated dienes and limited amounts of alkanes; vii) olefinic feedstock compositions consisting essentially of tri-olefins and having limited amounts of conjugated dienes and alkanes; viii) olefinic feedstock compositions comprised predominantly of mono-olefins and having limited amounts of dienes (both unconjugated and conjugated) and alkanes; and ix) olefinic feedstock compositions comprising substantial amounts of mono-olefins (e.g., at least about 50%, at least about 55%, at least about 60%, at least 65%, at least about 70%, at least about 75%, or at least about 80% mono-olefin) and limited amounts of di-olefins (e.g., at most about 10%, at most about 8%, at most about 5%, at most about 3%, at most about 2%, at most about 1% di-olefin, or at most about 0.5% di-olefin). In some variations, di-olefins that are present may be substantially unconjugated, e.g., so that a composition comprises at most about 2%, at most about 1%, at most about 0.5%, at most about 0.1%, or no detectable conjugated species.

Provided herein are specific species of partially hydrogenated hydrocarbon terpenes. For example, provided herein are alpha-olefins derived from a 1,3-diene conjugated hydrocarbon terpene (e.g., a $C_{10}$-$C_{30}$ conjugated hydrocarbon terpene such as farnesene, myrcene, ocimene, springene, or geranylfarnesene).

Provided herein are methods for making olefinic feedstocks from a conjugated alkene (e.g., a conjugated hydrocarbon terpene, which may be an acyclic or cyclic $C_{10}$-$C_{30}$ conjugated hydrocarbon terpene) comprising at least one conjugated diene and at least one additional carbon-carbon double bond by controlled (e.g., staged) partial hydrogenation.

A conjugated alkene comprising at least one conjugated diene and at least one additional C—C double bond is represented by structure A1 (or a stereoisomer thereof, including (E,E), (E,Z), (Z,E), and (Z,Z) stereoisomers and rotational isomers):

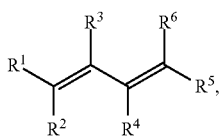
(A1)

where $R^1$, $R^2$, $R^3$, $R^4$, $R^5$, and $R^6$ are each independently H, or a $C_1$-$C_{25}$ linear or branched, cyclic or acrylic, saturated or unsaturated hydrocarbon group, and at least one of the group consisting of $R^1$, $R^2$, $R^3$, $R^4$, $R^5$, and $R^6$ contains at least one carbon carbon double bond. In some variations at least one of $R^1$, $R^2$, $R^3$, $R^4$, $R^5$, and $R^6$ may contain two, three, four, five, or six or more carbon carbon double bonds. In some variations, at least one of $R^1$, $R^2$, $R^3$, $R^4$, $R^5$, and $R^6$ is a monoene substituted with one or more methyl groups or a polyene substituted with one or more methyl groups (e.g.,

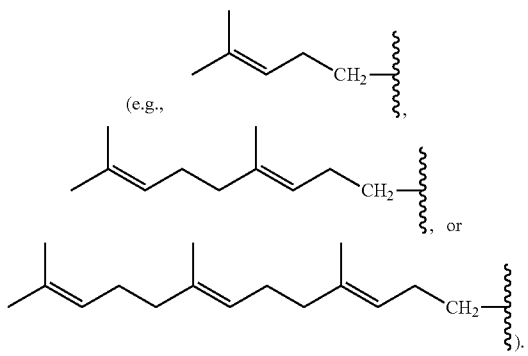

In some embodiments, the conjugated alkene comprises a terminal carbon-carbon double bond as part of the conjugated diene and at least one additional carbon-carbon double bond, and has structure A3 (or a stereoisomer thereof including (E,E), (E,Z), (Z,E), and (Z,Z) stereoisomers and rotational isomers):

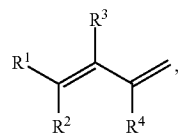
(A3)

where $R^1$, $R^2$, $R^3$, and $R^4$ are each independently H, or a $C_1$-$C_{25}$ linear or branched, cyclic or acyclic, saturated or unsaturated hydrocarbon group, and at least one of the group consisting of $R^1$, $R^2$, $R^3$, and $R^4$ contains at least one carbon carbon double bond. In some variations, at least one of $R^1$, $R^2$, $R^3$, and $R^4$ may contain two, three, four, five, or six or more carbon carbon double bonds. In some variations, at least one of $R^1$, $R^2$, $R^3$, and $R^4$ is a monoene substituted with one or more methyl groups or a polyene substituted with one or more methyl groups (e.g.,

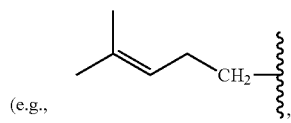

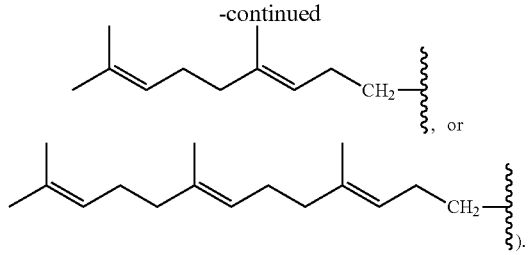

In some embodiments, the conjugated alkene has structure A5 (or a stereoisomer thereof):

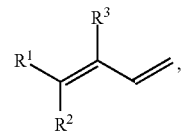
(A5)

where $R^1$, $R^2$ and $R^3$ are each independently H or a $C_1$-$C_{25}$ linear or branched, cyclic or acyclic, saturated or unsaturated hydrocarbon group, and at least one of the group consisting of $R^1$, $R^2$ and $R^3$ contains at least one carbon carbon double bond. In some variations, at least one of $R^1$, $R^2$ and $R^3$ may contain two, three, four, five, or six or more carbon carbon double bonds. In some variations, at least one of $R^1$, $R^2$ and $R^3$ is a monoene substituted with one or more methyl groups or a polyene substituted with one or more methyl groups (e.g.,

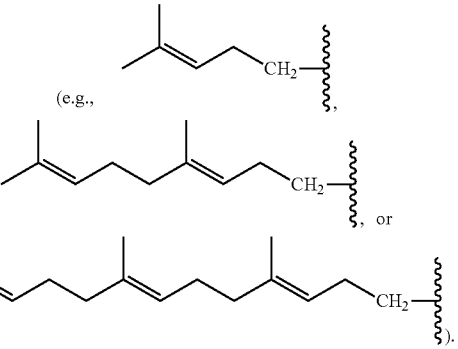

In some embodiments, the conjugated alkene has structure A7 (or a stereoisomer thereof including (E,E), (E,Z), (Z,E), and (Z,Z) stereoisomers and rotational isomers):

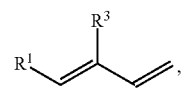
(A7)

where $R^1$ and $R^3$ are each independently H or a $C_1$-$C_{25}$ linear or branched, cyclic or acyclic, saturated or unsaturated hydrocarbon group, and at least one of the group consisting of $R^1$ and $R^3$ contains at least one carbon carbon double bond. In some variations, at least one of $R^1$ and $R^3$ may contain two, three, four, five, or six or more C—C double bonds. In some variations, at least one of $R^1$ and $R^3$ is a monoene substituted with one or more methyl groups, or a polyene substituted with one or more methyl groups (e.g.,

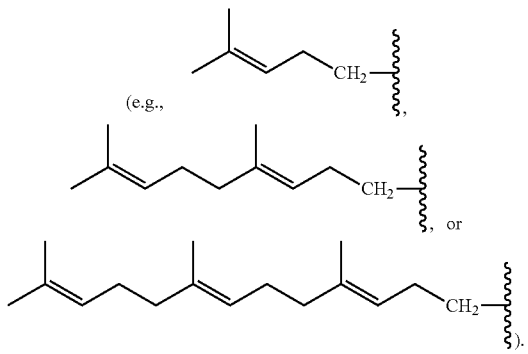

In some embodiments, the conjugated alkene has structure A9 (or a stereoisomer thereof including (E,E), (E,Z), (Z,E), and (Z,Z) stereoisomers and rotational isomers):

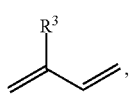 (A9)

where $R^3$ is a $C_5$-$C_{25}$ linear or branched, cyclic or acyclic unsaturated hydrocarbon group containing at least one carbon carbon double bond, or in some variations two, three, four, five, or six or more carbon carbon double bonds. In some variations, at $R^3$ is a monoene substituted with one or more methyl groups or a polyene substituted with one or more methyl groups, (e.g.,

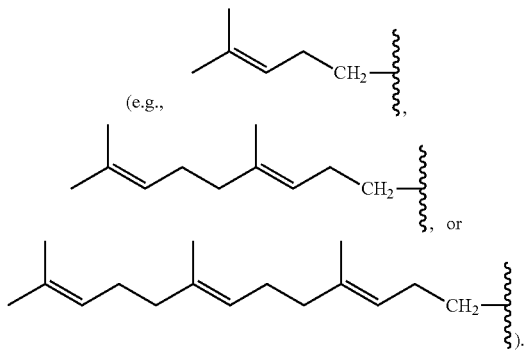

As stated above, in some variations, a conjugated alkene comprising at least one additional carbon-carbon double bond from which the olefinic feedstock is derived is a conjugated hydrocarbon terpene comprising at least one additional carbon-carbon double bond. Thus a conjugated hydrocarbon terpene having any of the above-listed structures A1-A9 (or stereoisomers thereof) may be used to make the olefinic feedstocks described herein. In some variations, a conjugated hydrocarbon terpene having structure A9 with $R^3$ being a $C_5$-$C_{25}$ monoene or polyene may be used to make the olefinic feedstocks described herein.

Nonlimiting examples of conjugated hydrocarbons comprising at least one additional carbon-carbon double bonds include: myrcene has structure A9 with

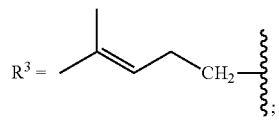 [SMILES: *CCC=C(C)C]

α-ocimene has structure A7 with $R^1$=$CH_3$ and

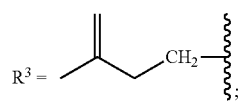

β-ocimene has structure A7 with $R^1$=$CH_3$ and

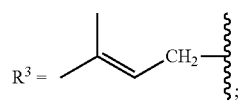

α-farnesene has structure A7 with

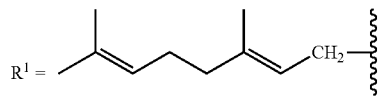 [SMILES: *C/C=C(\C)CCC=C(C)C]

and $R^3$=$CH_3$; β-farnesene has structure A9 with

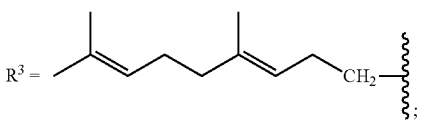 [SMILES: *CC/C=C(\C)CCC=C(C)C]

β-springene has structure A9 with

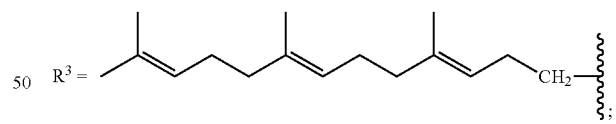

isodehydrosqualene has structure A1 with

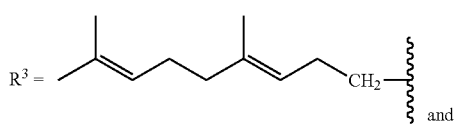

and

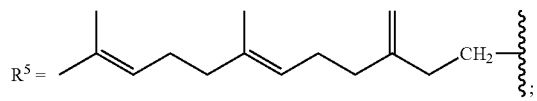

isosqualane precursor I has structure A1 with

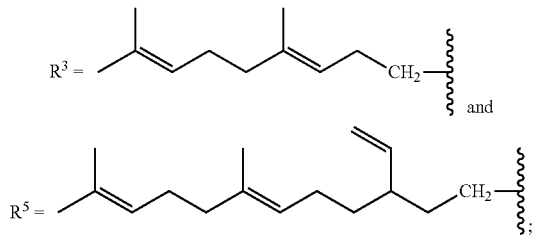

and isosqualane precursor II has structure A1 with $R^1$=H, $R^2$=H, $R^4$=H, $R^6$=H,

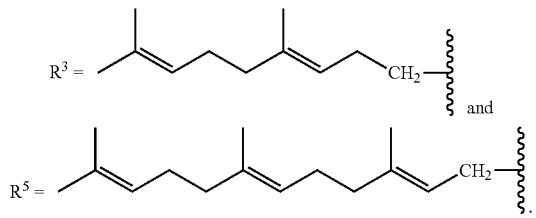

In certain embodiments, methods for making olefinic feedstocks from a conjugated alkene (e.g., a conjugated hydrocarbon terpene) comprising at least one conjugated diene and at least one additional carbon carbon double bond by controlled hydrogenation comprise selectively hydrogenating at least one olefinic bond in the conjugated diene in a first stage to produce a partially hydrogenated olefinic intermediate, and selectively hydrogenating the partially hydrogenated olefinic intermediate in one or more subsequent stages (e.g. a second stage for a two stage process) to produce the olefinic feedstock having a desired composition. Such staged partial hydrogenation methods may be applied to any of the aforementioned conjugated alkenes having structures A1-A9 to produce an olefinic feedstock, including but not limited to $C_{10}$-$C_{30}$ conjugated hydrocarbon terpenes such as myrcene, ocimene, farnesene, springene, geranylfarnesene, isodehydrosqualene, isosqualane precursor I, and isosqualane precursor II. In certain embodiments, an olefinic feedstock is produced by staged partial hydrogenation from a conjugated hydrocarbon terpene produced by a bioengineered microorganism using a renewable carbon source. In some variations, the staged partial hydrogenation is conducted in two stages. In some variations, the staged partial hydrogenation is conducted in three or more stages.

A model stepwise or staged hydrogenation process can be described as follows using farnesene as a model compound. The tetraene is reduced to a triene in a first hydrogenation stage having a first rate constant k[1]; the triene is reduced to a diene in a second hydrogenation stage having a second rate constant k[2]; the diene is reduced to a monoene in a third hydrogenation stage having a third rate constant k[3]; and the monoene is reduced to an alkane in a fourth hydrogenation stage having a fourth rate constant k[4]. The stepwise hydrogenation process can be described as follows:

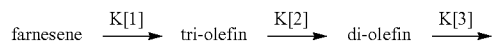
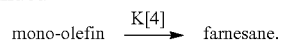

In an uncontrolled partial hydrogenation process, some or all of the four steps may happen nearly coincidentally or in a purely statistical manner so that no or insufficient selectivity as to degree of hydrogenation results. In devising a staged hydrogenation process to produce an olefinic feedstock it is desired to capitalize on the different reactivity of the conjugated diene moiety so as to essentially eliminate the conjugated diene functionality by reducing at least one of the olefinic bonds in the conjugated diene without producing alkane in a first stage so that k[1]>>k[2], followed by selective hydrogenation of one or more of the remaining olefinic bonds while minimizing formation of the alkane in a subsequent stage, e.g., by significantly increasing k[3] and/or reducing k[4] (increasing the ratio k[3]/k[4]). In some variations, it may be desired to produce an olefinic feedstock that comprises predominantly mono-olefinic species, so that a staged hydrogenation process can be devised in which k[3]>>k[4], i.e., so that the di-olefinic species is preferentially hydrogenated over the mono-olefinic species. For example, k[3] may be at least about two times, at least about three times, at least about five times, or at least about ten times k[4]. In some variations, k[1]:k[2] may be at least about 10:1, e.g., about 10:1, 20:1, 30:1, 40:1, 50:1, 60:1, 70:1, 80:1, 90:1, 100:1, 200:1, or even higher. In some variations, k[2] may be similar to k[3], e.g., a ratio k[2]:k[3] may be about 1:1, 2:1, or 1:2. In some variations, a ratio k[1]:k[4] may be at least about 20:1, e.g., about 20:1, 30:1, 40:1, 50:1, 60:1, 70:1, 80:1, 90:1, 100:1, 200:1, or even higher. In some variations, k[1]:k[2]:k[3]:k[4] may be about 80:10:5:1. In some variations, k[1]:k[2]:k[3]:k[4] may about 80:10:5:0.5 or 80:10:5:0.25. In some variations, reaction conditions may be selected such that the ratio k[3]:k[4] results a final olefinic feedstock in which the mono-olefinic content is at least about 60%, at least about 65%, at least about 70%, at least about 75%, or at least about 80%, the di-olefinic content is about 12% or less, about 10% or less, about 8% or less, about 5% or less, or less than 5%, and the alkane content is about 25% or less, about 20% or less, about 18% or less, about 15% or less, about 10% or less, or about 8% or less. The ratio k[3]:k[4] can be tuned using staged hydrogenation processes described herein to tune relative populations of mono-olefinic, di-olefinic, and alkane in an olefinic feedstock. In some variations, it may be desired to have as high a concentration of mono-olefin as possible while achieving as low a concentration of di-olefinic species as possible, as the di-olefinic species may cause side reactions, formation of undesired cross-products, and the like. In some variations, it may be desired to have as high a concentration of mono-olefin as possible while achieving as low a concentration of alkane as possible. Formation of the alkane may cause undesired yield loss. In some variations, it may be desired to have as high a concentration of mono-olefin as possible while achieving as low a concentration of di-olefin as possible. The presence of di-olefins may cause undesired side reactions, cross products, and the like.

As shown in the Examples, the conjugated diene is selectively hydrogenated in the first stage. After selectively reducing the concentration of conjugated diene (e.g., forming tri-olefin in the case of farnesene) in the first stage, hydrogenation in a subsequent stage or stages is controlled to form unconjugated polyenes (e.g., di-olefins) and to selectively favor hydrogenation of the unconjugated polyene (e.g., di-olefins) over hydrogenation of mono-olefin. In the case of farnesene, after the introduction of more than one equivalent of hydrogen in a subsequent stage, the di-olefin population increases, reaches a peak after about two equivalents of hydrogen have been added, and then monotonically decreases. The concentration of mono-olefin monotonically increases as until about three equivalents of hydrogen have been added, and subsequently begins to decrease as more saturated hydrocarbon is formed. As described herein, the degree of hydrogenation can be carefully controlled to achieve a composition in which mono-olefin content is maximized while di-olefin is minimized, to achieve a composition in which mono-olefin content is maximized while alkane is minimized, or to achieve a composition in which mono-olefin content is maximized by di-olefin and alkane are minimized.

In staged partial hydrogenation, the catalysis conditions are changed following a first hydrogenation stage. The catalysis conditions include amount of hydrogen, catalyst, catalyst loading, temperature, hydrogen pressure, and reaction time, and any one of or any combination of each of these variables may be independently varied between the first and subsequent (e.g. second) hydrogenation stages. In certain variations, catalysis conditions of a final (e.g., second stage in a two stage process) stage are selected to favor hydrogenation of polyene species present in an intermediate product over hydrogenation of mono-olefinic species in the intermediate product, thereby limiting the quantity of alkane produced in the final olefinic feedstock and reducing concentration of polyene species. The presence of polyene species in a mono-olefinic feedstock may lead to undesired side reactions and cross-products in some reactions.

In some variations, the amount of hydrogen delivered, the catalyst, catalyst loading, and reaction conditions (reaction temperature, hydrogen pressure and time) in a first stage are selected so that less than about 10%, less than about 5%, less than about 3%, less than about 1%, less than about 0.3% (or even fewer) of the molecules in the intermediate product have a conjugated diene moeity after the first hydrogenation stage.

In some variations, the catalyst type (and associated catalysis conditions) for the first stage are selected to be those that are known in the art to be selective for hydrogenating conjugated diene moieties and are active at temperatures below which thermal dimerization, cyclization, isomerization, or other competing or degradation process of the conjugated alkene occurs. For example, a catalyst system that is active at a temperature in a range from about 20° C. to about 110° C. may be used to catalyze hydrogenation of β-farnesene for a first stage to reduce probability that such a competing process occurs. In some variations, Lindlar's catalyst, palladium catalysts (e.g., palladium catalysts prepared via reduction by organoaluminum compounds of Pd(II) complexes (e.g., PdCl$_2$) with nitrogen-containing ligands; ruthenium compounds, rhodium compounds, chromium compounds, iridium compounds; and cobalt compounds (e.g., as described in U.S. Pat. No. 4,590,319, which is incorporated by reference herein in its entirety), may be selected as a catalyst for a first stage in which the conjugated diene is selectively reduced. Non-limiting examples of regioselective hydrogenation catalysts for 1,3-dienes are provided in Jong Tae Lee et al, "Regioselective hydrogenation of conjugated dienes catalyzed by hydridopentacyanocobaltate anion using β-cyclodextrin as the phase transfer agent and lanthanide halides as promoters," J. Org. Chem., 1990, 55 (6), pp. 1854-1856, in V. M. Frolov et al., "Highly active supported palladium catalysts for selective hydrogenation of conjugated dienes into olefins," Reaction Kinetics and Catalysis Letters, 1984, Volume 25, Numbers 3-4, pp. 319-322, in Tungler, A., Hegedüs, L., Fodor, K., Farkas, G., Fürcht, Á. and Karancsi, Z. P. (2003) "Reduction of Dienes and Polyenes," in *The Chemistry of Dienes and Polyenes*, Volume 2 (ed. Z. Rappoport), John Wiley & Sons, Ltd, Chichester, UK. doi: 10.1002/0470857226.ch12, and in Tungler, A., Hegedüs, L., Fodor, K., Farkas, G., Fürcht, Á. and Karancsi, Z. P., "Reduction of Dienes and Polyenes" in *Patai's Chemistry of Functional Groups* (John Wiley and Sons, Ltd, published online Dec. 15, 2009, DOI: 10.1002/9780470682531.pat0233), each of which is incorporated herein by reference in its entirety.

In some variations, a metal catalyst such as palladium, platinum, nickel, copper, copper-chromium, rhodium, ruthenium or molybdenum on various supports may be used in the first and/or second stage. Nonlimiting examples of palladium-containing catalysts that can be used in the first and/or second hydrogenation stage are Pd/C, Pd/Al$_2$O$_3$, Pd/titanium silicate, Pd/SiO$_2$, Pd on titania, Pd on zirconia, and Pd on alumina-silica). In some variations, catalysis conditions may be selected to be relatively mild in the first stage, e.g., lower activity catalyst, lower catalyst loading, and/or lower temperature (e.g., temperature of 110° C. or lower, or 100° C. or lower) to allow selective hydrogenation of at least one olefinic bond in the conjugated diene over other olefinic bonds that are present, without undesired levels of thermal dimerization, isomerization, or oligomerization. In some variations, a catalyst used in the first and/or subsequent stage is activated before use. For example, some copper-containing catalysts (e.g., Cu/SiO$_2$ or a Cu—Cr catalyst) is activated before use (e.g., at 150-180° C.). In some variations, catalysts that require activation at high temperatures are used in second or subsequent stages of hydrogenation to avoid exposure of the conjugated terpene to temperatures which may cause dimerization and the like. In some variations, more active catalysis conditions are selected for the second or subsequent stages.

In some variations, about 1-1.5 equivalents of hydrogen are consumed during the first hydrogenation stage in which at least one olefinic bond of the conjugated diene is selectively reduced. In some variations, about 1 equivalent of hydrogen is consumed in the first hydrogenation stage. In some variations, about 1.5 equivalents of hydrogen are consumed in the first hydrogenation stage. Thus, if the olefinic intermediate product produced after the first stage contains limited amounts of conjugated diene (e.g., less than about 10%) and limited amounts of alkane (e.g., less than about 1%), the intermediate product consists essentially of unconjugated polyenes in which the number of olefinic bonds is one less than in the starting conjugated alkene. Examples 21 and 22 herein provide non-limiting examples of a first stage of partial hydrogenation of β-farnesene in which one molar equivalent of hydrogen was consumed and the resulting olefinic mixture consists essentially of tri-olefinic species. Examples 30-46 herein provide non-limiting examples of a hydrogenation process in which about 1-1.5 equivalents of hydrogen are consumed in a first hydrogenation stage.

In some variations, about 2-2.5 molar equivalents of hydrogen are consumed during the first hydrogenation stage in which the conjugated diene is selectively reduced. In some variations, about 2 equivalents of hydrogen are consumed in the first hydrogenation stage. In some variations, about 2.5 equivalents of hydrogen are consumed in the first hydrogenation stage. Thus, if the intermediate product produced after the first stage contains limited amounts of conjugated diene (e.g., less than about 10%) and limited amounts of alkane (e.g., less than about 2%), the intermediate product consists essentially of a mixture of monoenes and unconjugated polyenes. Certain Examples herein provide non-limiting examples of partial hydrogenation of β-farnesene in which about 2.5 molar equivalents of hydrogen were consumed and the resulting olefinic mixture consists essentially of monoenes and unconjugated dienes, with less than about 10% trienes, and no detectable amount of alkane or conjugated diene.

The amount of hydrogen, catalyst, catalyst loading, and reaction conditions (reaction temperature, hydrogen pressure and time) can be independently varied in the second stage relative to the first stage to partially hydrogenate the olefinic intermediate product to produce a desired olefinic feedstock. For example, if a mono-olefinic feedstock is desired, the catalyst and catalysis conditions in the second stage may be selected to preferentially hydrogenate unconjugated polyenes over monoenes. In one example, hydrogen pressure and temperature are reduced in the second stage so as to favor hydrogenation of unconjugated polyenes over monoenes.

Although certain staged hydrogenation processes for a conjugated hydrocarbon terpene comprising at least one additional olefinic bond (e.g., α-farnesene or β-farnesene) may include three or more distinct hydrogenation stages, in some variations, a two stage hydrogenation process is used to produce an olefinic feedstock. In the first hydrogenation stage, catalysis conditions are such that at least one olefinic bond in the conjugated diene moiety is preferentially hydrogenated and sufficient hydrogen is delivered (e.g., at least about 1-1.5 molar equivalent of hydrogen, or in some cases about 2-2.5 molar equivalents of hydrogen) so that the quantity of conjugated diene remaining is low, e.g., less than about 10%, less than about 5%, less than about 2%, or less than about 1%. Hydrogenation conditions in the first stage may be relatively mild (e.g., temperature is in a range from about 40° C. to about 110° C.) so that essentially no alkane is formed and essentially no competing reactions (e.g., thermal dimerization, cyclization, isomerization, and the like) occur. In certain variations, about one molar equivalent of hydrogen is consumed and catalyst and catalyst conditions are selected so that the intermediate olefinic product produced after the first stage consists essentially of unconjugated polyenes (e.g., unconjugated trienes in the case of farnesene). In certain variations, the amount of hydrogen, catalyst and catalysis conditions (catalyst loading, temperature, hydrogen pressure and reaction time) are selected so that the intermediate product produced after the first stage consists predominantly of monoenes and unconjugated polyenes (monoenes and unconjugated dienes in the case of farnesene), e.g., at least about 80%, at least about 85%, at least about 90%, at least about 95% unconjugated polyenes, with little or no alkane and little or no conjugated diene.

In the second hydrogenation stage, the amount of hydrogen, the catalyst and the catalysis conditions (catalyst loading, hydrogen pressure, temperature and/or reaction time) may be selected based on the intermediate distribution of species formed in the first stage to produce a desired final distribution of species. For example, if the first stage produced an intermediate product consisting essentially of monoenes and unconjugated polyenes (e.g., monoenes and dienes in the case of farnesene), and a mono-olefinic feedstock is desired, catalysis conditions of the second stage may be tuned to selectively hydrogenate the unconjugated polyenes rather than the mono-olefins so as to produce a feedstock consisting of predominantly mono-olefins, e.g., at least about 60%, at least about 65%, at least about 70%, at least about 75%, at least about 80%, at least about 85%, at least about 90%, or at least about 95% monoolefins, and the amount of alkane produced is limited (e.g., to less than about 25%, less than about 20%, less than about 15%, less than about 10%, or less than about 5%). Certain Examples herein provide nonlimiting examples of two-stage partial hydrogenations of β-farnesene to produce mono-olefinic feedstocks.

In some variations, the temperature of a first hydrogenation stage of a conjugated hydrocarbon terpene (e.g., myrcene, ocimene, α-farnesene or β-farnesene) may be kept low (e.g., kept below about below about 120° C., below about 100° C., or below about 80° C., below about 50° C., or below about 40° C.) to preferentially hydrogenate at least one olefinic bond in the conjugated diene moiety over other olefinic bonds and to reduce occurrence of competing processes (e.g., thermal dimerization, cyclization, isomerization, and the like). After forming an intermediate partially hydrogenated product in which at least one olefinic bond in the conjugated diene moiety has been preferentially hydrogenated, catalysis conditions for a second stage may be selected to preferentially hydrogenate unconjugated polyenes (e.g., di-olefins and tri-olefins in the case of farnesene) over mono-olefins, without creating undesired amounts of completely saturated alkane. For example, a second hydrogenation stage may be conducted at a higher temperature (e.g. at least about 50° C., at least about 100° C., or at least about 150° C. higher than a first hydrogenation stage) to favor hydrogenation of unconjugated polyenes over mono-olefins, thereby enriching the population of mono-olefins in the final partially hydrogenated product. Since the conjugated diene moiety has been eliminated or reduced to a very low concentration by the first stage, probability of thermal dimerization or other competing reactions associated with the conjugated diene are greatly reduced, even at higher temperatures. In certain variations, the catalyst and catalyst loading are kept constant between the first and second stages, but the temperature is increased in the second stage relative to the first stage, e.g., as described here.

In some variations, a metal catalyst such as palladium, platinum, nickel, copper, copper-chromium, rhodium, ruthenium or molybdenum on various supports may be used in the second or subsequent hydrogenation stages. Nonlimiting examples of palladium-containing catalysts that can be used in the second hydrogenation stage are Pd/C, Pd/Al$_2$O$_3$, Pd/titanium silicate, Pd/SiO$_2$, Pd on titania, Pd on zirconia, and Pd on alumina-silica. In some variations, a catalyst used in a second or subsequent stage is activated before use. For example, some copper-containing catalysts (e.g., Cu/SiO$_2$ or a Cu—Cr catalyst) is activated before use (e.g., at 150-180° C.). In some cases, a metal catalyst known in the art for preferentially hydrogenating di-olefins or higher polyenes over mono-olefins is used in the second or subsequent stages.

In some variations, reaction conditions in latter hydrogenation stage are selected to favor dehydrogenation of paraffins. For example, temperature is increased and hydrogen pressure is reduced in a final hydrogenation stage so as to favor dehydrogenation of paraffins, without formation of undesired side products.

In some variations, a second hydrogenation stage may be conducted at a lower hydrogen pressure (e.g., a second stage hydrogen pressure of about 10-100 psig, such as about 10, 20, 30, 40, 50, 60, 70, 80, 90 or 100 psig) than the hydrogen pressure of a first stage to favor hydrogenation of unconjugated polyenes (e.g., di-olefins and tri-olefins in the case of farnesene) over mono-olefins. In some variations, the hydrogen pressure in the second stage is below 50 psig, e.g., about 10, 20, 30, or 40 psig. In some variations, a second hydrogenation stage may be conducted at a higher temperature (e.g., at least about 50° C., 100° C., or 150° C. higher than a first hydrogenation stage) and at a lower hydrogen pressure (e.g. at a pressure that is 10-990 psig lower than pressure in a first stage). In certain variations, the catalyst and catalyst loading are kept constant between the first and second stages, but the temperature is increased in the second stage relative to the first stage and the hydrogen pressure is lowered in the second stage relative to the first stage, e.g., as described here. In some variations, the temperature of the first stage is in a range from about 40° C. to about 160° C. and the hydrogen pressure in the first stage is in a range from about 100 psig to about 1000 psig, and the temperature in the second stage is in a range from about 120° C. to about 260° C. and the hydrogen pressure in the second stage is in a range from about 10 psig to about 100 psig.

In some variations, a staged partial hydrogenation process includes more than two temperature stages, e.g., three, four, five, or more temperature regimes. In some variations, a first temperature stage involves no external heating, and self-heat is provided by the exotherm of the hydrogenation reaction. In some variations, a staged partial hydrogenation process includes a first self-heated stage during which about 0.5 equivalents or less of hydrogen is added (e.g., about 0.3-0.5 equivalents of hydrogen), followed by a second temperature stage during which the temperature is raised (e.g., to about 80-110° C., such as about 80° C., 90° C., 100° C., or 110° C.) and the total hydrogen equivalents added is raised to about 1.5 (e.g., additional 1-1.2 equivalents), followed by a third stage during which an additional 1.5 equivalents hydrogen is added and the temperature is raised to about 160-240° C., e.g., about 160° C., 170° C., 180° C., 190° C., 200° C., 210° C., 220° C., 230° C., or 240° C.). In some cases, the hydrogen pressure is maintained at a relatively constant pressure (e.g., a pressure of about 50-200 psig, such as about 50, 100, 150 or 200 psig) throughout all three stages. In some variations, the hydrogen pressure is maintained (e.g., at about 50-200 psig for the first self-heating stage and the second stage (e.g., a pressure of about 50-200 psig, such as about 50, 100, 150 or 200 psig), and the hydrogen pressure is reduced during the third stage to a pressure less than about 50 psig (e.g., about 5, 10, 15, 20, 25, 30, 35, or 40 psig).

In some variations, a staged hydrogenation process comprises a first self-heat stage during which about 0.5 equivalents or less of hydrogen is added (e.g., about 0.3-0.5 equivalents), a second stage during which about 1-1.2 equivalents of hydrogen is added and the temperature is about 100° C., and a third stage during which about 1.5 equivalents of hydrogen is added and the temperature is about 160° C., where the hydrogen pressure is not varied (e.g., held at about 50 psig, 100 psig, 150 psig, or 200 psig). In one variant, the hydrogen pressure is about 100 psig throughout the hydrogenation process.

In one embodiment, a staged hydrogenation process comprises a first self-heat stage during which about 0.5 equivalents or less of hydrogen is added (e.g., about 0.3-0.5 equivalents) and the hydrogen pressure is about 50-200 psig (e.g., about 50, 100, 150, or 200 psig), a second stage during which about 1-1.2 equivalents of hydrogen is added and the temperature is about 100° C. and the hydrogen pressure is maintained as in the self-heat stage, and a third stage during which the temperature is increased to about 160-240° C. (e.g., about 160° C., 170° C., 180° C., 190° C., 200° C., 210° C., 220° C., 230° C. or 240° C.) and the hydrogen pressure is decreased to a pressure less than about 50 psig (e.g., about 5, 10, 15, 20, 25, 30, 35, or 40 psig). In one variant, the pressure in the first self-heat stage and the second stage is about 100 psig, the temperature in the third stage is about 210° C., and the hydrogen pressure in the third stage is about 20 psig or lower.

Nonlimiting examples of temperature and hydrogen pressure hydrogenation conditions for a first hydrogenation stage in which about 1-2.5 (e.g., about 1-1.5, or about 2-2.5) equivalents of hydrogen are consumed to selectively hydrogenate the conjugated diene are provided in Table 1A. It should be noted that the first hydrogenation stage may or may not be preceded by a self-heated hydrogenation stage as described above. Each "X" in Table 1A discloses reaction conditions comprising the temperature indicated in the column heading and the hydrogen pressure indicated in the row headings. Nonlimiting examples of catalysts that may be used together with the temperatures and hydrogen pressure combinations indicated in Table 1A include Pd/C (e.g., 5-10 wt % Pd), Pd/Al$_2$O$_3$ (e.g., 0.2-0.6 wt % Pd), Pd/SiO$_2$ (e.g., 0.2-0.6 wt % Pd), and Lindlar's catalyst.

TABLE 1A

| Hydrogen pressure (Psi) | Temperature (° C.) | | | | | | | | | | | | | |
|---|---|---|---|---|---|---|---|---|---|---|---|---|---|---|
| | 50 | 55 | 60 | 65 | 70 | 75 | 80 | 85 | 90 | 100 | 105 | 110 | 115 | 120 |
| 50 | X | X | X | X | X | X | X | X | X | X | X | X | X | X |
| 100 | X | X | X | X | X | X | X | X | X | X | X | X | X | X |
| 150 | X | X | X | X | X | X | X | X | X | X | X | X | X | X |
| 200 | X | X | X | X | X | X | X | X | X | X | X | X | X | X |
| 250 | X | X | X | X | X | X | X | X | X | X | X | X | X | X |
| 300 | X | X | X | X | X | X | X | X | X | X | X | X | X | X |
| 350 | X | X | X | X | X | X | X | X | X | X | X | X | X | X |
| 400 | X | X | X | X | X | X | X | X | X | X | X | X | X | X |
| 450 | X | X | X | X | X | X | X | X | X | X | X | X | X | X |
| 500 | X | X | X | X | X | X | X | X | X | X | X | X | X | X |
| 550 | X | X | X | X | X | X | X | X | X | X | X | X | X | X |
| 600 | X | X | X | X | X | X | X | X | X | X | X | X | X | X |
| 650 | X | X | X | X | X | X | X | X | X | X | X | X | X | X |
| 700 | X | X | X | X | X | X | X | X | X | X | X | X | X | X |
| 750 | X | X | X | X | X | X | X | X | X | X | X | X | X | X |
| 800 | X | X | X | X | X | X | X | X | X | X | X | X | X | X |
| 850 | X | X | X | X | X | X | X | X | X | X | X | X | X | X |
| 900 | X | X | X | X | X | X | X | X | X | X | X | X | X | X |
| 950 | X | X | X | X | X | X | X | X | X | X | X | X | X | X |

TABLE 1A-continued

| | Temperature (° C.) | | | | | | | | | | | | | |
|---|---|---|---|---|---|---|---|---|---|---|---|---|---|---|
| Hydrogen pressure (Psi) | 50 | 55 | 60 | 65 | 70 | 75 | 80 | 85 | 90 | 100 | 105 | 110 | 115 | 120 |
| 1000 | X | X | X | X | X | X | X | X | X | X | X | X | X | X |

Nonlimiting examples of hydrogenation conditions for a second hydrogenation stage after about 1-2.5 (e.g., about 1-1.5, or about 2-2.5) equivalents of hydrogen have already been consumed by the conjugated alkene are provided in Table 1B. Each "X" in Table 1B discloses reaction conditions comprising the temperature indicated in the column heading and the hydrogen pressure indicated in the row headings. Nonlimiting examples of catalysts that may be used together with the temperatures and hydrogen pressure combinations indicated in Table 1B include catalysts comprising Pt, Pd, Ni, Cu, Rh, Ru, and Mo on various supports, such as Pd/C (e.g., 5-10 wt % Pd), Pd/Al$_2$O$_3$ (e.g., 0.2-0.6 wt % Pd), Pd/SiO$_2$ (e.g., 0.2-0.6 wt % Pd), Cu-based catalyst (e.g., Cu/SiO2), zeolites impregnated or exchanged with noble metals (e.g., Pd or Pt), and Pt(S)/C. In some variations, the catalyst used for a second hydrogenation stage after about 1-2.5 equivalents of hydrogen have been consumed by the conjugated alkene is 0.3 wt % Pd/Al$_2$O$_3$, and the temperature is about 200-210° C. and the hydrogen pressure is about 1 bar (14 psi). For low hydrogen pressures (e.g., hydrogen pressures lower than about 2 bar), an inert gas such as dry nitrogen may be added to the reactor to increase the overall pressure while achieving a desired partial pressure of hydrogen.

50-150° C., e.g., by about 50° C., by about 60° C., by about 70° C., by about 80° C., by about 90° C., by about 100° C., by about 110° C., by about 120° C., by about 130° C., by about 140° C., or by about 150° C. In some variations, after the addition of 1-1.5 equivalents of hydrogen to farnesene in a first stage, in a second or subsequent stage hydrogen pressure is decreased so as to favor the reaction of di-olefin to form mono-olefin (k[3]) over the reaction of mono-olefin to form saturated hydrocarbon (k[4]). Without being bound by theory, reducing hydrogen pressure in the reactor limits the availability of hydrogen, which leads to favoring the reaction of di-olefin to form mono-olefin over the reaction of mono-olefin to form saturated hydrocarbon. The hydrogen pressure in a second or subsequent stage may be decreased by about 50-100 psig, e.g., by about 50 psig, about 60 psig, about 70 psig, about 80 psig, about 90 psig, or about 100 psig. In some variations, after the addition of 1-2.5 equivalents of hydrogen to farnesene in a first stage, in a second or subsequent stage temperature is increased and hydrogen pressure is decreased so as to favor the reaction of di-olefin to form mono-olefin (k[3]) over the reaction of mono-olefin to form saturated hydrocarbon (k[4]). The reaction temperature in a second or subsequent stage may be increased by about 50-150° C. (e.g., by about 50° C., about 60° C., about

TABLE 1B

| | Temperature (° C.) | | | | | | | | | | | | | |
|---|---|---|---|---|---|---|---|---|---|---|---|---|---|---|
| Hydrogen pressure (Psi) | 120 | 130 | 140 | 150 | 160 | 170 | 180 | 190 | 200 | 210 | 220 | 230 | 240 | 250 | 260 |
| 5 | X | X | X | X | X | X | X | X | X | X | X | X | X | X | X |
| 10 | X | X | X | X | X | X | X | X | X | X | X | X | X | X | X |
| 15 | X | X | X | X | X | X | X | X | X | X | X | X | X | X | X |
| 20 | X | X | X | X | X | X | X | X | X | X | X | X | X | X | X |
| 25 | X | X | X | X | X | X | X | X | X | X | X | X | X | X | X |
| 30 | X | X | X | X | X | X | X | X | X | X | X | X | X | X | X |
| 35 | X | X | X | X | X | X | X | X | X | X | X | X | X | X | X |
| 40 | X | X | X | X | X | X | X | X | X | X | X | X | X | X | X |
| 45 | X | X | X | X | X | X | X | X | X | X | X | X | X | X | X |
| 50 | X | X | X | X | X | X | X | X | X | X | X | X | X | X | X |

A hydrogenation process may comprise any combination of first stage temperature and hydrogen pressure conditions disclosed in Table 1A with second stage temperature and hydrogen pressure conditions described in Table 1B, with the proviso that the combination selected yields the desired selectivity, yield and reaction time. As described above, in some variations, the temperature in the second stage is higher than in the first stage. In some variations, the hydrogen pressure is lower in the second stage than in the first stage. In some variations, the temperature is higher and the hydrogen pressure is lower in the second stage relative to the first stage.

If farnesene is being selectively hydrogenated, after the addition of 1-2.5 equivalents of hydrogen in a first stage, in a second or subsequent stage temperature is increased so as to favor the hydrogenation of di-olefin to form mono-olefin (k[3]) over the hydrogenation of mono-olefin to form saturated hydrocarbon (k[4]). The reaction temperature in a second or subsequent stage may be increased by about 70° C., about 80° C., about 90° C., about 100° C., about 120° C., or about 150° C.), and the hydrogen pressure in a second or subsequent stage may be decrease by about 50-100 psig (e.g., decreased by about 50 psig, about 60 psig, about 70 psig, about 80 psig, about 90 psig, or about 100 psig).

Figure 18A:
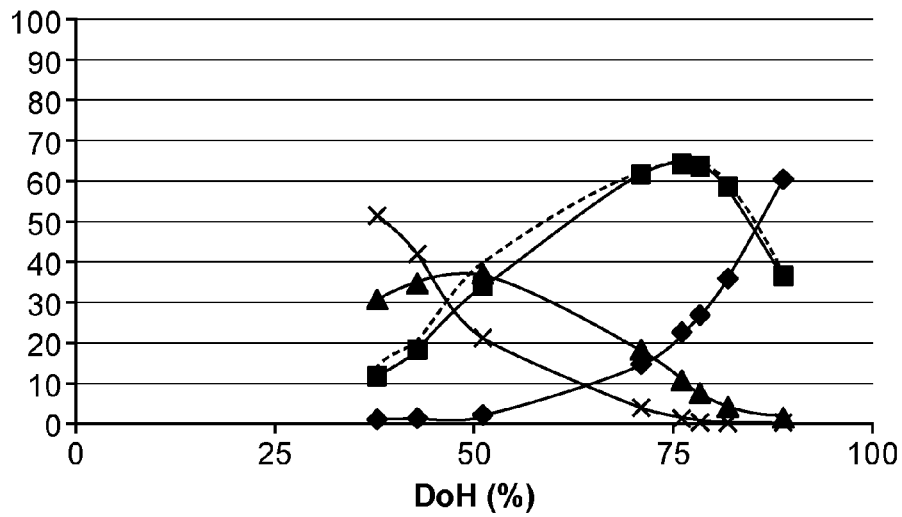
FIGS. 18A-18C provides graphs of populations of various species as hydrogenation proceeds in a second stage for Example 48. Second stage hydrogenation conditions for the data shown in FIG. 18A are 200° C., 2 bar hydrogen pressure; second stage hydrogenation conditions for the data shown in FIG. 18B are 200° C., 1 bar hydrogen pressure; second stage hydrogenation conditions for the data shown in FIG. 18C are 200° C., 0.5 bar hydrogen pressure. "X" represents farnesene content, solid squares represent mono-olefin content, solid triangles represent di-olefin content, and solid diamonds represent farnesane content.
Figure 18B:
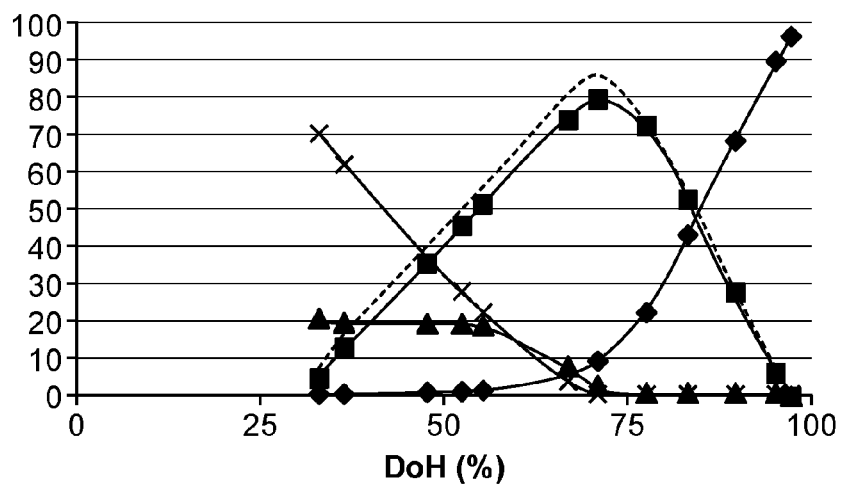
Figure 18C:
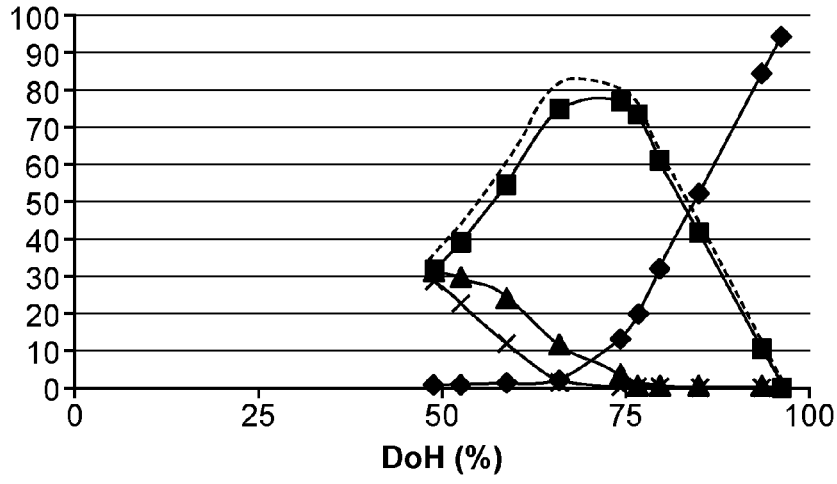

Although nominally the degree of hydrogenation to produce a mono-olefinic hydrocarbon terpene is adjusted to be about one hydrogen equivalent less than total hydrogenation (e.g., 75% hydrogenated for farnesene), the degree of hydrogenation is fine tuned to achieve a desired balance between mono-olefinic content, di-olefinic content and alkane content. In some variations, a desired balance is achieved when the degree of hydrogenation is slightly less than about one hydrogen equivalent less than total hydrogenation (e.g., slightly less than 75% for farnesene). Using farnesene as a model compound, as shown in FIGS. 18A-18C, it is possible to monitor the relative populations of each species as the total degree of hydrogenation proceeds and to identify a degree of hydrogenation at which a desired balance between mono-olefinic, di-olefinic, and alkane content is achieved. In some applications, it may be desired to maximize ratio mono-olefin:di-olefin. In some applications, it may be desired to maximize mono-olefin. As shown in FIG. 18A, under certain temperature and pressure conditions in a second stage, the hydrogenation degree at which mono-olefin is maximum occurs with a total degree of hydrogenation that is about 75% or slightly higher than 75%, and at a point at which alkane content has started to rise. Under these conditions, di-olefin content is not substantially reduced until alkane content has started to rise. Referring now to FIGS. 18B-18C, under other temperature and pressure conditions in a second stage, a degree of hydrogenation can be identified at which mono-olefin content is maximized before alkane content begins to rise steeply, and at a point at which di-olefin content has been substantially reduced. In the examples shown in FIGS. 18B and 18C, the degree of hydrogenation at which olefin content is maximized while both alkane and di-olefin content are minimized occurs at a degree of hydrogenation that is slightly lower than 75%, e.g., at about 70-74.5%, or about 70%, 70.5%, 71%, 72%, 72.5%, 73%, 73.5%, 74%, or 74.5% hydrogenated.

In some variations, hydrogenation conditions are adjusted so that the mono-olefin:di-olefin ratio is about 10:1 or greater, about 20:1 or greater, about 30:1 or greater, about 40:1 or greater, about 50:1 or greater, about 60:1 or greater, about 70:1 or greater, about 80:1 or greater, about 90:1 or greater, about 100:1 or greater, about 120:1 or greater, about 140:1 or greater, about 160:1 or greater, about 180:1 or greater, about 200:1 or greater, about 220:1 or greater, about 240:1 or greater, about 260:1 or greater, about 280:1 or greater, about 300:1 or greater, about 320:1 or greater, about 340:1 or greater, about 360:1 or greater, about 380:1 or greater, about 400:1 or greater, about 500:1 or greater, about 1000:1 or greater, or even greater.

Any suitable configuration for staged partial hydrogenation may be used to carry out the methods described herein. The catalysis conditions (structure of catalyst, type of catalyst, catalyst loading, reaction time, temperature and/or hydrogen pressure) of the first stage, second stage (and subsequent stages, if present) may be independently varied. In some variations, the hydrogenation may be conducted in a single reactor such that the catalyst is not changed between stages. In some variations, the hydrogenation may be conducted in one or more serial reactors so that the catalyst used in different stages may be different. If a single reactor is used for a multi-stage hydrogenation, a batch reactor (e.g., batch slurry reactor) or fixed bed or flow through type reactor may be used. If a batch reactor is used, any suitable type of batch reactor may be used, e.g., batch slurry reactor.

If a fixed bed or flow through reactor, any suitable type of fixed bed or flow through type reactor may be used. In a flow through reaction, efficient heat transfer to the hydrocarbon terpene and residence time in certain temperature zones are important for effective staged hydrogenation reaction to achieve desired selective hydrogenation as described herein. The reactor operates safely while removing exothermic heat due to the hydrogenation, and while controlling temperature in the desired ranges. In some variations, diameters of fixed bed reactors are limited to allow control of the exotherm and overall temperature control of the reactor. It is desired to tune reaction conditions to avoid formation of thermal dimers. Temperature in a first stage is limited to avoid formation of thermal dimers. Further, dilution by a diluent may be used limit formation of thermal dimers. Thermal dimer formation is second order with respect to terpene concentration, whereas hydrogenation rates are typically between zero order and first order with respect to the terpene, so that dilution by a diluent generally increases the ratio of hydrogenation rate to dimerization rate. Any suitable dilution is used, e.g., about 1:100, 1:50, 1:20, 1:10, 1:5, 1:4, 1:3, 1:2, 1:1, 2:1, 3:1, 4:1, 5:1, or 10:1 terpene: diluent. In some cases, the terpene is diluted about 25% in a diluent. In some variations, use of a higher first stage temperature is possible if sufficient dilution is used to limit formation of dimers. Residence times are adjusted so that the reactants experience hydrogenation conditions in the desired temperature and pressure range. Catalyst activity may be balanced such that activity is high enough to allow desired throughput rates but not so high as to produce undesired amounts of saturated alkane or to induce isomerization. In some variations, the hydrocarbon terpene is carried through the flow reactor in a liquid diluent to provide heat transfer between reactor walls and the terpene. The liquid diluent is selected to consume no hydrogen, to be inert under the reaction conditions, and to provide efficient thermal transfer between the terpene substrate and the source of heat in the reactor. In some variations, a suitable liquid diluent may have a higher boiling point than the terpene, such as a high boiling PAO (e.g., Durasyn® PAOs, such as Durasyn® 164, available from Ineos Oligomers, League City, Tex.), a higher boiling terpene oil (e.g., squalane). In some variations, the hydrocarbon terpene is carried through the flow reactor in an inert solvent such as toluene or heptane. A liquid diluent may be selected to be easily separated from the product, e.g., by distillation. In some variations, the hydrocarbon terpene is carried through the flow reactor in a gaseous diluent, e.g., excess hydrogen.

The multiple stage hydrogenation as described herein may be adapted to a variety of different reactor configurations. In some variations, multiple catalyst beds are used with interstage coolers. In some variations, a multiple tube reactor is used. In some variations, a continuous slurry reactor is used. In some variations, a fluidized bed reactor is used.

Figure 17:
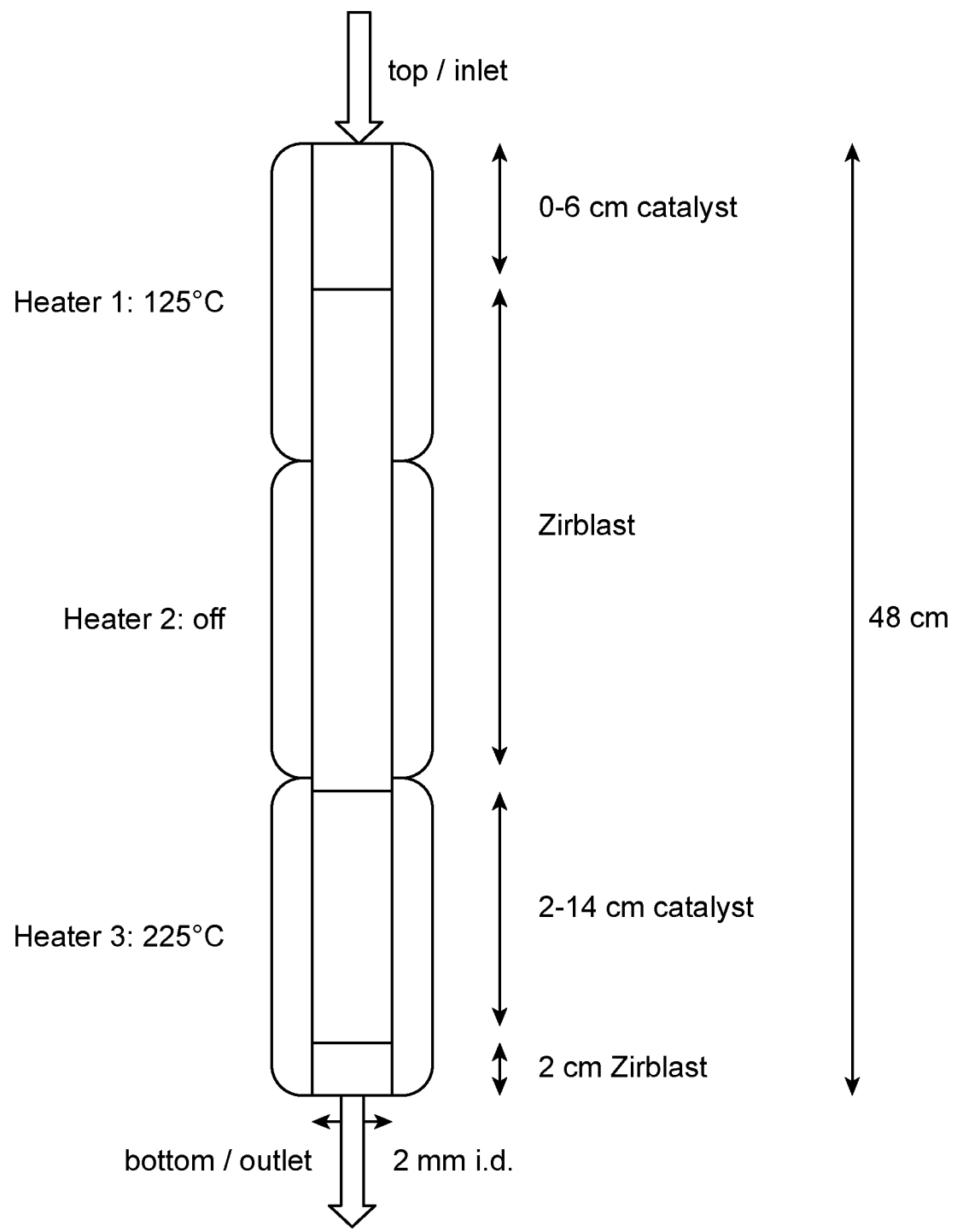
FIG. 17 provides a diagram of a fixed bed reactor used in Example 46.

In some variations, multiple hydrogenation stages are configured as multiple zones in a fixed bed reactor, e.g., as illustrated in FIG. 17. One non-limiting example of a multi-stage hydrogenation process adapted to a flow through reactor is provided in Example 46. If multiple reactors are used in a multi-stage hydrogenation, any combination of batch reactors and fixed bed or flow through type reactors may be used.

In some variations, the multi-stage hydrogenation is carried out in a batch reactor (e.g., batch slurry reactor), or in a series of more than one batch reactors, wherein one or more stages (e.g. a first stage) is carried out in a first batch reactor and one or more subsequent stages (e.g. a second stage) is carried out in a second batch reactor, and so on. In some variations, at least one stage (e.g. a first stage or a final stage) of a multi-stage hydrogenation is carried out in a fixed bed or flow through type reactor. In some variations, more than one stage (e.g., all stages) of a multi-stage hydrogenation is carried out in a fixed bed or flow through type reactor. In some variations, a first stage of a multi-stage hydrogenation is carried out in a fixed bed or flow through type reactor and a second or subsequent stage is carried out in a batch reactor. In some variations, a first stage of a multi-stage hydrogenation is carried out in a batch reactor and a second or subsequent stage is carried out in a fixed bed or flow through type reactor.

In some variations, the same catalyst is used in a first and subsequent stages, but the reaction time, temperature and/or hydrogen pressure is varied in the second or subsequent stages. In some variations, the temperature of the first stage is lower than the temperature of the second or subsequent stage, e.g. the temperature of the first stage is at least about 50° C., 75° C., 100° C., or 150° C. lower than the temperature of a second or subsequent stage. In some variations, the partial hydrogenation is conducted in three or more stages, and the temperature is increased with each stage, e.g., by at least about 50° C. In some variations, the temperature is increased with each stage, but the hydrogen pressure is maintained to be about the same in second and subsequent stages. In some variations, the hydrogen pressure of the first stage is higher than the pressure of the second or subsequent stage, e.g., the hydrogen pressure of the first stage is about 10-500 psig, or about 20-500 psig higher than the hydrogen pressure of the second or subsequent stage. In some variations, the temperature is increased with each stage and the hydrogen pressure is decreased with each stage. In some variations, the loading of the catalyst is varied between a first stage and a subsequent stage. In some variations, the same catalyst is used in first and second stages, and hydrogen pressure in the first stage is in a range from about 50 psig to about 500 psig (e.g., about 50, 100, 200, 300, 400, or 500 psig) and the temperature in the first stage is in a range from about 40° C. to about 160° C. (e.g., about 40° C., 50° C., 60° C., 70° C., 80° C., 90° C., 100° C., 110° C., 120° C., 130° C., 140° C., 150° C., or 160° C.), and the hydrogen pressure in the second stage is in a range from about 10 psig to about 50 psig (e.g., about 10, 20, 30, 40, or 50 psig) and the temperature in the second stage is in a range from about 180° C. to about 260° C. (e.g., about 180° C., 200° C., 220° C., 240° C., or 260° C.). In some variations, the same catalyst is used in the first and second stages, and the same hydrogen pressure is used in the first and second stages, but the temperature is increased in the second stage relative to the first stage, e.g., the temperature in the second stage may be about 50° C.-150° C. higher than the first stage. In one variation, the catalyst and hydrogen pressure are kept constant between the first and second stages, the temperature in the first stage is about 40° C.-80° C. (e.g., about 40° C., 50° C., 60° C., 70° C., or 80° C.) and the temperature in the second stage is in a range from about 100° C. to about 200° C. (e.g., about 100° C., 120° C., 140° C., 160° C., 180° C., or 200° C.).

In some variations, the catalysis conditions (structure of catalyst, type of catalyst, catalyst loading, reaction time, temperature and/or hydrogen pressure) are selected so that the total degree of hydrogenation after a first stage is about 20%, 25%, 30%, 35%, 40%, 45%, 50%, 55%, 60%, 65%, or 70%. In some variations, the catalysis conditions are selected so that the total degree of hydrogenation after a final stage (e.g. after a second stage in a two-stage hydrogenation) is about 50%, 55%, 60%, 65%, 70%, 75% or 80%. In some variations, the catalysis conditions are selected so that the total degree of hydrogenation after a first stage is about 20-70% (e.g., about 20%, 25%, 30%, 35%, 40%, 45%, 50%, 55%, 60%, 65% or 70%), and the total degree of hydrogenation after a final stage is about 50-80% (e.g., about 50, 55%, 60%, 65%, 70%, 75% or 80%).

In some variations, the catalysis conditions (structure of catalyst, composition of catalyst, catalyst loading, reaction time, temperature and/or hydrogen pressure) of a first hydrogenation stage are selected to hydrogenate the sample so that at least one olefinic bond in the conjugated diene is selectively hydrogenated. For example, catalysis conditions in a first stage may be selected so that there is less than about 10% starting material (e.g., about 9%, 8%, 7%, 6%, 5%, 4%, 3%, 2%, 1%, 0.5%, less than 0.3%, or no detectable amount as measured by GC-MS). In some variations, the conjugated diene species is effectively eliminated (e.g., so that the amount of species having a conjugated diene less than about 5%, such as about 3%, 2%, 1%, 0.5%, 0.3% or an undetectable amount by GC-MS in a first stage of the hydrogenation, so that the temperature of a second or subsequent stage may be increased without causing significant thermal dimerization. For example, in the case of farnesene, if the conjugated diene species remaining after the first stage is less than about 5%, the temperature of a second or subsequent stage may be increased to be 160° C. or higher, e.g., about 160° C., 170° C., 180° C., 190° C., 200° C., 210° C., 220° C., 230° C., 240° C., 250° C., or 260° C., without forming significant amounts of thermal dimers.

In some variations, a first stage of the hydrogenation produces less than about 10% of the completely hydrogenated alkane (e.g., about 9%, 8%, 7%, 6%, 5%, 4%, 3%, 2%, 1%, 0.5%, 0.3%, less than 0.3%, or no detectable amount as measured by GC/MS). In some variations, in a first stage of the hydrogenation, the catalysis conditions are selected such that there is less than about 10% starting material (e.g., about 9%, 8%, 7%, 6%, 5%, 4%, 3%, 2%, 1%, 0.5%, 0.3%, less than 0.3%, or no detectable amount as measured by GC/MS) and there is less than about 10% of the completely hydrogenated alkane (e.g., about 9%, 8%, 7%, 6%, 5%, 4%, 3%, 2%, 1%, 0.5%, 0.3%, less than 0.3%, or no detectable amount as measured by GC/MS).

If a feedstock comprising predominantly mono-olefins is desired, the catalysis conditions (catalyst composition, catalyst structure, reaction time, temperature and/or hydrogen pressure) of a first stage may be selected to produce a mixture comprising predominantly mono-olefins and di-olefins, without producing undesirably high amounts (e.g., greater than about 1%, 3%, 5% or 10%, depending on the application) of completely hydrogenated alkenes or leaving undesirably high amounts (e.g., greater than about 1%, 3%, 5%, or 10%, depending on the application) of starting material. The catalysis conditions of a second stage (catalyst composition, catalyst structure, reaction time, temperature and/or hydrogen pressure) may be selected to preferentially act on the di-olefins over the mono-olefins, thereby enriching the mono-olefin content without creating a concomitant increase in the amount of saturated alkane. For example, the temperature of a second stage may be increased so that the thermodynamics favor hydrogenation of the di-olefin to make a mono-olefin over hydrogenation of the mono-olefin to make saturated alkane.

If a feedstock comprising primarily hexahydrofarnesene is desired, the catalysis conditions (catalyst composition, catalyst structure, reaction time, temperature and/or hydrogen pressure) of a first stage may be selected to produce a mixture comprising predominantly hexahydrofarnesene and tetrahydrofarnesene while producing less than about 10% (e.g., less than 10%, less than 5%, less than 3%, less than 1%, less than 0.5%, or an undetectable amount by GC/MS) farnesene and less than about 10% (e.g., less than 10%, less than 5%, less than 3%, less than 1%, less than 0.5%, or an undetectable amount by GC/MS) farnesane. For example, a catalyst (e.g., a palladium catalyst such as Pd/Al$_2$O$_3$ (e.g., 0.3 wt %) or a Pd/C catalyst (e.g., 5 wt % or 10 wt %) may be used at a temperature in a range of about 80° C.-160° C. and a hydrogen pressure in a range of about 45 psig-1000 psig in a first stage to create an intermediate partially hydrogenated farnesene composition comprising predominantly hexahydrofarnesene and tetrahydrofarnesene, with less than about 5% (e.g., less than about 1% farnesene and less than about 5%) (e.g., less than about 1%) farnesane. A second stage using the same catalyst but higher temperature (e.g., about 200° C. or greater, such as about 200° C., 210° C., 220° C., 240° C. or 260° C.) and a hydrogen pressure lower than the first stage (e.g., a hydrogen pressure of about 10 psig, 20 psig, 30 psig, 40 psig, 50 psig, 60 psig, 70 psig, 80 psig, 90 psig, or 100 psig) can be implemented to preferentially hydrogenate the di-olefin and tri-olefin (if present) and create partially hydrogenated farnesene comprising at least about 70%, 71%, 72%, 73%, 74%, 75%, 76%, 77%, 78%, 79%, 80%, 81%, 82%, 83%, 84%, 85%, 86%, 87%, 88%, 89% or 90% hexahydrofarnesene.

If a feedstock comprising primarily hexahydrofarnesene with limited amounts of tetrahydrofarnesene is desired, the catalysis conditions (catalyst composition, catalyst structure, reaction time, temperature and/or hydrogen pressure) of a first stage may be selected to produce a mixture comprising predominantly hexahydrofarnesene and tetrahydrofarnesene while producing less than about 10% (e.g., less than 10%, less than 5%, less than 3%, less than 1%, less than 0.5%, or an undetectable amount by GC/MS) farnesene and less than about 10% (e.g., less than 10%, less than 5%, less than 3%, less than 1%, less than 0.5%, or an undetectable amount by GC/MS) farnesane. For example, a catalyst (e.g., a palladium catalyst such as $Pd/Al_2O_3$ (e.g., 0.3 wt %) or a Pd/C catalyst (e.g., 5 wt % or 10 wt %) may be used at a temperature in a range of about 80° C.-160° C. and a hydrogen pressure in a range from about 45 psig-1000 psig in a first stage to create an intermediate partially hydrogenated farnesene composition comprising predominantly hexahydrofarnesene and tetrahydrofarnesene, with less than about 5% (e.g., less than about 1% farnesene and less than about 5%) (e.g., less than about 1%) farnesane. A second stage using the same catalyst but higher temperature (e.g., about 200° C. or greater, such as about 200° C., 210° C., 220° C., 240° C. or 260° C.) and a hydrogen pressure lower than the first stage (e.g., a hydrogen pressure of about 10 psig, 20 psig, 30 psig, 40 psig, 50 psig, 60 psig, 70 psig, 80 psig, 90 psig, or 100 psig) can be implemented to preferentially hydrogenate the di-olefin and tri-olefin (if present) and create partially hydrogenated farnesene comprising at least about 70%, 71%, 72%, 73%, 74%, 75%, 76%, 77%, 78%, 79%, 80%, 81%, 82%, 83%, 84%, 85%, 86%, 87%, 88%, 89% or 90% hexahydrofarnesene and about 10% or less, 8% or less, 5% or less, 3% or less, 2% or less, 1% or less, or 0.5% or less tetrahydrofarnesene.

In another non-limiting example, controlled staged partial hydrogenation of β-farnesene to produce olefinic feedstocks is carried out as follows. One aliquot hydrogen corresponding to one molar equivalent hydrogen per mol β-farnesene or (two aliquots, each corresponding to about 0.5 mol equivalent $H_2$ per mol β-farnesene), may be delivered to a reactor containing β-farnesene, and the reaction allowed to proceed until the hydrogen is substantially consumed to form 25% hydrogenated β-farnesene. If 50% hydrogenated β-farnesene is desired, two molar equivalents of hydrogen are added, e.g., a first pair of 0.5 mol equivalents of $H_2$ may be delivered to the reactor and allowed to proceed until the hydrogen is substantially consumed, and a second pair of 0.5 mol equivalents of $H_2$ may be delivered to the reactor and allowed to proceed until the hydrogen is substantially consumed. In an example of a staged hydrogenation to form 75% hydrogenated β-farnesene, a first pair of 0.5 mol equivalents of $H_2$ is delivered to the reactor and allowed to proceed until the hydrogen is substantially consumed, a second pair of 0.5 mol equivalents of $H_2$ is delivered to the reactor and allowed to proceed until the hydrogen is substantially consumed in a first stage. In a second stage, the reactor is heated (e.g. to about 100° C.-140° C.) as the heat generated by the exothermic hydrogenation decreases, and a third pair of 0.5 mol equivalents of $H_2$ is delivered to the reactor while the reactor is heated to a temperature of about 100° C.-140° C. and allowed to proceed until the hydrogen is substantially consumed.

In some variations, the methods comprise reacting a controlled amount of hydrogen with a hydrocarbon terpene having a conjugated diene in the presence of a catalyst under controlled (without involving multiples stages) reaction conditions to produce an olefin comprising partially hydrogenated hydrocarbon terpene, wherein the catalyst and reaction conditions are selected to preferentially hydrogenate at least one olefinic bond in the conjugated diene and to preferentially produce mono-olefin species in the olefin comprising the partially hydrogenated hydrocarbon terpene. Some non-limiting examples of β-farnesene that has been partially hydrogenated to produce partially hydrogenated β-farnesene in which hexahydrofarnesene has been preferentially produced with less than 0.3% β-farnesene in a single stage hydrogenation are shown in the Examples herein.

In certain variations, a single stage partial hydrogenation process can be used to make an olefinic feedstock rich in a desired species (e.g., mono-olefins) if the catalyst is sufficiently selective, whereas a multi-stage partial hydrogenation process is used in those instances in which the catalyst itself is not particularly selective, but the process conditions (e.g., temperature and/or hydrogen pressure) can be changed between a first stage and a second stage to tune the composition of the final olefinic mixture by choosing process conditions that kinetically and/or thermodynamically favor hydrogenation of certain species over others (e.g., process conditions that favor hydrogenation of polyenes over monoenes to form a mono-olefinic feedstock that comprises limited amounts of alkane).

In some variations, the single stage hydrogenation methods comprise reacting a controlled amount of hydrogen with a hydrocarbon terpene having a conjugated diene in the presence of a catalyst under controlled reaction conditions to produce an olefin comprising partially hydrogenated hydrocarbon terpene, wherein the catalyst and reaction conditions are selected to preferentially hydrogenate one olefinic bond in the conjugated diene and to preferentially produce dihydro hydrocarbon terpene species (with one carbon-carbon double bond reduced). Non-limiting examples are shown in Examples 21-22 herein. The resulting dihydro hydrocarbon terpene species may be used as-is as an olefinic feedstock, or may be further hydrogenated in a second stage (in which one or more of or any combination of catalyst, catalyst loading, temperature and hydrogen pressure may be varied relative to the first stage) to produce an olefinic feedstock.

In some variations, the methods comprise reacting a controlled amount of hydrogen with a hydrocarbon terpene having a conjugated diene in the presence of a catalyst under controlled reaction conditions to produce an olefin comprising partially hydrogenated hydrocarbon terpene, wherein the catalyst and reaction conditions are selected to preferentially hydrogenate one olefinic bond in the conjugated diene and to produce predominantly dihydro hydrocarbon terpene species and tetrahydro hydrocarbon terpene species (e.g., the dihydro and tetrahydro species combined make up at least about 75%, at least about 80%, at least about 85%, at least about 90%, or at least about 95% of the partially hydrogenated product), with less than about 5% (or less than about 1%) conjugated hydrocarbon terpene remaining, and less than about 5% (or less than about 1%) alkane formed. In certain variations, the ratio of dihydro:tetrahydro species in the partially hydrogenated mixture is about 50:50, or 40:60, or 60:40. Non-limiting examples are shown in the Examples herein. The resulting mixture may be used as-is as an olefinic feedstock, or may be further hydrogenated in a second stage (in which one or more of or any combination of catalyst, catalyst loading, temperature and hydrogen pressure may be varied relative to the first stage) to produce an olefinic feedstock. In certain variations, the amount of hydrogen, catalyst and catalyst conditions may be selected in a second hydrogenation stage to selectively hydrogenate the tetrahydro species over the dihydro species to result in a composition rich in dihydro species while minimizing formation of alkane.

In one embodiment, a method for making an olefinic feedstock comprises reacting a controlled amount of hydrogen with a $C_{10}$-$C_{30}$ hydrocarbon terpene (e.g. β-farnesene or α-farnesene) in the presence of a catalyst under controlled reaction conditions in a single stage to produce a partially hydrogenated terpene that is rich in mono-olefin and comprises a limited amount of alkane. In some variations, such methods are capable of producing a composition comprising at least about 60% mono-olefin and less than about 25% alkane. In certain variations, the controlled amount of hydrogen, the catalyst, and the reaction conditions are selected to produce an olefin comprising at least about 65% mono-olefin and less than about 20% alkane. In certain variations, the controlled amount of hydrogen, the catalyst, and the reaction conditions are selected to produce an olefin comprising at least about 70% mono-olefin and less than about 20% alkane. In certain variations, the controlled amount of hydrogen, the catalyst, and the reaction conditions are selected to produce an olefin comprising at least about 75% mono-olefin and less than about 15% alkane, or less than about 10% alkane. In some variations, the hydrocarbon terpene is made by a bioengineered microorganism using a renewable carbon source.

In one embodiment, a method for making an olefinic feedstock comprises reacting a controlled amount of hydrogen with a $C_{10}$-$C_{30}$ hydrocarbon terpene (e.g. β-farnesene or α-farnesene) in the presence of a catalyst under controlled reaction conditions in a single stage to produce a partially hydrogenated terpene comprising a substantial amount of mono-olefin and a limited amount of di-olefin. In some variations, any di-olefin that is present may be substantially unconjugated, e.g., so that an amount of conjugated species in the composition is about 2% or less or about 1% or less. Such methods may be selected when a feedstock rich in mono-olefins is desired and di-olefins cause undesired side reactions, cross-products, and the like. In some variations, the methods are capable of producing a mono-olefinic feedstock comprising at least about 50% mono-olefin and about 10% or less di-olefin, at least about 50% mono-olefin and about 5% or less di-olefin, at least about 50% mono-olefin and about 3% or less di-olefin, at least about 55% mono-olefin and about 10% or less di-olefin, at least about 55% mono-olefin and about 5% or less di-olefin, at least about 55% mono-olefin and about 3% or less di-olefin, at least about 60% mono-olefin and about 10% or less di-olefin, at least about 60% mono-olefin and about 5% or less di-olefin, at least about 60% mono-olefin and about 3% or less di-olefin, at least about 65% mono-olefin and about 10% or less di-olefin, at least about 65% mono-olefin and about 5% or less di-olefin, at least about 65% mono-olefin and about 3% or less di-olefin, at least about 70% mono-olefin and about 10% or less di-olefin, at least about 70% mono-olefin and about 5% or less di-olefin, at least about 70% mono-olefin and about 3% or less di-olefin, at least about 75% mono-olefin and about 10% or less di-olefin, at least about 75% mono-olefin and about 5% or less di-olefin, at least about 75% mono-olefin and about 3% or less di-olefin, at least about 80% mono-olefin and about 10% or less di-olefin, at least about 80% mono-olefin and about 5% or less di-olefin, at least about 80% mono-olefin and about 3% or less di-olefin, at least about 85% mono-olefin and about 10% or less di-olefin, at least about 85% mono-olefin and about 5% or less di-olefin, at least about 85% mono-olefin and about 3% or less di-olefin. In some variations, the hydrocarbon terpene is made by a bioengineered microorganism using a renewable carbon source.

In one embodiment, a method for making an olefinic feedstock comprises reacting a controlled amount of hydrogen with a $C_{10}$-$C_{30}$ hydrocarbon terpene (e.g. β-farnesene or α-farnesene) in the presence of a catalyst under controlled reaction conditions in a multiple stages (e.g., two or more stages) to produce a partially hydrogenated terpene rich in mono-olefin and comprising a limited amount of alkane. In some variations, such methods are capable of producing a partially hydrogenated terpene comprising at least about 60% mono-olefin and less than about 25% alkane. In certain variations, the controlled amount of hydrogen, the catalyst, and the reaction conditions are selected to produce an olefin comprising at least about 65% mono-olefin and less than about 20% alkane. In certain variations, the controlled amount of hydrogen, the catalyst, and the reaction conditions are selected to produce an olefin comprising at least about 70% mono-olefin and less than about 20% alkane. In certain variations, the controlled amount of hydrogen, the catalyst, and the reaction conditions are selected to produce an olefin comprising at least about 75% mono-olefin and less than about 15% alkane, or less than about 10% alkane. In some variations, the hydrocarbon terpene is made by a bioengineered microorganism using a renewable carbon source. At least one of the group consisting of catalyst, catalyst loading, temperature, and hydrogen pressure is varied between a first stage and a subsequent stage of the multi-stage reaction. In some variations, the hydrocarbon terpene is made by a bioengineered microorganism using a renewable carbon source.

In one embodiment, a method for making an olefinic feedstock comprises reacting a controlled amount of hydrogen with a $C_{10}$-$C_{30}$ hydrocarbon terpene (e.g. β-farnesene or α-farnesene) in the presence of a catalyst under controlled reaction conditions in a multiple stages (e.g., two or more stages) to produce a partially hydrogenated terpene rich in mono-olefin and comprising a limited amount of di-olefin. In some variations, such methods are capable of producing a partially hydrogenated terpene comprising a substantial amount of mono-olefin and a limited amount of di-olefin. In some variations, any di-olefin that is present may be substantially unconjugated, e.g., so that an amount of conjugated species in the composition is about 2% or less or about 1% or less. Such methods may be selected when a feedstock rich in mono-olefins is desired and di-olefins cause undesired side reactions, cross-products, and the like. In some variations, the methods are capable of producing a mono-olefinic feedstock comprising at least about 50% mono-olefin and about 10% or less di-olefin, at least about 50% mono-olefin and about 5% or less di-olefin, at least about 50% mono-olefin and about 3% or less di-olefin, at least about 55% mono-olefin and about 10% or less di-olefin, at least about 55% mono-olefin and about 5% or less di-olefin, at least about 55% mono-olefin and about 3% or less di-olefin, at least about 60% mono-olefin and about 10% or less di-olefin, at least about 60% mono-olefin and about 5% or less di-olefin, at least about 60% mono-olefin and about 3% or less di-olefin, at least about 65% mono-olefin and about 10% or less di-olefin, at least about 65% mono-olefin and about 5% or less di-olefin, at least about 65% mono-olefin and about 3% or less di-olefin, at least about 70% mono-olefin and about 10% or less di-olefin, at least about 70% mono-olefin and about 5% or less di-olefin, at least about 70% mono-olefin and about 3% or less di-olefin, at least about 75% mono-olefin and about 10% or less di-olefin, at least about 75% mono-olefin and about 5% or less di-olefin, at least about 75% mono-olefin and about 3% or less di-olefin, at least about 80% mono-olefin and about 10% or less di-olefin, at least about 80% mono-olefin and about 5% or less di-olefin, at least about 80% mono-olefin and about 3% or less di-olefin, at least about 85% mono-olefin and about 10% or less di-olefin, at least about 85% mono-olefin and about 5% or less di-olefin, at least about 85% mono-olefin and about 3% or less di-olefin. In some variations, the hydrocarbon terpene is made by a bioengineered microorganism using a renewable carbon source.

For any of the methods described herein, any suitable hydrogenation catalyst may be used. For example, in some variations, a catalyst used for first and/or subsequent hydrogenation stages is selected from the group consisting of Pd, Pt, Ni, Ru, Ir, Cu, Fe, Raney-type porous catalysts such as Ni/Al, Co/Al and Cu/Al, alloys of platinum group catalysts with promoters or stabilizers such as Mo, Co, Mg and Zn, and hydroprocessing catalysts such as NiMoS and CoMoS. Exemplary catalysts are described in U.S. Pat. Nos. 6,403,844; 5,378,767; 5,151,172; and 3,702,348, each of which is incorporated herein by reference in its entirety. In some variations, the catalyst used for first and/or subsequent hydrogenation stages is or comprises Pd/C, e.g. 5 wt % Pd/C or 10 wt % Pd/C. In some variations, the catalyst for first and/or subsequent hydrogenation stages is or comprises $Pd/Al_2O_3$, e.g. 0.3 wt % $Pd/Al_2O_3$. In some variations, the catalyst for first and/or subsequent hydrogenation stages is or comprises a Lindlar catalyst, e.g., Pd on calcium carbonate or barium carbonate and treated with lead (e.g., lead oxide or lead acetate). For example, a Lindlar catalyst comprising $Pd/Pb/BaCO_3$ may be used. In some variations, the catalyst for first and/or subsequent hydrogenation stages is or comprises Ni, e.g. Raney Ni, sponge nickel, or skeletal nickel. In some variations, a nickel catalyst is used that is supported by $Al_2O_3$, e.g. about 20%, 12% or 8% $Ni/Al_2O_3$. In some variations the catalyst used for first and/or subsequent hydrogenation stages comprises nickel sulfide. In some variations, the catalyst used for first and/or subsequent hydrogenation stages comprises molybdenum sulfide, e.g. molybdenum sulfide catalysts having a Mo:S ratio of sulfur to molybdenum, e.g. $MoS_2$ supported on alumina, e.g. activated alumina having a surface area of about 300 square meters per gram or more, or silica gel, activated charcoal, acid treated clay, silica-alumina complexes, e.g. as disclosed in U.S. Pat. No. 2,674,634 which is incorporated by reference herein in its entirety.

For any of the methods described herein, the catalyst can be provided in any suitable form, e.g. with a minimum dimension of at least about 1 mm. Particle dimensions may be selected depending on catalyst type and catalysis conditions (e.g. slurry batch, fixed bed, fluidized bed, or continuous flow reactor). The catalyst may be selected to have a specified surface area to produce the desired distribution of partially hydrogenated hydrocarbon terpene species, and may be formed in any suitable form factor, e.g. cylinders, tablets, granules, spheres, lobed cylinders, and the like. In certain variations, the catalyst contains voids, e.g. in the form of channels, passages, or holes. In some variations, the catalyst used for first and/or subsequent hydrogenation stages comprises a shell type catalyst. In some variations, the catalyst comprises an extrudate, e.g., an extrude having a desired cross-sectional shape, such as a lobed extrude (e.g., trilobe extrudate). In some variations, the catalyst used for first and/or subsequent stages is or comprises $Pd/Al_2O_3$, e.g., 0.3 wt % $Pd/Al_2O_3$ trilobe extrudate.

A continuous flow reactor scheme may be designed to incorporate the multistage hydrogenation process as described herein. For example, multiple reactors may be placed in series, where the temperature and hydrogen pressure in each reactor are adjusted to reflect the stage of the hydrogenation process. Any of the hydrogenation processes described herein may be adapted to a continuous flow reactor using known techniques for supporting catalysts, selecting appropriate diluents, providing heat and temperature control, providing hydrogen and pressure control, and separation of product from diluents, byproducts, residual starting material and impurities. In some variations, two reactors are placed in series, where the temperature in the first reactor is in a range from about 80° C. to about 110° C. and the hydrogen pressure in the first reactor is in a range from about 50-300 psig, and the temperature in the second reactor is in a range from about 160° C. to about 240° C. and the hydrogen pressure in the second reactor is in a range from about 10-40 psig. In some variations, three reactors are placed in series, where the first reactor is self-heated and the hydrogen pressure in the first reactor is in a range from about 50-300 psig, the temperature in the second reactor is in a range from about 80° C. to about 240° C. and the hydrogen pressure in the second reactor is in a range from about 50-300 psig, and the temperature in the third reactor is in a range from about 160° C. to about 240° C. and the hydrogen pressure in the third reactor is in a range from about 10-40 psig. When multiple reactors are used in series, catalysts used in each of the reactors may be the same or different. For example, in some variations, a catalyst comprising Pd (e.g., $Pd/Al_2O_3$) is used in some or all series reactors in a continuous flow reactor scheme. In other variations, the catalyst is different in series reactors in a continuous flow reactor scheme. For example, a catalyst that selectively catalyzes hydrogenation of conjugated dienes may be used in a first reactor in some variations. In some variations, a catalyst that selectively hydrogenates dienes is used in a final reactor. In some variations, a catalyst that selectively catalyzes dehydrogenation of paraffins to form mono-olefins may be used in a final reactor.

In some variations, a single continuous flow reactor with multiple zones in series is used to carry out staged partial hydrogenation as described herein. The temperature and hydrogen pressure and catalyst may each be independently varied between zones to achieve a staged hydrogenation process as described herein within a single reactor. Any multi-zone reactor known in the art may be adapted for this purpose, and known techniques for use of diluents, catalyst support, heating and temperature control, feeding in of hydrogen and pressure control, and separation of products from diluents, reactants, byproducts, impurities and the like may be used. In some variations, a reactor comprises two zones in series, where the temperature in the first zone is in a range from about 80° C. to about 110° C. and the hydrogen pressure in the first zone is in a range from about 50-300 psig, and the temperature in the second zone is in a range from about 160° C. to about 240° C. and the hydrogen pressure in the second zone is in a range from about 10-40 psig. In some variations, a reactor comprises three zones in series, where the first zone is self-heated and the hydrogen pressure in the first zone is in a range from about 50-300 psig, the temperature in the second zone is in a range from about 80° C. to about 240° C. and the hydrogen pressure in the second zone is in a range from about 50-300 psig, and the temperature in the third zone is in a range from about 160° C. to about 240° C. and the hydrogen pressure in the third zone is in a range from about 10-40 psig. When a reactor comprising multiple zones in series is used, catalysts used in each of the zones may be the same or different. For example, in some variations, a catalyst comprising Pd (e.g., Pd/Al$_2$O$_3$) is used in some or all zones in a continuous flow reactor. In other variations, the catalyst is different between zones. For example, a catalyst that selectively catalyzes hydrogenation of conjugated dienes may be used in a first zone, or in first and second zones in some variations. In some variations, a catalyst that selectively hydrogenates dienes is used in a final zone. In some variations, a catalyst that selectively catalyzes dehydrogenation of paraffins to form mono-olefins may be used in a final zone.

It should be understood that in batch reactors or continuous flow reactors implementing the staged hydrogenation process described herein, there may be a gradual or ramped, rather than abrupt, change in temperature and/or hydrogen pressure between the different stages of the hydrogenation process. That is, a continuous process incorporating the multiple stages may be devised.

When the catalyst is used with a support, any suitable support can be used, e.g. carbon, silica, titania, zirconia, alumina, kieselguhr, magnesia, calcium aluminate cements, and other inorganic materials. In some cases, supports are activated. Modified versions of such supports can be used, e.g. base-treated supports or supports treated with stabilizing additives such as MgO. A support can have any suitable form factor (e.g. a pellet or extrudate) with dimensions on the order of about 0.1-5 mm, 0.5-5 mm, 1-5 mm, 1-4 mm, or 1-3 mm.

The hydrogenation catalyst may be used in any effective loading. In some variations (e.g. for 5 wt % Pd/C or 10 wt % Pd/C), an effective catalyst loading may be about 1/50, 1/100, 1/1000, 2/1000, 3/1000, 4/1000, 5/1000, 1/2000, 1/5000, or 1/10000 (ratio refers to weight metal/weight substrate). For example, in some variations β-farnesene can be partially hydrogenated using 5 wt % Pd/C at a loading of 1/10000, 1/7000, 1/6000, 1/5000, 1/4000, 1/3000, 1/2000, 1/1000, 2/1000, 3/1000, 4/1000, or 5/1000. In some variations (e.g., for 0.3 wt % Pd/Al$_2$O$_3$), an effective catalyst loading may be about 1/50, 1/100, 1/200, 1/300, 1/400, 1/500, 1/750, 1/1000, 1/2000, 1/5000, 1/10000 g metal/g substrate, or in a range from about 10-1000 ppm, 10-100 ppm, (e.g., 10-60 ppm), where ppm refers to g metal/g substrate. In some variations (e.g., for 0.3 wt % Pd/Al$_2$O$_3$), an effective catalyst loading may be about 10 ppm, about 12 ppm, about 14 ppm, about 16 ppm, about 18 ppm, about 20 ppm, about 30 ppm, about 40 ppm, about 50 ppm, about 60 ppm, about 70 ppm, about 80 ppm, about 90 ppm, or about 100 ppm in a first or a second hydrogenation stage.

During the partial hydrogenation process, it is desired to deliver a controlled amount of hydrogen under controlled reaction conditions so as to control the extent of and site selectivity of the hydrogenation. Such controlled hydrogenation can be accomplished in a variety of ways, and using a variety of equipment setups. For example, continuous hydrogen uptake by the sample may be controlled and/or measured using a flow meter, flow totalizer, or the like, or hydrogen may be delivered to the sample in discrete or quantized molar aliquots, e.g. discrete aliquots of 0.25, 0.5, or 1 mol H$_2$ per mol hydrocarbon terpene. In some variations, a batch slurry hydrogenation reactor is used. In some variations, a fixed bed reactor is used for partial hydrogenation. In some variations, a fluidized bed reactor is used for partial hydrogenation.

The temperature of the hydrogenation may be selected to control the rate of reaction, which may, in some situations, enhance site selectivity of the hydrogenation. In certain variations, a suitable hydrogenation temperature is in a range from about 40° C. to about 260° C., e.g. about 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., or 260° C. In some variations, the reaction is conducted at about 80° C. In some variations, the reaction is conducted at about 100° C. As described earlier, in some variations, the reaction temperature is varied between a first stage and a subsequent stage. In some variations, the reaction is at least partially self-heated during a first stage when the exothermic reaction is generating sufficient heat, and external heat is added (e.g., to heat the reaction to about 140° C., 150° C. or 160° C.) during a latter stage. In some variations, the reactor is cooled to keep the temperature of the exothermic hydrogenation process under control.

The hydrogen pressure used may be in a range from about 20 psig-1000 psig, e.g. about 20, 30, 40, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 psig. As described earlier, in some variations, the hydrogen pressure is varied between a first stage and a subsequent stage of the hydrogenation.

One variation of method for carrying out at least one stage of partially hydrogenating farnesene comprises immersing a catalyst into the liquid hydrocarbon terpene (e.g. β-farnesene) to form a slurry and delivering a controlled amount of hydrogen to the slurry in a closed reactor, where the controlled amount of hydrogen corresponds to a molar equivalent of desired hydrogenation degree. The method comprises hydrogenating the terpene at a temperature between about 50° C. and 260° C. until the controlled amount of hydrogen is substantially consumed, and removing the catalyst from the hydrogenated terpene. For example, in the case of β-farnesene, one molar equivalent of hydrogen delivered to the slurry in the closed reactor corresponds to 25% hydrogenation, two molar equivalents of hydrogen delivered to the slurry in the closed reactor corresponds to 50% hydrogenation, and three molar equivalents corresponds to 75% hydrogenation. The controlled amount of hydrogen may be delivered to the slurry in one or more discrete aliquots or as a continuous stream. In one variation, molar equivalents of hydrogen are delivered to the slurry (e.g. 5 wt % Pd/C at a loading of about 1-5 g/kg hydrocarbon terpene or about 3-5 g/kg hydrocarbon terpene, or 0.3 wt % Pd/Al$_2$O$_3$ at a loading of about 25 mg/20-35 ml hydrocarbon terpene) in the closed reactor in discrete aliquots, e.g. each aliquot corresponding to a known molar equivalent H$_2$ per mol hydrocarbon terpene in the reactor, at a pressure of 20-1000 psig. After each aliquot (or pair of aliquots) is delivered to the reactor, the hydrogenation reaction is allowed to proceed until the hydrogen is substantially consumed. If more extensive hydrogenation is desired, another aliquot (or multiple aliquots) is delivered to the reactor and allowed to proceed until the hydrogen is substantially consumed, and so forth. Following the reaction, the catalyst can be removed from the partially hydrogenated farnesene using known techniques.

In another variation of carrying out at least one stage of a partial hydrogenation, a controlled amount of hydrogen is delivered to a closed reactor in a continuous stream. For example, a catalyst (e.g. 5 wt % Pd/C or 10 wt % Pd/C) is immersed in liquid hydrocarbon terpene (e.g. β-farnesene) to form a slurry in a closed reactor. The reactor is evacuated. Hydrogen is delivered to the reactor (e.g. at about 50 psig), and the cumulative uptake of hydrogen is monitored, e.g. using a flow totalizer or a flow meter. The temperature of the reaction is controlled to control the rate of reaction, e.g. at about 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., or 260° C. When the desired molar equivalent of hydrogen has been consumed (e.g. 3 mol equivalents hydrogen/mol farnesene for 75% hydrogenated farnesene), the hydrogen flow is stopped. Catalyst can be removed from the partially hydrogenated hydrocarbon terpene using known techniques.

Any of the methods described herein can be used to produce a $C_{10}$ olefin comprising partially hydrogenated myrcene, a $C_{10}$ olefin comprising partially hydrogenated ocimene, a $C_{15}$ olefin comprising partially hydrogenated β-farnesene, a $C_{15}$ olefin comprising partially hydrogenated α-farnesene, a $C_{20}$ olefin comprising partially hydrogenated springene, a $C_{25}$ olefin comprising partially hydrogenated geranylfarnesene, a $C_{30}$ olefin comprising partially hydrogenated isodehydrosqualene, or a $C_{30}$ olefin comprising partially hydrogenated isosqualane precursor I or II.

Figure 11:
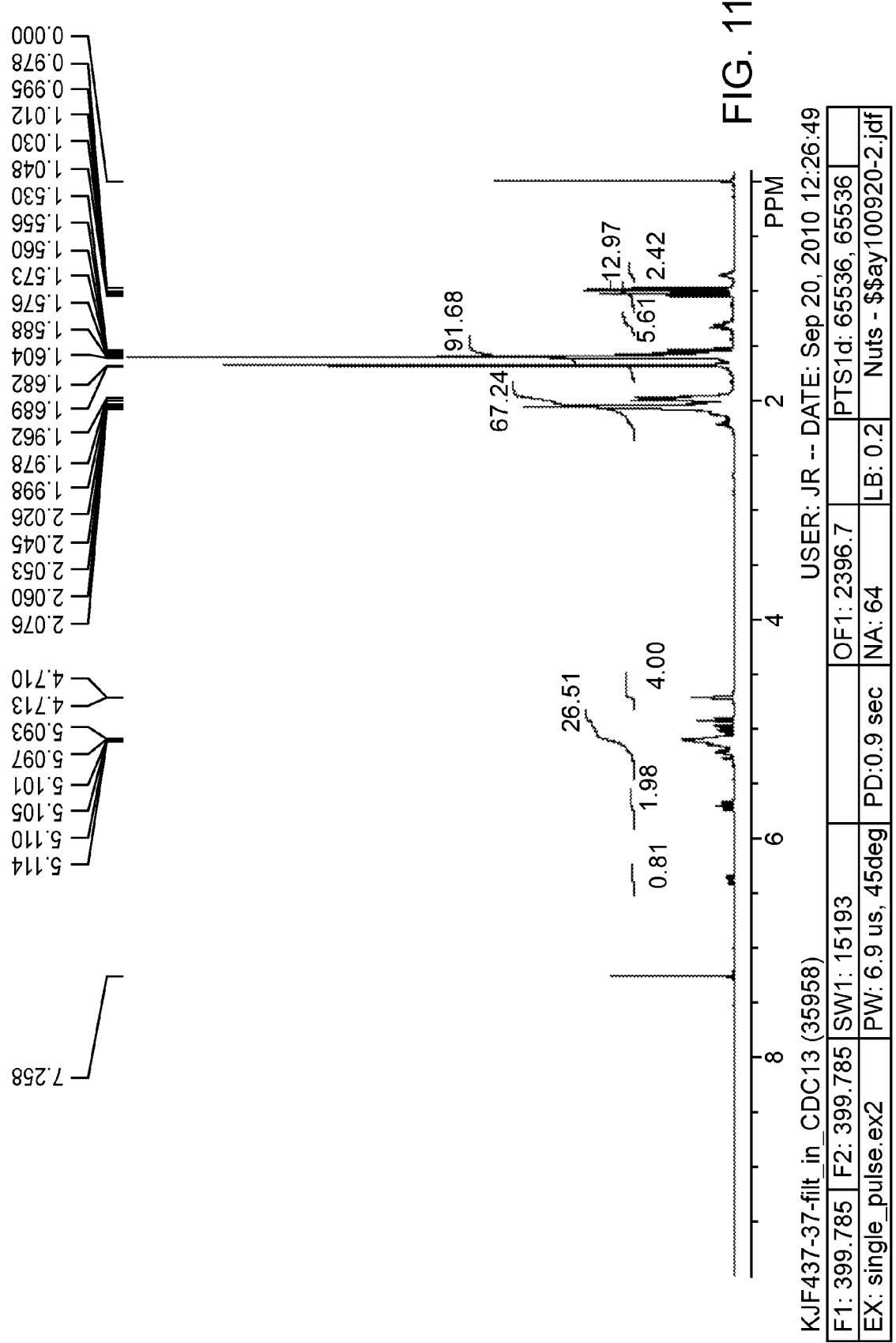
FIG. 11 provides a $^1$H NMR spectrum of β-farnesene that is 25% hydrogenated according to Example 21.

Referring now to FIG. 11 and Examples 21 and 22, microbial-derived farnesene is partially hydrogenated to produce a feedstock comprising a mixture of $C_{15}$ trienes. As shown in Example 21, delivering a controlled amount of hydrogen (1 mol equivalent hydrogen) under controlled reaction conditions with a suitable catalyst (5 wt % Pd/C at a loading of 3 g/kg) yields an olefinic mixture comprising almost exclusively dihydrofarnesene, with less than 10% of the mono-olefin molecules exhibiting a conjugated diene moiety. As shown in Example 22, delivering a controlled amount of hydrogen (1 molar equivalent of hydrogen) under controlled reaction conditions with a Lindlar catalyst yields an olefinic mixture comprising almost exclusively dihydrofarnesene, with less than 12% of the mixture attributed to tetrahydrofarnesene.

The methods described herein may be used to produce a partially hydrogenated β-farnesene feedstock that comprises about 60, 65, 70, 75, 76, 77, 78, 79, 80, 81, 82, 83, 84, 85, 86, 87, 88, 89 or 90% hexahydrofarnesene. For example, partially hydrogenated farnesene produced by delivering about 2.4-3.4 (or about 2.5-3.2, or about 2.7-3.1) mol equivalents $H_2$/mol farnesene in a controlled manner or multi-stage as described herein may comprise about 50, 55, 60, 65, 70, 75, 76, 77, 78, 79, 80, 81, 82, 83, 84, 85, 86, 87, 88, 89 or 90% hexahydrofarnesene. As described herein and illustrated in Example 48 and FIGS. 18A-18C, the amount of hydrogen delivered can be carefully controlled to achieve a desired balance between mono-olefinic, di-olefinic and alkane species.

In some variations, the olefinic feedstocks derived from partially hydrogenated hydrocarbon terpenes using the methods disclosed herein are suitable for catalytic oligomerization to form a mixture of isoparaffins. In some variations, at least a portion of the mixture of isoparaffins so produced may be used as a base oil.

In some variations, the olefinic feedstocks derived from partially hydrogenated hydrocarbon terpenes using the methods disclosed herein are suitable for catalytic reaction with one or more alphaolefins to form a mixture of isoparaffins comprising adducts of the terpene and the one or more alphaolefins. In some variations, at least a portion of the mixture of isoparaffins so produced may be used as a base oil.

Methods are disclosed herein that comprise using an olefinic feedstock comprising a partially hydrogenated $C_{10}$-$C_{30}$ hydrocarbon terpene as a monomer or reactant in any industrial process, e.g., an industrial oligomerization, polymerization, hydroformylation, or carbonylation process. Products produced by such methods are disclosed, e.g. alcohols, detergents, surfactants, polymers, plastics, rubbers, or oils.

Compositions

If hydrogenation of a conjugated alkene (e.g. a $C_{10}$-$C_{30}$ hydrocarbon terpene such as myrcene, ocimene or farnesene) is carried out with insufficient hydrogen to saturate substantially all carbon-carbon double bonds, a mixture comprising molecules having different degrees of hydrogenation may be produced. For conjugated alkenes containing a conjugated diene and at least one additional olefinic bond, partial hydrogenation (e.g. with about 2 molar equivalents of hydrogen, or about 1 molar equivalent or less of hydrogen) may preferentially reduce or eliminate at least one olefinic bond of the conjugated diene moiety, as described herein.

Partial hydrogenation of a conjugated alkene may result in a distribution of species. For example, myrcene can be partially hydrogenated to result in distribution of hexahydromyrcene, tetrahydromyrcene, dihydromyrcene, and myrcene. Farnesene can be partially hydrogenated to result in a distribution of farnesane, hexahydrofarnesene, tetrahydrofarnesene, dihydrofarnesene, and farnesene.

However, the distribution of species produced by partial hydrogenation can be tuned through selecting the type, activity and loading of the catalyst, and the catalysis conditions (e.g. temperature and/or controlled hydrogen delivery).

As described herein, in some variations, the hydrogenation may be accomplished in two or more stages to produce a desired distribution of species in a partially hydrogenated terpene hydrocarbon. For example, the amount of hydrogen, catalysis conditions (structure and type of catalyst, catalyst loading, reaction time, temperature and/or hydrogen pressure) of a first stage may be selected to produce an intermediate distribution of species, and the amount of hydrogen and catalysis conditions (structure and type of catalyst, temperature and/or hydrogen pressure) for a second hydrogenation stage may be selected based on the intermediate distribution of species formed in the first stage to produce a desired final distribution of species. In certain variations, the catalysis conditions of a second stage may be selected so as to minimize formation of alkane.

For example, the catalysis conditions (catalyst type, catalyst structure, catalyst loading, temperature, hydrogen pressure and/or reaction time used in one or more hydrogenation stages as described herein) may be selected so that partial hydrogenation of a hydrocarbon terpene (e.g. myrcene, ocimene, or farnesene) results in a distribution that is unexpectedly rich in mono-olefinic species. Myrcene can be hydrogenated to produce partially hydrogenated myrcene in which tetrahydromyrcene is the predominant species (e.g. at least about 50%, 55%, 60%, 70% or 80% of the sample is tetrahydromyrcene). Farnesene can be hydrogenated to produce partially hydrogenated farnesene in which hexahydrofarnesene is the predominant species (e.g. at least about 50%, 55%, 60%, 70% or 80% of the sample is hexahydrofarnesene).

In certain variations, the hydrogenation is conducted in a single stage, and the catalyst and/or catalysis conditions are selected to provide a desired distribution of species. In one non-limiting example, a catalyst and catalyst conditions that are known to selectively reduce at least one olefinic bond in a conjugated diene moiety may be used to produce a composition rich in tri-olefinic species. In another non-limiting example, a catalyst and catalysis conditions that are known to selectively produce mono-olefins may be used to produce a composition rich in mono-olefinic species.

Provided herein are examples of specific compositions for olefinic feedstocks derived by partial hydrogenation of conjugated hydrocarbon terpenes. For example, the following classes of olefinic feedstock compositions are disclosed herein: i) olefinic feedstocks compositions that have very low amounts of conjugated dienes (e.g., less than about 10% conjugated diene, less than about 5% conjugated diene, or less than about 1% conjugated diene); ii) olefinic feedstocks comprised predominantly of mono-olefins and di-olefins (e.g., at least about 80%, or at least about 90%, or at least about 95% mono-olefins and di-olefins); iii) olefinic feedstock compositions comprised predominantly of mono-olefinic species (e.g., at least about 60%, at least about 65%, at least about 70%, at least about 75%, or at least about 80% mono-olefins); v) olefinic feedstock compositions that have limited amounts of alkanes (e.g., less than about 25%, less than about 20%, less than about 15%, less than about 10%, or less than about 5%); vi) olefinic feedstock compositions that have limited amounts of conjugated dienes and limited amounts of alkanes; vii) olefinic feedstock compositions consisting essentially of tri-olefins and having limited amounts of conjugated dienes and alkanes; viii) olefinic feedstock compositions comprised predominantly of mono-olefins and having limited amounts of conjugated dienes and alkanes; and ix) olefinic feedstock compositions comprising substantial amounts of mono-olefins (e.g., at least about 50%, at least about 55%, at least about 60%, at least 65%, at least about 70%, at least about 75%, or at least about 80% mono-olefin) and limited amounts of di-olefins (e.g., at most about 10%, at most about 8%, at most about 5%, at most about 3%, at most about 2%, at most about 1% di-olefin, or at most about 0.5% di-olefin). In some variations, di-olefins that are present may be substantially unconjugated, e.g., so that a composition comprises at most about 2%, at most about 1%, at most about 0.5%, at most about 0.1%, or no detectable conjugated species.

Partially hydrogenated α-farnesene or β-farnesene may comprise any amount of and any combination of dihydrofarnesene, tetrahydrofarnesene, hexahydrofarnesene, farnesane, and farnesene. Nonlimiting, exemplary structures for various species of dihydrofarnesene, tetrahydrofarnesene and hexahydrofarnesene are shown below.

Dihydrofarnesene:

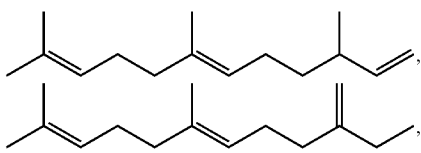

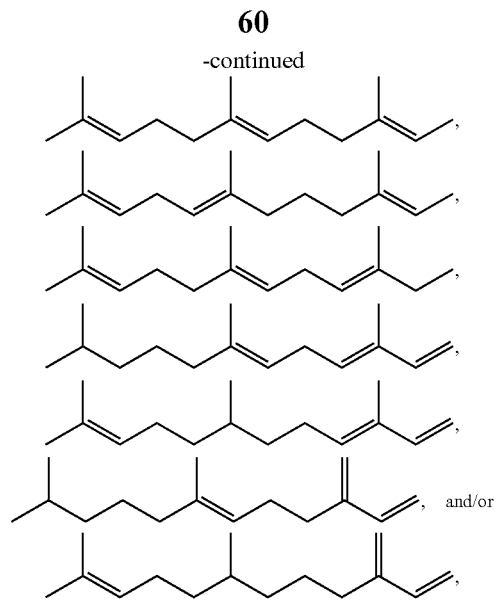

including isomers of the foregoing.

Tetrahydrofarnesene:

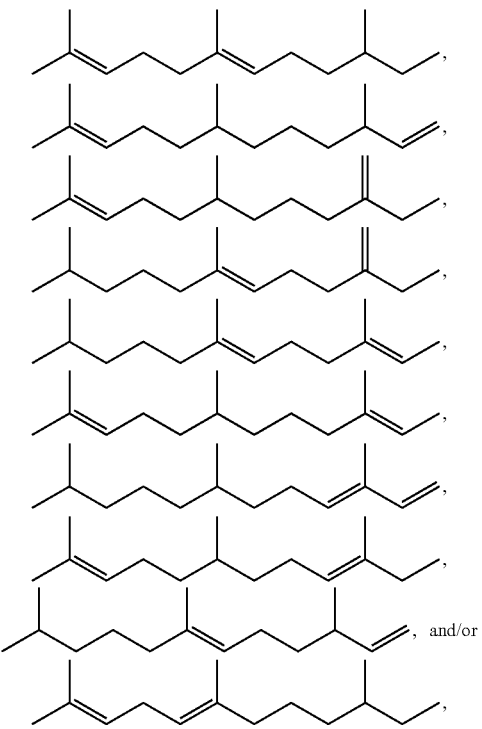

including any isomers of the foregoing.

Hexahydrofarnesene:

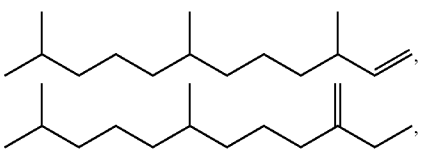

-continued

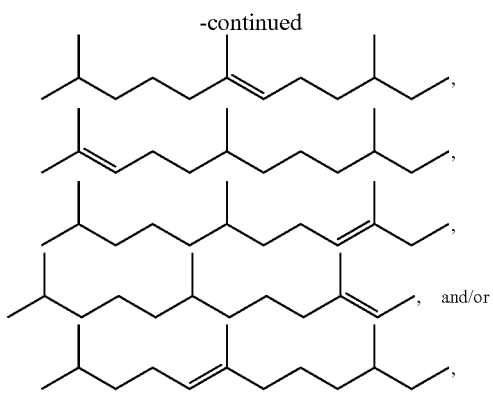

including any isomers of the foregoing.

Partially hydrogenated myrcene may comprise any amount of and any combination of dihydromyrcene, tetrahydromyrcene, 2,6-dimethyloctane, and myrcene. Nonlimiting exemplary structures for various species of dihydromyrcene and tetrahydromyrcene are shown below.

Dihydromyrcene:

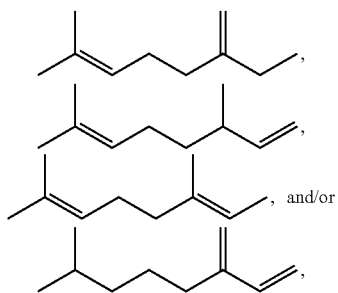

including any isomers of the foregoing.

Tetrahydromyrcene:

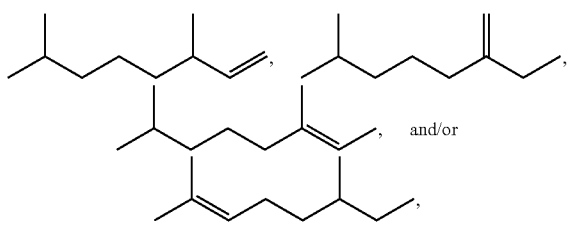

including any isomers of the foregoing.

Partially hydrogenated ocimene may comprise any amount of and any combination of dihydroocimene, tetrahydroocimene, 2,6-dimethyloctane, and ocimene. Nonlimiting exemplary structures for various species of dihydroocimene and tetrahydroocimene are shown below.

Dihydroocimene:

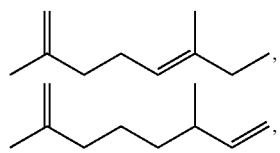

-continued

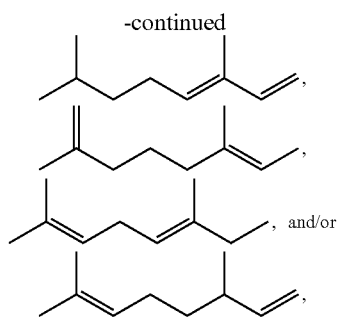

including any isomers of the foregoing.

Tetrahydroocimene:

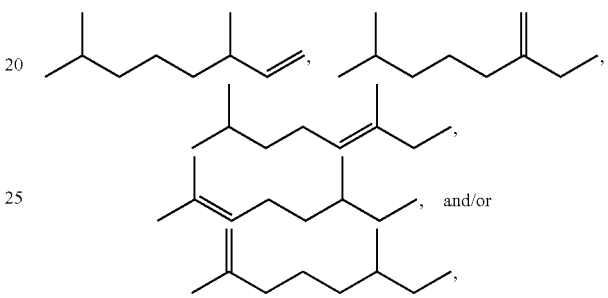

including any isomers of the foregoing.

The degree of hydrogenation in a partially hydrogenated hydrocarbon terpene (e.g., farnesene) sample can be quantified by a variety of methods, e.g. by mol of $H_2$ consumed per mol hydrocarbon terpene (e.g. per mol farnesene) in the hydrogenation process, by an analysis of the degree of unsaturation in the sample (e.g. by Bromine number, which may be measured according to ASTM D1159-07 "Standard Test Method for Bromine Numbers of Petroleum Distillates and Commercial Aliphatic Olefins by Electrometric Titration" which is incorporated herein by reference in its entirety, or by Bromine index, which may be measured according to ASTM D2710-09 "Standard Test Method for Bromine Index of Petroleum Hydrocarbons by Electrometric Titration" which is incorporated herein by reference in its entirety), or by measuring the relative populations of each species (e.g., farnesene, farnesane, hexahydrofarnesene, tetrahydrofarnesene, and dihydrofarnesene), e.g. by GC-MS or GC-FID. In some variations, species in a partially hydrogenated sample may be determined by GC-MS or GC-FID as follows. Peak areas associated with ions corresponding to each of farnesane, hexahydrofarnesene, tetrahydrofarnesene, and dihydrofarnesene can be calculated, and the resulting relative populations of each species can be determined. Alternatively, if the degree of unsaturation (e.g., as measured by Br number) and the area % farnesane for a sample are known, and assuming only mono-olefinc and di-olefinic species are present in significant amounts (e.g. greater than about 1 area % in a GC-MS measurement), the relative amounts of mono-olefinic and di-olefinic species can be calculated. Table 1 shows a theoretical correlation between % unsaturation and Bromine number, assuming that partially hydrogenated farnesene responds to bromine as a tri-unsaturate. An experimentally measured Bromine number may be used to estimate a % hydrogenation in a sample using Table 1. An experimentally measured % hydrogenation (e.g., by GC-FID or GC-MS) can be used to estimate a Br number in a number using Table 1.

Table 1 provides an expected Bromine number for various partially hydrogenated farnesene feedstocks.

TABLE 1

| Mol H$_2$/mol farnesene | % hydrogen saturation | Corresponding Br number |
|---|---|---|
| 0.25 | 6.3 | 293 |
| 0.5 | 12.5 | 272 |
| 0.75 | 18.8 | 252 |
| 1 | 25 | 232 |
| 1.25 | 31.3 | 212 |
| 1.5 | 37.5 | 193 |
| 1.75 | 43.8 | 173 |
| 2 | 50 | 153 |
| 2.25 | 56.3 | 134 |
| 2.5 | 63.5 | 115 |
| 2.75 | 68.8 | 95 |
| 3 | 75 | 76 |
| 3.25 | 81.3 | 57 |
| 3.5 | 87.5 | 38 |
| 3.75 | 93.8 | 19 |
| 4 | 100 | 0 |

In some variations, partially hydrogenated farnesene (e.g. β-farnesene) used as a feedstock comprises hexahydrofarnesene, and may additionally comprise tetrahydrofarnesene and/or farnesane. In some variations, the feedstock may comprise hexahydrofarnesene, tetrahydrofarnesene and farnesane. In some variations, the feedstock may comprise hexahydrofarnesene, tetrahydrofarnesene and dihydrofarnesene. Some feedstocks may comprise hexahydrofarnesene, tetrahydrofarnesene, dihydrofarnesene and farnesane. Some feedstocks may comprise hexahydrofarnesene, tetrahydrofenesene, dihydrofarnesene, farnesane, and farnesene (or an isomer thereof).

In some variations, partially hydrogenated myrcene used as a feedstock comprises tetrahydromyrcene, and, in certain variations, may additionally comprise dihydromyrcene and/or hexahydromyrcene. Partially hydrogenated ocimene used as a feedstock comprises tetrahydroocimene and may, in certain variations, additionally comprise dihydroocimene and/or hexahydroocimene.

Described herein are feedstocks in which the partial hydrogenation proceeds so as to selectively reduce at least one olefinic bond in a conjugated diene moiety in a hydrocarbon terpene (e.g. a C$_{10}$-C$_{30}$ hydrocarbon terpene such as myrcene, ocimene, or farnesene (e.g. β-farnesene)). For example, some feedstocks comprise partially hydrogenated β-farnesene in which the partial hydrogenation proceeds so as to selectively reduce the conjugated diene, so that a sample that is 25% hydrogenated consists essentially of dihydrofarnesene (e.g. one or more dihydrofarnesene structures shown in Examples 21 and 22 herein).

Described herein are feedstocks in which the partial hydrogenation proceeds so as to selectively produce a mono-olefin (e.g. hexahydrofarnesene in the case of farnesene (e.g. β-farnesene) and tetrahydromyrcene in the case of myrcene) in greater quantities than would be statistically expected. The mono-olefin-rich feedstock produced from partial hydrogenation of hydrocarbon terpenes (e.g. hydrocarbon terpenes microbially produced via genetically engineered cells using a renewable carbon source as described herein) can be used in place of, or in addition to, an olefinic feedstock derived from fossil fuel sources (e.g. a linear or branched mono-olefin or a linear or branched alpha-olefin derived from petroleum products).

In one embodiment, described herein are olefinic feedstocks comprising partially hydrogenated acyclic or cyclic C$_{10}$-C$_{30}$ hydrocarbon terpene (e.g. myrcene, ocimene, or farnesene), wherein the partially hydrogenated hydrocarbon terpene comprises at least about 60% mono-olefin and less than about 25% alkane. In some variations, the hydrocarbon terpene is produced by bioengineered microorganisms using a renewable carbon source. In some variations, the olefinic feedstock comprises at least about 65% mono-olefin and less than about 25% alkane. In some variations, the olefinic feedstock comprises at least about 70% mono-olefin and less than about 20% alkane. In some variations, the olefinic feedstock of comprises at least about 75% mono-olefin and about 10% or less alkane. For example, some olefinic feedstocks comprise at least about 60% hexahydrofarnesene and less than about 25% farnesane, at least about 65% hexahydrofarnesene and less than about 25% farnesane, at least about 70% hexahydrofarnesene and less than about 20% farnesane, at least about 75% hexahydrofarnesene and about 10% or less farnesane. In certain variations, β-farnesene used to make the feedstocks is made by bioengineered microorganisms using a renewable carbon source.

Described herein are feedstock compositions derived from β-farnesene that are about 60-80% (e.g. about 60%, 61%, 62%, 63%, 64%, 65%, 66%, 67%. 68%. 69%, 70%, 71%, 72%, 73%, 74%, 75%, 76%, 77%, 78%, 79%, or 80%) hydrogenated and hexahydrofarnesene is produced in an amount greater than about 50%, e.g. hexahydrofarnesene is present at about 50-80% of the total partially hydrogenated farnesene sample, e.g. about 50, 55, 60, 65, 70, 75, or 80% (as measured by area %). The hexahydrofarnesene-rich feedstock can be used in place of, or in addition to an olefinic feedstock having a similar molecular weight (e.g. a linear or branched mono-olefin, or a linear or branched alpha-olefin). For example, the hexahydrofarnesene-rich feedstock may be used in place of or in addition to a C$_{12}$-C$_{15}$ linear or branched mono-olefin derived from fossil fuels. In some reactions, the hexahydrofarnesene-rich feedstock may be used to substitute for or to supplement a C$_{12}$-C$_{15}$ linear or branched alpha-olefin feedstock.

Described herein are feedstock compositions derived from β-farnesene that are about 70-80% (e.g. about 70%, 71%, 72%, 73%, 74%, 75%, 76%, 77%, 78%, 79%, or 80%) hydrogenated and hexahydrofarnesene is produced in an amount greater than about 50%, e.g. hexahydrofarnesene is present at about 50-80% of the total partially hydrogenated farnesene sample, e.g. about 50, 55, 60, 65, 70, 75 or 80%. The hexahydrofarnesene-rich feedstock may be used in place of, or in addition to an olefinic feedstock having a similar molecular weight (e.g. a linear or branched mono-olefin, or a linear or branched alpha-olefin). For example, the hexahydrofarnesene-rich feedstock may be used in place of or in addition to a C$_{12}$-C$_{15}$ linear or branched mono-olefin derived from fossil fuels. In some reactions, the hexahydrofarnesene-rich feedstock may be used to substitute for or to supplement a C$_{12}$-C$_{15}$ linear or branched alpha-olefin feedstock.

Described herein are feedstock compositions derived from myrcene that are about 60-70% (e.g. about 60%, 61%, 62%, 63%, 64%, 65%, 66%, 67%, 68%, 69% or 70%) hydrogenated and tetrahydromyrcene is produced in an amount greater than about 50% (e.g. about 50, 55, 60, 65, 70, 75, 80, 85, 90 or 95%). The tetrahydromyrcene-rich feedstock may be used in place of, or in addition to, an olefinic feedstock In some variations, a feedstock comprises partially hydrogenated β-farnesene in which least about 2 but less than about 3.8 mol $H_2$ was consumed per mol β-farnesene during hydrogenation. In some variations, a feedstock comprises partially hydrogenated β-farnesene in which about 2, 2.25, 2.5, 2.75, 3, 3.25 or 3.5 mol $H_2$ was consumed per mol β-farnesene during hydrogenation. In some variations, a feedstock comprises partially hydrogenated β-farnesene in which about 2.5, 2.6, 2.7, 2.8, 2.9, 3.0, 3.1, 3.2, 3.3, 3.4 or 3.5 mol $H_2$ was consumed per mol β-farnesene during hydrogenation. In some variations, a feedstock comprises partially hydrogenated β-farnesene in which the degree of hydrogenation is about 60-85%, e.g. about 60, 61, 62, 63, 64, 65, 66, 67, 68, 69, 70, 71, 72, 73, 74, 75, 76, 77, 78, 79, 80, 81, 82, 83, 84 or 85%, corresponding to about 2.5 to about 3.5 mol $H_2$ (e.g. 2.5, 2.6, 2.7, 2.8, 2.9, 3.0, 3.1, 3.2, 3.3, 3.4 or 3.5 mol $H_2$) per mol β-farnesene consumed during hydrogenation.

In some variations, a partially hydrogenated β-farnesene feedstock comprises at least about 50% hexahydrofarnesene, e.g. about 50, 55, 60, 65, 70, 75, or 80% hexahydrofarnesane. In some variations, a partially hydrogenated farnesene feedstock comprises at least about 50% hexahydrofarnesene (e.g. about 50, 55, 60, 65, 70, 75 or 80%) and less than about 10% (e.g. less than about 10%, less than about 5%, less than about 4%, less than about 3%, less than about 2%, or less than about 1%) dihydrofarnesene. In some variations, a partially hydrogenated farnesene feedstock comprises at least about 50% hexahydrofarnesene (e.g. about 50, 55, 60, 65, 70, 75 or 80%) and about 5% or less (e.g. less than about 5%, less than about 4%, less than about 3%, less than about 2%, or less than about 1%) farnesene (or isomers thereof). For example, in some variations, a partially hydrogenated farnesene feedstock comprises at least about 50% hexahydrofarnesene (e.g. about 50, 55, 60, 65, 70, 75 or 80%) and less than about 1% dihydrofarnesene and less than about 1% farnesene (or isomers thereof).

In some variations, a partially hydrogenated farnesene feedstock comprises at least about 50% hexahydrofarnesene (e.g. about 50, 55, 60, 65, 70, 75 or 80%) and about 25% or less farnesane, e.g. about 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, 10% or less, 9% or less, 8% or less, 7% or less, 6% or less, or 5% or less farnesane. For example, some partially hydrogenated farnesene feedstocks comprise about 60-80% hexahydrofarnesane, and about 5-25% farnesane.

In some variations, a partially hydrogenated farnesene feedstock comprises at least about 50% hexahydrofarnesene (e.g. about 50, 55, 60, 65, 70, 75 or 80%) and about 25% or less tetrahydrofarnesene, e.g. about 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, or 10% or less tetrahydrofarnesene.

In some variations, a partially hydrogenated farnesene feedstock comprises at least about 50%, or at least about 60% hexahydrofarnesene (e.g. about 50, 55, 60, 65, 70, 75 or 80%), about 25% or less farnesane, (e.g. about 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, 10% or less, 9% or less, 8% or less, 7% or less, 6% or less, or 5% or less farnesane), and about 25% or less tetrahydrofarnesene, (e.g. about 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, or 10% or less). For example, some feedstocks comprise about 50-80% hexahydrofarnesene, about 0-25% tetrahydrofarnesene, and about 5-25% farnesane. Some feedstocks comprise about 60-80% hexahydrofarnesene, about 0-15% tetrahydrofarnesene, and about 5-25% farnesane. Some feedstocks comprise about 65-80% hexahydrofarnesene, about 0-5% tetrahydrofarnesene, and about 0-20% farnesane.

Some specific non-limiting examples of compositions of partially hydrogenated farnesene feedstocks are provided in Table 2A. Each "X" specifically discloses a feedstock comprising hexahydrofarnesene in the area % indicated on the horizontal axis and farnesane in the area % indicated on the vertical axis. Each of the ranges in Table 2A specifically discloses the numerical values provided as lower limits RL and upper limits RU, and also specifically discloses values within the range limits, e.g., each of the following numbers within each range are specifically disclosed: R=RL+k*(RU−RL), wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. For any of the compositions in Table 2A, the amount of aromatic compounds may be less than about 1 ppm. For any of the compositions in Table 2A, the amount of sulfur and the amount of aromatic compounds may each be less than 1 ppm. For any of the compositions in Table 2A, the terpene is microbially derived from renewable carbon sources, and has a renewable carbon content of about 100%.

TABLE 2A

| | area % of hexahydrofarnesene | | | | | | | | | |
|---|---|---|---|---|---|---|---|---|---|---|
| area % of farnesane | 50-55 | 55-60 | 60-65 | 65-70 | 70-75 | 75-80 | 80-85 | 85-90 | 90-95 | >95 |
| <4 | X | X | X | X | X | X | X | X | X | X |
| 4-6 | X | X | X | X | X | X | X | X | X | X |
| 6-8 | X | X | X | X | X | X | X | X | X | |
| 8-10 | X | X | X | X | X | X | X | X | X | |
| 10-12 | X | X | X | X | X | X | X | X | X | |
| 12-14 | X | X | X | X | X | X | X | X | | |
| 14-16 | X | X | X | X | X | X | X | | | |
| 16-18 | X | X | X | X | X | X | X | | | |
| 18-20 | X | X | X | X | X | X | X | | | |
| 20-22 | X | X | X | X | X | X | | | | |
| 22-24 | X | X | X | X | X | X | | | | |

Also provided herein are each of the compositions specifically disclosed in Table 2A individually, and about 25% or less tetrahydrofarnesene, e.g. about 25, 24, 23, 22, 21, 20, 19, 18, 17, 16, 15, 14, 13, 12, 11, 10, 9, 8, 7, 6, 5, 4, 3, 2, or %, or no detectable amount of tetrahydrofarnesene, individually. Provided herein are each of the compositions specifically disclosed in Table 2A individually, and about 10% or less tetrahydrofarnesene, e.g. about 10, 9, 8, 7, 6, 5, 4, 3, 2, or %, or no detectable amount of tetrahydrofarnesene, individually. Provided herein are each of the compositions specifically disclosed in Table 2A individually, and about 6% or less tetrahydrofarnesene, e.g. about 5, 4, 3, 2, or %, or no detectable amount of tetrahydrofarnesene, individually. For example, some feedstocks comprise about at least about 70-80% hexahydrofarnesene, about 5-10% farnesane, and about 10-20% tetrahydrofarnesene. Some feedstocks comprise at least about 70-80% hexahydrofarnesene, about 5-15% farnesane, and about 5% or less tetrahydrofarnesene.

In some variations, described herein are olefinic feedstocks comprising partially hydrogenated acyclic or cyclic $C_{10}$-$C_{30}$ conjugated hydrocarbon terpene (e.g., myrcene, ocimene, or farnesene), wherein the partially hydrogenated hydrocarbon terpene comprises less than about 10% of the corresponding alkane and less than about 10% of the starting hydrocarbon terpene. In some variations, the partially hydrogenated hydrocarbon terpene comprises about 5% or less (e.g., about 5%, 4%, 3%, 2% or 1%) of the corresponding alkane and about 5% or less of the starting hydrocarbon terpene. For example, in one variation, an olefinic feedstock comprises about 5% or less (e.g., about 5%, 4%, 3%, 2%, 1% or less) farnesene and about 5% or less (e.g., about 5%, 4%, 3%, 2%, 1%, or even less, e.g., an amount not detected by GC/MS) farnesane, with the remainder being comprised of tetrahydrofarnesene and hexahydrofarnesene in any relative amounts. For example, in some variations, partially hydrogenated farnesene comprises less than about 10% farnesene and less than about 10% farnesane, such that the combined total of hexahydrofarnesene and tetrahydrofarnesene comprises at least about 80% of the partially hydrogenated farnesene (e.g., about 80%, about 85%, about 90%, about 95%, 96%, 97%, 98% or 99% of the partially hydrogenated farnesene), wherein any relative amounts of hexahydrofarnesene and tetrahydrofarnesene may be present.

Some specific non-limiting examples of partially hydrogenated farnesene compositions wherein the combined total of hexahydrofarnesene and tetrahydrofarnesene comprises about 80% of the total composition are provided in Table 2B below, where each "X" specifically discloses a feedstock comprising hexahydrofarnesene in the area % indicated on the horizontal axis and tetrahydrofarnesene in the area % indicated on the vertical axis. For any of the compositions in Table 2B, the amount of sulfur may be less than about 1 ppm. For any of the compositions in Table 2B, the amount of aromatic compounds may be less than about 1 ppm. For any of the compositions in Table 2B, the amount of sulfur and the amount of aromatic compounds may each be less than 1 ppm. For any of the compositions in Table 2B, the terpene is microbially derived from renewable carbon sources, and has a renewable carbon content of about 100%.

TABLE 2B

| Area % of hexahydrofarnesene | Area % of hexahydrofarnesene | | | | | | | | | |
|---|---|---|---|---|---|---|---|---|---|---|
| | <10 | 10-20 | 20-30 | 30-40 | 40-50 | 50-60 | 60-70 | 70-80 | 80-90 | >90 |
| <0.5 | | | | | | | | | | |
| <1 | | | | | | | | X | X | X |
| 2-3 | | | | | | | | X | X | X |
| 4-5 | | | | | | | | X | X | X |
| 5-10 | | | | | | | | X | X | X |
| 10-20 | | | | | | X | X | X | X | X |
| 20-30 | | | | | X | X | X | X | X | |
| 30-40 | | | | X | X | X | X | X | | |
| 40-50 | | | X | X | X | X | X | | | |
| 50-60 | | X | X | X | X | X | | | | |
| 60-70 | | X | X | X | X | | | | | |
| 70-80 | X | X | X | X | | | | | | |
| 80-90 | X | X | X | | | | | | | |
| >90 | X | | | | | | | | | |

For each of the compositions disclosed in Table 2B, the amount of farnesene may be, individually, about 10%, 9%, 8%, 7%, 6%, 5%, 4%, 3%, 2%, 1%, 0.5%, 0.3%, or less than 0.3%, e.g., an amount not detectable by GC/MS. For each of the compositions disclosed in Table 2B, the amount of farnesane may be, individually, about 10%, 9%, 8%, 7%, 6%, 5%, 4%, 3%, 2%, 1%, 0.5%, 0.3%, or less than 0.3%, e.g., an amount not detectable by GC/MS. For example, in one variation, a partially hydrogenated farnesene feedstock that is about 60-65% hydrogenated comprises about 40-50% hexahydrofarnesene, about 40-50% tetrahydrofarnesene, less than about 10% dihydrofarnesene, less than about 1% (e.g., less than about 0.5% or no detectable amount by GC/MS) farnesane, and less than about 1% (e.g., less than about 0.5% or no detectable amount by GC/MS) farnesene.

In some variations, a partially hydrogenated farnesene composition comprises substantial amounts of hexahydrofarnesene and limited amounts of tetrahydrofarnesene. It some situations, diolefinic species may contribute to undesired branching, cross-reactions, and the like. In some variations, limited amounts of tetrahydrofarnesene present are substantially unconjugated, e.g., so that the composition comprises about 2% or less or about 1% or less conjugated diene. Some specific non-limiting examples of partially hydrogenated farnesene compositions comprising substantial amounts of hexahydrofarnesene and limited amounts of tetrahydrofarnesene are provided in Table 2C below, where each "X" specifically discloses a feedstock comprising hexahydrofarnesene in the area % indicated on the horizontal axis and tetrahydrofarnesene in the area % indicated on the vertical axis. For any of the compositions in Table 2C, the amount of sulfur may be less than about 1 ppm. For any of the compositions in Table 2C, the amount of aromatic compounds may be less than about 1 ppm. For any of the compositions in Table 2C, the amount of sulfur and the amount of aromatic compounds may each be less than 1 ppm. For any of the compositions in Table 2C, the terpene is microbially derived from renewable carbon sources, and has a renewable carbon content of about 100%.

TABLE 2C

| | Area % of hexahydrofarnesene | | | | | | | | | |
|---|---|---|---|---|---|---|---|---|---|---|
| area % of tetrahydrofarnesene | 50-55 | 55-60 | 60-65 | 65-70 | 70-75 | 75-80 | 80-85 | 85-90 | 90-95 | >95 |
| <0.3 | X | X | X | X | X | X | X | X | X | X |
| <0.5 | X | X | X | X | X | X | X | X | X | X |
| <1 | X | X | X | X | X | X | X | X | X | X |
| 1-2 | X | X | X | X | X | X | X | X | X | X |
| 2-3 | X | X | X | X | X | X | X | X | X | X |
| 3-4 | X | X | X | X | X | X | X | X | X | X |
| 4-5 | X | X | X | X | X | X | X | X | X | X |
| 5-6 | X | X | X | X | X | X | X | X | X | X |
| 6-7 | X | X | X | X | X | X | X | X | X | X |
| 7-8 | X | X | X | X | X | X | X | X | X | X |
| 8-9 | X | X | X | X | X | X | X | X | X | X |
| 9-10 | X | X | X | X | X | X | X | X | X | X |
| 10-11 | X | X | X | X | X | X | X | X | X | X |
| 11-12 | X | X | X | X | X | X | X | X | X | X |

For each of the compositions disclosed in Table 2C, the amount of farnesene may be, individually, about 10%, 9%, 8%, 7%, 6%, 5%, 4%, 3%, 2%, 1%, 0.5%, 0.3%, or less than 0.3%, e.g., an amount not detectable by GC/MS. For each of the compositions disclosed in Table 2C, the amount of farnesane may be, individually, about 10%, 9%, 8%, 7%, 6%, 5%, 4%, 3%, 2%, 1%, 0.5%, 0.3%, or less than 0.3%, e.g., an amount not detectable by GC/MS.

In some variations, a suitable hydrocarbon terpene feedstock comprises about 70-85% mono-olefin, about 12-17% farnesane, and about 5% or less di-olefin. In some variations, a suitable hydrocarbon terpene feedstock comprises about 70-85% mono-olefin, about 12-17% farnesane, and about 3% or less di-olefin. In some variations, a suitable hydrocarbon terpene feedstock comprises about 70-85% mono-olefin, about 12-17% farnesane, and about 2% or less di-olefin. In some variations, a suitable hydrocarbon terpene feedstock comprises about 70-85% mono-olefin, about 12-17% farnesane, and about 1% or less di-olefin. In some variations, a suitable hydrocarbon terpene feedstock comprises about 75-85% mono-olefin, about 15% or less farnesane, and about 5% or less di-olefin. In some variations, a suitable hydrocarbon terpene feedstock comprises about 75-85% mono-olefin, about 15% or less farnesane, and about 3% or less di-olefin. In some variations, a suitable hydrocarbon terpene feedstock comprises about 75-85% mono-olefin, about 15% or less farnesane, and about 2% or less di-olefin. In some variations, a suitable hydrocarbon terpene feedstock comprises about 75-85% mono-olefin, about 15% or less farnesane, and about 1% or less di-olefin.

It should be understood that analogous compositions to those shown in Table 2A, 2B, and 2C are contemplated in which the hydrocarbon terpenee is a hydrocarbon terpene other than farnesene, e.g., myrcene, springene, or geranylfarnesene.

In certain embodiments, one partially hydrogenated acyclic or cyclic $C_{10}$-$C_{30}$ hydrocarbon terpene as described herein is combined with one or more different partially hydrogenated acyclic or cyclic $C_{10}$-$C_{30}$ hydrocarbon terpenes as described herein to make a mixed olefinic feedstock. For example, a mixed olefinic feedstock may comprise partially hydrogenated myrcene mixed with partially hydrogenated farnesene. Any relative amounts of each of the partially hydrogenated terpenes are contemplated, and any relative degree of hydrogenation of each of the partially hydrogenated terpenes is contemplated. For example, mixed olefinic feedstocks are contemplated in which a ratio of a first partially hydrogenated hydrocarbon terpene to a second partially hydrogenated hydrocarbon terpene is about 0.1:1, 0.2:1, 0.3:1, 0.4:1, 0.5:1, 1:1, 2:1, 3:1, 4:1, 5:1, 6:1, 7:1, 8:1, 9:1 or 10:1.

In certain embodiments, a mixed olefinic feedstock comprises one or more partially hydrogenated acyclic or cyclic $C_{10}$-$C_{30}$ hydrocarbon terpenes and one or more olefins not derived from an acyclic or cyclic $C_{10}$-$C_{30}$ hydrocarbon terpene. For example, the olefin may be selected from the group consisting of a $C_5$-$C_{30}$ linear alphaolefin, a $C_5$-$C_{30}$ branched alphaolefin, a $C_5$-$C_{30}$ linear internal olefin, and a $C_5$-$C_{30}$ branched internal olefin. For example, mixed olefinic feedstocks are contemplated in which a ratio of a partially hydrogenated hydrocarbon terpene to another olefin (e.g., an alphaolefin) is about 0.1:1, 0.2:1, 0.3:1, 0.4:1, 0.5:1, 1:1, 2:1, 3:1, 4:1, 5:1, 6:1, 7:1, 8:1, 9:1 or 10:1.

In some variations, an additive is added to a hydrogenation catalyst to increase selectivity. For example, zirconium sulfate may be added to certain catalysts (e.g., palladium containing catalysts such as Pd/C) to increase selectivity. In some variations, a catalyst poison or additive is deliberately introduced to limit reactivity of a catalyst system and to increase selectivity. Any catalyst poison known in the art may be used in an effective amount. Non-limiting examples of additives that may be used to limit reactivity of certain catalysts include triethylamine, carbon monoxide, pyridine, acetone, and ethylene diamine. In some cases, an acidic heterogeneous additive (e.g., $Nb_2O_5$) is used to increase selectivity for mono-olefins by enhancing double bond isomerization, e.g., without skeletal isomerization.

In certain variations, a partially hydrogenated feedstock as described herein is stabilized by storing under an inert atmosphere (e.g., nitrogen) or by addition of an antioxidant such as 4-tert-butylcatechol (e.g., at 25-200 ppm).

Partially Hydrogenated Conjugated Terpenes

Also provided herein are specific species of partially hydrogenated conjugated hydrocarbon terpenes and methods for making the same. It should be noted that a specific species of partially hydrogenated conjugated terpenes may or may not be produced by a hydrogenation process. In certain variations, a partially hydrogenated hydrocarbon terpene species is prepared by a method that includes one or more steps in addition to or other than catalytic hydrogenation.

Nonlimiting examples of specific species partially hydrogenated conjugated hydrocarbon terpenes include any of the structures provided herein for dihydrofarnesene, tetrahydrofarnesene, and hexahydrofarnesene; any of the structures provided herein for dihydromyrcene and tetrahydromyrcene; and any of the structures provided herein for dihydroocimene and tetrahydroocimene.

One example of a particular species of partially hydrogenated conjugated hydrocarbon terpene that may have utility as a feedstock is a terminal olefin having a saturated hydrocarbon tail with structure (A11):

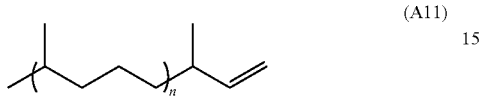

(A11)

where n=1, 2, 3, or 4.

In some variations, a mono-olefinic alphaolefin having structure A11 may be derived from a conjugated hydrocarbon terpene wherein the conjugated diene is at the 1,3-position of the terpene. Provided herein are alphaolefins derived from a 1,3-diene conjugated hydrocarbon terpene (e.g., a $C_{10}$-$C_{30}$ conjugated hydrocarbon terpene such as farnesene, myrcene, ocimene, springene, geranylfarnesene, neophytadiene, trans-phyta-1,3-diene, or cis-phyta-1,3-diene). In one nonlimiting example of an alphaolefin having the general structure A11, 3,7,11-trimethyldodec-1-ene having structure A12 and methods for making the same are provided herein.

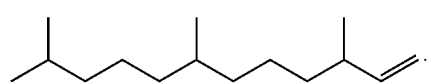

(A12)

A mono-olefinic alphaolefin having structure A11 may be prepared from the appropriate conjugated hydrocarbon terpene using any suitable method. In some variations, the mono-olefinic alphaolefin having structure A11 is produced from primary alcohol of corresponding to the hydrocarbon terpene (e.g., farnesol in the case of farnesene, or geraniol in the case of myrcene). The methods comprise hydrogenating the primary alcohol, forming a carboxylic acid ester or carbamate ester from the hydrogenated alcohol, and pyrolizing the ester (or heating the ester to drive the elimination reaction) to form the alphaolefin with a saturated hydrocarbon tail, e.g., as described in Smith, L. E.; Rouault, G. F. J. Am. Chem. Soc. 1943, 65, 745-750 for the preparation of 3,7-dimethyloct-1-ene, which is incorporated by reference herein in its entirety. The primary alcohol of the corresponding hydrocarbon terpene may be obtained using any suitable method. The Examples herein describe nonlimiting examples of methods for making an alphaolefin having structure A12, 3,7,11-trimethyldodec-1-ene, from farnesol.

It should be noted that other schemes for making alphaolefins having the general structure A11 from conjugated hydrocarbon terpenes are contemplated. For example, in some variations, the hydrocarbon terpene has a conjugated diene at the 1,3-position, and the conjugated diene can be functionalized with any suitable protecting group known to one of skill in the art in a first step (which may comprise one reaction or more than one reaction). The remaining olefinic bonds can be saturated in a second step (which may comprise one reaction or more than one reaction), and the protecting group can be eliminated to produce an alphaolefin having the general structure A11 in a third step (which may comprise one reaction or more than one reaction).

Any suitable protecting group and elimination scheme may be used. For example, a hydrocarbon terpene having a 1,3-conjugated diene (e.g., β-farnesene) may be reacted with an amine (e.g., a dialkyl amine such as dimethylamine or diethylamine) in the first step to produce an amine having the formula $N(R_1)(R_2)(R_3)$, where $R_1$ and $R_2$ are alkyl groups such as methyl or ethyl, and $R_3$ is an unsaturated hydrocarbon originating from the conjugated terpene. (In the case of β-farnesene, (In the case of β-farnesene, $R_3$ =

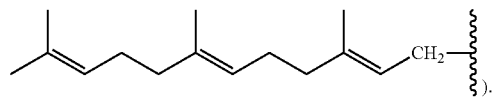

).

The resulting amine may be oxidized to the N oxide using hydrogen peroxide followed by elimination to the aldehyde using acetic anhydride. Hydrogenation of the aldehyde in the presence of a catalyst may be carried out to saturate any remaining olefinic bonds on the aliphatic tail originating from the hydrocarbon terpene, and the aldehyde functionality may be eliminated to produce an alphaolefin having structure A11. Scheme I below illustrates an example of such a preparation of an alphaolefin having structure A11 using β-farnesene as a model compound.

SCHEME I

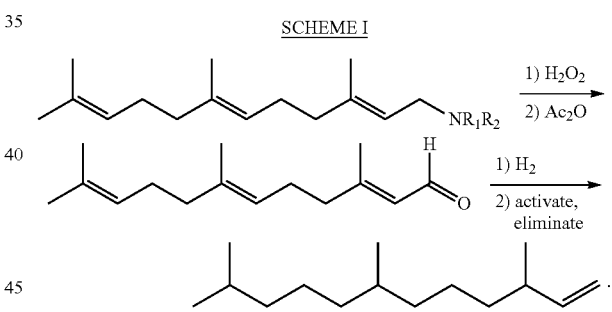

Another variation of a method to make an alphaolefin from a hydrocarbon terpene having a 1,3-conjugated diene follows Scheme II below. Here, the hydrocarbon terpene is reacted with a dialkyl amine (e.g., dimethylamine). The resulting amine has the general formula $N(R_1)_2(R_2)$, where $R_1$ and $R_2$ are alkyl groups such as methyl and $R_3$ is an unsaturated hydrocarbon originating from the hydrocarbon terpene (e.g., in the case of β-farnesene, (In the case of β-farnesene, $R_3$ =

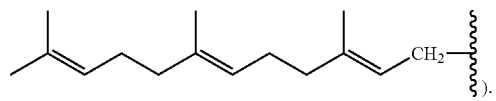

).

The amine $N(R_1)(R_2)(R_3)$ can be hydrogenated (e.g., using an appropriate catalyst), treated with peroxide, and heated to undergo elimination to form an alphaolefin having structure A11 (e.g., compound A12 if β-farnesene is used as the starting hydrocarbon terpene). Scheme II illustrates this method using β-farnesene as a model compound.

SCHEME II

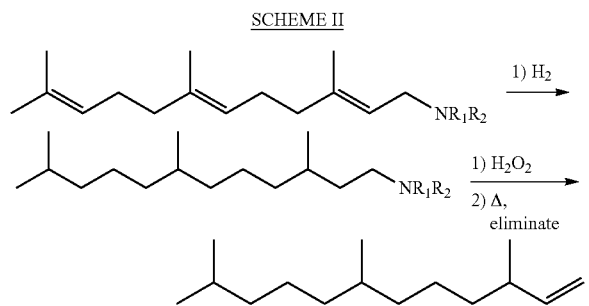

In another variation, a hydrogenated primary alcohol corresponding to a hydrocarbon terpene (e.g., hydrogenated farnesol or hydrogenated geraniol) can be dehydrated using basic aluminum oxide (e.g., at a temperature of about 250° C.) to make an alphaolefin having the general structure A11. Any suitable dehydration apparatus can be used, but in some variations, a hot tube reactor (e.g., at 250° C.) is used to carry out a dehydration of a primary alcohol. In one variation, hydrogenated farnesol can be dehydrated using basic aluminum oxide (e.g., in a hot tube reactor at 250° C.) to make compound A12, or an isomer thereof.

Other examples of particular species of partially hydrogenated conjugated hydrocarbon terpene that may have utility as a feedstock are mono-olefins having a saturated hydrocarbon tail with structure (A13) or structure (A15):

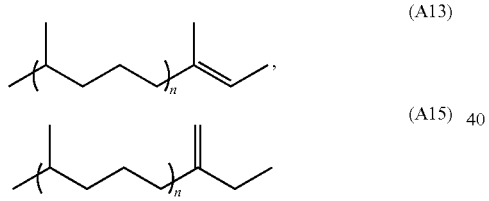

where n=1, 2, 3, or 4. A mono-olefin having the general structure A13, A15 or A11 may in certain instances be derived from a conjugated hydrocarbon terpene having a 1,3-diene moiety, such as myrcene, farnesene, springene, geranylfarnesene, neophytadiene, trans-phyta-1,3-diene, or cis-phyta-1,3-diene. Here again, the conjugated may be functionalized with a protecting group (e.g., via a Diels-Alder reaction) in a first step, exocyclic olefinic bonds hydrogenated in a second step, and the protecting group eliminated in a third step. In one non-limiting example of a method for making mono-olefins having the structure A13, A15 or A11, a conjugated hydrocarbon terpene having a 1,3-diene is reacted with SO₂ in the presence of a catalyst to form a Diels-Alder adduct. The Diels-Alder adduct may be hydrogenated with an appropriate hydrogenation catalyst to saturate exocyclic olefinic bonds. A retro Diels-Alder reaction may be carried out on hydrogenated adduct (e.g., by heating, and in some instances in the presence of an appropriate catalyst) to eliminate the sulfone to form a 1,3-diene. The 1,3-diene can then be selectively hydrogenated using a catalyst known in the art to result in a mono-olefin having structure A11, A13 or A15, or a mixture of two or more of the foregoing. Non-limiting examples of regioselective hydrogenation catalysts for 1,3-dienes are provided in Jong Tae Lee et al, "Regioselective hydrogenation of conjugated dienes catalyzed by hydridopentacyanocobaltate anion using β-cyclodextrin as the phase transfer agent and lanthanide halides as promoters," J. Org. Chem., 1990, 55 (6), pp. 1854-1856, in V. M. Frolov et al., "Highly active supported palladium catalysts for selective hydrogenation of conjugated dienes into olefins," Reaction Kinetics and Catalysis Letters, 1984, Volume 25, Numbers 3-4, pp. 319-322, in Tungler, A., Hegedüs, L., Fodor, K., Farkas, G., Fürcht, Á. and Karancsi, Z. P. (2003) "Reduction of Dienes and Polyenes," in *The Chemistry of Dienes and Polyenes*, Volume 2 (ed. Z. Rappoport), John Wiley & Sons, Ltd, Chichester, UK. doi: 10.1002/0470857226.ch12, and in Tungler, A., Hegedüs, L., Fodor, K., Farkas, G., Fürcht, Á. and Karancsi, Z. P., "Reduction of Dienes and Polyenes" in *Patai's Chemistry of Functional Groups* (John Wiley and Sons, Ltd, published online Dec. 15, 2009, DOI: 10.1002/9780470682531.pat0233), each of which is incorporated herein by reference in its entirety. For example, a catalyst known in the art for 1,4 hydrogen addition to 1,3-dienes results in a mono-olefin having structure A13. In one non-limiting example, β-farnesene can be reacted with SO₂ in the presence of a catalyst to form a Diels-Alder adduct, which is subsequently hydrogenated, and the sulfone eliminated to form a 1,3-diene, which is subsequently selectively hydrogenated using a catalyst known in the art for regioselective hydrogen additions to 1,3-dienes to form 3,7,11-trimethyldodec-2-ene, 3,7,11-trimethyldodec-1-ene, or 3-methylene-7,11-dimethyldodecane, or a mixture of any two or more of the foregoing.

In yet another example of a particular species of partially hydrogenated hydrocarbon terpene that may have utility as a feedstock, a terminal olefin of the general structure A14 may be made from a conjugated hydrocarbon terpene having a 1,3-conjugated diene and at least one additional olefinic bond (e.g., myrcene, farnesene, springene, or geranylfarnesene):

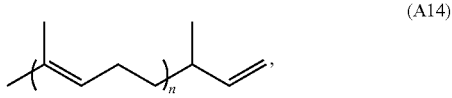

where n=1, 2, 3, or 4. In one nonlimiting variation, a compound having the structure A14 may be derived from an unsaturated primary alcohol corresponding to the relevant hydrocarbon terpene (e.g., farnesol in the case of farnesene, or geraniol in the case of myrcene). The unsaturated primary alcohol may be exposed to a suitable catalyst under suitable reaction conditions to dehydrate the primary alcohol to form the terminal olefin A14.

In one non-limiting example, a stoichiometric deoxygenation-reduction reaction may be conducted to form compounds having structure A14 from a primary alcohol (e.g., farnesol or geraniol) of a hydrocarbon terpene. One prophetic example of such a reaction can be conducted according to a procedure described in Dieguez et al., "Weakening C—O Bonds: Ti(III), A New Reagent for Alcohol Deoxygenation and Carbonyl Coupling Olefination," J. Am. Chem. Soc. 2010, vol. 132, pp. 254-259, which is incorporated by reference herein in its entirety: A mixture of titanocene dichloride (η⁵-C₅H₅)₂TiCl₂(Cp₂TiCl₂) (3.88 mmol) and Mn dust (2.77 mmol) in strictly deoxygenated tetrahyrofuran (THF) (7 mL) can be heated at reflux under stirring until the red solution turns green. Then, to this mixture can be added a solution of the primary alcohol (e.g., farnesol or geraniol) (1.85 mmol) in strictly deoxygenated THF (4 mL). After the starting materials disappear, the reaction can be quenched with 1N HCl and extracted with tert-butylmethyl ether (t-BuOMe). The organic phase can be washed with brine, filtered and concentrated in vacuo to yield a crude product, which can be purified, e.g., by column chromatography (hexane/t-BuOMe, 8:1) over silica gel column to afford a compound having structure A14 (e.g., 3,7,11-trimethyldodeca-1,6,10-triene if farnesol is used as the starting material).

Other reactions may be conducted to form compounds having structure A14 from a primary alcohol (e.g., farnesol or geraniol) of a hydrocarbon terpene. One prophetic example of such a reaction can be conducted according to another procedure described in Dieguez et al., "Weakening C—O Bonds: Ti(III), a New Reagent for Alcohol Deoxygenation and Carbonyl Coupling Olefination," J. Am. Chem. Soc. 2010, vol. 132, pp. 254-259, which is incorporated herein by reference in its entirety: A mixture of Cp2TiCl2 (0.639 mmol) and Mn dust (17.04 mmol) in thoroughly deoxygenated THF (8 mL) and under Ar atmosphere can be stirred until the red solution turned green. This mixture may then be heated at reflux and the corresponding trimethylsilylchloride (TMSCl) (8.52 mmol) may be added. The primary alcohol (e.g., farnesol) (1.92 mmol) in strictly deoxygenated THF (2 mL) may then be added. After the starting materials disappear, the reaction may be quenched with t-BuOMe, washed with 1 N HCl, brine, dried, and concentrated under reduced pressure. The resulting crude may be purified, e.g., by column chromatography (hexane/t-BuOMe, 8:1) on silica gel to afford compound having structure A14 (e.g., 3,7,11-trimethyldodeca-1,6,10-triene if farnesol is used as the starting material).

An olefinic feedstock as described herein may comprise any useful amount of the particular species (e.g., alphaolefinic species having structure A11, A12 or A15, mono-olefinic species having structure A13, or unsaturated terminal olefin species having structure A14), made either by a partial hydrogenation route or by another route, e.g., as described herein. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% species having structure A11, A12, A13, A14, or A15. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7,11-trimethyldodec-1-ene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3-methylene-7,11-dimethyldodecane. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7,11-trimethyldodec-2-ene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7,11-trimethyldodeca-1,6,10-triene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7-dimethyloct-1-ene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7-dimethyloct-2-ene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7-dimethylocta-1,6-diene.

As described herein, in some variations, the hydrocarbon terpene feedstock comprising alpha-olefinic species or internal olefinic species of partially hydrogenated hydrocarbon terpenes are suitable for catalytic reaction with one or more alpha-olefins to form a mixture of isoparaffins comprising adducts of the terpene and the one or more alpha-olefins. In some variations, at least a portion of the mixture of isoparaffins so produced may be used as a base oil.

B. Olefin Co-Monomer

In certain embodiments, the one or more olefin co-monomers are not terpenes. In certain embodiments, a non-terpene co-monomer is linear or only lightly branched, e.g., containing one or two branches. In the instances in which a hydrocarbon terpene and a linear or only lightly branched non-terpene olefin co-monomer are coupled together, the resulting adducts comprise one or more sections with regularly spaced methyl branching originating from the one or more terpenes and one or more sections with little or no branching originating from the one or more olefin co-monomers. A nonlimiting example of one 1:1 terpene: unbranched non-terpene olefin comonomer adduct is depicted as follows in Scheme B:

SCHEME B

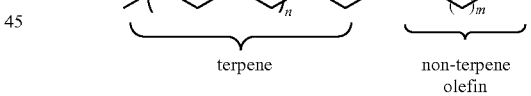

terpene      non-terpene olefin

The wavy bond in Scheme B is determined by the coupling mechanism between the terpene feedstock and the olefin co-monomer. The terpene segments contain regularly spaced methyl groups, and the length of the terpene segment is determined by n. For β-farnesene, n=2. In certain variations, the non-terpene olefin segment contains little or no branching. In Scheme B, an example in which the non-terpene olefin is a linear olefin is depicted. The length of the olefin co-monomer is determined by m. For a co-monomer that is 1-tetradecene, m is 13. It should be noted that the 1:1 adduct shown in Scheme B is only one example of the type of adducts that can be formed between hydrocarbon terpene feedstocks and non-terpene olefin co-monomers. For example, 1:2, 2:1, 3:1, 2:2, and 1:3 terpene:non-terpene olefin adducts are contemplated. The length of the terpene segment or segments and the length and linearity of the non-terpene olefin co-monomer or co-monomers can be adjusted to tune the properties of the resulting adducts. For example, a relatively longer terpene segment introduces an increased amount of methyl branching to the adducts, and a relatively longer olefin co-monomer that is linear or only lightly branched decreases the overall branching in the adducts. The degree of branching, molecular weight and adduct structure can each be varied by selecting the hydrocarbon terpene feedstock, the olefin co-monomer, and the coupling mechanism to tune overall properties of adducts to yield a desired product.

Non-terpene olefin co-monomers may comprise one or more olefins selected from the group consisting of linear or branched acyclic $C_2$-$C_{30}$ olefins (e.g., $C_2$-$C_{20}$, $C_4$-$C_{20}$, $C_4$-$C_{30}$, $C_6$-$C_{20}$, $C_6$-$C_{30}$, $C_8$-$C_{20}$, $C_8$-$C_{30}$, $C_{10}$-$C_{20}$, or $C_{10}$-$C_{30}$ olefins). In certain coupling reactions described herein, the olefin co-monomer comprises one or more alpha-olefins. Alpha-olefins used as olefin co-monomers as described herein may be selected from the group consisting of linear or branched acyclic $C_2$-$C_{30}$ alpha-olefins, ($C_2$-$C_{30}$ alpha-olefins (e.g., $C_2$-$C_{20}$, $C_4$-$C_{20}$, $C_4$-$C_{30}$, $C_6$-$C_{20}$, $C_6$-$C_{30}$, $C_8$-$C_{20}$, $C_8$-$C_{30}$, $C_{10}$-$C_{20}$, or $C_{10}$-$C_{30}$ alpha-olefins).

A non-terpene olefin co-monomer can be produced by any manner now known or later developed. For example, an alpha-olefin co-monomer may comprise linear or branched alpha-olefins that are produced by a Fischer Tropsch process, by dehydrogenating a paraffinic feedstock, such as a paraffinic feedstock derived by a Fischer Tropsch process, or by cracking wax, diesel, or other petroleum products. In other variations, an alpha-olefin co-monomer comprises linear or branched alpha-olefins produced by dehydration of alcohols or by decarboxylation of acids. In some variations, an alpha-olefin co-monomer comprises linear or branched alpha-olefins made by oligomerizing ethylene or propylene.

In some variations, a non-terpene olefin co-monomer (e.g., an alpha-olefin co-monomer) comprises linear or branched olefins (e.g., alpha-olefins) produced from renewable carbon sources. For example, a non-terpene alpha-olefin co-monomer may be produced by oligomerization of ethylene derived from dehydration of ethanol produced from a renewable carbon source. In some variations, an alpha-olefin co-monomer may be produced by dehydration of a primary alcohol other than ethanol that is produced from a renewable carbon source.

In some variations, an olefin co-monomer is or is derived from a terpene. In one non-limiting example, an alpha-olefin terpenoid co-monomer may be prepared from the appropriate conjugated hydrocarbon terpene using any suitable method. In some variations, the mono-olefinic alpha-olefin having structure A11:

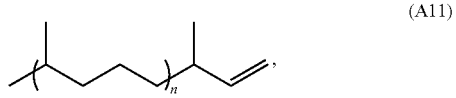

(A11)

may be produced from primary alcohol of corresponding to the hydrocarbon terpene (e.g., farnesol in the case of farnesene, or geraniol in the case of myrcene). The methods comprise hydrogenating the primary alcohol, forming a carboxylic acid ester or carbamate ester from the hydrogenated alcohol, and pyrolizing the ester (or heating the ester to drive the elimination reaction) to form the alphaolefin with a saturated hydrocarbon tail, e.g., as described in Smith, L. E.; Rouault, G. F. J. Am. Chem. Soc. 1943, 65, 745-750 for the preparation of 3,7-dimethyloct-1-ene, which is incorporated by reference herein in its entirety. The primary alcohol of the corresponding hydrocarbon terpene may be obtained using any suitable method. In some variations, the olefin co-monomer comprises a terpenoid alpha-olefin having structure A12

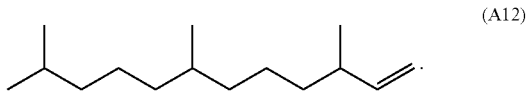

(A12)

In some variations, the olefin co-monomer comprises an unsaturated terminal terpenoid olefin having structure A14

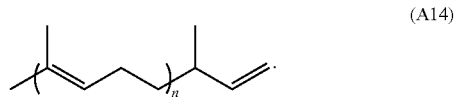

(A14)

An olefin co-monomer having structure A14 may be produced using any suitable method, including those described herein.

In some variations, a non-terpene olefin co-monomer comprises one or more linear $C_2$-$C_{20}$ alpha-olefins selected from the group consisting of ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene.

In some variations, the olefin co-monomer may comprise two or more alpha-olefins, e.g., two or more non-terpene linear alpha-olefins selected from the group consisting of ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene.

Some non-limiting examples of mixtures of two non-terpene alpha-olefins that may be used in an olefin co-monomer feed include: ethylene and propylene, 1-hexene and 1-octene; 1-hexene and 1-decene; 1-hexene and 1-dodecene; 1-hexene and 1-tetradecene; 1-hexene and 1-hexadecene, 1-hexene and 1-octadecene; 1-octene and 1-dodecene, 1-octene and 1-tetradecene; 1-octene and 1-hexadecene; 1-octene and 1-octadecene; 1-nonene and 1-decene; 1-nonene and 1-dodecene; 1-nonene and 1-tetradecene; 1-nonene and 1-hexadecene; 1-nonene and 1-octadecene; 1-decene and 1-dodecene; 1-decene and 1-tetradecene; 1-decene and 1-hexadecene; 1-decene and 1-octadecene; 1-dodecene and 1-tetradecene; 1-dodecene and 1-hexadecene; 1-dodecene and 1-octadecene; 1-tetradecene and 1-hexadecene; 1-tetradecene and 1-octadecene; and 1-hexadecene and 1-octadecene. If a mixture of two or more alpha-olefins is used, the relative amounts of each of the alpha-olefins may be any suitable amount. For example, for each of the above-identified pairs of alpha-olefins, the relative amounts of each of the alpha-olefins in the pair may be varied from 1:100 to 100:1. In some variations, an olefin co-monomer comprises a mixture of 1-hexadecene and 1-tetradecene, wherein the ratio of quantity 1-hexadecene to 1-tetradecene is about 1:20, 1:15, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 15:1, or 20:1. In some variations, an olefin comonomer comprises a mixture of 1-hexadecene and 1-tetradecene, wherein a ratio of quantity of 1-hexadecene to 1-tetradecene is about 10:90, 20:80, 30:70, 40:60, 50:50, 60:40, 70:30, 80:20, or 90:10. In some cases, an olefin co-monomer comprises a 60:40 1-hexadecane:1-tetradecene mixture. In some cases, an olefin co-monomer comprises a 50:50 1-hexadecene:1-tetradecene mixture. In some cases, an olefin co-monomer comprises a 40:60 1-hexadecene:1-tetradecene mixture. In some cases, an olefin co-monomer comprises a 10:90 1-hexadecene:1-tetradecene mixture. In some cases, an olefin co-monomer comprises a 20:80 1-hexadecene:1-tetradecene mixture. In some cases, an olefin co-monomer comprises a 30:70 1-hexadecene:1-tetradecene mixture.

Some non-limiting examples of mixtures of three non-terpene alpha-olefins that may be used in an olefin co-monomer feed include: 1-hexene, 1-octene and 1-decene; 1-hexene, 1-decene and 1-dodecene; 1-octene, 1-nonene, and 1-decene; 1-octene, 1-decene and 1-dodecene; 1-octene, 1-nonene and 1-dodecene; 1-hexene, 1-decene and 1-tetradecene; 1-octene, 1-nonene and 1-tetradecene; 1-octene, 1-decene and 1-tetradecene; 1-hexene, 1-decene and 1-hexadecene; 1-hexene, 1-nonene and 1-hexadecene; 1-octene, 1-decene and 1-hexadecene; 1-octene, 1-nonene and 1-hexadecene; 1-hexene, 1-dodecene and 1-hexadecene; 1-octene, 1-dodecene and 1-hexadecene; 1-decene, 1-dodecene, and 1-tetradecene; 1-nonene, 1-dodecene, and 1-tetradecene; 1-decene, 1-dodecene, and 1-hexadecene; 1-decene, 1-tetradecene, and 1-hexadecene; 1-nonene, 1-tetradecene and 1-hexadecene; and 1-dodecene, 1-tetradecene and 1-hexadecene. In those variations in which an olefin co-monomer comprises a mixture of three alpha-olefins, the three alpha-olefins may be present in any suitable relative proportions. For example, for any of the above-identified groups of 3 alpha-olefins, the amount of any one of the 3 alpha-olefins may be independently varied from about 1% to 99%. In some cases, each of the 3 alpha-olefins may be present in relative amounts of about 1:1:1.

Some non-limiting examples of mixtures of four non-terpene alpha-olefins that may be used in a an olefin co-monomer feed include: 1-octene, 1-decene, 1-dodecene and 1-tetradecene; 1-octene, 1-nonene, 1-dodecene and 1-tetradecene; 1-octene, 1-decene, 1-dodecene and 1-hexadecene; 1-octene, 1-nonene, 1-dodecene and 1-hexadecene; 1-octene, 1-decene, 1-dodecene and 1-octadecene; 1-octene, 1-nonene, 1-dodecene and 1-octadecene; 1-hexene, 1-decene, 1-dodecene and 1-tetradecene; 1-hexene, 1-nonene, 1-dodecene and 1-tetradecene; 1-hexene, 1-octene, 1-decene, and 1-dodecene; 1-hexene, 1-octene, 1-nonene, and 1-dodecene; 1-hexene, 1-octene, 1-decene and 1-tetradecene; and 1-hexene, 1-octene, 1-nonene and 1-tetradecene. In those variations in which an olefin co-monomer comprises a mixture of four alpha-olefins, the four alpha-olefins may be present in any suitable relative proportions. For example, for any of the above-identified groups of 4 alpha-olefins, the amount of any one of the 4 alpha-olefins may be independently varied from about 1% to 99%. In some cases, each of the 4 alpha-olefins may be present in relative amounts of about 1:1:1:1. In some variations, an olefin co-monomer comprises a mixture of 1-tetradecene, 1-hexadecene, 1-octadecene and 1-eicosene, wherein $C_{14}$ species are present at about 2%, $C_{16}$ species are present about 65%, $C_{18}$ species are present at about 55%, and $C_{20}$ species are present at about 10%.

In some variations, an olefin co-monomer feed may include more than four alpha-olefins, e.g., a mixture of 1-decene, 1-dodecene, 1-tetradecene, 1-hexadecene, and 1-eicosene. In those variations in which an olefin co-monomer comprises a mixture of more than four alpha-olefins, the alpha-olefins may be present in any suitable relative proportions. For example, for any of the above-identified group of 5 alpha-olefins, the amount of any one of the 5 alpha-olefins may be independently varied from about 1% to 99%. In some cases, each of the 5 alpha-olefins may be present in relative amounts of about 1:1:1:1:1.

In some variations, an olefin co-monomer feed comprises one or more branched $C_4$-$C_{20}$ or $C_6$-$C_{20}$ alpha-olefins that may or may not be derived from terpenes. In some variations, an alpha-olefin co-monomer is selected from the group consisting of $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ and $C_{20}$ branched alpha-olefins. Non-limiting examples of branched alpha-olefin co-monomers include 2-methylpropene, 2-methylbut-1-ene, 2-methylpent-1-ene, 2-methylhept-1-ene, 2-methylnon-1-ene, 2-methylundec-1-ene, 2-methyltridec-1-ene, 2-methylpentadec-1-ene, 2-methylheptadec-1-ene, 2-methylnonadec-1-ene. In some variations, a olefin co-monomer feed comprises two or more alpha-olefins selected from the group consisting of $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ and $C_{20}$ branched alpha-olefins. In some variations, an olefin co-monomer feed comprises three or more alpha-olefins selected from the group consisting of $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ and $C_{20}$ branched alpha-olefins. In certain variations, an olefin co-monomer feed comprises four or more $C_4$-$C_{20}$ or $C_6$-$C_{20}$ branched alpha-olefins.

In some variations, an olefin co-monomer comprises one or more non-terpene linear alpha-olefins and one or more branched alpha-olefins that may or may not be derived from terpenes. For example an olefin co-monomer may comprise a $C_2$-$C_{20}$ (e.g., $C_6$-$C_{20}$) linear alpha-olefin and a $C_4$-$C_{20}$ (e.g., $C_6$-$C_{20}$) branched alpha-olefin. In some variations, a co-monomer comprises three alpha-olefins, where two of the three are $C_2$-$C_{20}$ (e.g., $C_6$-$C_{20}$) linear alpha-olefins and one of the three is a $C_4$-$C_{20}$ (e.g., $C_6$-$C_{20}$) branched alpha-olefin, or where two of the three are $C_4$-$C_{20}$ (e.g., $C_6$-$C_{20}$) branched alpha-olefins and one of the three is a $C_2$-$C_{20}$ (e.g., $C_6$-$C_{20}$) linear alpha-olefin. In some variations, a co-monomer feed comprises four or more $C_2$-$C_{20}$ (e.g., $C_6$-$C_{20}$) alpha-olefins, where any combination of $C_2$-$C_{20}$ (e.g., $C_6$-$C_{20}$) linear alpha-olefins and $C_2$-$C_{20}$ (e.g., $C_6$-$C_{20}$) branched alpha-olefins is contemplated.

In some variations, an olefin co-monomer comprises one or more non-terpene linear $C_4$-$C_{20}$ (e.g., $C_6$-$C_{20}$) internal olefins. In some variations, an olefin co-monomer comprises one or more branched $C_4$-$C_{20}$ (e.g., $C_6$-$C_{20}$) internal olefins. In some cases, branched internal olefin co-monomers are derived from terpenes and in some cases, branched internal olefin co-monomers are not derived from terpenes. In some cases, an olefin co-monomer feed comprises a mixture of linear or branched $C_2$-$C_{20}$ (e.g., $C_6$-$C_{20}$) alpha-olefins and linear or branched $C_2$-$C_{20}$ (e.g., $C_6$-$C_{20}$) internal olefins, e.g. a mixture in which the wt. % of internal olefin is about 80 wt % or less, about 70 wt % or less, about 60 wt % or less, about 50 wt % or less, about 40 wt % or less, about 30 wt % or less, about 25 wt % or less, about 20 wt % or less, about 15 wt % or less, about 10 wt % or less, or about 5 wt % or less, based on the total weight of the mixture.

In some variations, an olefin co-monomer (e.g., an alpha-olefin co-monomer) may comprise non-terpene linear dienes, trienes or tetraenes. In some variations, an olefin co-monomer (e.g., an alpha-olefin co-monomer may comprise branched dienes, trienes, or tetraenes that may or may not be terpenoid. Nonlimiting examples of polyene co-monomers include a linear or branched $C_8$ diene, a linear or branched $C_8$ triene, a linear or branched $C_8$ tetraene, a linear or branched $C_9$ diene, a linear or branched $C_9$ triene, a linear or branched $C_9$ tetraene, a linear or branched $C_{10}$ diene, a linear or branched $C_{10}$ triene, a linear or branched $C_{10}$ tetraene, a linear or branched $C_{11}$ diene, a linear or branched $C_{11}$ triene, a linear or branched $C_{ii}$ tetraene, a linear or branched $C_{12}$ diene, a linear or branched $C_{12}$ triene, a linear or branched $C_{12}$ tetraene, a linear or branched $C_{13}$ diene, a linear or branched $C_{13}$ triene, a linear or branched $C_{13}$ tetraene, a linear or branched $C_{14}$ diene, a linear or branched $C_{14}$ triene, a linear or branched $C_{14}$ tetraene, a linear or branched $C_{15}$ diene, a linear or branched $C_{15}$ triene, a linear or branched $C_{15}$ tetraene, a linear or branched $C_{16}$ diene, a linear or branched $C_{16}$ triene, a linear or branched $C_{16}$ tetraene, a linear or branched $C_{17}$ diene, a linear or branched $C_{17}$ triene, a linear or branched $C_{17}$ tetraene, a linear or branched $C_{18}$ diene, a linear or branched $C_{18}$ triene, a linear or branched $C_{18}$ tetraene, a linear or branched $C_{19}$ diene, a linear or branched $C_{19}$ triene, a linear or branched $C_{19}$ tetraene, a linear or branched $C_{20}$ diene, a linear or branched $C_{20}$ triene, or a linear or branched $C_{20}$ tetraene. In some variations, an olefin co-monomer that is a polyene is terpenoild. For example, an olefin co-monomer may comprise a $C_{10}$-$C_{30}$ hydrocarbon terpene, e.g. myrcene, ocimene, farnesene, springene, or geranylfarnesene, or a partially hydrogenated $C_{10}$-$C_{30}$ hydrocarbon terpene as described herein or in U.S. Pat. App. Ser. No. 61/493,316 entitled "Olefins and methods for making the same" and filed Jun. 3, 2011, which is incorporated by reference in its entirety herein as if put forth fully below, such as partially hydrogenated myrcene, partially hydrogenated ocimene, partially hydrogenated farnesene, partially hydrogenated springene, or partially hydrogenated geranylfarnesene.

In some variations, an olefin co-monomer may comprise a mixture of two or more of the following: non-terpene $C_2$-$C_{30}$ (e.g. $C_6$-$C_{30}$) linear alpha-olefins, non-terpene $C_4$-$C_{30}$ (e.g., $C_6$-$C_{30}$) branched alpha-olefins, terpenoid $C_{10}$-$C_{30}$ branched alpha-olefins, non-terpene $C_4$-$C_{30}$ (e.g., $C_6$-$C_{30}$) linear internal olefins, terpenoid $C_{10}$-$C_{30}$ branched internal olefins, non-terpene $C_6$-$C_{30}$ linear dienes, terpenoid $C_{10}$-$C_{30}$ branched dienes, non-terpene $C_{10}$-$C_{30}$ linear trienes, terpenoid $C_{10}$-$C_{30}$ branched trienes, non-terpene $C_{12}$-$C_{30}$ linear tetraenes, and terpenoid $C_{15}$-$C_{30}$ branched tetraenes.

C. Catalysts

As described herein, any suitable catalyst that effectively catalyzes the formation of desired adducts between the hydrocarbon terpene feedstock and the olefin co-monomer (e.g., a non-terpene olefin co-monomer) may be used in the methods described herein. In some variations, the coupling reaction relies at least in part on a reaction mechanism involving a conjugated diene, so that the hydrocarbon terpene or the olefin co-monomer contains a conjugated diene. For example, in some cases the coupling reaction involves addition of an alpha-olefin (e.g., a non-terpene alpha-olefin) to a hydrocarbon terpene feedstock containing a conjugated diene. In other variations, the presence of a conjugated diene moiety produces undesired adducts or side reactions, so that a hydrocarbon terpene feedstock can be partially hydrogenated to remove or substantially reduce the population of molecules containing conjugated diene moieties. For example, partially hydrogenated hydrocarbon terpene feedstock containing very few or no conjugated diene moieties may be reacted with an olefin co-monomer (e.g., a non-terpene olefin co-monomer) in the presence of certain catalysts comprising a cationic initiator (e.g., a strong acid such as $H_2SO_4$ or $BF_3$ with one or more protic co-catalysts).

In some variations of the methods, a hydrovinylation reaction (e.g., a 1,4-hydrovinylation reaction of a hydrocarbon terpene comprises a 1,3-diene) is used to couple a hydrocarbon terpene feedstock with one or more alpha-olefins (e.g., a non-terpene alpha-olefin) to make one or more branched alkenes, which may be subsequently hydrogenated to form isoparaffins.

In some variations, a cationic initiator is used to couple a hydrocarbon terpene feedstock with one or more olefin co-monomers (e.g., one or more non-terpene olefin co-monomers) to make one or more branched alkenes, which may be subsequently hydrogenated to form isoparaffins. In some variations, the olefin co-monomer coupled with the terpene feedstock comprises one or more alpha-olefins (e.g., one or more non-terpene alpha-olefins).

In certain variations, a metal catalyst that is selected from the group consisting of early transition metal catalysts, late transition metal catalysts, and lanthanide metal catalysts is used to catalytically couple a hydrocarbon terpene feedstock with an olefin co-monomer (e.g., one or more non-terpene olefins) to make one or more branched alkenes, which may be subsequently hydrogenated to form isoparaffins. In certain variations, a homogeneous or heterogeneous Ziegler-Natta catalyst is used to couple a hydrocarbon terpene feedstock with one or more alpha-olefins (e.g., non-terpene alpha-olefins) to make one or more branched alkenes, which may be subsequently hydrogenated to form isoparaffins. In certain variations, a metallocene catalyst is used to couple a hydrocarbon terpene feedstock with one or more alpha-olefins (e.g., a non-terpene alpha-olefin) to make one or more branched alkenes.

1. Catalysts for Coupling Reactions Involving Reaction of Conjugated Diene in Hydrocarbon Terpene Feedstock with Alpha-Olefin Co-Monomer In certain variations, the methods comprise catalytically coupling a hydrocarbon terpene feedstock comprising a conjugated diene moiety to one or more alpha-olefins (e.g., non-terpene alpha-olefins) to produce one or more acyclic branched alkenes, which may be hydrogenated to obtain isoparaffins.

Any reaction mechanism or scheme may be employed to accomplish formation of a new carbon-carbon bond between a conjugated diene moiety on the hydrocarbon terpene and the terminal vinyl moiety on an alpha-olefin to produce one or more branched alkenes. In some variations, the coupling reaction conditions are sufficiently mild that no or minor isomerization occurs. In certain variations, the reaction conditions result in some isomerization along with coupling.

In some variations, the coupling reaction comprises a hydrovinylation reaction to couple a hydrocarbon terpene comprising a conjugated diene moiety with an alpha-olefin (e.g., non-terpene alpha-olefin). In certain variations, the coupling reaction comprises a hydrovinylation reaction in which the predominant products do not exhibit substantial isomerization. "Hydrovinylation reaction" as used herein refers to any reaction in which hydrogen and a vinyl group (or alkenyl group) are added across a carbon-carbon double bond to form a new carbon-carbon bond. In some variations, the coupling reaction comprises a 1,4-addition of the alpha-olefin to the conjugated diene moiety on the hydrocarbon terpene.

A hydrovinylation reaction employing a hydrocarbon terpene comprising a conjugated diene and having the general formula

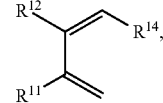

wherein $R^{11}$, $R^{12}$ and $R^{14}$ are each independently H or a $C_1$-$C_{30}$ saturated or unsaturated, branched aliphatic group, with the proviso that $R^{11}$, $R^{12}$ and $R_{14}$ are not each H in the same compound, and a linear or branched alpha-olefin having the general formula

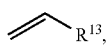

wherein $R^{13}$ is a $C_1$-$C_{30}$ linear or branched alkyl group, or a $C_1$-$C_{30}$ linear or branched alkenyl group, is illustrated in Scheme III below.

SCHEME III

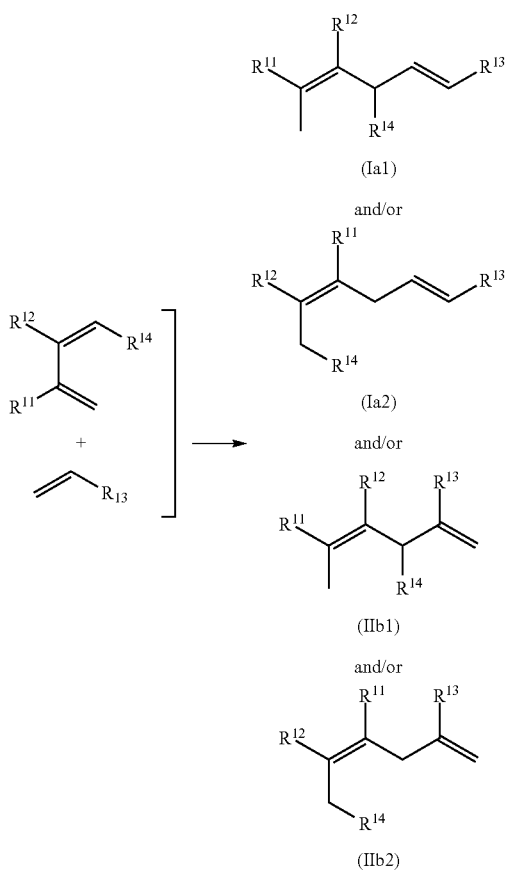

For a hydrovinylation reaction as shown in Scheme III, non-limiting examples of the hydrocarbon terpene feedstock include myrcene, ocimene, α-farnesene, β-farnesene, β-springene, geranylfarnesene, neophytadiene, trans-phyta-1,3-diene and cis-phyta-1,3-diene refers, isodehydrosqualene, isosqualane precursor I, and isosqualane precursor II. Non-limiting examples of the alpha-olefin co-monomer include propylene, 1-butene, 1-pentene, 1-hexene, 1-octene, 1-decene, 1-dodecene, 1-tetradecene, 1-hexadecene, 1-octadecene, 1-eicosene, 2-methylhex-1-ene, 2-methyloct-1-ene, 2-methyldec-1-ene, 2-methyldodec-1-ene, 2-methyltetradec-1-ene, 2-methylhexadec-1-ene, 2-methyloctadec-1-ene, 2-methyleicos-1-ene, a compound having structure A11, and a compound having structure A14.

For the hydrovinylation reaction illustrated in Scheme III, catalysis conditions can be selected to produce a linear adduct in which the new carbon-carbon bond is formed at the 1-position on the alpha-olefin (structure Ia1 or structure Ia2) and/or a branched adduct (structure Ib1 or structure Ib2) in which the new carbon-carbon double bond is formed at the 2-position on the alpha-olefin. For example, any one of or any combination of the catalyst, co-catalyst (if any), ligand (if any), counterion (if any), catalyst loading, temperature, pressure, solvent, concentration, and reaction time can be selected so that coupling between the hydrocarbon terpene and the alpha-olefin occurs preferentially at the 1-position of the alpha-olefin. In other variations, any one of or any combination of the catalyst, co-catalyst (if any), ligand (if any), counterion (if any), catalyst loading, temperature, pressure, solvent, concentration, and reaction time can be selected so that coupling between the hydrocarbon terpene and the alpha-olefin occurs preferentially at the 2-position of the alpha-olefin. In certain variations, any one of or any combination of the catalyst, co-catalyst (if any), ligand (if any), counterion (if any), catalyst loading, temperature, pressure, solvent, concentration, and reaction time are selected so that coupling between the hydrocarbon terpene and the alpha-olefin occurs to produce a desired mixture of alkenes having structure Ia1 or Ia2 and alkenes having structure Ib1 or Ib2. In some variations, catalyst conditions are selected to predominantly produce a desired regioisomer, e.g., structure Ia1 over Ia2 or vice versa, or structure Ib1 over Ib2 or vice versa. In some variations, catalysis conditions are selected to produce a desired mixture of regioisomers, e.g., a mixture of alkenes having structure Ia1 and alkenes having structure Ia2 and/or a mixture of alkenes having structure Ib1 and alkenes having structure Ib2.

In some variations, the regioselectivity is determined by steric effects of the hydrocarbon terpene and the alpha-olefin. For example, if $R^{11}$=H and $R^{12}$ is a $C_5$-$C_{30}$ aliphatic tail, regioisomer Ib1 may be favored over regioisomer Ib2 due to steric effects, where the addition tends to occur on the mono-substituted carbon due to steric hindrance. In some variations, the regioselectivity is determined by steric and/or electronic effects of ligands in the catalyst complex. For example, regioselectivity may be decreased if phenyl substituents on a ligand are replaced by methyl groups. If electron poor substituents are used, regioselectivity may be increased in some cases.

Any suitable catalyst can be used to create desired adducts between a hydrocarbon terpene feedstock comprising a conjugated diene and an alpha-olefin. For example, in some variations, a catalyst known in the art to dimerize or oligomerize alpha-olefins may be used. In some variations, a catalyst known in the art to catalyze hydrovinylation between a conjugated diene and an alpha-olefin is used. In some variations, a catalyst selected from the group consisting of rhodium compounds, ruthenium compounds, iridium compounds, iron compounds, cobalt compounds, copper compounds, nickel compounds, chromium compounds, palladium compounds, and platinum compounds.

In certain variations, a cobalt catalyst is used to carry out a hydrovinylation reaction between a conjugated hydrocarbon terpene and an olefin co-monomer (e.g., a non-terpene olefin co-monomer such as a non-terpene alpha-olefin). In some variations, a cobalt(I) catalyst is used. Any suitable method of making a cobalt(I) catalyst may be used. Some non-limiting examples of suitable Co(I) catalysts are provided in Hilt et al., Synthesis, 2002, No. 5, pp. 609-618, which is incorporated by reference herein in its entirety. Suitable catalysts can be formed by combining a cobalt(II) salt (e.g., $CoCl_2$ or $CoBr_2$) and a Lewis acid (e.g., a zinc(II)

salt such as $ZnI_2$ or $ZnBr_2$) together with a suitable chelating ligand (e.g., dppe, $PPh_3$ (2 eq), pmpe, dmpe, $P(OMe)_3$ or dpype) and a reducing agent (e.g., tetrabutylammonium borohydride or zinc), where dppe=1,2-Bis(diphenylphosphino)ethane, pmpe=1,2-bis-(methylphenylphosphino)ethane, dpype=1,2-bis-(dipyrrolylphosphino)ethane, dmpe=1,2-bis-(dimethylphosphino)ethane, $P(OMe)_3$=trimethylphosphite, PPh3=triphenylphosphine. In certain instances, a cobalt(I) catalyst as described herein preferentially forms branched adducts of the form Ib1 and/or Ib2. In one example, β-farnesene is reacted with a C5-C30 alpha-olefin in the presence of a cobalt(II) salt (e.g., Co(dppe)$Br_2$), a Lewis acid (e.g., a zinc(II) salt such as $ZnI_2$ or $ZnBr_2$), and a reducing agent (e.g., tetrabutylammonium borohydride or zinc) to form a mixture of compounds having structure Ib1 and structure Ib2, with structure Ib1 present as the major product. Any suitable solvent may be used for the hydrovinylation reaction using a Co(I) catalyst. For example, for a hydrovinylation reaction between β-farnesene and a C5-C30 alpha-olefin in the presence of a cobalt(II) salt (e.g., Co(dppe)$Br_2$), a Lewis acid (e.g., a zinc(II) salt such as $ZnI_2$ or $ZnBr_2$), and a reducing agent (e.g., tetrabutylammonium borohydride or zinc), no solvent may be used, or a solvent may be selected from the group consisting of methylene chloride, ethyl acetate, toluene, 2-methyltetrahydrofuran, 2-butanone, and 3-methylbutanone. The olefinic mixture comprising compounds of structure Ib1 and structure Ib2 may be hydrogenated to form a mixture of isoparaffins. The isoparaffins so formed may be used as a base oil, or as a component in a base oil. Examples 1-5 herein illustrate examples of isoparaffins formed using a Co(I) catalyst from β-farnesene and 1-octadecene, 1-hexadecene, 1-tetradecene, 1-dodecene, and 1-decene, respectively.

In some variations, a catalyst comprises a complex of the form $L_nCoX_2$, where L is a ligand such as a mono-phosphine or a di-phosphine, X is a halogen such as chlorine or bromine, and n=1 or 2. In certain variations, the ligand is a α,ω-bis-diphenylphosphinoalkane having the general formula $Ph_2P(CH_2)_nPPh_2$, where n=1, 2, 3 or 4, in the presence of a trialkylaluminum compound such as trimethylaluminum ($Me_3Al$), where the Co:Al ratio is about 1:1, 1:2, 1:3, or 1:4. In some variations, the catalyst comprises $CoCl_2$ with a ligand selected from the group consisting of dppb, dppm, dppe, dppp, and 2 $PPh_3$, in the presence of a trialkylaluminum compound such as trimethylaluminum, where dppb=1,4-bis-diphenylphosphinobutane, dppm=1,4-bis-diphenylphosphinomethane, dppe=1,4-bis-diphenylphosphinoethane, and 2 $PPh_3$ is two equivalents of triphenylphosphine ligands. In certain variations, a catalyst comprises dppb-$CoCl_2$ in the presence of $Me_3Al$ (Co:Al=1:3), which may for example be carried out in toluene or in a mixture of toluene and methylene chloride. In some variations, cobalt catalysts having the form $L_nCoX_2$, with n=1 or 2 and X=Cl or Br as described herein or in Sharma et al., J. Am. Chem. Soc. 2010, 132, 3295-3297, which is incorporated herein by reference in its entirety, may selectively produce compounds having formula Ia1 or Ia2.

In certain variations, a rhodium or ruthenium catalyst is used to couple a hydrocarbon terpene comprising a conjugated diene with an alpha-olefin (e.g., a non-terpene alpha-olefin) in a hydrovinylation reaction to form branched alkenes, which may be hydrogenated to form isoparaffins. At least a portion of the isoparaffins so formed may be used as a base oil, or as a component of a base oil. Non-limiting examples of suitable catalysts include hydrated rhodium salts or hydrated ruthenium salts, e.g., $RuCl_3 \cdot xH_2O$ and/or $RuCl_4 \cdot xH_2O$. Another non-limiting example of a suitable ruthenium catalyst is $(PCy_3)_2(CO)RuClH$ used with $HBF_4 \cdot OEt_2$, as described in Yi et al., Organometallics, 2001, 20, 802. Non-limiting examples of suitable rhodium catalysts are provided in Alderson et al., J. Am. Chem. Soc. 1965, 87, 5638, which is incorporated by reference herein in its entirety. In some variations, a ruthenium catalyst is used in a hydrophilic solvent. Certain examples of ruthenium catalyst used in hydrophilic solvents for regioselective addition reactions of a substituted conjugated diene and a terminal olefin are described in U.S. Pat. No. 6,239,324, which is incorporated herein by reference in its entirety. In some variations $(Ph_3P)_3RuCl_2$ in the presence of hydrogen may be used to carry out a hydrovinylation reaction between a conjugated terpene and an alpha-olefin.

In certain variations, a nickel catalyst is used to catalyze coupling of a hydrocarbon terpene comprising a conjugated diene with an alpha-olefin (e.g., a non-terpene alpha-olefin). Non-limiting examples of suitable nickel catalysts include π-allyl nickel complexes. In certain variations, a nickel catalyst is derived from $[[(R_1)(R_2)(R_3)P]_2NiCl_2]$ and $(R_4)(R_5)AlX$ or $(R_4)AlX_2$, where P=phosphine, X=Cl, Br, or I, $R_1$, $R_2$, $R_3$ can be the same or different, and are independently H or acyclic or cyclic C1-C10 alkyl groups, phenyl groups, or napthyl groups, and $R_4$ and $R_5$ are the same or different and are independently H or C1-C6 alkyl groups. In one instance, $R_1=R_2=R_3$=n-butyl, and $R_4=R_5$=ethyl, so that a catalyst comprising $[Ni(PBu_3)_2Cl_2]$ activated by diethylaluminum chloride is used. In one variation, a heterogeneous catalyst comprising nickel oxide on a support is used.

In certain variations, an iron catalyst is used to catalyze coupling of a hydrocarbon terpene comprising a conjugated diene with an alpha-olefin (e.g., a non-terpene alpha-olefin). In one variation, the catalyst may comprise $Fe(acac)_3/Et_3Al$ mixtures. Iron complexes of diphosphine or iron complexes of diphosphine and an organoaluminum compound may be used in some variations. Suitable non-limiting examples of iron complexes of diphosphine and iron complexes of diphosphine and organoaluminum compounds are provided in U.S. Pat. No. 3,475,509, which is incorporated by reference herein in its entirety. In other variations, $FeCl_2$ complexes can be reduced in situ with activated magnesium metal in diethylether to catalyze carbon-carbon bond formations between a conjugated diene and an alpha-olefin. Suitable ligands for the $FeCl_2$ include iminopyridine ligands and bisiminopyridine ligands. Non-limiting examples of specific ligands that can be used with $FeCl_2$ to make an effective catalyst include

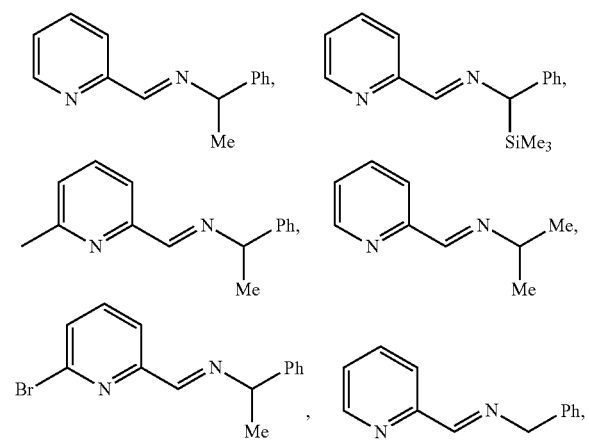

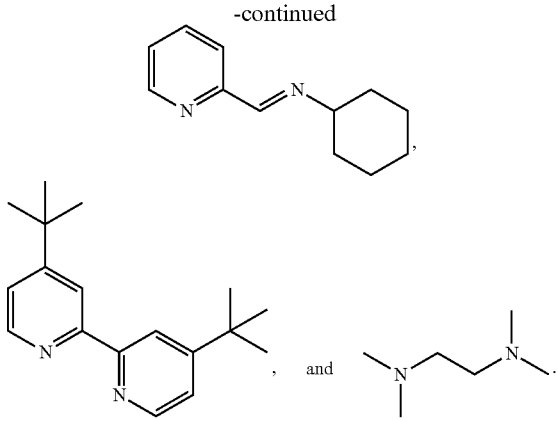

, and

Non-limiting examples of suitable iron containing catalysts are described in Moreau et al., Organic Letters, 2009, 11(2), 337-339, including Supporting Information S1 (available at www.pubs.acs.org), which is incorporated herein by reference in its entirety. In one variation, Fe—Co—Al type catalysts are used.

In certain variations, a palladium catalyst is used to catalyze coupling of a hydrocarbon terpene comprising a conjugated diene with an alpha-olefin (e.g., a non-terpene alpha-olefin). In one variation, a catalyst comprises a π-allyl palladium complex produced by a mixture of a palladium salt and an allylic compound. Some suitable palladium catalysts are described in U.S. Pat. No. 3,398,168, which is incorporated herein by reference in its entirety. The palladium salt precursors are palladium(II) salts, e.g., palladium nitrate, palladium carbonate, palladium acetate, palladium acetylacetonate, palladium chloride, or palladium bromide. The allylic compounds may be allyl chloride, allyl bromide, crotyl chloride, 1,4-dichlorobut-2-ene, allyl methyl ether, allyl acetate, allyl cyanide, 3,40dichlorobut-1-ene, 1-chloro-4-methoxybut-2-ene, mesityl oxide, cloroprene, 2-chloropent-3-ene, 3-chlorcylhexene, or 3-methoxycyclooctene. In some variations, Pd—Al type catalyst are used. In one variation, Pd—P type catalyst are used, e.g., bis(triphenylphosphine) (maleic anhydride palladium) $[(Ph)_3P]_z$ $Pd(C_4H_2O_3)$, or bis(triphenylphosphine) p-benzoquinone (palladium) $[(Ph)_3P]_2$ $Pd(C_6H_4O)$. In one variation, a suitable catalyst is prepared by reacting a palladium compound, a compound having an anion selected from tetra- and hexafluoro-complex anion and perchlorate anion, and a phosphorus compound selected from a tertiary phosphine and a tertiary phosphite.

Table 3 below provides non-limiting examples of possible routes to isoparaffins having a desired molecular weight range by making hydrogenated 1:1 hydrocarbon terpene: alpha-olefin adducts using 1,4 addition of an alpha-olefin to a conjugated diene moiety on the hydrocarbon terpene feedstock. Adducts having structures Ia1, Ia2, Ib1 and/or Ib2 as illustrated for Scheme III are hydrogenated to form the isoparaffins having desired molecular weights as shown in Table 3, where $R^{11}$, $R^{12}$, $R^{13}$, and $R^{14}$ have been provided for each entry. As described herein, the structure or structures (and hence degree of branching) of compounds in the isoparaffins having the desired molecular weight may in some instances be tuned by using regioselective catalysts as described herein. For example, a cobalt(I) catalyst as described herein may produce predominantly structures Ib1 and/or Ib2, so that the isoparaffins produced correspond to the hydrogenated structures Ib1 and/or Ib2. It should be noted that although Table 3 provides non-limiting examples of 1,4 addition products, in certain instances 1,2 addition products may be obtained instead of or in combination with 1,4 addition products.

TABLE 3

Non-limiting examples of hydrogenated 1:1 hydrocarbon terpene:alpha-olefin adducts

| Hydrocarbon terpene feedstock | Alpha-olefin co-monomer | $R^{11}$ | $R^{12}$ |
|---|---|---|---|
| Myrcene | 1-decene | H | (CH₃)₂C=CH–CH₂– |
| Myrcene | 1-hexadecene | H | (CH₃)₂C=CH–CH₂– |
| Myrcene | 1-eicosene | H | (CH₃)₂C=CH–CH₂– |
| β-ocimene | 1-decene | H | CH₃ |
| β-ocimene | 1-hexadecene | H | CH₃ |
| β-ocimene | 1-eicosene | H | CH₃ |

TABLE 3-continued

Non-limiting examples of hydrogenated 1:1 hydrocarbon terpene:alpha-olefin adducts

| Hydrocarbon terpene feedstock | Alpha-olefin co-monomer | R¹⁴ | (structure) | R¹³ | Possible products |
|---|---|---|---|---|---|
| β-farnesene | 1-decene | H | [farnesene-derived structure with CH₂] | | |
| β-farnesene | 1-dodecene | H | [farnesene-derived structure with CH₂] | | |
| β-farnesene | 1-tetradecene | H | [farnesene-derived structure with CH₂] | | |
| β-farnesene | 1-hexadecene | H | [farnesene-derived structure with CH₂] | | |
| β-farnesene | 1-octadecene | H | [farnesene-derived structure with CH₂] | | |
| β-farnesene | Compound A12 | H | [farnesene-derived structure with CH₂] | | |
| α-farnesene | 1-decene | H | | CH₃ | |
| α-farnesene | 1-dodecene | H | | CH₃ | |
| α-farnesene | 1-tetradecene | H | | CH₃ | |
| α-farnesene | 1-hexadecene | H | | CH₃ | |
| α-farnesene | 1-octadecene | H | | CH₃ | |
| β-springene | 1-hexene | H | | [springene-derived structure with CH₂] | |
| β-springene | 1-decene | H | | [springene-derived structure with CH₂] | |
| Isodehydro-squalene | 1-hexene | | [structure with CH₂] | H | |
| Isosqualane precursor I | 1-hexene | | [structure with CH₂] | H | |
| Myrcene | 1-decene | H | | n-octyl | C20 isoparaffins |
| Myrcene | 1-hexadecene | H | | n-dodecyl | C26 isoparaffins |
| Myrcene | 1-eicosene | | | n-octadecyl | C30 isoparaffins |

TABLE 3-continued

Non-limiting examples of hydrogenated 1:1 hydrocarbon terpene:alpha-olefin adducts

| Terpene | Olefin | | Structure | R group | Product |
|---|---|---|---|---|---|
| β-ocimene | 1-decene | | 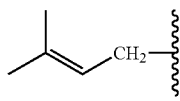 [SMILES: *CC=C(C)C] | n-octyl | C20 isoparaffins |
| β-ocimene | 1-hexadecene | | 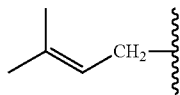 [SMILES: *CC=C(C)C] | n-dodecyl | C26 isoparaffins |
| β-ocimene | 1-eicosene | | 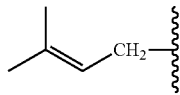 [SMILES: *CC=C(C)C] | n-octadecyl | C30 isoparaffins |
| β-farnesene | 1-decene | H | | n-octyl | C25 isoparaffins |
| β-farnesene | 1-dodecene | H | | n-decyl | C27 isoparaffins |
| β-farnesene | 1-tetradecene | H | | n-dodecyl | C29 isoparaffins |
| β-farnesene | 1-hexadecene | H | | n-tetradecyl | C31 isoparaffins |
| β-farnesene | 1-octadecene | H | | n-hexadecyl | C33 isoparaffins |
| β-farnesene | Compound A12 | H | 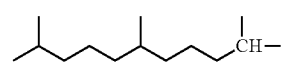 | | C30 isoparaffins |
| α-farnesene | 1-decene | | 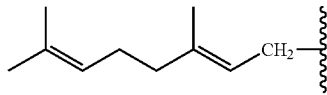 [SMILES: *C/C=C(\C)CCC=C(C)C] | n-octyl | C25 isoparaffins |
| α-farnesene | 1-dodecene | | 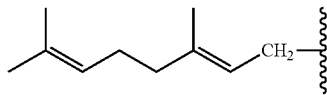 [SMILES: *C/C=C(\C)CCC=C(C)C] | n-decyl | C27 isoparaffins |
| α-farnesene | 1-tetradecene | | 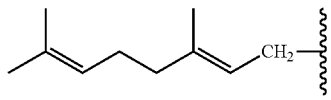 [SMILES: *C/C=C(\C)CCC=C(C)C] | n-dodecyl | C29 isoparaffins |
| α-farnesene | 1-hexadecene | | 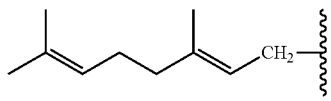 [SMILES: *C/C=C(\C)CCC=C(C)C] | n-tetradecyl | C31 isoparaffins |
| α-farnesene | 1-octadecene | | 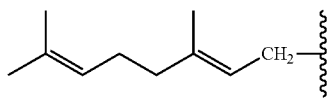 [SMILES: *C/C=C(\C)CCC=C(C)C] | n-hexadecyl | C33 isoparaffins |
| β-springene | 1-hexene | H | | n-butyl | C26 isoparaffins |
| β-springene | 1-decene | H | | n-octyl | C30 isoparaffins |
| Isodehydrosqualene | 1-hexene | | 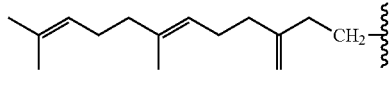 [SMILES: *CCC(=C)CC/C=C(\C)CCC=C(C)C] | n-butyl | C36 isoparaffins |
| Isosqualane precursor I | 1-hexene | | 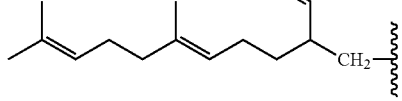 | n-butyl | C36 isoparaffins |

If β-farnesene is used as a model compound, and a cobalt(I) catalyst as described herein in used as a model catalyst so as to produce branched alkenes having structures Ib1 and Ib2, Table 4A shows the structures of the corresponding isoparaffins. If α-farnesene is used as a model compound and a cobalt(I) catalyst as described herein is used as a model catalyst so as to produce alkenes having structures Ib1 and Ib2, Table 4B shows predicted possible structures of the corresponding isoparaffins. If myrcene is used as a model compound and a cobalt(I) catalyst as described herein is used as a model catalyst so as to produce structures Ib1 and Ib2, Table 4C shows predicted possible structures of the corresponding isoparaffins. If isodehydrosqualene used as a model compound, and a cobalt(I) catalyst as described herein is used as a model catalyst so as to produce structures Ib1 and Ib2, Table 4D shows predicted structures of the corresponding isoparaffins. Any of the isoparaffins described herein formed as 1:1 hydrocarbon terpene:alpha-olefin adducts by hydrovinylation may be used as a base oil, or as a component of a base oil.

TABLE 4A

Structures of isoparaffins formed from hydrovinylation reactions of β-farnesene with alpha-olefins using a cobalt(I) catalyst.

| Alpha-olefin | Products | Structures |
|---|---|---|
| 1-octadecene | C33 iso-paraffins | 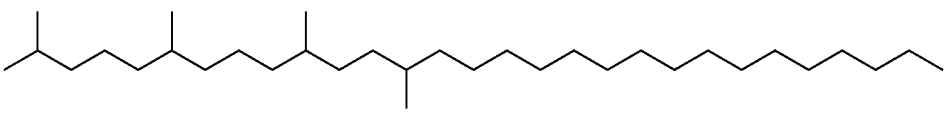 (major) <br> 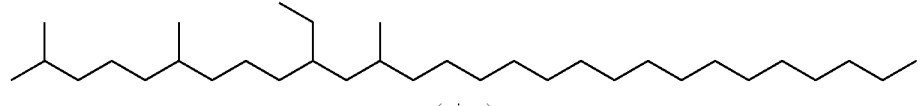 (minor) |
| 1-hexadecene | C31 iso-paraffins | 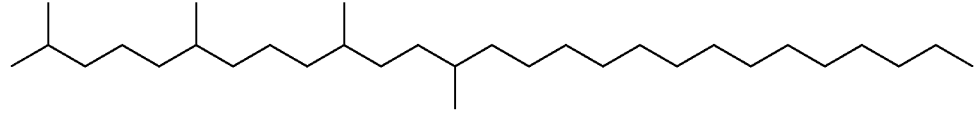 (major) <br> 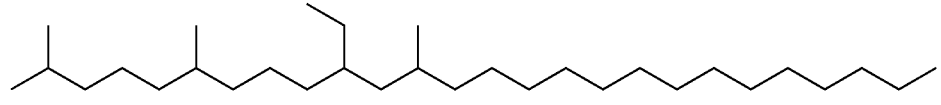 (minor) |
| 1-tetradecene | C29 iso-paraffins | 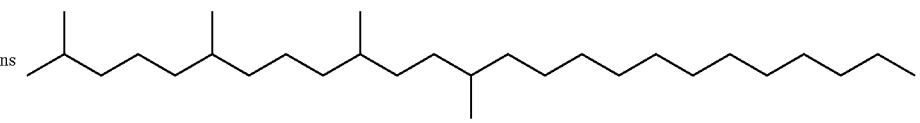 (major) <br> 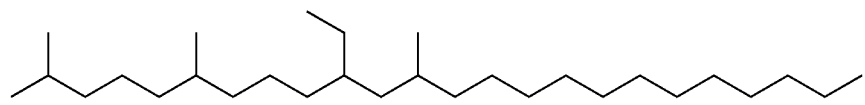 (minor) |
| 1-dodecene | C27 iso-paraffins | 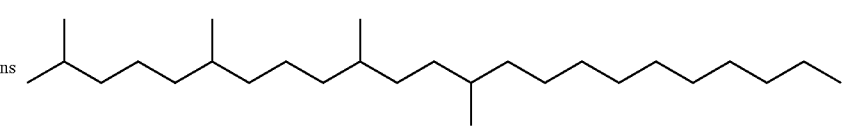 (major) <br> 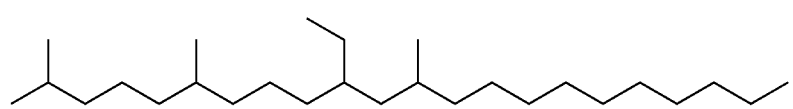 (minor) |

TABLE 4A-continued

Structures of isoparaffins formed from hydrovinylation reactions of β-farnesene with alpha-olefins using a cobalt(I) catalyst.

| Alpha-olefin | Products | Structures |
|---|---|---|
| 1-decene | C25 iso-paraffins | 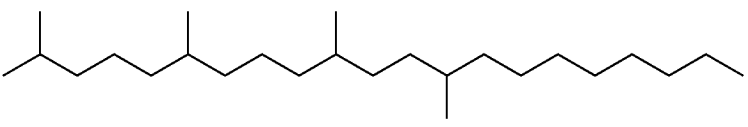<br>(major)<br>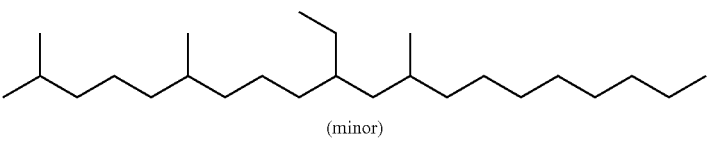<br>(minor) |

TABLE 4B

Predicted possible structures of isoparaffins formed from hydrovinylation reactions of α-farnesene with alpha-olefins using a cobalt(I) catalyst.

| Alpha-olefin | Products | Structures |
|---|---|---|
| 1-octadecene | C33 iso-paraffins | 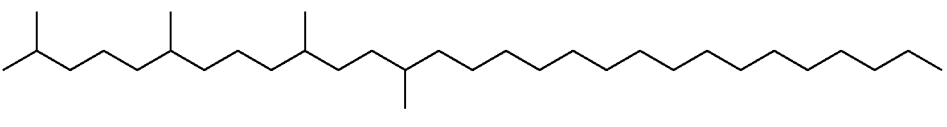<br>(major)<br>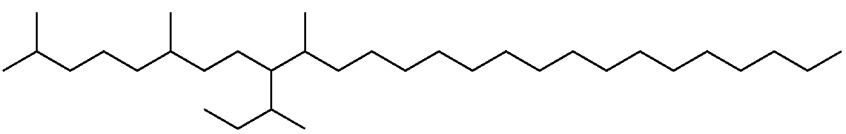<br>(minor) |
| 1-hexadecene | C31 iso-paraffins | 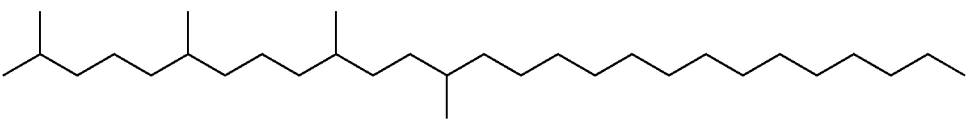<br>(major)<br>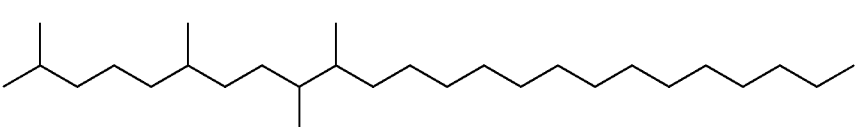<br>(minor) |

TABLE 4B-continued
Predicted possible structures of isoparaffins formed from hydrovinylation reactions of α-farnesene with alpha-olefins using a cobalt(I) catalyst.
| Alpha-olefin | Products | Structures |
|---|---|---|
| 1-tetradecene | C29 iso-paraffins | 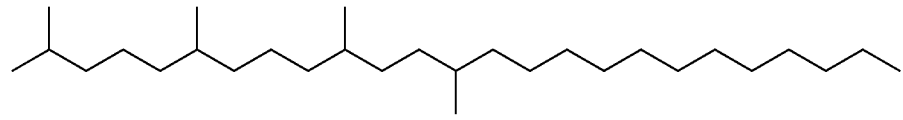 (major)<br>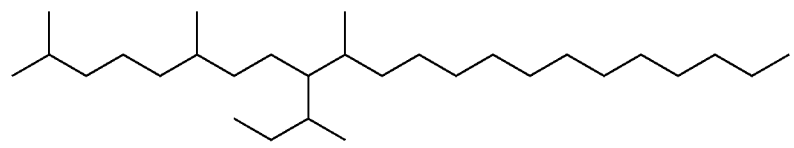 (minor) |
| 1-dodecene | C27 iso-paraffins | 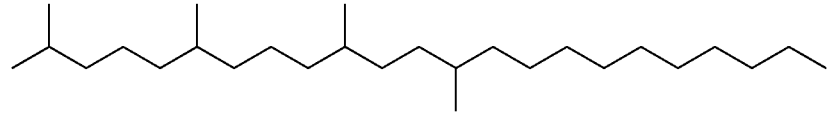 (major)<br>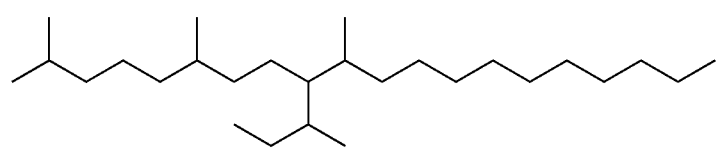 (minor) |
| 1-decene | C25 iso-paraffins | 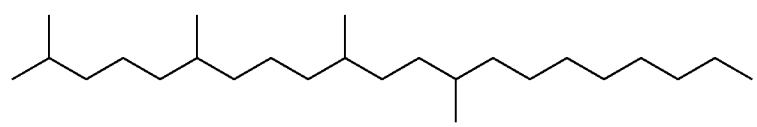 (major)<br>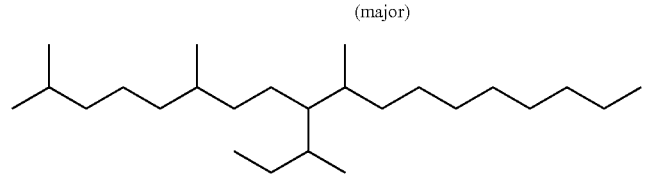 (minor) |

TABLE 4C

Possible structures of isoparaffins formed from hydrovinylation reactions of myrcene with alpha-olefins using a cobalt(I) catalyst.

| Alpha-olefin | Products | Structures |
| --- | --- | --- |
| 1-octadecene | C28 isoparaffins | (major) / (minor) |
| 1-hexadecene | C26 isoparaffins | (major) / (minor) |
| 1-tetradecene | C24 isoparaffins | (major) / (minor) |
| 1-dodecene | C22 isoparaffins | (major) / (minor) |

TABLE 4C-continued

Possible structures of isoparaffins formed from hydrovinylation reactions of myrcene with alpha-olefins using a cobalt(I) catalyst.

| Alpha-olefin | Products | Structures |
|---|---|---|
| 1-decene | C20 isoparaffins | 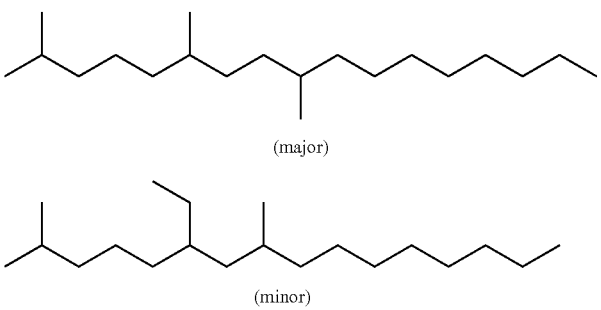 (major) / (minor) |

TABLE 4D

Predicted possible structures of isoparaffins formed from hydrovinylation reactions of isodehydrosqualene with alpha-olefins using a cobalt(I) catalyst.

| Alpha-olefin | Products | Structures |
|---|---|---|
| 1-hexene | C36 isoparaffins | 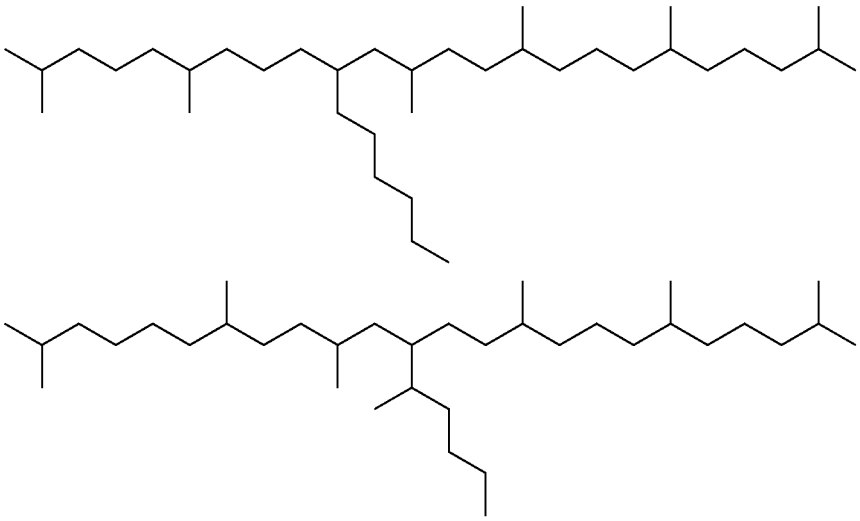 |

It is noted that the alpha-olefin co-monomer to be coupled to the hydrocarbon terpene via a hydrovinylation reaction may comprise a single alpha-olefin, or a blend of two or more alpha-olefins to form branched alkenes, which may be subsequently hydrogenated to form isoparaffins, at least a portion of which has utility as a base oil, or as a component of a base oil. A blend of two or more alpha-olefins may for example be a blend of two or more of the group consisting of 1-hexene, 1-octene, 1-nonene, 1-decene, 1-dodecene, 1-tetradecene, 1-hexadecene, 1-octadecene, and 1-eicosene. If a mixture of alpha-olefins is used, any suitable combination of alpha-olefins may be used (e.g., combination of molecular weights, combination of linear and branched alpha-olefins, or a combination of molecular weights and a combination of linear and branched alpha-olefins), and any suitable relative amounts of multiple alpha-olefins may be used. In some variations, the mixture of two or more alpha-olefins comprises a mixture of a first linear alpha-olefin and a second linear alpha-olefin, wherein the ratio of the amount first linear alpha-olefin:amount second linear alpha-olefin may be about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or 1:10. Table 5A below provides non-limiting examples of blends of linear alpha-olefins that may be used to react with a hydrocarbon terpene via hydrovinylation, where each "X" represents the presence of the alpha-olefin indicated in the column heading as a component in a blend of alpha-olefins.

TABLE 5A

Non-limiting examples of blends of linear alpha-olefins that may be used to react with a hydrocarbon terpene via a hydrovinylation reaction.

| Entry | 1-octene | 1-decene | 1-dodecene | 1-tetradecene | 1-hexadecene | 1-octadecene |
|---|---|---|---|---|---|---|
| 1 | X | X | | | | |
| 2 | X | | | X | | |

TABLE 5A-continued

Non-limiting examples of blends of linear alpha-olefins that may be used to react with a hydrocarbon terpene via a hydrovinylation reaction.

| Entry | 1-octene | 1-decene | 1-dodecene | 1-tetradecene | 1-hexadecene | 1-octadecene |
|---|---|---|---|---|---|---|
| 3 | X | | | X | | |
| 4 | X | | | | X | |
| 5 | X | | | | | X |
| 6 | X | X | X | | | |
| 7 | X | X | | X | | |
| 8 | X | X | | | X | |
| 9 | X | X | | | | X |
| 10 | X | | X | X | | |
| 11 | X | | X | | X | |
| 12 | X | | X | | | X |
| 13 | X | | | X | X | |
| 14 | X | | | X | | X |
| 15 | X | | | | X | X |
| 16 | | X | X | | | |
| 17 | | X | | X | | |
| 18 | | X | | | X | |
| 19 | | X | | | | X |
| 20 | | X | X | X | | |
| 21 | | X | X | | X | |
| 22 | | X | X | | | X |
| 23 | | X | | X | X | |
| 24 | | X | | X | | X |
| 25 | | X | | | X | X |
| 26 | | | X | X | | |
| 27 | | | X | | X | |
| 28 | | | X | | | X |
| 29 | | | X | X | X | |
| 30 | | X | X | | | X |
| 31 | | X | | | X | X |
| 32 | | | | X | X | |
| 33 | | | | X | | X |
| 34 | | | | X | X | X |
| 35 | | X | | X | X | X |
| 36 | | X | X | X | X | |
| 37 | X | X | X | X | | |

It is noted that it is possible to make 2:1 hydrocarbon terpene:alpha-olefin adducts using hydrovinylation reactions as described herein. For example, if the alpha-olefin is an α,ω-diene, comprising two terminal olefinic bonds, then 1,4 hydrovinylation reactions can take place at opposite ends of the α,ω-diene, where each terminal carbon-carbon double bond on the α,ω-diene adds across a conjugated diene moiety of two separate hydrocarbon terpenes. Nonlimiting examples of α,ω-dienes include 1,5-hexadiene, 1,6-heptadiene, 1,7-octadiene, 1,8-nonadiene, and 1,9-decadiene. An example is illustrated in Scheme IV, where $R^{11}$, $R^{12}$ and $R^{14}$ are as described herein in connection with Scheme III, and $R^{15}$ is a $C_1$-$C_{30}$ linear or branched, saturated or unsaturated hydrocarbon chain. In certain variations, the alpha-olefin is 1,5-hexadiene, so that $R^{15}$=—$CH_2CH_2$—.

SCHEME IV

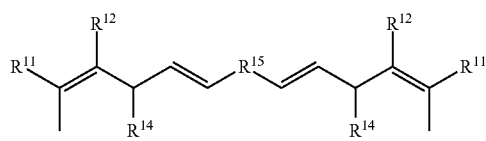

(IIa1)

and/or

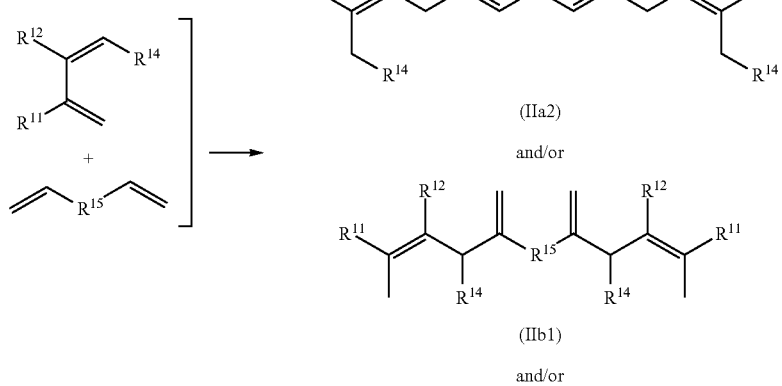

(IIa2)

and/or (IIb1)

and/or

-continued

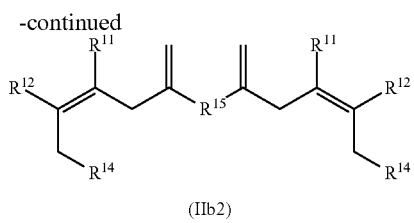

(IIb2)

Table 5B provides exemplary structures of hydrogenated 2:1 hydrocarbon terpene:α,ω-diene adducts, where β-farnesene has been used as a model hydrocarbon terpene, 1,5-hexadiene has been used as a model α,ω-diene, and a cobalt(I) catalyst has been used as a model catalyst so as to form structures (IIb1) and (IIb2).

For the methods using a cationic initiator to catalyze formation of hydrocarbon terpene:olefin adducts, any one of or any combination of the following may be varied, each of which is described in more detail herein: hydrocarbon terpene feedstock; olefin co-monomer; and cationic initiator. It should be understood that the methods for making

TABLE 5B

Non-limiting examples of 2:1 hydrocarbon terpene:α,ω-diene adducts formed by hydrovinylation reaction

| α,ω-diene | Potential product | Potential Structures |
|---|---|---|
| 1,5-hexadiene | C36 isoparaffins | |

2. Coupling Reactions Involving Cationic Initiator Catalyzed Addition of Olefin Co-Monomer to Hydrocarbon Terpene Feedstock In some variations, the methods comprise reacting a hydrocarbon terpene feedstock with one or more olefin co-monomers (e.g., non-terpene olefin co-monomers) in the presence of a cationic initiator to form one or more branched alkenes, which may be hydrogenated to form isoparaffins.

As used herein, a cationic initiator refers to any catalyst that generates a proton or a carbocation. The cationic initiator initiates or catalyzes coupling between the olefin co-monomer and the hydrocarbon terpene feedstock. Any cationic initiator known in the art to initiate oligomerization or alkylation of olefins (e.g., alpha-olefins) may be used. Non-limiting examples of cationic initiators that may be used in the methods described herein include protic acids, and Lewis acids used together with one or more optional co-catalysts capable of generating a carbocation. As used herein, "carbocation" refers to any species containing a positively charged carbon atom.

In one variation, provided herein are methods comprising reacting a hydrocarbon terpene feedstock that contains few or no conjugated olefinic bonds with olefin co-monomer (e.g., one or more alpha-olefins) in the presence of a cationic initiator to form branched alkenes, which may be hydrogenated to form isoparaffins.

In another variation, provided herein are methods comprising reacting a saturated hydrocarbon terpene feedstock with olefin co-monomer (e.g., one or more alpha-olefins) in the presence of a cationic initiator to form an alkylate. The alkylate may be hydrogenated to form a mixture of isoparaffins. Any known hydrogenation method may be used to produce the saturated hydrocarbon terpene.

branched alkenes or isoparaffins may employ any combination of i) any variation of the hydrocarbon terpene feedstock described herein or otherwise known, ii) any variation of the cationic initiator described herein or otherwise known; and iii) any variation of the olefin co-monomer described herein or otherwise known.

As described above, any suitable cationic initiator can be used in the methods to couple a hydrocarbon terpene feedstock with one or more olefin co-monomers (e.g., one or more alpha-olefin co-monomers) to form one or more branched alkenes, and saturating the branched alkenes to form isoparaffins, at least a portion of which may be used as a base oil or as a component of a base oil. In some variations, the cationic initiator comprises a protic acid. In other variations, the cationic initiator comprises a Lewis acid and a co-catalyst capable of generating a cation. For example, the cationic initiator may comprise a Lewis acid and a protic co-catalyst. In certain variations, the cationic initiator comprises an ionic liquid.

In certain variations when using a cationic initiator to catalyze a coupling reaction between a hydrocarbon terpene feedstock and one or more olefin co-monomers, it is desired that the hydrocarbon terpene feedstock contain few or no conjugated diene moieties. In those variations, a partially hydrogenated hydrocarbon terpene feedstock as described herein that contains about 10% or less, about 5% or less, about 3% or less, about 1% or less, or about 0.5% or less conjugated bonds of all carbon-carbon double bonds.

In some variations, a hydrocarbon terpene feedstock used with a cationic initiator comprises at least about 50%, at least about 55%, at least about 60%, at least about 65%, at least about 70%, at least about 75%, at least about 80%, at least about 85%, at least about 90%, or at least about 95% mono-olefin. In some variations, a hydrocarbon terpene feedstock used with a cationic initiator comprises less than about 25%, less than about 20%, less than about 15%, less than about 10%, or less than about 5% alkane. In some variations, a hydrocarbon terpene feedstock used with a cationic initiator comprises at least about 65% mono-olefin and less than about 25% alkane, at least about 70% mono-olefin and less than about 20% alkane, at least about 70% mono-olefin and less than about 10% alkane, at least about 75% mono-olefin and less than about 15% alkane, at least about 75% mono-olefin and less than about 10% alkane, at least about 80% mono-olefin and less than about 10% alkane, or at least about 80% mono-olefin and less than about 5% alkane. In some variations, a hydrocarbon terpene feedstock used with a cationic initiator has a composition disclosed in Table 2A, Table 2B, or Table 2C. In some variations, a hydrocarbon terpene feedstock used with a cationic initiator comprises about 40-60% mono-olefin and about 40-60% di-olefin, with less than about 5%, or less than about 1% conjugated diene, and less than about 5%, or less than about 1% alkane. In some variations, a hydrocarbon terpene feedstock used with a cationic initiator comprises about 50-90% mono-olefin and about 10% or less di-olefin (e.g., about 5% or less, about 3% or less, about 1% or less, or about 0.5% or less). In those particular instances where the hydrocarbon terpene is β-farnesene, the hydrocarbon terpene feedstock used with a cationic initiator may comprise about 65% hexahydrofarnesene and less than about 25% farnesene, at least about 70% hexahydrofarnesene and less than about 20% farnesane, at least about 70% hexahydrofarnesene and less than about 10% farnesane, at least about 75% hexahydrofarnesene and less than about 15% farnesane, at least about 75% hexahydrofarnesene and less than about 10% farnesane, at least about 80% hexahydrofarnesene and less than about 10% farnesane, at least about 80% hexahydrofarnesene and less than about 5% farnesane, at least about 50 hexahydrofarnesene and about 10% or less tetrahydrofarnesene, at least about 50% hexahydrofarnesene and about 5% or less tetrahydrofarnesene, at least about 50% hexahydrofarnesene and about 3% or less tetrahydrofarnesene, at least about 60% hexahydrofarnesene and about 10% or less tetrahydrofarnesene, at least about 60% hexahydrofarnesene and about 5% or less tetrahydrofarnesene, at least about 60% hexahydrofarnesene and about 3% or less tetrahydrofarnesene, at least about 70% hexahydrofarnesene and about 10% or less tetrahydrofarnesene, at least about 70% hexahydrofarnesene and about 5% or less tetrahydrofarnesene, or at least about 70% hexahydrofarnesene and about 3% or less tetrahydrofarnesene. In some variations in which the hydrocarbon terpene is β-farnesene, the hydrocarbon terpene feedstock used with a cationic initiator is about 40-60% hexahydrofarnesene, about 40-60% tetrahydrofarnesene, less than about 5% or less than about 1% farnesene, and less than about 5% or less than about 1% farnesane.

a. Liquid Protic Acids

In some variations, a protic acid is used as a cationic initiator to catalyze coupling between an alpha-olefin (e.g., a non-terpene alpha-olefin) and the hydrocarbon terpene feedstock to form branched alkenes, which may be hydrogenated to form isoparaffins. A protic acid generates protons or protonated species to catalyze formation of adducts between the hydrocarbon terpene feedstock and an olefin co-monomer, which in certain variations comprises one or more alpha-olefins. Non-limiting examples of suitable protic acids include $H_2SO_4$, $HOSOCF_3$, $H_3PO_4$, HF, HCl, and HBr. In some variations, $H_2SO_4$ or HF is used to catalyze formation of adducts between a hydrocarbon terpene feedstock and an olefin co-monomer (e.g., one or more alpha-olefins). In some variations, a protic acid comprises an alkylation catalyst known in the art to catalyze alkylation of olefins.

When using a protic acid to catalyze formation of adducts between a hydrocarbon terpene and an alpha-olefin, any one of or any combination of the following reaction parameters can be tuned to determine the composition of the final mixture of branched alkenes or the final isoparaffinic mixture: i) type of protic acid; ii) concentration of protic acid; iii) reaction temperature; iv) ratio of hydrocarbon terpene to olefin co-monomer; v) amount of alpha-olefin present in the olefin co-monomer; vi) degree of branching olefin co-monomer; vii) degree of saturation in the olefin co-monomer; viii) whether a single olefin or a mixture of olefins is used as a co-monomer; ix) degree of hydrogenation in the hydrocarbon terpene feedstock; x) reaction time; and xi) reaction quench conditions.

For the methods described herein, the protic acid catalyst may be any catalyst now known or later developed to catalyze alkylation of olefins. The protic acid catalyst may be used in any suitable concentration and may be present in any suitable amount to effectively catalyze the reaction.

If sulfuric acid is used as the catalyst, a sulfuric acid that is 96-98 wt % pure in aqueous solution may be used. The sulfuric acid (e.g. 88-98 wt %, 88-90 wt %, 90-92 wt %, 92-94 wt %, 94-96 wt %, or 96-98 wt %) may be present in the reaction at about 1-60 wt % (based on the total acid combined with hydrocarbon), e.g. at about 1-5 wt %, 5-10 wt %, 10-15 wt %, 15-20 wt %, 20-25 wt %, 25-30 wt %, 30-35 wt %, 35-40 wt %, 40-45 wt %, 45-50 wt %, 50-55 wt %, or 55-60 wt %. In some variations, the concentration of the sulfuric acid is monitored as the reaction progresses, and additional acid is added if the concentration drops below a desired level, or water is added if the concentration increases above a desired level. For example, the concentration of the sulfuric acid may be maintained in the reaction at about 1 wt %, 5 wt %, 10 wt %, 15 wt %, 20 wt %, 25 wt %, 30 wt %, 35 wt %, 40 wt %, 45 wt %, 50 wt %, 55 wt %, or 60 wt %.

If hydrofluoric acid is used as the catalyst, the concentration of hydrofluoric acid in the acid phase entering the reactor may be maintained below strengths titrating to 60 wt % HF/water, e.g. 1-5 wt %, 5-10 wt %, 10-15 wt %, 15-20 wt %, 20-25 wt %, 25-30 wt %, 30-35 wt %, 35-40 wt %, 40-45 wt %, 45-50 wt %, 50-55 wt %, or 55-60 wt %. In some variations, the concentration of hydrofluoric acid may be monitored as the reaction progresses, and additional acid may be added if the concentration drops below a desired level, or water may be added if the concentration increases above a desired level. For example, the concentration of the hydrofluoric acid may be maintained in the reaction at about 1 wt %, 5 wt %, 10 wt %, 15 wt %, 20 wt %, 25 wt %, 30 wt %, 35 wt %, 40 wt %, 45 wt %, 50 wt %, 55 wt %, or 60 wt %.

Figure 5:
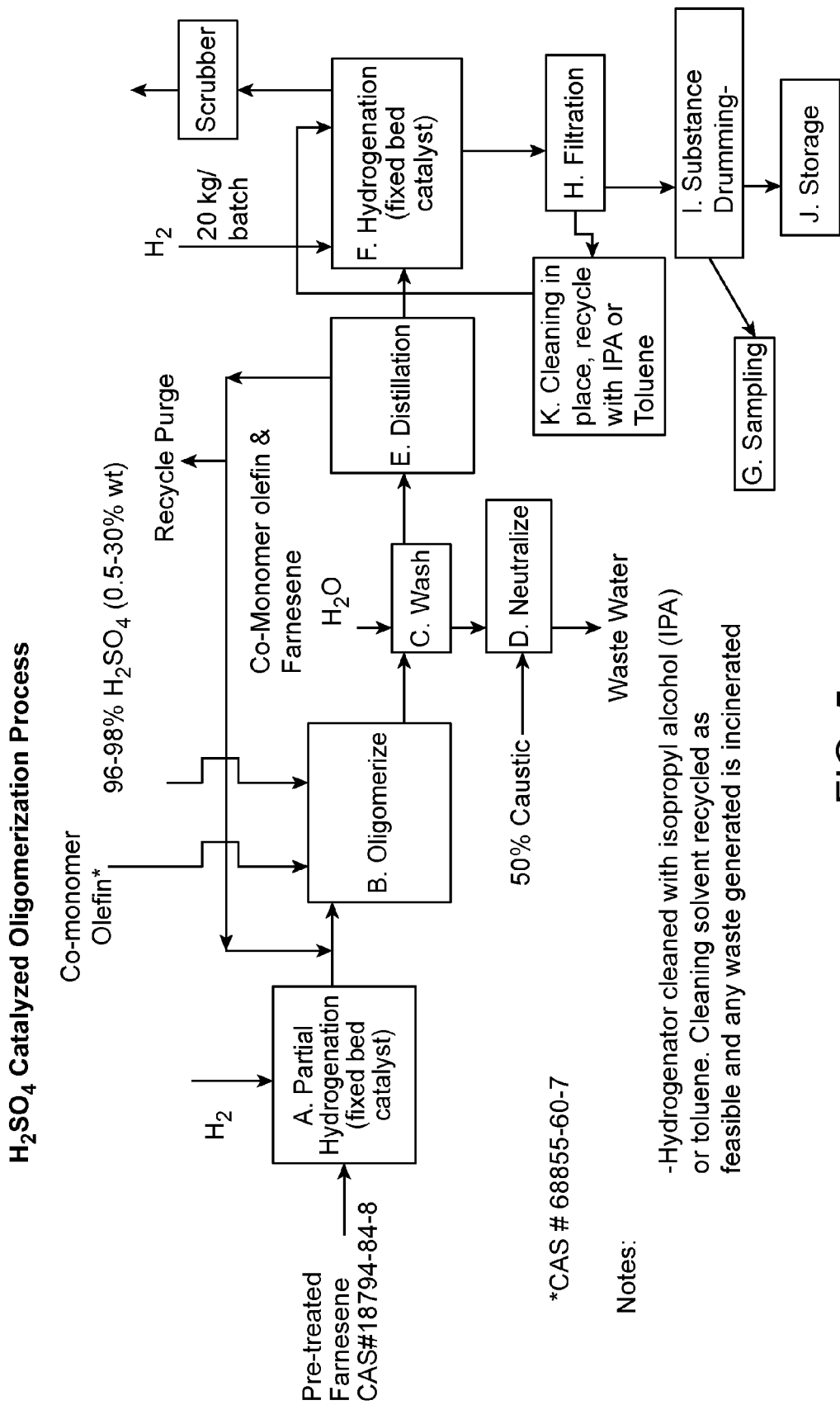
FIG. 5 provides another non-limiting example of a process flow diagram for reacting a hydrocarbon terpene feedstock comprising partially hydrogenated hydrocarbon terpene (β-farnesene is shown as a model hydrocarbon terpene) with one or more olefin co-monomers in the presence of a cationic initiator (the protic acid $H_2SO_4$ is shown as a model cationic initiator) to form one or more base oils.

An example of a process flow diagram in which hydrocarbon terpene feedstock (e.g., partially hydrogenated hydrocarbon terpene or saturated hydrocarbon terpene) is reacted with one or more olefin co-monomers in the presence of a protic acid catalyst is provided in FIG. 5. In FIG. 5, partially hydrogenated β-farnesene is used as a model hydrocarbon terpene feedstock, but it should be understood that any hydrocarbon terpene feedstock as described herein may be used in the process illustrated in FIG. 5. As shown, the hydrocarbon terpene feedstock (e.g., partially hydrogenated farnesene) is provided in Step A. In certain variations, the partially hydrogenated feedstock may be produced in situ as needed from a hydrocarbon terpene (e.g. β-farnesene), e.g. using a fixed bed catalyst or other continuous flow through catalytic reactor. Any suitable source of hydrocarbon terpene feedstock may be used. For example, if partially hydrogenated β-farnesene is used, microbially-produced β-farnesene as described in U.S. Pat. No. 7,399,323 may be used, and partially hydrogenated as described in U.S. Pat. App. Ser. No. 61/493,316, filed Jun. 3, 2011. In some variations, a hydrocarbon terpene (e.g., β-farnesene) is pretreated prior to partial hydrogenation. In some variations, it may be desired to remove oxygen-containing compounds (e.g., alcohols, alcohols, acids, epoxies, and the like) from the hydrocarbon terpene feedstock, e.g., to prevent or reduce formation of emulsions. For example, a hydrocarbon terpene (e.g., β-farnesene) may be distilled (under conditions that do not result in undesired thermal reactions such as dimerization), filtered using silica or activated alumina (e.g., aluminum oxide, 150 mesh, 58 Å, Brockman standard grade, available from Sigma Aldrich), treated with molecular sieves (e.g., 13× molecular sieves), or a caustic wash followed by a water wash may be conducted followed by centrifuge and separation of aqueous portions, prior to use. It should be noted that such a pretreatment step may occur prior to and/or following a partial hydrogenation step for the hydrocarbon terpene. Although not shown explicitly in FIG. 5, in some variations, Step A is performed prior to the coupling reaction, where the hydrocarbon terpene feedstock (e.g., partially hydrogenated farnesene) is partially hydrogenated ahead of time (e.g. using a batch slurry reactor, fixed bed reactor, or any other suitable hydrogenation apparatus) and drummed or otherwise stored. In some variations, partially hydrogenated hydrocarbon terpene (e.g., farnesene) is stored is stored under inert atmosphere. In some cases, a stabilizer or an antioxidant, e.g. 50-100 ppm t-butyl catechol, is added to the partially hydrogenated hydrocarbon terpene (e.g., farnesene). In some circumstances, partially hydrogenated hydrocarbon (e.g., farnesene) is treated to remove oxygenates and/or other impurities (e.g., distilled, filtered using activated alumina or silica, treated using molecular sieves, or using a caustic wash followed by a water wash) just prior to use.

The coupling process occurs in Step B, in some variations in a continuously stirred reactor. The hydrocarbon terpene feedstock, olefin co-monomer(s) and catalyst may be fed into the reactor using any procedure applicable to the particular reaction. For example, in some variations, the hydrocarbon terpene feedstock is added to the reactor first with the catalyst, with the other olefin co-monomers added thereafter. In some variations, the one or more olefin co-monomers (or a portion of the one or more olefin co-monomers) is added to the reactor first with the catalyst and the hydrocarbon terpene feedstock is added thereafter. In some variations, the hydrocarbon terpene feedstock and the one or more olefin co-monomers are mixed prior to being fed into the reactor and contacted with the catalyst. In some variations, the catalyst is added slowly to a mixture of hydrocarbon terpene feedstock and the one or more olefins. In some variations, the hydrocarbon terpene feedstock and the one or more olefins are co-fed into the reactor.

The reactor is cooled to maintain a temperature between about −20° C. and 20° C., e.g. about −20° C., −10° C., −5° C., 0° C., 5° C., 10° C., 15° C., or 20° C. In some variations, the reaction temperature is controlled to within about +/−10, +/−5, +/−2, +/−1, or +/−0.5° C. One or both of the rate of feed of the hydrocarbon terpene feedstock and the rate of feed of the one or more olefins may be adjusted to assist in controlling reaction temperature.

In some variations, the concentration of the cationic initiator is monitored as the reaction proceeds. For example, the concentration of the cationic initiator may be maintained at about 1, 5, 10, 15, 20, 25, 30, 35, 40, 45, 50, 55, or 60 wt % as the reaction proceeds.

The molar ratio of hydrocarbon terpene feedstock to the olefin co-monomer(s) may be about 10:1, 8:1, 6:1, 4:1, 2:1, 1:1, 1:2, 1:4, 1:6, 1:8, or 1:10 mol hydrocarbon terpene feedstock:mol other olefin reactants. In some variations, about one mol hydrocarbon terpene feedstock is used per mol olefin co-monomer.

The protic acid catalyzed reaction may be allowed to run for any suitable time. In some variations, the reaction may be allowed to run for up to about 1-48 hours, e.g. about 1-2 hours, 2-4 hours, 4-6 hours, 6-8 hours, 8-10 hours, 10-12 hours, 12-14 hours, 14-16 hours, 16-18 hours, 18-20 hours, 20-22 hours, 22-24 hours, 24-36 hours, or 36-48 hours.

It is desired to adjust reaction conditions so that formation of cross-products (hydrocarbon terpene feedstock:olefin adducts) is favored over olefin:olefin adduct formation. Further, catalysis conditions may be tuned to adjust the relative quantities of dimers (1:1 hydrocarbon terpene:olefin adducts), trimers (1:2 hydrocarbon terpene:olefin adducts and/or 2:1 hydrocarbon terpene:olefin adducts), tetramers (1:3 hydrocarbon terpene:olefin adducts, 3:1 hydrocarbon terpene:olefin adducts, and/or 2:2 hydrocarbon terpene: olefin adducts), etc. As an illustrative example, for olefin co-monomers having lower molecular such as C8 (e.g. 1-octene), C10 (e.g. 1-decene), or C12 (e.g. 1-dodecene), it may be desirable to adjust catalysis conditions to produce trimers and tetramers and other higher oligomers over dimers. For heavier molecular weight co-monomers such as C16 (e.g. 1-hexadecene), it may be desirable to adjust catalysis conditions to produce dimers and trimers over tetramers and higher oligomers. For isoparaffins containing relatively large amounts of branching, it may be desired to adjust catalysis conditions to produce trimers and tetramers and other higher oligomers over dimers, e.g., to increase viscosity index of one or more cuts obtained from the mixture of isoparaffins.

Referring again to FIG. 5, following the protic acid catalyzed coupling reaction, the reaction mixture is washed (Step C) and neutralized (Step D). In some variations, the reaction mixture is neutralized prior to washing. The neutralization may, for example, be carried out until Total Acid Number (TAN)≤1 mg KOH/100 g liquid. Any suitable neutralization method may be used. In some variations, a dialkylamine (e.g. diethylamine, dibutylamine, or dicyclohexylamine) is used to neutralize the reaction, e.g. at about 2:1, 1.5:1, 1:1, or 0.5:1 mol diethylamine:mol $H_2SO_4$. For example, about 1 g dialkylamine/1 g sulfuric acid catalyst can be used to neutralize the reaction mixture. The organic layer is isolated from the aqueous layer using any suitable method, e.g. gravity separation, centrifuge and/or filtration (not shown). The crude, unsaturated reaction mixture is distilled (Step E) to remove low molecular weight species, e.g. those having carbon numbers less than or equal to that of the reactants. Any suitable distillation apparatus may be used. In some variations, a single stage flash distillation apparatus may be used. In some variations, a distillation apparatus with multiple stages (e.g. 2, 3, 4 or 5 stages) may be used. In some variations, it is desirable to remove at least about 99% or 99.9% of monomer from the mixture of unhydrogenated reaction product obtained in Step E. In some variations, unreacted reactants are recovered through the distillation and reintroduced to the oligomerization. Following the distillation step, the reaction mixture is hydrogenated (Step F) to form a mixture of isoparaffins, e.g. hydrogenated using a batch slurry reactor, a fixed bed reactor, or a fluidized bed reactor, as is described herein or known in the art. The hydrogenated reaction product obtained in Step F is filtered to remove catalyst, e.g., prior to sampling (Step G), drumming (Step I), and storage (Step J). In some variations, the filtered mixture of isoparaffins obtained in Step H is fractionated to obtain one or more distillation cuts (not shown). Here again, any suitable distillation apparatus may be used, e.g. batch or continuous distillation using any suitable distillation method such as flash distillation, single stage distillation, fractional distillation (e.g., a packed column distillation), a multiple stage distillation apparatus having multiple stages (e.g. 2, 3, 4, 5, 6, 7, or 8 stages)), wiped film evaporator, steam distillation, vacuum distillation, or short path distillation. In some variations, distillation cuts may be obtained at pot temperatures of up to 300° C. under a maximum pressure of 1-2 mm Hg, which may correspond to one or more distillation cuts that are collected in a temperature range from about 350° C. to about 500° C., e.g. 350° C. to 380° C., 380° C. to 400° C., 400° C. to 420° C., 420° C. to 435° C., 435° C. to 445° C., 445° C. to 460° C., or 460° C. to 480° C. (with temperatures corresponding to boiling points at atmospheric pressure, or atmospheric equivalent temperatures (AET)). Certain fractions may be blended together, depending on the desired characteristics for the final product. In some variations, the residue remaining in the pot after distillation is collected, e.g., residue remaining after distillation up to about 420° C., 430° C., 440° C., 450° C., 455° C., 460° C., 465° C., 470° C., 475° C., or 480° C. (AET if distilled below ambient pressures). Additional distillation schemes that can be used with any of the isoparaffinic mixtures described herein are described in Section II below. In some cases, the mixture of isoparaffins is not fractionated. In some variations, the mixture of isoparaffins (or a desired fraction thereof) is filtered, e.g., with alumina or silica. In some situations, an antioxidant may be added to the isoparaffins (which may have been filtered, e.g., with alumina or silica), e.g., at a level of about 50-100 ppm.

Figure 6:
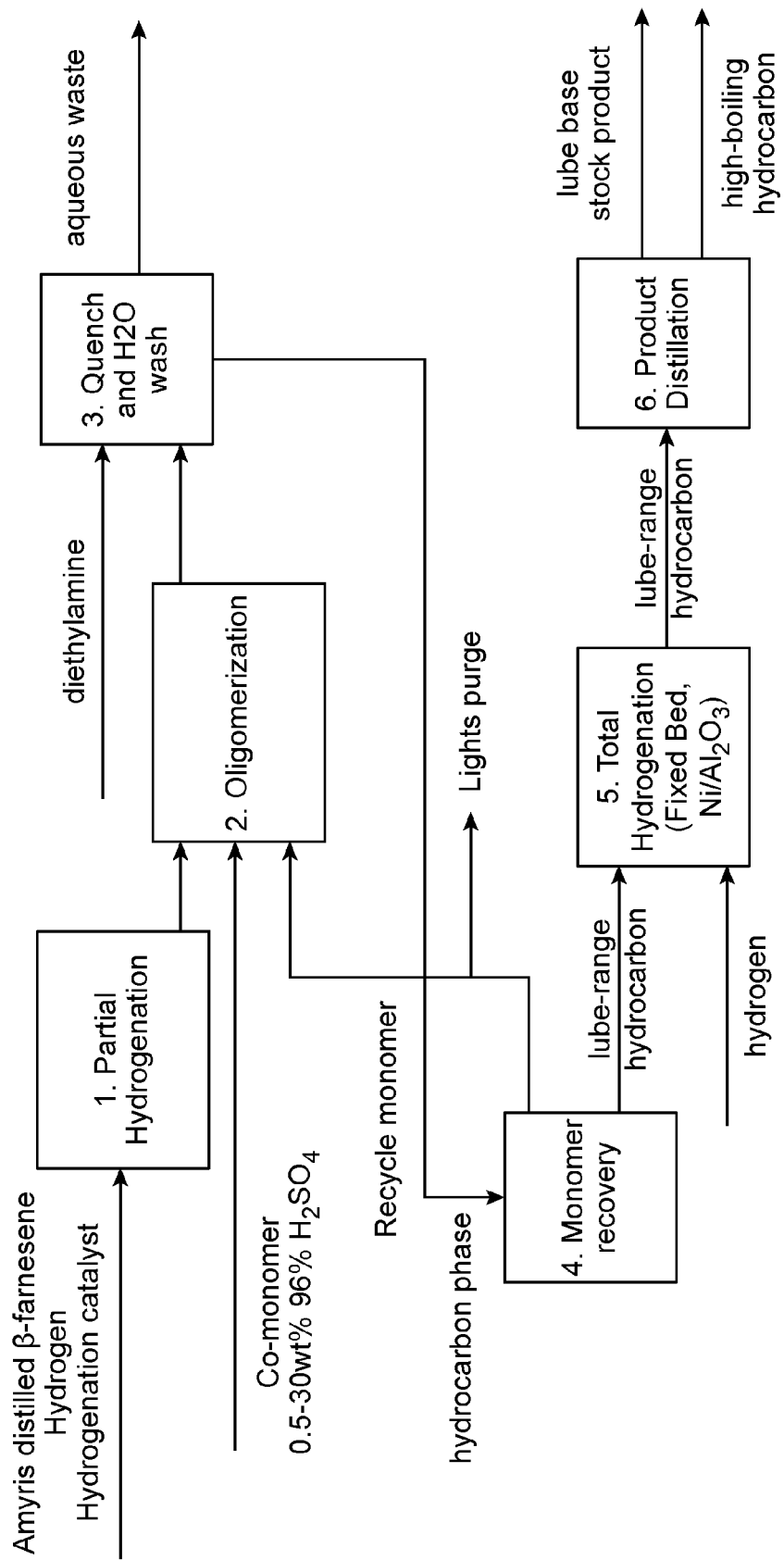
FIG. 6 provides another non-limiting example of a process flow diagram for reacting a hydrocarbon terpene feedstock comprising partially hydrogenated hydrocarbon terpene (β-farnesene is shown as a model hydrocarbon terpene) with one or more olefin co-monomers in the presence of a cationic initiator (the protic acid $H_2SO_4$ is shown as a model cationic initiator) to form one or more base oils.
Figure 7A:
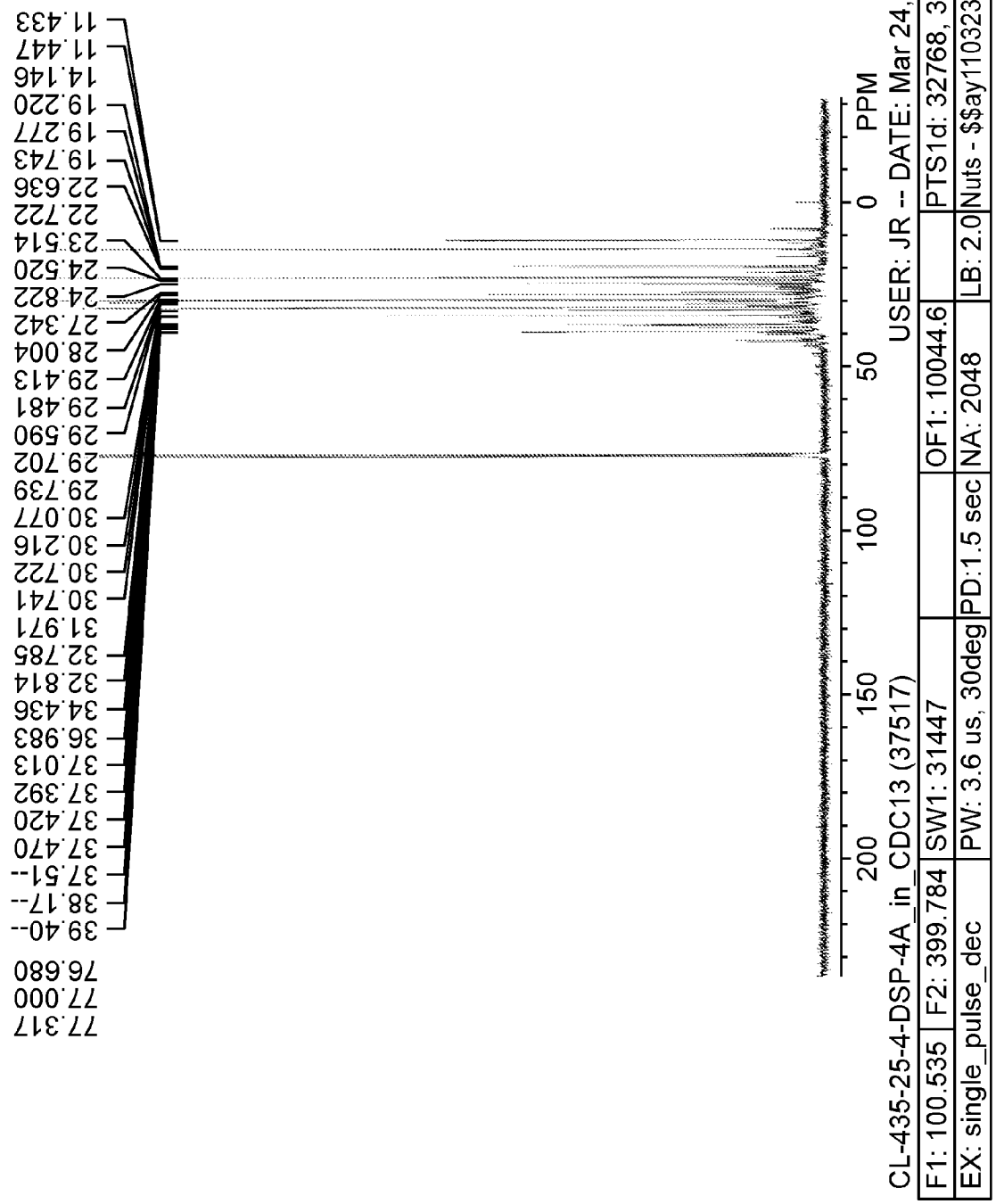
FIG. 7A provides a $^{13}C$ NMR spectrum (in $CDCl_3$) of a mixture of isoparaffins prepared by Example 6.
Figure 7B:
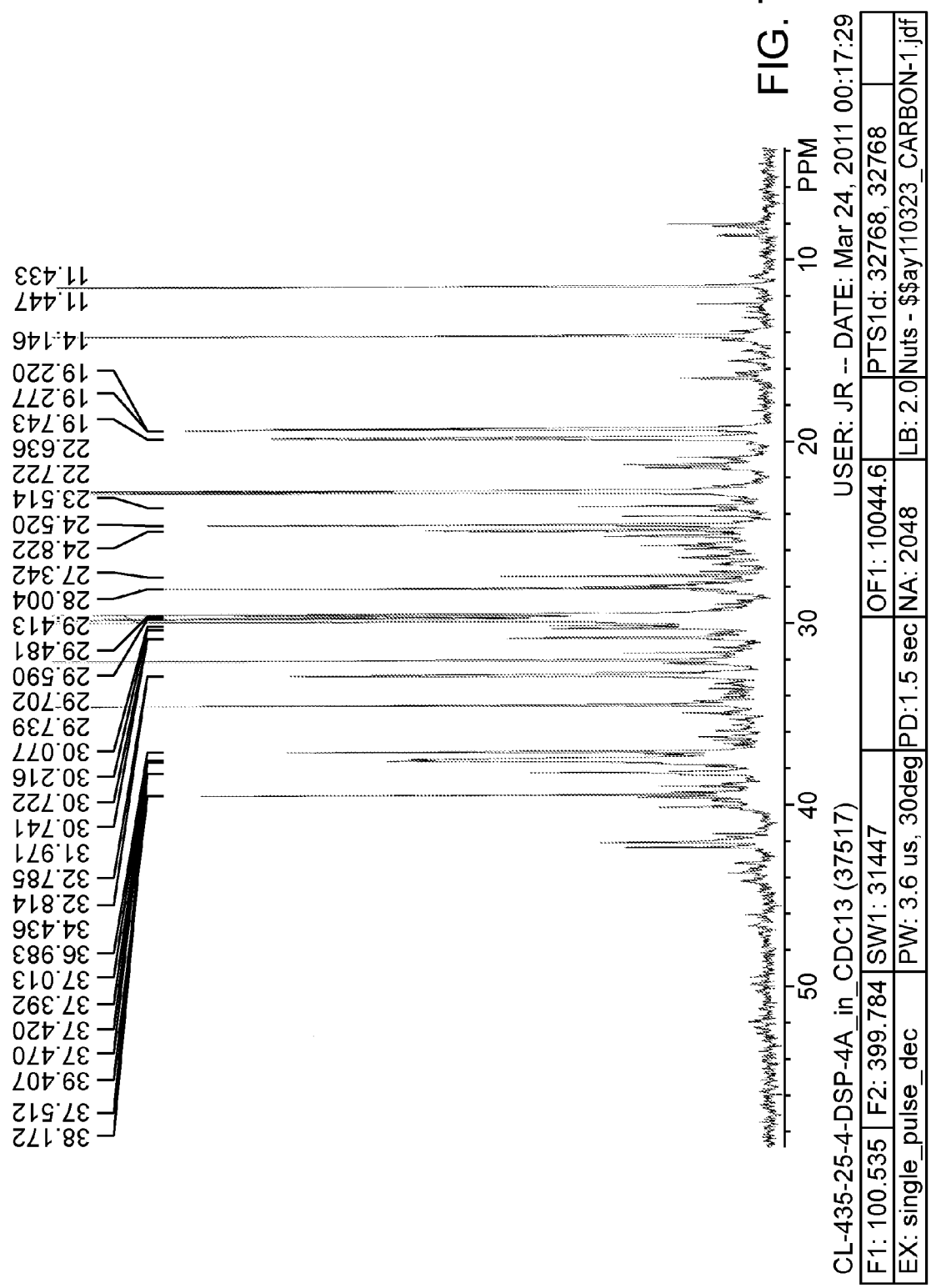
FIG. 7B provides a $^{13}C$ NMR spectrum of the mixture of isoparaffins as in FIG. 7A, on an expanded scale of about 4 ppm-60 ppm.
Figure 7C:
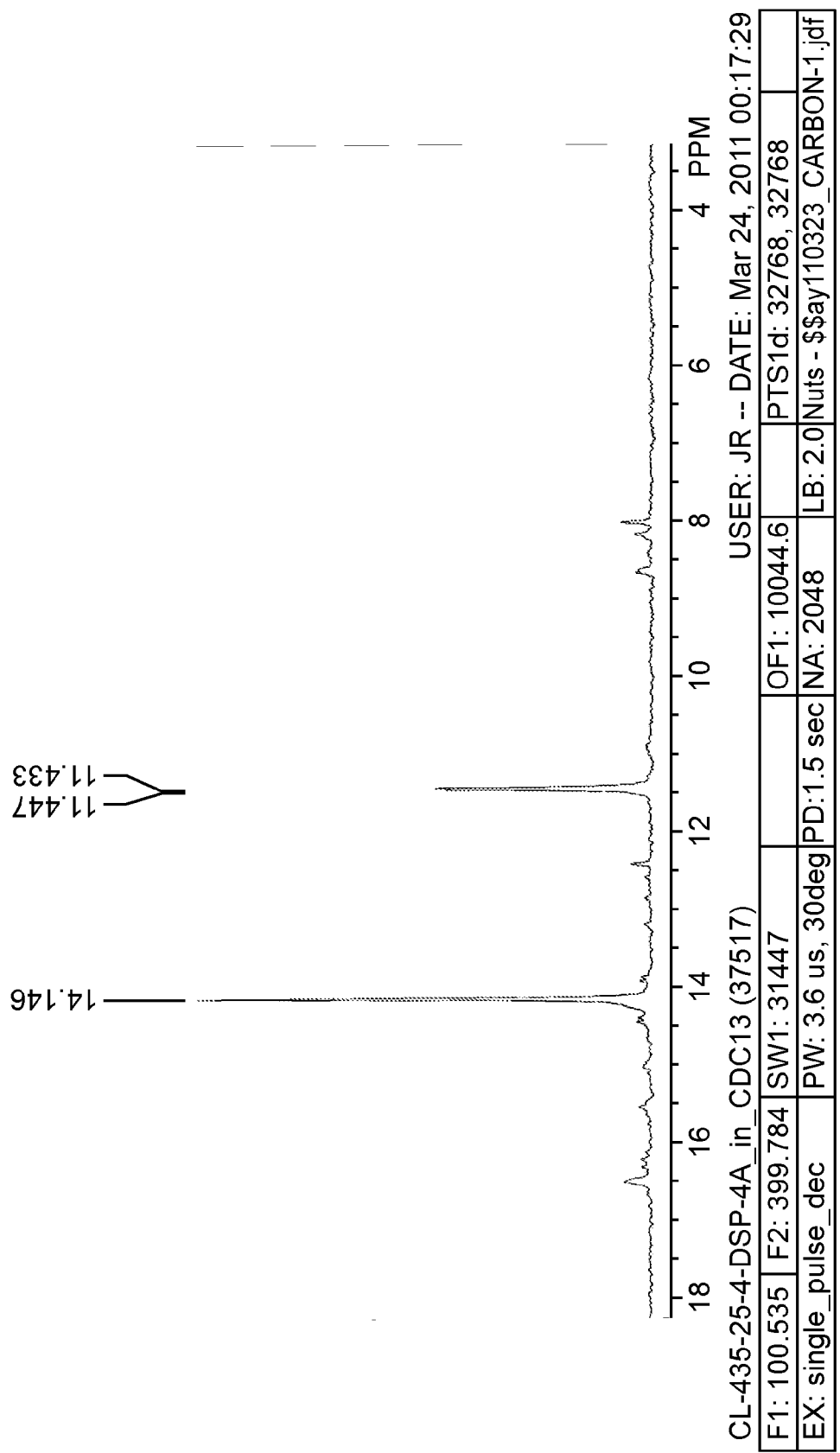
FIG. 7C provides a $^{13}C$ NMR spectrum of the mixture of isoparaffins as in FIG. 7A, on an expanded scale of about 3 ppm-18 ppm.
Figure 7D:
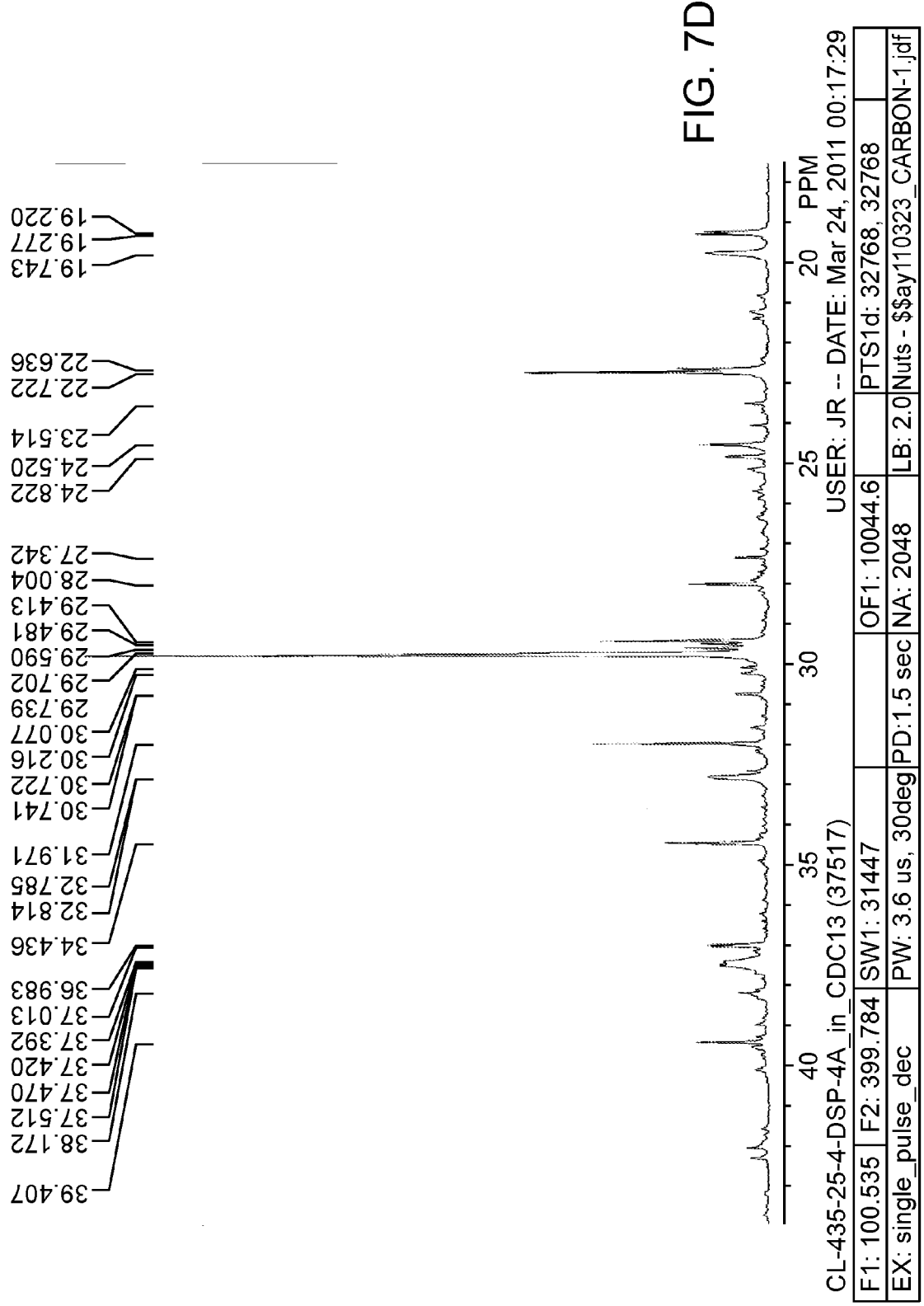
FIG. 7D provides a $^{13}C$ NMR spectrum of the mixture of isoparaffins as in FIG. 7A, on an expanded scale of about 18 ppm-44 ppm.

An example of an alternate process flow diagram is provided in FIG. 6. Here again, partially hydrogenated β-farnesene is used as a model hydrocarbon terpene feedstock, but it should be understood that any hydrocarbon terpene feedstock as described herein may be used in the reaction. If applicable, partial hydrogenation of a hydrocarbon terpene to make the hydrocarbon terpene feedstock is Step 1. If the hydrocarbon terpene is β-farnesene, any suitable source of β-farnesene may be used, e.g., microbially-produced β-farnesene as described in U.S. Pat. No. 7,399,323. In some variations, β-farnesene is pretreated prior to partial hydrogenation. For example, β-farnesene may be filtered using silica or activated alumina. Although not explicitly shown in FIG. 6, in some variations of the methods, the hydrocarbon terpene feedstock (e.g., partially hydrogenated farnesene) is produced prior to the protic acid catalyzed coupling reaction. In some variations, a partially hydrogenated hydrocarbon terpene that has been produced earlier and stored is stored under inert atmosphere. In some cases, a stabilizer or an antioxidant, e.g., 50-100 ppm t-butyl catechol, is added to the partially hydrogenated hydrocarbon terpene. In some variations, partially hydrogenated farnesene is filtered (e.g., using activated alumina or silica) just prior to use in the reaction.

One or more olefin co-monomers is reacted with the hydrocarbon terpene feedstock, using a protic acid catalyst (e.g. 0.5-60 wt % $H_2SO_4$ having a purity of 96% or greater as described herein) (Step 2). The total liquid feed can have any suitable ratio between the hydrocarbon terpene feedstock and the one or more olefins, e.g. about 10:1, 8:1, 6:1, 4:1, 2:1, 1:1, 1:2, 1:4, 1:6, 1:8 or 1:10 mol hydrocarbon terpene feedstock:mol other olefin co-monomer(s). In some variations, the molar ratio between the hydrocarbon terpene feedstock and other olefin co-monomers is about 1:1. The reaction is carried out at a temperature controlled to be a range from about −20° C. to about 20° C. (e.g., about −20° C., −15° C., −10° C., −5° C., 0° C., 5° C., 10° C., 15° C., or 20° C.). The reaction may be allowed to run for any suitable time. In some variations, the reaction may be allowed to run for up to about 1-48 hours, e.g., about 1-2 hours, 2-4 hours, 4-6 hours, 6-8 hours, 8-10 hours, 10-12 hours, 12-14 hours, 14-16 hours, 16-18 hours, 18-20 hours, 20-22 hours, 22-24 hours, 24-36 hours, or 36-48 hours.

In some variations, the catalyst (e.g., $H_2SO_4$) is added slowly to the hydrocarbon mixture with sufficient mixing. In some variations, the hydrocarbon mixture is added slowly to the catalyst with mixing. In some variations, the hydrocarbon terpene feedstock is contacted with the catalyst prior to addition of the other olefin reactants. In some variations, the one or olefin co-monomers is contacted with the catalyst prior to addition of hydrocarbon terpene feedstock. Following the reaction, the reaction mixture is neutralized and washed (Step 3). To neutralize, any suitable base may be used. In some variations, a dialkylamine such as dicyclohexylamine, dibutylamine, or diethylamine is used. For example, about 1 g dialkylamine/1 g sulfuric acid catalyst used can be used to neutralize the reaction mixture. In some variations, the reaction is neutralized such that TAN≤1 mg KOH/100 g liquid. Following neutralization, the product mixture is washed using about 1 kg water per 1 kg product mixture. The hydrocarbon is separated from the water, e.g., using a settler for about 2-8 hours, or a liquid/liquid separation centrifuge. In some variations, unreacted monomer can be recovered from the hydrocarbon phase by distillation (Step 4) and recycled as a reactant.

Optionally, if $H_2SO_4$ is used as a catalyst, sulfur can be removed from the hydrocarbon prior to hydrogenation, e.g., by adsorption. The hydrocarbon can be passed through packed silica, the silica can be washed one or more times using isopropyl alcohol, and the washings can be collected and evaporated to recover unsaturated hydrocarbon product.

The unsaturated hydrocarbon product is hydrogenated (Step 5), e.g., in a fixed bed reactor or in a batch slurry reactor. If a fixed bed reactor is used, a nickel catalyst supported by $Al_2O_3$ can be used in some variations. If a batch slurry reactor is used, a nickel catalyst such as Johnson-Matthey 62/15 P 60% $Ni/SiO_2$ catalyst can be used, e.g., at a loading of 0.5 g/100 g hydrocarbon and a pressure of about 1000 psig and 150° C. for about 12 hours, or a palladium catalyst such as 10 wt % Pd/C at a loading of 1 g/200 g hydrocarbon at a pressure of about 50-1000 psig and a temperature of about 50° C.-150° C. The hydrogenation can be continued until the degree of unsaturation is suitably low, as determined by any suitable analysis (e.g., Br index measured to be less than or equal to about 500, 200, or 100 mg Br/100 g liquid). If a slurry reactor is used for the hydrogenation, the hydrogenation catalyst can be removed using any suitable method, e.g., so that no sediment is observed when centrifuged at 10000 g×2 min.

The hydrogenated hydrocarbon product can be distilled (Step 6) in some variations. First the hydrogenated hydrocarbon product can be heated to selectively remove low boiling components including hydrogenated residual monomers originating from the hydrocarbon terpene feedstock and/or the olefin co-monomers. For example, the hydrogenated hydrocarbon product can be heated at 200° C. at 1 torr to remove C15 hydrocarbons. Optionally, the mixture can be distilled at 1 torr and 250-300° C. to isolate the desired product from higher boiling components (e.g., oligomers having more than about 45 carbons).

It should be understood that additional embodiments are contemplated in which the hydrocarbon terpene feedstock comprises a saturated hydrocarbon terpene (e.g., farnesane) which is reacted with one or more olefin co-monomers in the presence of a protic acid catalyst to produce an unsaturated reaction product comprising branched alkenes. The unsaturated reaction product can be subsequently hydrogenated to form isoparaffins. At least a portion of the isoparaffins can be used as a base oil, or as a component of a base oil. Any suitable olefin co-monomer(s) as described herein can be reacted with the saturated hydrocarbon terpene (e.g., one or more $C_2$-$C_{20}$ linear alpha-olefins, one or more $C_2$-$C_{20}$ branched alpha-olefins, one or more $C_2$-$C_{20}$ linear or branched internal olefins, or any combination of the foregoing) in the presence of a protic acid catalyst (e.g. sulfuric acid or hydrofluoric acid). In those instances, the process may be carried out as described herein with farnesane substituted for partially hydrogenated farnesene.

In still other embodiments, one or more $C_3$-$C_{20}$ paraffins (e.g. one or more $C_3$-$C_{20}$ isoparaffins) is reacted with a partially hydrogenated hydrocarbon terpene feedstock (e.g., partially hydrogenated myrcene or partially hydrogenated farnesene which comprises at least about 60%, 65%, 70%, 75%, 80% or even more mono-olefin) in the presence of a protic acid catalyst to produce an unsaturated reaction product comprising branched alkenes. The unsaturated reaction product can be subsequently hydrogenated to form isoparaffins. At least a portion of the isoparaffins so formed can be used as a base oil, or as a component of a base oil.

In some embodiments, a saturated hydrocarbon terpene (e.g., farnesane) is reacted with a partially hydrogenated hydrocarbon terpene feedstock as described herein in the presence of a protic acid catalyst (e.g., sulfuric acid or hydrofluoric acid) to make crude unsaturated product, which is subsequently hydrogenated to form isoparaffins which have utility as base oils or as additives to base oils. For example, in some variations, farnesane is reacted with partially hydrogenated farnesene in the presence of a protic acid catalyst (e.g., sulfuric acid or hydrofluoric acid) to make a mixture of isoparaffins, at least a portion of which may be used as a base oil.

b. Solid Acid Catalysts

In some variations, a solid acid catalyst may be used to catalyze the coupling of a hydrocarbon terpene feedstock with one or more olefin co-monomers (e.g., one or more non-terpene co-monomers). In some variations, an olefin co-monomer may be an alpha-olefin. For example, any solid acid catalyst known to oligomerize olefins (e.g., alpha-olefins) may be used in certain variations. In some cases, a solid acid catalyst known to dimerize or trimerize olefins (e.g., alpha-olefins) may be used. In other variations, any solid acid catalyst known to alkylate isoparaffins with olefins may be used. Non-limiting examples of solid acid catalysts that may be used include amorphous or crystalline aluminosilicates, clays, ion-exchange resins, mixed oxides, and acids supported by a carrier, e.g., sulfonic acid, sulfuric acid, hydrofluoric acid, or phosphoric acid supported by a carrier. In some variations, Y-type zeolites or ZSM-5 (e.g., H-ZSM-5) solid acid catalysts may be used.

In some variations, a solid acid catalyst comprising an acid (e.g., sulfonic acid) supported on a polymeric resin is used, e.g., AMBERLYST™ resin or AMBERLITE™ resin, available from Dow Chemical Co., Midland, Mich. For example, AMBERLYST™ 36 or 15 grade heterogeneous acid catalyst systems may be adopted for cross coupling oligomerization reaction of partially hydrogenated hydrocarbon terpene feedstock (e.g., partially hydrogenated b-farnesene) with one or more olefin co-monomers (e.g., one or more alpha-olefins).

A heterogeneous catalyst (e.g., heterogeneous acid catalysts such as AMBERLYST™ catalysts) may be advantageous in some circumstances as the need for post-oligomerization process such as neutralization, separation, and purification may be reduced or eliminated. Heterogeneous catalysts may be recyclable multiple times while still maintaining acceptable activity in some cases.

In some variations, a solid phosphoric acid catalyst is used. Any suitable carrier may be used in the catalyst, and may in some variations comprise a molded product of siliceous carrier such as diatomaceous earth, infusorial earth, Celite earth, Kieselguhr, kaoline clay, fuller's earth, silica, and any combination thereof. If the support is molded, any suitable mold and molding process may be used, e.g., to produce granular, plate-like, pellet-like product can be made by tablet molding, extrusion molding, spray dry, tumbling granulation, granulation in oil and the like, and the granulation size can be made to approximately 0.5-5 mm. The phosphoric acid used in the solid acid catalysts may in certain variations comprise orthophosphoric acid and its condensation products (pyrophosphoric acid, polyphosphoric acid and the like). In other variations, the phosphoric acid may comprise a precursor that can be hydrolyzed to form the phosphoric acid, e.g., a phosphoric acid ester. and the chemical compounds which is hydrolyzed to the phosphoric acid (the precursor of the phosphoric acid).

If a zeolite solid acid catalyst is used (e.g., ZSM-5 or Y-type) the characteristics of the zeolite may be tuned to adjust the properties of the adducts formed. For example, the Si/Al ratio, the crystal size, the morphology of the crystals, pore structure (size, shape), and charge distribution may be varied. In some variations, characteristics of the zeolite are adjusted to form desired adducts. For example, zeolite characteristics may be adjusted using known techniques to favor production of linear adducts over production of highly branched adducts.

c. Lewis Acids

In some variations, a Lewis acid and one or more co-catalysts is used as a cationic initiator to catalyze coupling between one or more olefin co-monomers and the hydrocarbon terpene feedstock to form branched alkenes, which may be hydrogenated to form isoparaffins. In some variations, non-terpene olefin co-monomers are used. In some variations, the one more olefin co-monomers comprise one or more alpha-olefins (e.g., one or more non-terpene alpha-olefins). The Lewis acid and a co-catalyst capable of generating cations catalyzes formation of adducts between a hydrocarbon terpene and one or more olefin co-monomers (e.g., one or more alpha-olefins).

Some non-limiting examples of suitable Lewis acids include metalloid halides and metal halides typically used as Friedel-Crafts catalysts, e.g. $AlCl_3$, $BF_3$, $BF_3$ complexes, $BCl_3$, $AlBr_3$, $TiCl_3$, $TiCl_4$, SnCl4, or $SbCl_5$. Any of the metalloid halide or metal halide catalysts can be used with or without a co-catalyst protic promoter (e.g. water, alcohol, acid, or ester). A Lewis acid catalyst can be used in any suitable amount, but in some cases, a catalyst is used in an amount from 0.1 wt % to 10 wt %, from 0.2 wt % to 5 wt %, or from 0.2 wt % to 3 wt % based on the total feed.

In some variations, the catalyst comprises $BF_3$ as a gas, and in some variations the catalyst comprises $BF_3$ complexed to form a liquid or solid, and in some variations the catalyst comprises $BF_3$ as a gas and $BF_3$ complexed to form a liquid or solid. For example, $BF_3$ may be complexed with an ether, an alcohol, an ester, an amine, a carboxylic acid, or an inorganic acid. Non-limiting examples of $BF_3$ complexes that may be used as oligomerization catalysts include $BF_3$: acetonitrile, $BF_3$:diacetic acid, $BF_3$:acetic acid, $BF_3$ dihydrate, $BF_3$:phosphoric acid, $BF_3$:dimethyl ether, $BF_3$:diethyl ether, $BF_3$:methyl ethyl ether, $BF_3$:phenol, $BF_3$:tetrahydrofuran, and $BF_3$:propionic acid, $BF_3$:methanol, $BF_3$:ethanol, $BF_3$:n-propanol, $BF_3$:isopropanol, $BF_3$:n-butanol, and $BF_3$: 2-butanol.

When $BF_3$ is used as a catalyst, one or more protic co-catalysts may be used. Some non-limiting examples of protic promoters that may be used in combination with $BF_3$ include: water; alcohols such as the $C_1$-$C_{10}$ (e.g., $C_1$-$C_6$) straight chain or branched alcohols, such as methanol, ethanol, isopropanol, n-propanol, n-butanol, 2-butanol, n-pentanol, n-hexanol and mixtures thereof; organic acids, e.g., carboxylic acids or anhydrides of organic acids, such as acetic acid, propionic acid, butanoic acid, acetic anhydride; inorganic acids such as phosphoric acid; esters such as ethyl acetate; alcohol alkoxylates such as glycol ethers, e.g., ethylene glycol monomethyl ether, or propylene glycol monoethyl ether, or an ethoxylate derived from $C_2$ to $C_{24}$ straight chain alcohols; ethers such as dimethyl ether, diethyl ether, methyl ethyl ether; ketones such as methyl ethyl ketone; aldehydes; and alkyl halides. In certain embodiments, the oligomerization is carried out using the protic promoter to form a complex with $BF_3$, and a molar excess of $BF_3$ in relation to the protic promoter is present, e.g., by sparging the reactor with $BF_3$ gas or by conducting the reaction under slight $BF_3$ pressure, e.g., a $BF_3$ pressure of about 1, 2, 3, 4, 5, 6, 7, 8. 9. 10, 11, or 12 psig.

In those variations in which more than one co-catalyst is used with $BF_3$, any suitable combination of co-catalysts may be used. For example, two different co-catalysts can be used together with a $BF_3$ catalyst, where one co-catalyst comprises an alcohol and one co-catalyst comprises an ester. Any suitable alcohol can be used, e.g., a $C_1$-$C_{10}$ straight chain or branched alcohol, or a $C_1$-$C_6$ straight chain or branched alcohol. Non-limiting examples of alcohols that may be used as co-catalysts with $BF_3$ include methanol, ethanol, isopropanol, n-propanol, n-butanol, 2-butanol, n-pentanol, n-hexanol and mixtures thereof. Any suitable ester co-catalyst may be used in combination with an alcohol co-catalyst and $BF_3$. In some variations, the ester is derived from a $C_1$-$C_6$ linear or branched alcohol and a low molecular weight carboxylic acid such as acetic acid, formic acid, propionic acid, butanoic acid, and the like. Non-limiting examples of ester co-catalysts that can be used include methyl acetate, ethyl acetate, n-propyl acetate, isopropyl acetate, n-butyl acetate, and 2-butyl acetate. In some cases, an alcohol co-catalyst having the formula R'OH is used with an ester co-catalyst having the formula $R^2CO_2R^1$, where $R^1$ is a linear or branched $C_1$-$C_{10}$ (e.g., a $C_1$-$C_6$) alkyl group, and $R^2$ is H or a linear or branched $C_1$-$C_4$ alkyl group, e.g., n-butyl acetate and n-butanol may be used together as protic co-catalysts with $BF_3$.

If more than one protic co-catalyst is used with $BF_3$, the co-catalysts may be present in any suitable molar relation to each other. For example, a molar ratio of alcohol co-catalyst: ester co-catalyst may be about 0.1 to about 20, e.g., about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 or 20. In some variations, a molar ratio of alcohol co-catalyst:ester co-catalyst is about 0.5 to about 10, or about 0.5 to about 5, about 0.5 to about 3, or about 1.

Figure 3A:
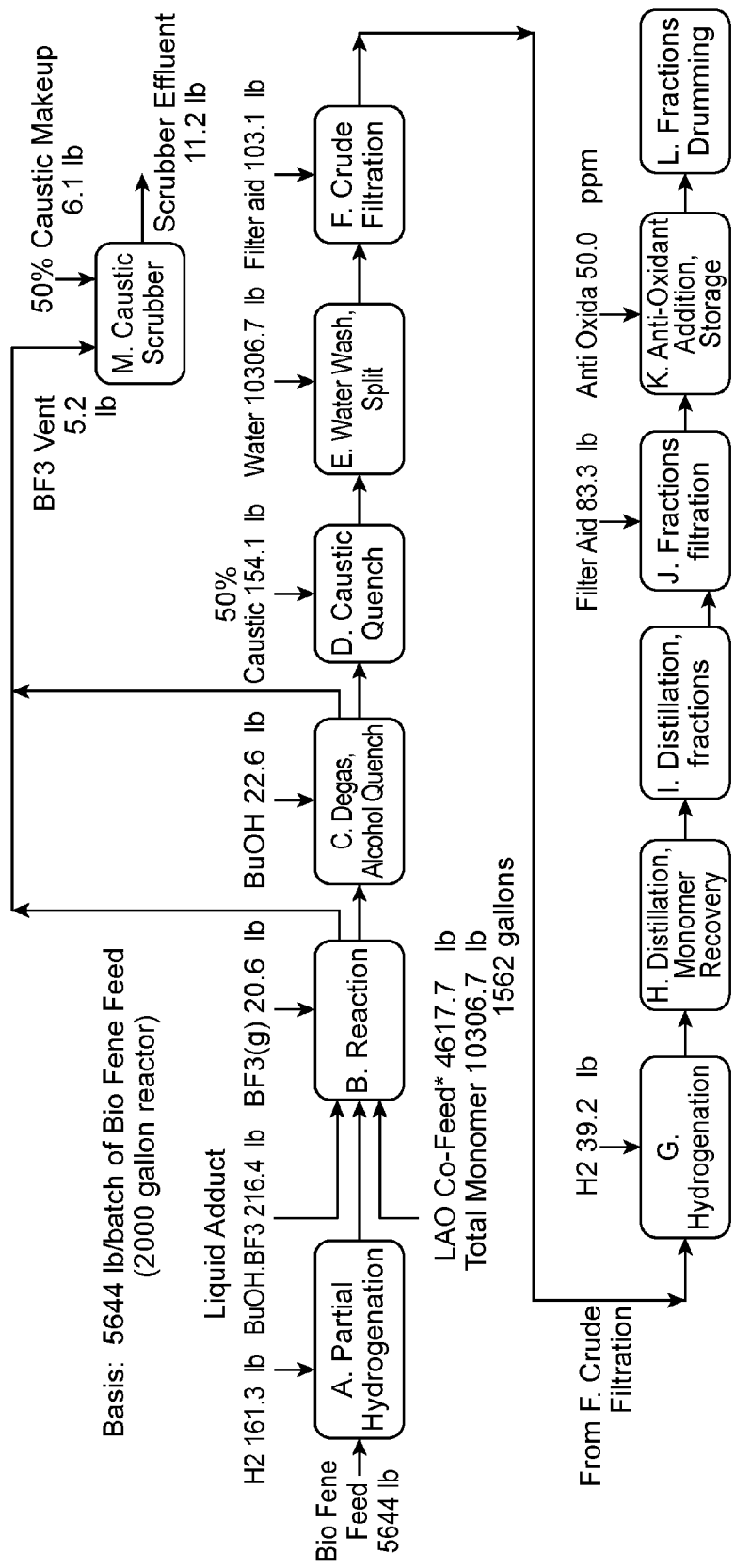
FIG. 3A provides a non-limiting example of a process flow diagram for reacting a hydrocarbon terpene feedstock comprising partially hydrogenated hydrocarbon terpene (β-farnesene is shown as a model hydrocarbon terpene) with one or more olefin co-monomers (a linear alpha-olefin, or LAO, is shown as a model olefin co-monomer) in the presence of a cationic initiator ($BF_3(g)$ with n-butanol as a co-catalyst is shown as a model catalyst system) to form one or more base oils.

One non-limiting example of process using $BF_3$ as a cationic initiator is provided in FIG. 3A. In FIG. 3A, β-farnesene is shown as a model hydrocarbon terpene, but it should be understood that the process illustrated in FIG. 3A applies to hydrocarbon terpene feedstocks in general. As shown, partially hydrogenated hydrocarbon terpene feedstock is provided in Step A. It should be understood that in some cases, the hydrocarbon terpene feedstock is treated prior to use, e.g., filtered using basic alumina, silica, or the like, to remove impurities such as oxygenates (e.g., alcohols, acids, glycerides, and/or epoxides), residual catalyst if partially hydrogenated, and any other contaminants that may be present. In some variations, the hydrocarbon terpene feedstock is treated prior to use to remove oxygenates and/or other impurities using molecular sieves (e.g., 13× molecular sieves), or by caustic wash followed by water wash, centrifuge, and removal of aqueous layer. In some cases the hydrocarbon terpene is treated using any suitable method (e.g., filtered using basic alumina, silica, or the like, treated with molecular sieves, or by caustic wash followed by water wash, centrifuge, and removal of aqueous layer) prior to partial hydrogenation to remove impurities such as oxygenates. The partially hydrogenated feedstock may be produced in situ as needed (e.g., as described in connection with FIGS. 5 and 6), or may be produced ahead of time and drummed or otherwise stored. Although not shown explicitly in FIG. 3A, in some variations, a step prior to Step A is included in which the hydrocarbon terpene (e.g., β-farnesene) is partially hydrogenated to produce a partially hydrogenated feedstock used in Step A. The coupling reaction occurs in a closed, continuously stirred reactor in step B. Although FIG. 3A indicates one or more olefin co-monomers, this process flow diagram also applies to the situation in which the only feedstock is partially hydrogenated hydrocarbon terpene (e.g., partially hydrogenated farnesene, β-farnesene or α-farnesene). The feedstocks and catalysts may be fed into the reactor using any procedure applicable to the particular feedstocks and catalysts.

Figure 3B:
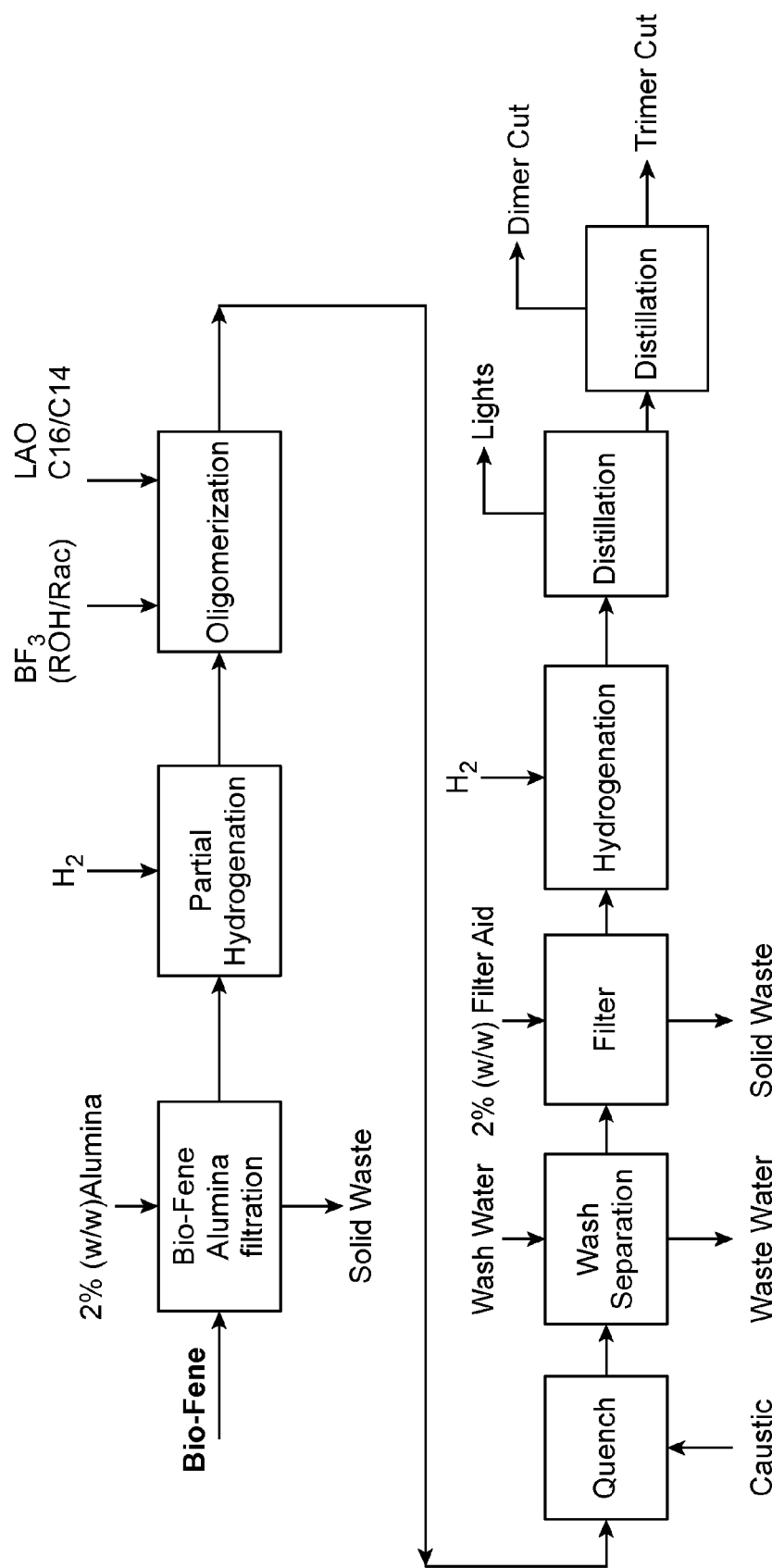
FIG. 3B provides an additional non-limiting example of a process flow diagram for reacting a hydrocarbon terpene feedstock comprising partially hydrogenated hydrocarbon terpene (β-farnesene is shown as a model hydrocarbon terpene) with one or more olefin co-monomers (a mixture of $C_{14}$ and $C_{16}$ LAO is shown as a model olefin co-monomer) in the presence of a cationic initiator (BF3(g) with an alkyl alcohol (ROH) and an alkyl acetate (Rac) as co-catalysts is shown as a model catalyst system) to form one or more base oils.
Figure 3C:
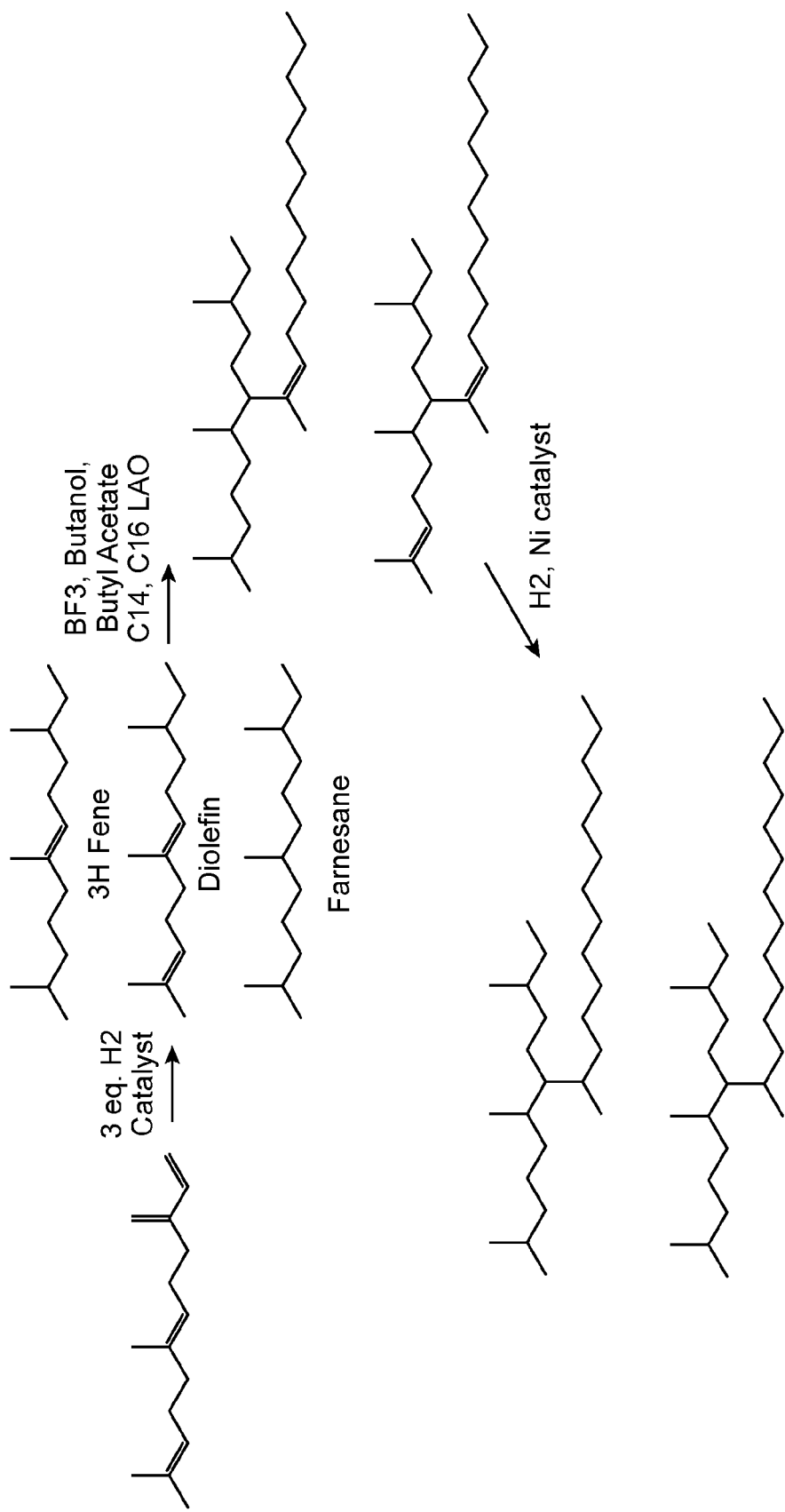
FIG. 3C provides a non-limiting example of a reaction scheme for converting a hydrocarbon terpene to a base oil.

FIG. 3B shows another non-limiting example of a coupling reaction using $BF_3$ as a cationic initiator to couple a hydrocarbon feedstock with one or more olefin comonomers, and FIG. 3C shows a representative reaction scheme. It should be noted that the dimer structures shown in FIG. 3C are representative only. Other dimer structures are contemplated, and trimers and other higher order oligomers may be formed. In FIG. 3B, β-farnesene is shown as a model hydrocarbon terpene. Optionally, the hydrocarbon terpene is treated prior to partial hydrogenation to remove oxygenates. For example, about 2 wt % basic alumina may be sufficient to remove oxygenates such as alcohols, acids, glycerides and epoxides. In the example shown in FIG. 3B, the catalyst system used is BF3(g) with an alcohol having formula ROH and an alkyl acetate denoted as Rac, where the alkyl group R of the acetate Rac is the same as R for the alcohol ROH. In the example shown in FIG. 3B, the olefin comonomer comprises a mixture of 1-hexadecene and 1-tetradecene. Following the oligomerization reaction, the reaction mixture is quenched using caustic, followed by a water wash and separation. The washed reaction mixture is then filtered using a filter aid (e.g., about 2 wt % filter aid), to produce solid waste and a filtered crude olefinic mixture. The crude olefinic mixture is hydrogenated using standard techniques (e.g., a nickel catalyst) to produce a crude saturate. The crude saturate undergoes one or more stripping or distillation steps to remove monomeric species and other light ends.

In some variations, unreacted hydrogenated monomers may be recovered and used for another purpose, e.g., as a solvent for lubricant products, or as a diesel fuel. The crude saturate with the monomeric species removed may be used as is, or may undergo one or more additional distillation steps. In the example shown in FIG. 3B, a distillation step is used to separate a dimer cut, and to leave as residue trimers and any higher order oligomers that may have been produced by the reaction. It should be pointed out that a variety of distillation schemes are contemplated, where distillation conditions can be set to provide any desired carbon number range. In some variations, residue remaining after distilling out the dimer cut is further distilled under high vacuum to selectively remove trimers. Further details on possible distillation schemes are provided in Section II below.

In certain variations in which the oligomerization catalyst comprises $BF_3$ gas, at least a portion of the $BF_3$ may be introduced into the reactor simultaneously with a co-catalyst (or with two co-catalysts if two are being used). A molar excess (in relation to the co-catalyst or co-catalysts) of $BF_3$ is maintained in the reaction zone of the reactor, e.g., by pressurizing the reactor with $BF_3$ at a pressure of about 1 to 500 psig, e.g. about 1-5 psig, about 2-5 psig, about 1-10 psig, or about 1-20 psig, or about 1-50 psig, or about 1-100 psig, or about 1-200 psig, or about 1-300 psig, or about 1-400 psig, or about 1-500 psig. In some variations, the reactor is pressurized at a pressure of about 1, 2, 3, 4, 5, 6, 7, 8, 9, 10, 11 or 12 psig. In certain variations, the pressure of $BF_3$ is maintained to within about +/−1 psig, or +/−0.5 psig. In some variations, a molar excess of $BF_3$ may be achieved by sparging $BF_3$ through the reaction mixture.

If $BF_3$ and a co-catalyst used, the co-catalyst (which may be delivered as an adduct of $BF_3$ and a protic catalyst) may be added to the reactor together with one or more of the olefinic feeds, or separately. If more than one protic co-catalyst is used with $BF_3$, the co-catalysts may be added to the reactor together with each other, or each co-catalyst may be added separately to the reactor. Two or more co-catalysts may be added together or separately with one or more of the olefinic feed (with partially hydrogenated hydrocarbon terpene feedstock, with one or more olefin co-monomers, or with partially hydrocarbon terpene feedstock and one or more olefin co-monomers). For example, in some variations, multiple co-catalysts may be added together with partially hydrogenated hydrocarbon terpene feedstock, with one or more olefin co-monomers, or with partially hydrogenated hydrocarbon terpene feedstock and one or more olefin co-monomers. In other variations, a first co-catalyst may be added together with one component of an olefinic feed, while another co-catalyst is added with a different component of the olefinic feed, or separately altogether from the first co-catalyst. In another variation, each co-catalyst is added separately to the reactor.

In certain variations, a liquid adduct of $BF_3$ and one or more protic catalysts may be made as follows. The protic co-catalyst or co-catalysts (e.g., an alcohol, an ester (e.g., an acetate), or an alcohol and an ester if two co-catalysts are used) are fed into a glass-lined reactor. The reactor is evacuated (e.g., to less than 50 torr). $BF_3$ gas is fed into the reactor. The reactor is cooled to maintain a temperature between 0° C. and 20° C., e.g., about 0° C., 5° C., 10° C., 15° C., or 20° C. In some variations, the $BF_3$ feed is stopped when a desired molar ratio of $BF_3$:co-catalyst is reached. In some variations, the $BF_3$ feed is stopped when a desired pKa value is reached. For example, it may be desired that the liquid adduct have a pKa that is about equal to or about 90% of the value of an expected pKa for the saturated adduct. In certain variations, a liquid adduct of $BF_3$ and one or more co-catalysts is prepared in a separate reactor, and stored under inert atmosphere and at a sufficiently low temperature (e.g., at a temperature of 15° C. or lower for a $BF_3$:n-butanol or $BF_3$:n-butyl acetate adduct) to keep the adduct stable. When needed, the liquid adduct is fed into the oligomerization reactor that is under $BF_3$ atmosphere. In certain variations, a liquid adduct of $BF_3$ and one or more co-catalysts is prepared in situ in the oligomerization reactor, e.g., by adding one or more co-catalysts to olefinic feed, and delivering $BF_3$ to the reactor to react with the one or more co-catalysts in the presence of the olefinic feed. For example, $BF_3$ can be bubbled or sparged through the reaction mixture containing one of more co-catalysts.

The oligomerization reaction may be carried out at any suitable temperature, e.g., at a temperature in a range from about −20° C. to about 70° C. For example, a reaction temperature may be about −20, −15, −10, −5, 0, 5, 10, 15, 20, 25, 30, 35, 40, 45, 50, 55, 60, 65, or 70° C. In some variations, the reaction temperature is controlled to within about +/−2, +/−1, or +1-0.5° C. One or both of the rate of feed of the olefinic monomers (partially hydrogenated β-farnesene and in some variations one or more olefinic co-monomers) and the rate of deliver of a liquid catalyst adduct may be varied to aid in maintaining a desired temperature.

In certain variations, the oligomerization reaction is carried out using $BF_3$ gas at a pressure of about 1-12 psig (e.g., about 1, 2, 3, 4, 5, 6, 7, 8, 8, 10, 11 or 12 psig), with a liquid adduct of $BF_3$ and an alcohol (e.g., $BF_3$:n-butanol) or a liquid adduct of $BF_3$ and an alcohol and an ester (e.g., $BF_3$:n-butanol and $BF_3$:n-butyl acetate). The relative amounts of olefinic feed, $BF_3$ gas, and liquid adducts of $BF_3$ may be adjusted to tune the oligomerization reaction products, but in some variations, about 0.2 to 1 lb $BF_3$ gas and 2-3 pounds liquid adduct are used per 100 pound of combined olefinic feed (100 lbs partially hydrogenated β-farnesene or 100 lbs partially hydrogenated β-farnesene and olefin co-monomer).

In those variations in which an olefinic feed comprises partially hydrogenated hydrocarbon terpene (e.g., partially hydrogenated β-farnesene) and one or more olefin co-monomers, it is desired to tune the catalysis conditions to minimize coupling between olefin co-monomers (e.g. alpha-olefins) and to maximize cross-coupling between the partially hydrogenated β-farnesene and the olefin co-monomer. In certain variations, such tuning may be accomplished by adjusting the pressure of $BF_3$ in the oligomerization reactor. In some variations, a $BF_3$ pressure in the reactor of about 5 psig or less (e.g., about 5, about 4, about 3, about 2, or about 1 psig) may minimize coupling between olefin co-monomers and maximize cross-coupling between partially hydrogenated β-farnesene and olefin co-monomer.

In some variations, catalyst conditions may be tuned to adjust the relative quantities of dimers, trimers, tetramers, pentamers, etc. For example, for lower molecular weight monomers such as $C_8$ (e.g., 1-octene), $C_{10}$ (e.g., 1-decene), or $C_{12}$ (e.g., 1-dodecene) olefins, it may be desirable to adjust catalysis conditions to produce trimers and tetramers and other higher oligomers over dimers. For heavier molecular weight monomers such as C14 (e.g., 1-tetradecene) or $C_{16}$ (e.g., 1-hexadecene) olefins, it may be desirable to adjust catalysis conditions to produce dimers and trimers over tetramers and higher oligomers. For isoparaffins containing relatively large amounts of branching, it may be desired to adjust catalysis conditions to produce trimers and tetramers and other higher oligomers over dimers, e.g., to increase viscosity index of one or more cuts obtained from the mixture of isoparaffins.

If $BF_3$ and one or more protic co-catalysts is used to catalyze the coupling of a hydrocarbon terpene feedstock with one or more olefin co-monomers, higher conversions the olefin can be achieved by any one of or any combination of two or more of the following: increasing the amount of protic co-catalyst (e.g., a $C_1$-$C_{10}$ primary alcohol such as n-butanol) relative to the amount of $BF_3$; increasing federate; increasing hold times; increasing reaction temperature; and/or increasing $BF_3$. The relative concentration of 1:1 terpene feedstock:olefin adducts as compared to terpene:terpene, olefin:olefin, or trimeric adducts may be increased by any one of or any combination of two or more of the following: increasing reaction temperature; using a primary alcohol in combination with an ester (e.g., n-butanol in combination with n-butyl acetate) as co-catalyst to the $BF_3$, and increase the ratio ester:alcohol (e.g., n-butyl acetate:n-butanol). The use of an ester (e.g., an alkyl acetate such as n-butyl acetate) in combination with a primary alcohol (e.g., n-butanol) may provide a "chain stopper" in which formation of 1:1 terpene feedstock:olefin adduct is favored over higher order adducts.

Referring again to FIGS. 3A-3B, following the oligomerization reaction, the $BF_3$ head pressure may be relieved through a caustic scrubber (e.g., scrubber utilizing 10% caustic solution). Nitrogen is sparged through the crude reaction product and reactor to sweep out $BF_3$ gas from the reactor. The reaction product is pumped out and quenched with an alcohol (e.g., n-butanol, as an inline mixture) (Step C), and subsequently quenched with caustic (e.g., 50% caustic) (Step D), with about 1.5 to 2 lb caustic solution per 100 lb of combined monomer feed. The mixture is water washed (Step E) with about 50 lb water per 100 lb of combined monomer feed. The organic layer separates from the aqueous layer by gravity, and in some variations the organic layer is water washed a second time as in Step E. A crude filtration of the isolated organic layer follows (Step F) using a filter having a mesh of about 10-20 microns. In some variations, a filter designed to remove water particles (e.g., a coalescer filter) is used to filter the crude unhydrogenated reaction product. Following the crude filtration, the reaction mixture is hydrogenated (Step G) to form a mixture of isoparaffins, e.g., hydrogenated using a batch slurry reactor, a fixed bed reactor, or a fluidized bed reactor, as is described herein or known in the art. In some variations, the mixture of isoparaffins obtained in Step G is distilled to remove hydrocarbons corresponding to monomers or other low molecular weight species (Step H). A distillation to remove monomers or other low molecular weight species may, for example, be carried out at about 200° C. to about 250° C. under about 10 mm Hg. Any suitable distillation apparatus may be used. In some variations, a single stage flash distillation apparatus may be used. In some variations, a wiped film distillation apparatus may be used, and in some variations, a fractionation distillation column may be used. In some variations, a distillation apparatus with multiple stages (e.g., 2, 3, 4 or 5 stages) may be used. It is desirable to remove at least about 99% or 99.9% of monomer from the mixture of unhydrogenated isoparaffins obtained in Step G. In some variations, the mixture of isoparaffins (in some cases, with monomers distilled off), can be fractionated to obtain one or more distillation cuts (Step I). Here again, any suitable distillation apparatus using any suitable distillation technique may be used. For example, simple distillation, fraction distillation, or steam distillation may be used. Non-limiting examples of distillation apparatus include a flash distillation apparatus, a wiped film apparatus, a column, or a packed column distillation apparatus having multiple stages (e.g., 2, 3, 4, 5, 6, 7, or 8 stages). In some variations, distillation cuts may be obtained at pot temperatures of up to 300° C. under a maximum pressure of about 1-2 mm Hg, which may correspond to one or more distillation cuts that are collected in a temperature range from about 350° C. to about 500° C., e.g., 350° C. to 380° C., 380° C. to 400° C., 400° C. to 420° C., 420° C. to 435° C., 435° C. to 445° C., 445° C. to 460° C., or 460° C. to 480° C. (with temperatures corresponding to boiling points at atmospheric pressure or atmospheric equivalent temperatures (AET). In some variations, a first distillation cut corresponds to a mixture containing predominantly monomers, and has an initial boiling point of 200° C. and a final boiling point of 370° C., a second distillation cut corresponds to a mixture containing predominantly dimers, and has an initial boiling point of 370° C. and a final boiling point of 450° C., 455° C., 460° C., 465° C., 470° C., or 475° C. Additional distillation schemes that can be used with any of the isoparaffinic mixtures described herein are described in Section II below. Certain fractions may be blended together, depending on the desired characteristics for the final product. In some variations, the residue remaining in the pot after distillation is collected, e.g., residue remaining after distillation up to about 420° C., 430° C., 440° C., 450° C., 455° C., 460° C., 465° C., 470° C., 475° C., or 480° C. (AET if distilled below ambient pressure).

In some variations, the distillation conditions are set to selectively remove monomeric species in a first stage, to vaporize and collect dimeric species in a second cut, and retain trimeric and higher oligomeric species as the residue in the pot. The distillation conditions can be set so that the amount of monomeric species remaining is less than about 1 wt %, less than about 0.5 wt %, less than about 0.2 wt %, or less than about 0.1 wt % in a base oil made from one or more distillation cuts. In some cases, the distillation conditions for the second cut are set so that the distillate contains about 1-15 wt % or about 1-20 wt % trimeric species in addition to dimeric species. In some cases, a higher boiling distillation cut (e.g., a trimer cut) is collected and some of the higher boiling distillation cut is blended with a lower boiling distillation cut (e.g., a dimer cut) to make a base oil. For example, in some variations about 60 wt %, about 50 wt %, about 40 wt %, about 30 wt %, about 20 wt %, about 10 wt %, about 5 wt %, or about 2 wt % of a higher boiling distillation cut (e.g., a trimer cut) is blended with a lower boiling cut (e.g., a dimer cut) to make a base oil having a higher kinematic viscosity, or to increase viscosity index of a base oil. As used herein, "monomer cut" or "monomer fraction" refers to a distillation cut that contains predominantly monomeric species. As used herein, "dimer," "dimer cut" or "dimer fraction" refers to a distillation cut that preferentially selects adducts comprising two monomeric units, e.g., 1:1 terpene:olefin adducts (e.g., so that a product of the distillation is at least about 70%, 75%, 80%, 85%, 90%, 95%, 97%, 98%, or 99% dimeric species). As used herein, "trimer," "trimer cut" "trimer fraction" or "trimer-enriched" cut or fraction refers to a distillation cut that preferentially selects adducts comprising three monomeric units, e.g., 1:2 or 2:1 hydrocarbon terpene:olefin adducts. A trimer cut, trimer fraction or trimer-enriched cut or fraction may in some cases comprise at least about 55%, 60%, 65%, 70%, 75%, 80%, 85%, 90%, or 95% trimeric species). It should be noted that in some circumstances a trimer cut may contain higher oligomers such as tetramers, pentamers, and even higher oligomers. For example, a trimer cut may contain about 5%, 10%, 15%, 20%, 25%, 30%, 35%, 40%, or 45% tetramers and higher oligomers. In some cases, the mixture of isoparaffins is not fractionated (Step I is skipped). The desired isoparaffinic mixture is filtered (Step J) to filter out any solids or other impurities (e.g., oxygenates) remaining after distillation. Any suitable filter may be used, e.g., a filter having a mesh size of 10-20 microns. For example, a filter used for polishing hydrocarbon liquids having limited amounts of solids may be used, e.g., a filter available from Sparkler Filters, Inc., Conroe, Tex. In some cases, a precoat filter or filter aid may be used to increase throughput of the liquid. In some situations, an antioxidant may be added to the filtered isoparaffins, e.g., at a level of about 50-100 ppm.

Figure 4:
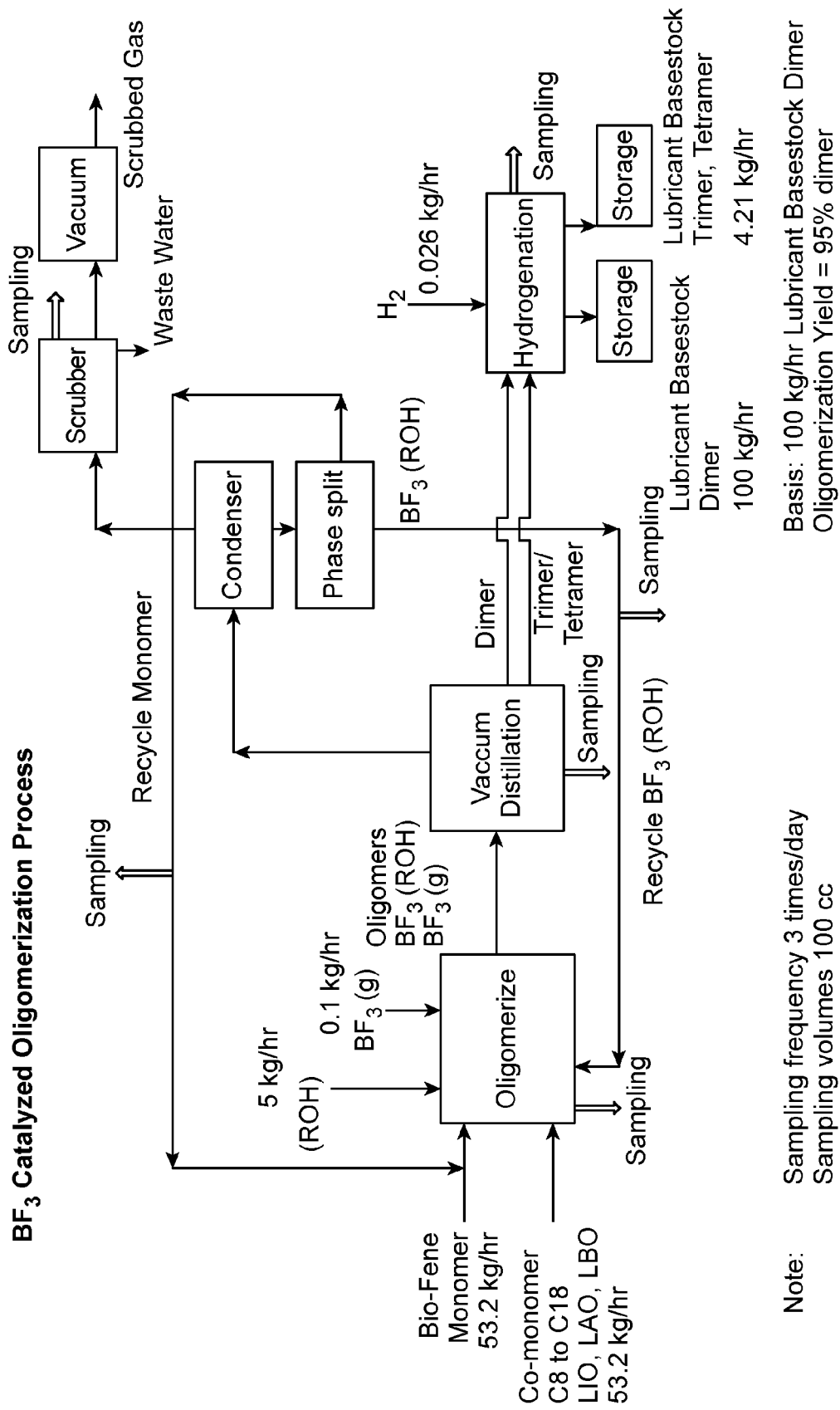
FIG. 4 provides a non-limiting example of a process flow diagram for reacting a hydrocarbon terpene feedstock comprising partially hydrogenated hydrocarbon terpene (β-farnesene is shown as a model hydrocarbon terpene) with one or more olefin co-monomers ($C_8$-$C_{18}$ olefins are shown as model olefin co-monomers) in the presence of a cationic initiator ($BF_3(g)$ with an alcohol co-catalyst having the formula ROH, where R as used in the context of FIG. 4 refers to a $C_1$-$C_{10}$ linear or branched alkyl group, is shown as a model cationic initiator) to form one or more base oils.

An example of an alternate process flow diagram is provided in FIG. 4. Here again, β-farnesene is shown as a model hydrocarbon terpene feedstock. It should be understood that the process flow shown in FIG. 4 applies to the situation in which partially hydrogenated hydrocarbon terpene feedstock (e.g., partially hydrogenated β-farnesene) is the only olefin feed, as well as to the situation in which partially hydrogenated farnesene and an olefin co-monomer are used in an olefinic feed. The process illustrated in FIG. 4 includes a distillation step following the oligomerization and prior to hydrogenation. Such a scenario may be used, for example, when it is desired to recycle unreacted monomer back into the olefinic feed to the oligomerization reactor. As shown in FIG. 4, in some variations, a catalyst may be recycled.

In some variations of a process, β-farnesene is charged to a reactor equipped with a mechanical stirrer and a nitrogen purge. 25 g alumina (Selexorb CDX) per 1000 g farnesene is added to the reactor. The reactor is agitated for 120 minutes at 25-30° C. under a nitrogen headspace. The TAN of the mixture is monitored until it reaches a TAN value of about 0.1. The alumina is removed by filtration (e.g., through 25 micron filter). Nitrogen atmosphere is maintained over the treated β-farnesene. The treated β-farnesene is charged to a reactor and 4.5 g 0.3 wt % $Pd/Al_2O_3$ per 750 g β-farnesene is added to the reactor and the reactor is sealed. The reactor is purged with dry nitrogen several times. After the nitrogen purge, the reactor is purged with hydrogen several times (20 psig to 0). After purging, the reactor is pressurized to 100 psig with hydrogen. The reaction is heated to 100° C. using the exotherm from the reaction and external heat, and is controlled to <100° C. using external heating and cooling and by controlling hydrogen flow into the reactor. The hydrogen delivered to the reactor is monitored using an in-line mass meter or a pre-weighed hydrogen reservoir. After approximately 1.5 equivalents of hydrogen have been delivered to the reactor, the temperature of the reactor is raised to 220° C. and the hydrogen pressure is reduced to less than 10 psig, followed by back addition of hydrogen to 15 psig so that the desired total equivalents of hydrogen are consumed (e.g., about 2.9, 3.0, or 3.1 equivalents). The composition of the selectively hydrogenated b-farnesene can be monitored by GC-FID or GC-MS as described in the Examples so that hydrogenation is stopped after a desired mono-olefin and di-olefin content are reached (e.g., about 70-85% mono-olefin and about 5% or less or about 3% or less or about 2% or less di-olefin). Following the selective hydrogenation, the reactor is allowed to cool and the catalyst is removed using a filter pre-coated with filter aid. A pre-mix is made in a flask comprising selectively hydrogenated farnesene, 1-tetradecene, 1-hexadecene, n-butanol and n-butyl acetate. The mass ratios of partially hydrogenated farnesene:1-tetradecene:1-hexadence:n-butanol:n-butyl acetate are 931:502:332:8:12.5. A vacuum of 50 mm Hg is applied to a reactor for about 15 minutes. $BF_3$ gas is slowly charged to the reactor until a pressure of 3 psig is reached. The pre-mix is delivered to the reactor over a period of about 2 hours. The reaction temperature is maintained between 25-35° C. and the $BF_3$ pressure is maintained at 3 psig+−0.5 psig. After the pre-mix has been delivered to the reactor, the reactor is held and temperature and pressure for about 1 hour. A quench solution of 95 g of 30% NaOH is charged to another flask equipped with a stirring bar. The reaction mixture is charged to the quench flask using a pump. The quenching reaction is stirred for about 30 minutes and the temperature is controlled between 45-55° C. The quenched reaction mixture is allowed to settle for about 1 hour, and the lower aqueous layer is separated, while the intermediate rag layer remains with the hydrocarbon layer. A water wash of the hydrocarbon/rag layer is performed using 890 g water and mixing for 30 minutes at 45-50° C., and settling for 1 hour. The lower aqueous layer is removed, and any rag layer remains with the hydrocarbon phase. The water wash is repeated. After the final water wash, the organic phase is filtered through Celite. A target product contains less than 35% monomer and greater than 65% oligomers. The unsaturated crude reaction product is hydrogenated in a pressure reactor capable of operating at 500 psig. Any suitable hydrogenation catalyst can be used (e.g., Pricat Ni 62-15P by Johnson Matthey). The mixture is nitrogen purged, purged with hydrogen, and pressurized with hydrogen to 100 psig. A combination of self-heat from the exotherm and external heat are used to raise the hydrogenation pressure to 190-200° C. After the reactor reaches temperature, the hydrogen pressure is increased to 500 psig. The hydrogenation reaction is allowed to proceed until complete, typically 6-10 hours. The target bromine index (measured by ASTM D2710) is less than 100. The catalyst is removed from the hydrogenated mixture by filtration.

More than one reactor in series may be used. The particular arrangement and staging of reactions in serial reactors can be adjusted according to the nature of the oligomerization reaction. For example, an initial stage of the reaction may be completed in a first reactor, and a final stage in which the reaction is allowed to reach steady state or proceed to a desired degree of completion is completed in a second reactor. In some variations in which more than one reactor in series are used, $BF_3$ catalyst, co-catalyst (or co-catalysts if appropriate) and olefinic feed are added only to the first reactor, and a second reactor in series is used to hold to allow steady state to be achieved, and to hold the reaction for a desired time thereafter. The progress of the reaction may be monitored by sampling from the second reactor.

In some variations, β-farnesene or partially hydrogenated β-farnesene (e.g., partially hydrogenated β-farnesene that has been about 75% hydrogenated and comprises at least about 50%, at least about 55%, at least about 60%, at least about 65%, at least about 70%, at least about 75%, at least about 80%, or at least about 85% mono-olefin) is reacted with an olefin co-monomer selected from the group consisting of 1-hexadecene, 1-tetradecene, and a mixture of 1-hexadecene and 1-tetradecene in the presence of a cationic initiator to form branched alkenes, which are hydrogenated to form isoparaffins. In some variations, partially hydrogenated β-farnesene that has been about 75% hydrogenated and comprises at least about 50% mono-olefin and about 10% or less di-olefin, at least about 50% mono-olefin and about 5% or less di-olefin, at least about 50% mono-olefin and about 3% or less di-olefin, at least about 60% mono-olefin and about 10% or less di-olefin, at least about 60% mono-olefin and about 5% or less di-olefin, at least about 60% mono-olefin and about 3% or less di-olefin, at least about 70% mono-olefin and about 10% or less di-olefin, at least about 70% mono-olefin and about 5% or less di-olefin, at least about 70% mono-olefin and about 3% or less di-olefin, at least about 80% mono-olefin and about 10% or less di-olefin, at least about 80% mono-olefin and about 5% or less di-olefin, or at least about 80% mono-olefin and about 3% or less di-olefin is reacted with an olefin co-monomer selected from the group consisting of 1-hexadecene, 1-tetradecene, and a mixture of 1-hexadecene and 1-tetradecene in the presence of a cationic initiator to form branched alkenes, which are hydrogenated to form isoparaffins.

Monomeric species can be removed from the isoparaffins by distillation. If distillation is conducted before hydrogenation, monomeric species may be recycled for reuse in the coupling reaction. If distillation is conducted after hydrogenation, distilled off monomeric species may be used as a diesel fuel comprising farnesane and tetradecane, or farnesane and hexadecane, or farnesane, tetradecane and hexadecane. Farnesane may comprise about 80-85 wt % of the distilled off monomer fraction, with alkane originating from olefin comonomer comprising about 15-20 wt % of the distilled off monomer fraction. The monomeric species may be collected as species having boiling points in the range from about 200° C. to about 370° C. After removal of the monomeric species, the isoparaffins can be further fractionated to produce two distillation cuts: a lower boiling distillation cut comprising predominantly dimeric species (less than about 0.5% monomer or less than about 0.2% monomer, about 5% or less trimer, and higher oligomers) and having a boiling point range between about 370° C. and 450° C., about 370° C. and about 455° C., about 370° C. and about 460° C., about 370° C. and about 465° C., about 370° C. and about 470° C., about 370° C. and about 475° C., and a higher boiling distillation cut comprising predominantly trimeric species and higher oligomers (no detectable monomer, and less than about 5% dimer, or less than about 2% dimer) corresponding to the residue having a boiling point range higher than about 450° C., 455° C., 460° C., 465° C., 470° C., or 475° C. The lower boiling distillation cut may be used to make a base oil having a kinematic viscosity at 100° C. of about 4 cSt, and the higher boiling distillation cut (residue) may be used to make a base oil having a kinematic viscosity of about 10 cSt, about 11 cSt, about 12 cSt, or greater than about 12 cSt. In some variations, one or more further distillation cuts may be obtained from the residue having a boiling point range higher than about 450° C., 455° C., 460° C., 465° C., 470° C., or 475° C. For example an additional distillation step may be added that is conducted at a reduced pressure (e.g., about 0.5 mm Hg or less, about 0.1 mm Hg or less, about 0.05 mm Hg or less, about 0.01 mm Hg or less, about 0.005 mm Hg or less, about 0.001 mm Hg or less, which may in some instances be achieved using a wiped film evaporator or a short path distillation) to selectively vaporize trimeric species (e.g., to produce a composition comprising at least about 80%, at least about 85%, at least about 90%, or at least about 95% trimeric species, with the balance being tetramers and higher order oligomers), and to produce a new residue comprising an increased concentration of higher order oligomers (e.g., about 60:40, about 65:35, about 70:30, or about 75:25 trimer:tetramer and higher order oligomers). Additional distillation schemes that can be used with any of the isoparaffinic mixtures described herein are described in Section II below. If a mixture of 1-hexadecene and 1-tetradecene is used as the olefin co-monomer, the relative quantities of 1-hexadecene and 1-tetradecene may be varied to tune the properties of the resulting base oils. For example, the ratio of 1-hexadecene to 1-tetradecene may be varied to result in a composition that has desired viscosity index and cold temperature flow properties (e.g., pour point or cold cranking simulator viscosity). For example, the relative amount of 1-hexadecene may be increased to increase kinematic viscosity and/or viscosity index, and the relative amount of 1-tetradecene may be increased to lower cold cranking simulator viscosity. In some variations, β-farnesene or partially hydrogenated β-farnesene is reacted with a mixture of 1-hexadecene and 1-tetradecene in the presence of a cationic initiator (e.g., BF3, a $C_1$-$C_6$ alcohol and a $C_1$-$C_6$ alkyl acetate such as n-butanol and n-butyl acetate) to form branched alkenes, which can be hydrogenated to form isoparaffins. Monomeric species can be removed (e.g., by distillation) so that the resulting isoparaffins contain less than 1 wt %, less than 0.5 wt %, less than 0.2 wt %, or less than 0.1 wt % monomeric species. The isoparaffins can be fractionated into multiple distillation cuts, which can be used to form more than one base oil. For example, the isoparaffins can be fractionated into a dimer cut, which can be used as a base oil having a kinematic viscosity at 100° C. of about 4-5 cSt, and a trimer-enriched cut, which can be used as a base oil having a kinematic viscosity at 100° C. of about 10 cSt, about 11 cSt, about 12 cSt, or greater than about 12 cSt. The molar ratio of 1-hexadecene:1-tetradecene may be about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some variations, the ratio of 1-hexadecene:1-tetradecene is about 80:20, 70:30, 60:40, 50:50, 40:60, 30:70, or 20:80. In some cases, the ratio of 1-hexadecene:1-tetradecene is about 60:40. In some cases, the ratio of 1-hexadecene:1-tetradecene is about 50:50. In some cases, the ratio of 1-hexadecane:1-tetradecene is about 40:60. In some cases, the ratio of 1-hexadecene:1-tetradecene is about 2:98. In some cases, the ratio of 1-hexadecene:1-tetradecene is about 5:95. In some cases, the ratio of 1-hexadecene:1-tetradecene is about 10:90. In some cases, the ratio 1-hexadecene:1-tetradecene is 20:80. In some cases, the ratio 1-hexadecene:1-tetradecene is about 30:70. In some variations, the ratio of 1-hexadecene:1-tetradecene may be adjusted so that the dimer cut (or a blend of the dimer cut with the trimer cut) has a viscosity index of about 120 or greater (e.g., about 120-125, or 122-125) and a cold cranking simulator viscosity at −30° C. of about 1800 cP or less (e.g., about 1800 or less, 1500 or less, 1300 or less, 1200 or less, 1100 or less, or 1000 or less). In one variation, a dimer cut has a viscosity index of about 120-124 and a cold cranking simulator viscosity at −30° C. of about 1000-1500 cP. In one variation, a dimer cut blended with about 10 wt % or less, or about 5 wt % or less trimer cut has a viscosity index of about 120-124 and a cold cranking simulator viscosity at −30° C. of about 1000-1500 cP. In one variation, a blend comprising about 50% dimer cut and 50% trimer-enriched cut makes a base oil having a KV at 100° C. of about 6 cSt, a viscosity index of about 130-135, and a CCS viscosity at −30° C. of about 2800-3000 cP. In one variation, a distillation blend is devised to have a kinematic viscosity at 100° C. of about 6 cSt, a viscosity index for about 125-135, and a CCS viscosity at −35° C. of about 5000-8000 cP (e.g., about 7000 cP or less, or about 6500 cP or less). In one variation, a trimer-enriched cut has a kinematic viscosity of about 12 cSt and a viscosity index of about 120 or greater, about 125 or greater, or about 130 or greater. Example 29 provides non-limiting examples of a family of base oils with KV at 100° C. ranging from 4-12 cSt that can be made derived from a single oligomerization reaction between partially hydrogenated β-farnesene and a mixture of 1-hexadecene and 1-tetradecene using $BF_3(g)$ with n-butanol and n-butyl acetate as a catalyst system. Tables 29A and 29B, and FIGS. 14A-14D illustrate some of the possible base oils that can be made using the methods described herein. It should be pointed out that the distillation cuts and blends illustrated in Example 29 are non-limiting examples. Additional distillation cuts and schemes, and additional blended mixtures are envisioned that may be used to tune properties of base oils. Distillation schemes may be used that produce a mixture of dimers and trimers directly, without a blending step. Even if the C14-C16 olefin co-monomer is derived from a petroleum source, if the β-farnesene is derived from a renewable carbon source (e.g., by microorganisms), the dimer cut may have a renewable carbon content of at least about 40%, or at least about 50%, and the trimer-enriched cut may have a renewable carbon content of at least about 25% or at least about 30%.

As shown, the methods described herein provide a family of base oils that have high viscosity index for base oils having KV at 100° C. ranging from 4 cSt to 12 cSt. Base oils having renewable carbon content of about 50%, KV at 100° C. of 4 cSt, viscosity index of 124 and CCS at −30° C. of about 1000 cP have been made. Base oils having renewable carbon content in a range from about 30-40%, KV at 100° C. of 6 cSt, viscosity index of 132 and CCS at −30° C. of about 3000 cP, and CCS at −25° C. of about 1740 cP have been made. A variety of base oils having renewable carbon content of at least about 30%, KV at 100° C. of 7-12 cSt and viscosity index>128 have been made. In some variations, the base oils made by the methods described herein have additional specifications. For examples, base oils as described herein may have a bright and clear appearance, a color of <0.5 as measured by ASTM D1500, a Bromine index (measured by ASTM D2710) of less than 200, and an evaporative weight loss (e.g., Noack evaporative weight loss measured by ASTM D5800 or TGA-Noack evaporative weight loss measured by ASTM D6375) of about 4-15 wt %, or 4-12 wt %, and a pour point (measured by ASTM D97) in a range from about −35° C. to about −65° C.

In some variations, a mono-olefinic hydrocarbon terpene feedstock containing very low quantities of diene, very low quantities of triene, and no detectable amount of conjugated species is reacted with one or more non-terpene olefin co-monomers (e.g., one or more alpha-olefins) in the presence of a Lewis acid catalyst (e.g., $BF_3$ and one or more protic co-catalysts as described herein) to make a base oil. The presence of dienes (or higher polyenes) may cause formation of undesired side products or cross-reactions, e.g., low boiling branched species. The quantity of dienes may be limited to about 5% or less, about 4% or less, about 3% or less, about 2% or less, about 1% or less, about 0.5% or less, about 0.3% or less, or about 0.1% or less. The quantity of higher polyenes may be limited to about 0.5% or less, about 0.3% or less, about 0.1% or less, or may be undetectable. The use of a hydrocarbon terpene feedstock containing essentially only mono-olefin and saturated alkane may result in oligomerization products that contain reduced quantities of low-boiling species that may cause undesired reduction of viscosity index and/or degradation of low temperature properties (e.g., increase pour point or increase CCS viscosity at −30° C. or −35° C.). Such low boiling species may be due to more branched terpene:terpene adducts in some cases. Non-limiting examples of low diene content feedstocks are described in Section B herein, and also provided in the Examples. In some variations, a mono-olefinic feedstock comprising at least about 50%, at least about 60%, at least about 70%, or at least about 80% hexahydrofarnesene, at most about 5%, at most about 3%, at most about 2%, at most about 1%, or at most about 0.5% tetrahydrofarnesene, less than about 0.3% or less than about 0.1% dihydrofarnesene, with the balance being farnesane is reacted with a non-terpene alpha-olefin co-monomer comprising a mixture of 1-tetradecene:1-hexadecene (e.g., about 50:50, 60:40, 70:30, 80:20, 90:10, or 95:5 1-tetradecene:1-hexadecene) using $BF_3$ and a co-catalyst comprising a $C_1$-$C_{10}$ primary alcohol and optionally a corresponding alkyl acetate (e.g., 1-butanol and n-butyl acetate) to form an unsaturated crude mixture. The unsaturated crude mixture is hydrogenated (after removal of the catalyst) to form a mixture of isoparaffins. The isoparaffins are distilled into a variety of distillation cuts to make a family of base oils as described herein. As shown in Example 48, the use of a low diene content hydrocarbon terpene can produce a base oil having low temperature CCS viscosities that are comparable to that of Group III or Group III plus base oils.

In some variations, the base oils made by oligomerizing a hydrocarbon terpene with one or more non-terpene alpha-olefins using a Lewis acid catalyst comprise controlled and tunable amounts of dimers, trimers, and higher oligomers. As described herein, reaction conditions can be controlled to limit formation of higher oligomers. Distillation conditions can be devised to select certain fractions. For example, certain base oils comprise essentially all dimeric species, with about 3% trimeric species, and no detectable amount of tetramer or higher oligomers. In some variations, base oils comprise a mixture of dimers and trimers, with limited amounts of tetramers and higher oligomers (e.g., about 1% or less). In some variations, base oils comprise a mixture of trimers and tetramers, with limited amounts of dimers (e.g., about 1% or less).

d. Acidic Ionic Liquids

In certain variations, acidic ionic liquids (e.g., acidic room temperature ionic liquids) can be used to catalyze the coupling between a hydrocarbon terpene feedstock as described herein and one or more olefin co-monomers (e.g., one or more alpha-olefin co-monomers). In some cases, the ionic liquid acts as both a catalyst and a solvent for the reaction.

"Ionic liquids" as used herein refers to molten salts containing only cations and anions that have low melting points (e.g., between about −100° C. and 200° C.). Ionic liquids have negligible vapor pressure, and exhibit air and moisture stability. Their properties (e.g., hydrophilicity and/or lipophilicity) can be tuned by varying the pairing of cations and anions. Depending on their structures and compositions, ionic liquids are able to dissolve a variety of organic, inorganic, and organometallic compounds. In certain variations, an ionic liquid can be recycled after use. Ionic liquids generally demonstrate poor miscibility with common organic solvents but high compatibility with transition metals, so that ionic liquids may be used in multi-phase reaction scheme in which the ionic liquid provides a first liquid phase, and reactants or products are in a second liquid phase.

In certain variations, a pyridinium or imidazolium ionic liquid can be used as a catalyst, or as both a solvent and a catalyst. The pyridinium or imidazolium rings can be alkylated to incorporate alkyl groups onto the nitrogen, e.g., linear, branched or cyclic $C_1$-$C_{20}$ alkyl groups. In some variations, cyclic or non-cyclic quaternary ammonium salts are used. In still other variations, phosphonium or sulphonium based salts are used. Non-limiting examples of ionic liquid include acidic chloraluminate ionic liquids such as acidic pyridinium chloroaluminates or alkyl-substituted pyridinium chloraluminates, e.g., n-butylpyridinium chloroaluminate. In certain variations, an ionic liquid as disclosed herein or otherwise known is used in combination with a co-catalyst or promoter, such as a proton donating acid, e.g., sulfuric acid, hydrochloric acid, hydrofluoric acid, phosphoric acid, hydrobromic acid, or hydroiodic acid.

3. Coupling Reactions Involving Transition Metal or Lanthanide Metal Catalyzed Addition of Olefin Co-Monomer to Hydrocarbon Terpene Feedstock In some embodiments, the catalyst used for coupling the hydrocarbon terpene feedstock with one or more alpha-olefin co-monomers comprises a transition metal catalyst or a lanthanide metal catalyst that known in the art to be capable of catalyzing oligomerization of alpha-olefins. In some variations, the alpha-olefin comonomers are non-terpenes. In some variations, a catalyst comprises an early transition metal (e.g., a Group 4, Group 5, Group 6, or Group 7 transition metal). In other variations, a catalyst comprises a late transition metal (e.g., a Group 8, Group 9, or Group 10 transition metal). In still other variations, a catalyst comprises a metal from the lanthanide series (e.g., La, Ce, Pr, Nd, Pm, Gd, Tb, Dy, Ho, Er, Tm, Yb or Lu). Certain metal containing catalysts may be classified as Ziegler-Natta catalysts or metallocene catalysts, as described in more detail below.

The hydrocarbon terpene feedstock used together with the early transition metal, late transition metal, lanthanide metal, Ziegler-Natta, or metallocene catalysts described herein or otherwise known may be any hydrocarbon terpene feedstock as described herein or otherwise known. In some variations, the hydrocarbon terpene feedstock used together with the early transition metal, late transition metal, lanthanide metal, Ziegler-Natta or metallocene catalysts described herein or otherwise known may be a hydrocarbon terpene feedstock comprising conjugated diene moieties, e.g., myrcene, ocimene, β-farnesene, or α-farnesene. In other variations, the hydrocarbon terpene feedstock used together with these catalysts is a partially hydrogenated hydrocarbon terpene feedstock, e.g., partially hydrogenated farnesene or partially hydrogenated myrcene may be used as a hydrocarbon terpene feedstock in certain situations. In still other variations, a single species of partially hydrogenated hydrocarbon terpene feedstock may be used with the early transition metal, late transition metal, lanthanide metal, Ziegler-Natta, or metallocene catalysts described herein or otherwise known. For example, a hydrocarbon terpene feedstock comprising a compound having formula A11, A12, A13 or A14 may be used.

Non-limiting examples of early transition metals that can be used in catalysts that can be used in the methods described herein include Group 4 elements such as titanium, zirconium or hafnium, Group 5 elements such as vanadium, niobium, or tantalum, Group 6 elements such as chromium, molybdenum or tungsten, and Group 7 elements such as technetium or rhenium. For example, catalysts comprising $ZrCl_4$, $HfCl_4$, $CrCl_3$, $CrCl_3(THF)_3$, $VCl_3$, or $TiCl_4$ may be used in certain instances, where THF refers to tetrahydrofuran. In some variations, a catalyst comprising an early transition metal (e.g., early transition metal halide, early transition metal alkyl, early transition metal amide, or early transition metal alkoxide) is used in combination with an aluminum co-catalyst and/or one or more non-coordinating anions. Non-limiting examples of early transition metal containing compounds that can be used with an aluminum co-catalyst and/or one or more non-coordinating anions include early transition metal halides, metal benzyls, metal amides, and metal alkoxides. For example, $ZrCl_4$, $HfCl_4$, $TiCl_4$, $ZrBz_4$ and $HfBz_4$, where Bz refers to a benzyl group, may be used with an aluminum co-catalyst and/or one or more non-coordinating anions. Non-limiting examples of early transition metal amides that can be used with an aluminum co-catalyst and/or one or more non-coordinating anions include $Zr(NMe_2)_4$, $Hf(NMe_2)_4$ and $Ti(NMe_2)_4$. Non-limiting examples of early transition metal alkoxides that can be used with an aluminum co-catalyst and/or one or more non-coordinating anions include $Zr(OtBu)_4$, $Zr(OEt)_4$, $Zr(OnBu)_4$, $Ti(OEt)_4$ and $Ti(OnBu)_4$. Other non-limiting examples of early transition metal catalysts that can be used with an aluminum co-catalyst and/or one or more non-coordinating anions include $CrPh_3(THF)_3$ and $Cr(acac)_3$, where acac refers to acetylacetonate. The aluminum co-catalyst that may be used in combination with the aforementioned early transition metal catalysts may be $AlR^{21}R^{22}R^{23}$, where $R^{21}$, $R^{22}$ and $R^{23}$ are the same or different, and each of $R^{21}$, $R^{22}$, and $R^{23}$ may independently be hydrogen, a $C_1$-$C_{30}$ alkyl group, or a halide, or in some variations the aluminum co-catalyst may be a methylaluminoxane. Non-limiting examples of non-coordinating anions that can be used either in addition to or instead of an aluminum co-catalyst include boron-containing compounds such as $B(C_6F_5)_3$ or aluminum tetrakispentafluorophenylborate. If an aluminum co-catalyst is used, aluminum to metal (Al:M) ratios can vary from about 0.5 to 1000. In some variations, increasing Al:M ratio may decrease molecular weight of the oligomer.

In some variations, coordination complex catalysts such as catalyst systems comprising an alkylaluminum compound together with $TiCl_4$ or alkyl halides (e.g., ethylaluminum sesquichloride/$TiCl_4$) may be used.

In some variations, an early transition metal catalyst comprising a mono-cyclopentadienyl metal halide is used in the methods described herein for catalytically coupling a hydrocarbon terpene feedstock with one or more alpha-olefins. Non-limiting examples of early transition metal catalysts comprising a mono-cyclopentadienyl metal halide include $CpTiCl_3$ and $CpZrCl_3$, where Cp refers to a cyclopentadienyl group.

In some variations, a metallocene catalyst is used in the methods described herein for catalytically coupling a hydrocarbon terpene feedstock with one or more alpha-olefins. Any suitable metallocene catalyst known in the art for oligomerizing alpha-olefins may be used, including non-bridged and bridged metallocene catalysts. Non-limiting examples of suitable metallocene catalysts include $Cp_2ZrCl_2$, $Cp_2HfCl_2$, where Cp is cyclopentadienyl group. If a bridged metallocene catalyst is used, the bridge may be any suitable alkyl-substituted silicon or carbon linkage (e.g., carbon linkage containing 1 or 2 carbons). Additional description of suitable metallocene catalysts is provided in sections below.

In certain variations, post-metallocene catalysts based on early transition metals may be used in the methods described herein. Non-limiting examples of post-metallocene catalysts include Ti, Zr, and Hf catalyst precursors bearing carbon, nitrogen and/or oxygen atoms coordinated to the metal center, and examples of ancillary ligands in this family include pyridyl amines, biphenyl phenols, phenoxyketimine, and amine phenolate ligands.

Chromium-containing catalysts that may be used include those shown to be selectivity for ethylene trimerization and tetramerization. For example the diphosphine ligand (o-MeO—$C_6H_4$)$_2$PN(Me)P(o-MeO—$C_6H_4$)$_2$ may be used in combination with CrCl$_3$(THF)$_3$ and methylaluminoxane. Other examples include ligands with sulfur or oxygen coordination to chromium.

Late transition metal catalysts that may be used in the methods described herein include catalyst systems based on Group 8 elements such as iron, Group 9 elements such as cobalt or rhodium, and Group 10 elements such as nickel or palladium. Non-limiting examples of catalysts comprising late transition metals that can be used in the methods described herein include nickel catalysts with alpha-diimine ligands, palladium catalysts with alpha-diimine ligands, and iron catalysts bearing bulky bis-imine ligands. In certain variations, Ziegler-Natta type metal precursors (e.g., neodymium, titanium, cobalt or nickel catalyst precursor systems) are used with aluminum alkyl or halide additives. In certain variations, Ziegler-Natta type heterogeneous catalysts, such as those based on combinations of Ti and Al or Mg salts are used.

In some variations, a catalyst used is a Ziegler-Natta catalyst. Ziegler-Natta catalysts can be heterogeneous or homogeneous. In some embodiments, the catalyst comprises a heterogeneous Ziegler-Natta catalyst. Some useful Ziegler-Natta catalysts are disclosed in J. Boor, "Ziegler-Natta Catalysts and Polymerizations," Saunders College Publishing, pp. 1-687 (1979); and Malcolm P. Stevens, "Polymer Chemistry, an Introduction," Third Edition, Oxford University Press, pp. 236-245 (1999), both of which are incorporated herein by reference.

Heterogeneous Ziegler-Natta catalysts generally comprise (1) a transition metal compound comprising an element from groups 4 to 8; and (2) an organometallic compound comprising a metal from groups 1 to 3 of the periodic table. The transition metal compound is referred as the catalyst while the organometallic compound is regarded as the co-catalyst or activator. The transition metal compound generally comprises a metal and one or more anions and ligands. Some non-limiting examples of suitable metals include titanium, vanadium, chromium, molybdenum, zirconium, iron and cobalt. Some non-limiting examples of suitable anions or ligands include halides, oxyhalides, alkoxy, acetylacetonyl, cyclopentadienyl, and phenyl.

Any co-catalyst or activator that can ionize the organometallic complex to produce an active oligomerization catalyst can be used herein. Generally, the organometallic co-catalysts are hydrides, alkyls, or aryls of metals, such as aluminum, lithium, zinc, tin, cadmium, beryllium, and magnesium. Some non-limiting examples of suitable co-catalysts include alumoxanes (methyl aluminoxane (MAO), PMAO, ethyl aluminoxane, diisobutyl aluminoxane), alkylaluminum compounds (trimethylaluminum, triethylaluminum, diethyl aluminum chloride, trimethylaluminum, triisobutylaluminum, trioctylaluminum), diethylzinc, di(i-butyl)zinc, di(n-hexyl)zinc, and ethylzinc (t-butoxide) and the like. Other suitable co-catalysts include acid salts that contain non-nucleophilic anions. These compounds generally consist of bulky ligands attached to boron or aluminum. Some non-limiting examples of such compounds include lithium tetrakis(pentafluorophenyl)borate, lithium tetrakis(pentafluorophenyl)aluminate, aluminum tetrakis(pentafluorophenyl)borate, and the like. Some non-limiting examples of suitable co-catalysts also include organoboranes, which include boron and one or more alkyl, aryl, or aralkyl groups. Other non-limiting examples of suitable co-catalysts include substituted and unsubstituted trialkyl and triarylboranes such as tris(pentafluorophenyl)borane, triphenylborane, tri-n-octylborane, and the like. These and other suitable boron-containing co-catalysts or activators are described in U.S. Pat. Nos. 5,153,157, 5,198,401, and 5,241,025, each of which is incorporated herein by reference.

In certain embodiments, the Ziegler-Natta catalyst can be impregnated on a support material. Some suitable support materials are disclosed in Malcolm P. Stevens, "Polymer Chemistry, an Introduction," Third Edition, Oxford University Press, p. 251 (1999), which is incorporated herein by reference.

The support material is generally a material inert or substantially inert to olefin oligomerization reactions. Non-limiting examples of suitable support materials include MgCl$_2$, MgO, alumina such as activated alumina and microgel alumina, silica, magnesia, kieselguhr, fuller's earth, clays, alumina silicates, porous rare earth halides and oxylalides, and combinations thereof. The support material can have a surface area between about 5 m$^2$/g and about 450 m$^2$/g, as determined by the BET (Brunauer-Emmet-Teller) method of measuring surface area, as described by S. Brunauer, P. H. Emmett, and E. Teller, Journal of the American Chemical Society, 60, 309 (1938), which is incorporated herein by reference. In some embodiments, the surface area of the support material is between about 10 m$^2$/g and about 350 m$^2$/g. In further embodiments, the surface area of the support material is between about 25 m$^2$/g and about 300 m$^2$/g.

The support material can have an average particle size ranging from about 20 to about 300 microns, from about 20 to about 250 microns, from about 20 to about 200 microns, from about 20 to about 150 microns, from about 20 to about 120 microns, from about 30 to about 100 microns, or from about 30 to about 90 microns. The compacted or tamped bulk density of the support material can vary between about 0.6 and about 1.6 g/cc, between about 0.7 and about 1.5 g/cc, between about 0.8 and about 1.4 g/cc, or between about 0.9 and about 1.3 g/cc.

In certain embodiments, the catalyst used herein is or comprises a Kaminsky catalyst, also known as homogeneous Ziegler-Natta catalyst. The Kaminsky catalyst can be used to produce branched alkenes herein with unique structures and physical properties. Some Kaminsky catalysts or homogeneous Ziegler-Natta catalysts are disclosed in Malcolm P. Stevens, "Polymer Chemistry, an Introduction," Third Edition, Oxford University Press, pp. 245-251 (1999); and John Scheirs and Walter Kaminsky, "Metallocene-Based Polyolefins: Preparation, Properties, and Technology," Volume 1, Wiley (2000), both of which are incorporated herein by reference.

In some embodiments, the Kaminsky catalyst suitable for making oligomers disclosed herein comprises a transition-metal atom sandwiched between ferrocene ring structures. In other embodiments, the Kaminsky catalyst can be represented by the formula Cp$_2$MX$_2$, where M is a transition metal (e.g., Zr, Ti or Hf); X is halogen (e.g., Cl), alkyl or a combination thereof; and Cp is a cyclopentadienyl group. In further embodiments, the Kaminsky catalyst has formula (XXVI):

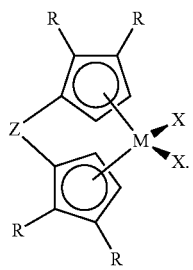

(XXVI)

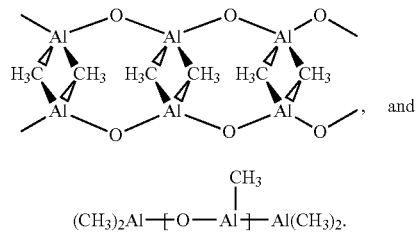

(XXX)

and

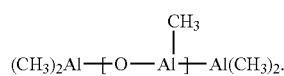

(XXXI)

wherein Z is an optional divalent bridging group, usually $C(CH_3)_2$, $Si(CH_3)_2$, or $CH_2CH_2$; R is H or alkyl; M is a transition metal (e.g., Zr, Ti or Hf); X is halogen (e.g., Cl), alkyl or a combination thereof. Some non-limiting examples of Kaminsky catalysts have formulae (XXVII) to (XXIX):

(XXVII)

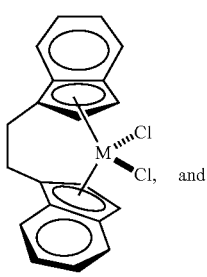

(XXVIII)

and

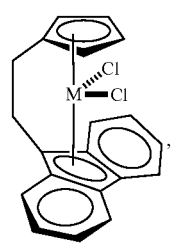

(XXIX)

wherein M is Zr, Hf or Ti.

In some embodiments, a co-catalyst is used with the Kaminsky catalyst. The co-catalyst may be any of the co-catalyst disclosed herein. In certain embodiments, the co-catalyst is methylaluminoxane (MAO). MAO is an oligomeric compound having a general formula $(CH_3AlO)_n$, where n is from 1 to 10. MAO may play several roles: it alkylates the metallocene precursor by replacing chlorine atoms with methyl groups; it produces the catalytic active ion pair $Cp_2MCH_3^+/MAO^-$, where the cationic moiety is considered responsible for polymerization and $MAO^-$ acts as weakly coordinating anion. Some non-limiting examples of MAO include formulae (XXX) and (XXXI):

In certain embodiments, the catalyst for making the polyfarnesene disclosed herein is or comprises a metallocene catalyst. Some metallocene catalysts are disclosed in Tae Oan Ahn et al., "*Modification of a Ziegler-Natta catalyst with a metallocene catalyst and its olefin polymerization behavior*," Polymer Engineering and Science, 39(7), p. 1257 (1999); and John Scheirs and Walter Kaminsky, "*Metallocene-Based Polyolefins: Preparation, Properties, and Technology*," Volume 1, Wiley (2000), both of which are incorporated herein by reference.

In other embodiments, the metallocene catalyst comprises complexes with a transition metal centre comprising a transition metal, such as Ni and Pd, and bulky, neutral ligands comprising alpha-diimine or diketimine. In further embodiments, the metallocene catalyst has formula (XXXII):

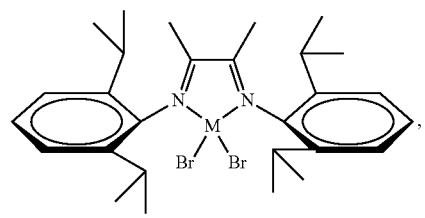

(XXXII)

wherein M is Ni or Pd.

In some embodiments, the catalyst used herein is or comprises a metallocene catalyst bearing mono-anionic bidentate ligands. A non-limiting example of such a metallocene catalyst has structure (XXXIII):

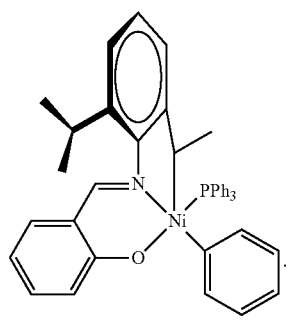

(XXXIII)

In other embodiments, the catalyst used herein is or comprises a metallocene catalyst comprising iron and a pyridyl is incorporated between two imine groups giving a tridentate ligand. A non-limiting example of such a metallocene catalyst has structure (XXXIV):

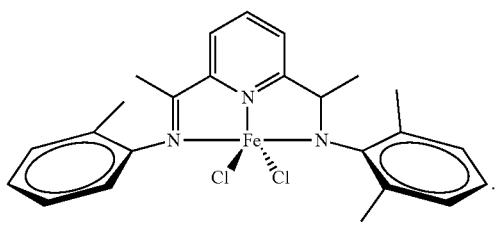

(XXXIV)

In some embodiments, the catalyst used herein is or comprises a metallocene catalyst comprising a salicylimine catalyst system based on zirconium. A non-limiting example of such a metallocene catalyst has structure (XXXV):

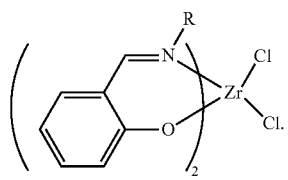

(XXXV)

In certain embodiments, the early transition metal, late transition metal, lanthanide metal, Ziegler-Natta, or metallocene catalysts described herein or otherwise known are used to catalytically couple a hydrocarbon terpene feedstock with ethylene and/or propylene to form oligomers or polymers. For example, a conjugated diene containing hydrocarbon terpene, a partially hydrogenated hydrocarbon terpene, or a particular species of partially hydrogenated hydrocarbon terpene as described herein may be catalytically coupled with ethylene or propylene to produce oligomers or copolymers, at least a portion of which may be used as a base oil. In some variations, β-farnesene, α-farnesene, partially hydrogenated farnesene, or alpha-olefins derived from α-farnesene or β-farnesene are catalytically coupled with ethylene and/or propylene to form oligomers or copolymers. The properties of the oligomers or copolymers so formed may be tuned by any one or any combination of the following: the metal, ligand, co-catalyst, temperature, solvent, and relative proportions of hydrocarbon terpene and olefin comonomer(s). Degree of branching in the oligomers or copolymers so formed may be determined by methyl branching on the hydrocarbon terpene feedstock as well as by the polymerization mechanism and enchainment (e.g., 1,2-, 3,4-, or cis- or trans-1,4-addition). Copolymers so formed may be hydrogenated, or in some variations, left unhydrogenated. In certain variations, the early transition metal, late transition metal, lanthanide metal, Ziegler-Natta, or metallocene catalysts as described herein can be used to make homopolymers from a hydrocarbon terpene feedstock, e.g., a hydrocarbon terpene comprising conjugated diene moieties, a partially hydrogenated hydrocarbon terpene, or a particular species of partially hydrogenated hydrocarbon terpene. In some variations, polymers or copolymers so formed may be useful as very high index base oils, as is described herein in more detail below. Additional non-limiting examples of homopolymers, interpolymers and copolymers derived from farnesene are described in U.S. Pat. Publ. 2010/0056743, published Mar. 4, 2010, entitled "Polyfarnesenes," which is incorporated herein by reference in its entirety.

For any of the catalysts described herein, the methods may comprise using a reaction quench or chain terminating method to limit or otherwise control formation of higher oligomers or polymers. Any suitable reaction quench or chain terminating method may be used.

In one embodiment, provided herein are methods for making a base oil, comprising oligomerizing a partially hydrogenated terpene feedstock in the presence of a catalyst to form an unsaturated reaction product, and hydrogenating the unsaturated reaction product to form a mixture of isoparaffins, at least a portion of which are used to form a base oil.

In another embodiment, provided herein are methods for making a base oil, comprising hydrogenating a terpene to produce a partially hydrogenated terpene feedstock, oligomerizing the partially hydrogenated terpene feedstock in the presence of a catalyst to form an unsaturated reaction product, and hydrogenating the unsaturated reaction product to form a mixture of isoparaffins, at least a portion of which are used to form a base oil.

In one embodiment, provided herein are methods of making a base oil, comprising oligomerizing partially hydrogenated terpene feedstock in the presence of a catalyst to form an unsaturated reaction product, distilling the unsaturated reaction product to selectively remove lower molecular weight hydrocarbons corresponding to monomeric species or lighter to produce an unsaturated bottoms product, and hydrogenating the unsaturated bottoms product to form a mixture of isoparaffins, at least a portion of which are used to form a base oil. In some variations of the methods, the lower molecular weight hydrocarbons selectively removed by distillation may comprise unreacted monomer, which may, in certain circumstance, be redirected for reuse in the oligomerization reaction.

In one embodiment, provided herein are methods of making a base oil, comprising hydrogenating a terpene to produce a partially hydrogenated terpene feedstock, oligomerizing the partially hydrogenated terpene feedstock in the presence of a catalyst to form an unsaturated reaction product, distilling the unsaturated reaction product to selectively remove lower molecular weight hydrocarbons corresponding to monomeric species or lighter to produce an unsaturated bottoms product, and hydrogenating the unsaturated bottoms product to form a mixture of isoparaffins, at least a portion of which are used to make a base oil.

In one embodiment, provided herein are methods of making a base oil, comprising coupling a hydrocarbon terpene feedstock and one or more olefin co-monomers (e.g. one or more alpha-olefin co-monomers) in the presence of a catalyst to form an unsaturated reaction product, and hydrogenating the unsaturated reaction product to form a mixture of isoparaffins, at least a portion of which is used to make a base oil. An exemplary flow chart for such methods is shown in FIG. 1.

In one embodiment, provided herein are methods of making a base oil, comprising hydrogenating terpene to produce a partially hydrogenated terpene feedstock, and coupling the partially hydrogenated farnesene feedstock and one or more olefin co-monomers (e.g. one or more alpha-olefin co-monomers) in the presence of a catalyst to form an unsaturated reaction product, and hydrogenating the unsaturated reaction product to form a mixture of isoparaffins. An exemplary flow chart for such methods is shown in FIG. 1.

In one embodiment, provided herein are methods of making a base oil, comprising coupling a partially hydrogenated terpene feedstock and one or more olefin co-monomers (e.g. one or more alpha-olefin co-monomers) in the presence of a catalyst to form an unsaturated reaction product, distilling the unsaturated reaction product to selectively remove lower molecular weight hydrocarbons corresponding to unreacted monomers to produce an unsaturated bottoms product, and hydrogenating the unsaturated bottoms product to form a mixture of isoparaffins, at least a portion of which is used to make a base oil. In some variations of the methods, the lower molecular weight hydrocarbons selectively removed by distillation may comprise unreacted monomer, which may, in certain circumstance, be redirected for reuse in the oligomerization reaction. An exemplary flow chart for such methods is shown in FIG. 2.

In one embodiment, provided herein are methods of making a base oil, comprising hydrogenating terpene to produce a partially hydrogenated terpene feedstock, coupling the partially hydrogenated farnesene feedstock and one or more olefin co-monomers (e.g. one or more alpha-olefins) in the presence of a catalyst to form an unsaturated reaction product, distilling the unsaturated reaction product to selectively remove lower molecular weight hydrocarbons corresponding to unreacted monomers or lighter species to produce an unsaturated bottoms product, and hydrogenating the unsaturated bottoms product to form a mixture of isoparaffins, at least a portion of which may be used to make a base oil. In some variations of the methods, the lower molecular weight hydrocarbons selectively removed by distillation may comprise unreacted monomer, which may, in certain circumstance, be redirected for reuse in the oligomerization reaction. An exemplary flow chart for such methods is shown in FIG. 2.

II. Compositions

In one variation, provided herein are base oils comprising hydrogenated adducts between a hydrocarbon terpene and one or more olefin co-monomers (e.g., one or more alpha-olefins). In some variations, branching in the base oil may be due predominantly to the hydrocarbon terpene. In some variations, branching in the base oil may be due predominantly to the olefin co-monomer. In some variations, branching in the base oil may be at least in part determined by a point of attachment between the hydrocarbon terpene and the alpha-olefin. In some variations, the base oil comprises predominantly hydrogenated 1:1 hydrocarbon terpene feedstock:olefin adducts. In some variations, the base oil comprises predominantly hydrogenated 2:1 hydrocarbon terpene feedstock:olefin adducts. In some variations, the base oil comprises predominantly 1:2 hydrocarbon terpene feedstock:olefin adducts. In some variations the base oil comprises a hydrogenated mixture comprising 1:1 hydrocarbon terpene feedstock:alpha-olefin adducts and 1:2 hydrocarbon terpene feedstock:alpha-olefin adducts. In some variations, the base oil comprises a hydrogenated mixture comprising 1:1 hydrocarbon terpene feedstock:alpha-olefin adducts and 2:1 hydrocarbon terpene feedstock:alpha-olefin adducts.

Disclosed herein are lubricant base stocks comprising at least a portion of a mixture of isoparaffins produced by any of the methods described herein. Disclosed herein are lubricant base stocks comprising one or more distillation cuts obtained from a mixture of isoparaffins produced by any of the methods described herein.

Table C1 below provides non-limiting examples of adducts formed by the methods described herein. "HCT" refers to hydrocarbon terpene feedstock and "OC" refers to olefin co-monomer(s). Each "X" in Table C1 below specifically discloses a composition comprising the HCT:OC cross-adducts indicated in the vertical columns and HCT only adducts indicated in the horizontal rows. It should be noted that the adducts may or may not be hydrogenated.

TABLE C1

| HCT only adducts | Cross-adducts between HCT and OC | | | | |
|---|---|---|---|---|---|
| | 1:1 HCT:OC | 1:2 HCT:OC | 2:1 HCT:OC | 3:1 HCT:OC | 1:3 HCT:OC |
| — | X | — | — | — | — |
| — | X | X | — | — | — |
| — | X | — | X | — | — |
| — | X | X | X | — | — |
| — | — | X | — | — | — |
| — | — | — | X | — | — |
| — | X | X | — | — | X |
| — | X | — | X | X | — |
| — | X | X | X | X | X |
| — | — | — | — | X | — |
| — | — | — | — | — | X |
| HCT dimers | — | — | — | — | — |
| HCT dimers | X | — | — | — | — |
| HCT dimers | X | X | — | — | — |
| HCT dimers | X | — | X | — | — |
| HCT dimers | X | X | X | — | — |
| HCT dimers | — | X | — | — | — |
| HCT dimers | — | — | X | — | — |
| HCT dimers | X | X | — | — | X |
| HCT dimers | X | — | X | X | — |
| HCT dimers | X | X | X | X | X |
| HCT dimers | — | — | — | X | — |
| HCT dimers | — | — | — | — | X |
| HCT trimers | — | — | — | — | — |
| HCT trimers | X | — | — | — | — |
| HCT trimers | X | X | — | — | — |
| HCT trimers | X | — | X | — | — |
| HCT trimers | X | X | X | — | — |
| HCT trimers | — | X | — | — | — |
| HCT trimers | — | — | X | — | — |
| HCT trimers | X | X | — | — | X |
| HCT trimers | X | — | X | X | — |
| HCT trimers | X | X | X | X | X |
| HCT trimers | — | — | — | X | — |
| HCT trimers | — | — | — | — | X |

Described herein are compositions comprising isoparaffins derived from β-farnesene, and in some cases derived from farnesene and one or more alpha-olefins, and methods for making the same. In some variations, the isoparaffinic compositions disclosed here can be used as base oils. Described herein are lubricants and lubricant formulations comprising base oils derived from farnesene as disclosed herein.

For isoparaffins made by the oligomerization of partially hydrogenated terpene as described herein, the isoparaffins may comprise dimers, trimers, tetramers, pentamers of terpene and so forth. For example, the isoparaffins may comprise dimers of farnesene, trimers of farnesene, tetramers of farnesene, pentamers of farnesene, etc.

For isoparaffins made by the oligomerization of partially hydrogenated farnesene with one or more olefin co-monomers, the isoparaffins may comprise 1:1 farnesene:olefin adducts, 1:2 farnesene:olefin adducts, 2:1 farnesene:olefin adducts, 1:3 farnesene olefin adducts, 3:1 farnesene olefin adducts, etc., as well as farnesene dimers, farnesene trimers, farnesene tetramers, olefin dimers, olefin trimers, olefin tetramers, etc. If more than one olefin co-monomer is formed, additional adducts are contemplated. In certain circumstances, the reaction conditions are adjusted to favor the formation of farnesene:olefin cross adducts, as opposed to olefin:olefin adducts. For example, if $BF_3$ and one or more co-catalysts as described herein or known in the art is used as the catalyst, keeping the $BF_3$ pressure low (e.g., lower than about 5 psig, such as at about 1, 2, 3, 4, or 5 psig) may favor the formation of farnesene:olefin cross adducts in some cases.

In some variations, an isoparaffin composition is used (e.g., as a base stock or lubricant) as produced by the oligomerization of a feed comprising β-farnesene as described herein.

In some variations, an isoparaffin composition is distilled to produce one or more distillation cuts, e.g. as illustrated in FIGS. 1 and 2, and one or more of these distillation cuts is used to make a base stock or lubricant. It should be understood that the residue remaining after distillation may also be used to make a base stock or lubricant. In some variations, a dimer cut may be used to make a base oil or lubricant. In some variations, a trimer cut may be used to make a base oil or lubricant. In some variations, a dimer cut may be blended with a trimer cut to make a base oil or lubricant, where the ratio of dimer:trimer may be about 100:1, 50:1, 20:1, 10:1, 1:1, 1:10, 1:20, 1:50, or 1:100.

Some isoparaffin compositions comprise at least about 20%, at least about 30%, at least about 40%, at least about 50%, at least about 60%, at least about 70%, at least about 80%, or at least about 90% dimers (where dimers encompasses hydrocarbon terpene (e.g., farnesene) dimers, olefin dimers, and 1:1 terpene:olefin adducts). Some isoparaffins comprise at least about 20%, at least about 30%, at least about 40%, at least about 50%, at least about 60%, at least about 70%, at least about 80%, or at least about 90% trimers (where trimers encompasses hydrocarbon terpene (e.g., farnesene) trimers, olefin trimers and 1:2 and 2:1 terpene:olefin adducts). Some isoparaffins comprise at least about 10%, at least about 20%, at least about 30%, at least about 40%, or at least about 50% tetramers (where tetramers encompasses hydrocarbon terpene (e.g., farnesene) tetramers, olefin tetramers, 1:3 terpene:olefin adducts, 3:1 terpene:olefin adducts, and 2:2 terpene:olefin adducts). Some isoparaffin compositions comprise dimers and trimers. Some isoparaffin compositions comprise dimers, trimers and tetramers. Some isoparaffin compositions comprise trimers and tetramers. Some isoparaffin compositions comprise pentamers, hexamers, or higher oligomers. Some isoparaffin compositions comprise copolymers.

A mixture of oligomers formed by any of the coupling reactions described herein may be separated into different molecular weight ranges or by boiling point using known techniques. Any desirable molecular weight or boiling point ranges may be selected. In some variations, it may be desirable to separate components having different boiling points by distillation. Any suitable type of distillation method, and any suitable distillation process using any desirable number of distillation passes may be carried out to obtain one or more distillation cuts having desirable properties. A distillation pass may be accomplished in a single stage or in multiple stages. A distillation pass may be accomplished using a single distillation apparatus or multiple distillation apparatus. Non-limiting examples of distillation methods that may be used include simple distillation, fractionation distillation, extractive distillation, steam distillation, vacuum distillation, and flash distillation. Distillation may be carried out in batch mode, or in a continuous mode. The combination of distillation steps may be set up in any suitable manner to collect desired distillates and residues under temperature, pressure, and time at temperature conditions that result in no (or an acceptably low amount) of thermal breakdown (e.g., due to cracking).

A distillation unit may be any suitable distillation apparatus known in the art. For example, a distillation unit may comprise one or more fractionation columns, one or more wiped film evaporators (WFE), a flash distillation unit (single stage flash or multiple stage flash), or the like. Any suitable type and size of fractionationation column may be used, and may include any suitable number of plates, and in some cases, a fractionationation column may be a packed column, or a partially packed column. Distillation units may be operated using any suitable reflux ratio (or no reflux). A distillation unit is run under temperature, pressure, and time at temperature conditions which undesired thermal breakdown (e.g., cracking) occurs. For example, a distillation unit may be run at a pot temperature of 300° C. or less.

Where multiple distillation units are used in series in a single distillation pass, the distillation units may be the same or different. For example, one or more fractionating columns may be used in series with one or more WFEs, or a first fractionating column may be arranged in series with a second fractionating column, where the second fractionating column may be set up to do a similar fractionation to the first fractionating column, or to do a different fractionation than the first column. In some variations, one or more fractionating columns are used in a distillation scheme where high throughput is desired. In some variations, one or more fractionating columns are used to remove monomeric species to a desired level (e.g., to about 0-1 wt %, 0-0.7 wt %, 0-0.5 wt %, 0-0.4 wt %, 0-0.3 wt %, 0-0.2 wt %, 0-0.1 wt %, 0-0.05 wt %, or 0-0.01 wt %) while maintaining a loss of dimeric species to a desired level (e.g, (e.g., to about 0-10 wt %, 0-7 wt %, 0-5 wt %, 0-4 wt %, 0-3 wt %, 0-2 wt %, 0-1 wt %, 0-0.5 wt %, or 0-0.1 wt %). In some variations, a WFE is used in which a deeper vacuum is used to achieve a desired separation (e.g., at a pressure of about 1 mm Hg or below, or about 0.5 mm Hg, or below). For example, a WFE operating at a pressure of about 0.5 mm Hg or lower and at or near the maximum allowed distillation temperature (e.g., 300° C.) to accomplish a more difficult separation of a mixture of species having boiling points that a close together, e.g., to separate trimers from a mixture of trimers and tetramers, or a mixture of trimers, tetramers, and higher oligomers.

In some variations, a first distillation pass is used to selectively remove monomeric species. A first distillation pass may comprise a single distillation apparatus, or in other variations, a first distillation pass comprises multiple (e.g., two) distillation units in series, where pressures, temperatures, and residence times in each of the distillation units may be set independently. In some applications the presence of a small amount of low boiling species can decrease flash point, increase volatility and/or decrease viscosity. In some cases, it is desired to remove light ends in a stripping step or in a first stage of a first distillation pass, e.g., to prevent loss by bumping. Light ends in some variations may include acetate (e.g., butyl acetate) and/or alcohol (e.g., butanol) that was used as a co-catalyst in the coupling reaction. Monomeric content may include species having molecular weight corresponding to unreacted monomers (or hydrogenated unreacted monomers), and may in some variations include other small molecule species such as catalyst and/or co-catalyst that boil at temperatures near or below unreacted monomers. For example, if a cationic initiator such as $BF_3$ or $AlCl_3$ is used in combination with one or more co-catalysts such as an alkyl alcohol (e.g., a $C_1$-$C_6$ alkyl alcohol such as n-propanol, n-butanol, n-pentanol, or n-hexanol), or an alkyl alcohol in combination with an ester (e.g., a $C_1$-$C_6$ alkyl acetate such as n-propyl acetate, n-butyl acetate, n-pentyl acetate or n-hexyl acetate), the monomeric content may include the one or more co-catalysts and/or adducts comprising the catalyst and one or more co-catalysts. In some variations, monomeric species remaining in the residue following the first distillation pass is less than about 5 wt %, less than about 4 wt %, less than about 3 wt %, less than about 2 wt %, less than about 1 wt %, less than about 0.7 wt %, less than about 0.5 wt %, less than about 0.4 wt %, less than about 0.3 wt %, less than about 0.2 wt %, less than about 0.1 wt %, less than about 0.05 wt %, less than about 0.02 wt %, or less than about 0.01 wt % monomeric species. In some variations, essentially all monomeric content is selectively removed from other distillation cuts that will be collected. The residue following the first distillation pass may contain dimers, or dimers and trimers, or dimers, trimers, and tetramers, or dimers, trimers, tetramers, pentamers, or dimers, trimers, tetramers, pentamers, and higher oligomers. The residue remaining after the first distillation pass may be used as a distillation cut without further distillation, or may be subjected to a second distillation pass. In some variations, the quantity of dimeric species that is removed by distillation in the first pass is less than about 2%, and essentially no trimeric or higher oligomers are removed in the first pass.

A second distillation pass (which may comprise a single distillation unit, or two or more distillation units in series) may be used to selectively remove dimer species, or a dimer-enriched fraction. A dimer-enriched fraction may contain at least about 70 wt %, least about 75 wt %, at least about 80 wt %, at least about 85 wt %, at least about 90 wt %, at least about 95 wt %, at least about 98 wt %, or at least about 99 wt % dimers. In some variations, a dimer-enriched fraction may contain about 95% or more dimer and about 5% or less trimer and higher oligomers. The residue following the second distillation pass may contain dimers and trimers; trimers; dimers, trimers, and tetramers; trimers and tetramers; dimers, trimers, tetramers and pentamers; trimers, tetramers and pentamers; dimers, trimers, tetramers, pentamers and higher oligomers; or trimers, tetramers, pentamers and higher oligomers. The residue remaining after the second distillation pass may be used as a distillation cut without further distillation, or may be subjected to a third distillation pass.

A third distillation pass (which may comprise a single distillation unit, or two or more distillation units in series) may be used to selective remove trimer species. For example, a third distillation pass may be devised to produce a fraction that comprises at least about 80%, at least about 85%, at least about 90%, or at least about 95% trimer, with the residue comprising trimers, tetramers, and potentially higher order oligomers depending on the coupling reaction conditions, where the concentration of trimers has decreased and the concentration of tetramers and higher oligomers has increased relative to the residue following the second stage.

Figure 12:
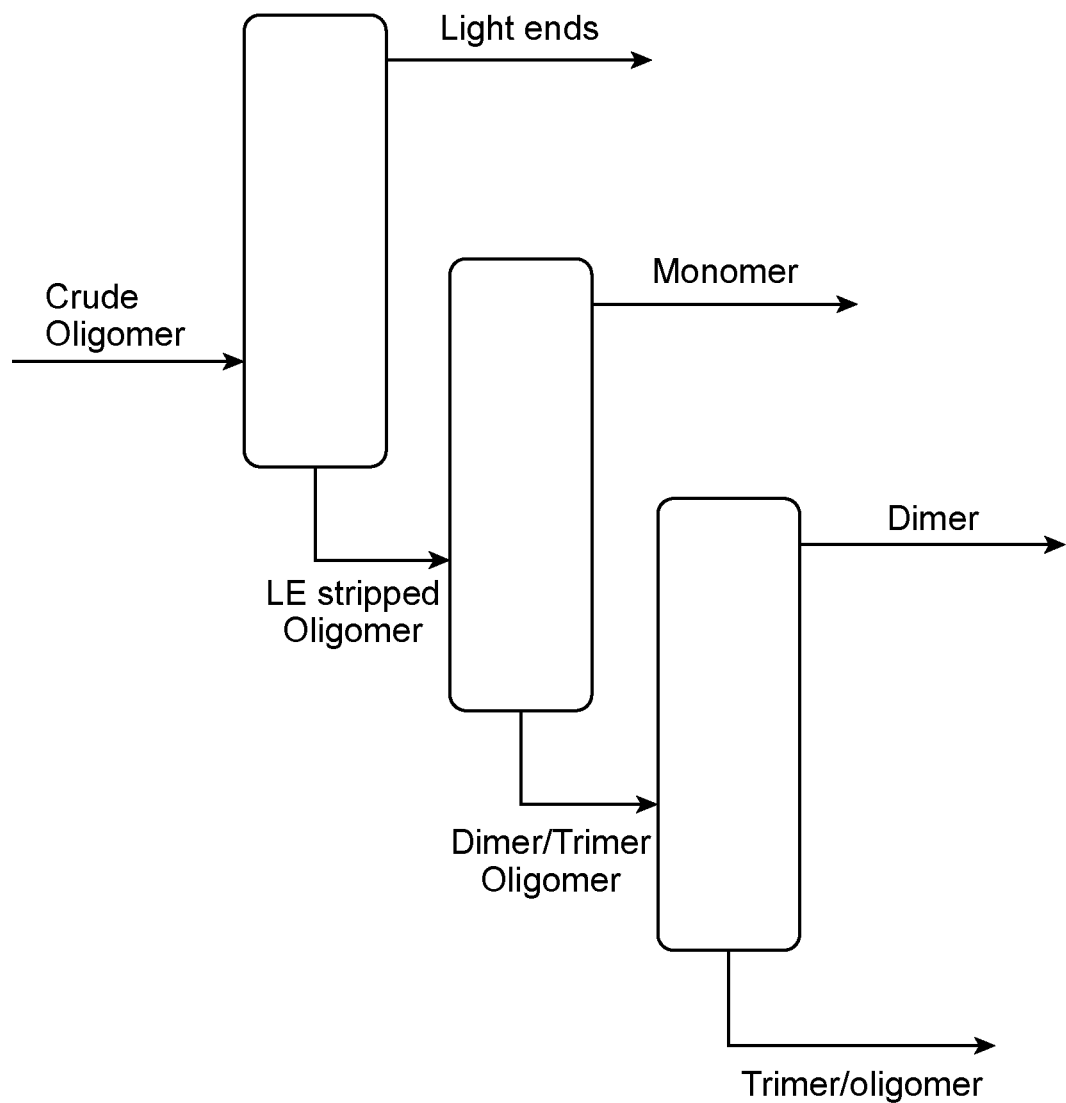
FIG. 12 provides a non-limiting example of a distillation scheme that can be used to produce distillation cuts useful for making base oils as described herein.

FIG. 12 provides a non-limiting example of a distillation scheme comprising a first stripping step to selectively remove light ends, a first distillation pass to selectively remove unreacted monomeric species, and a second distillation pass to selectively remove dimeric species and leave as bottoms a trimer-enriched mixture comprising trimer, tetramer, pentamer and potentially higher order oligomers depending on the coupling reaction conditions.

Figure 13:
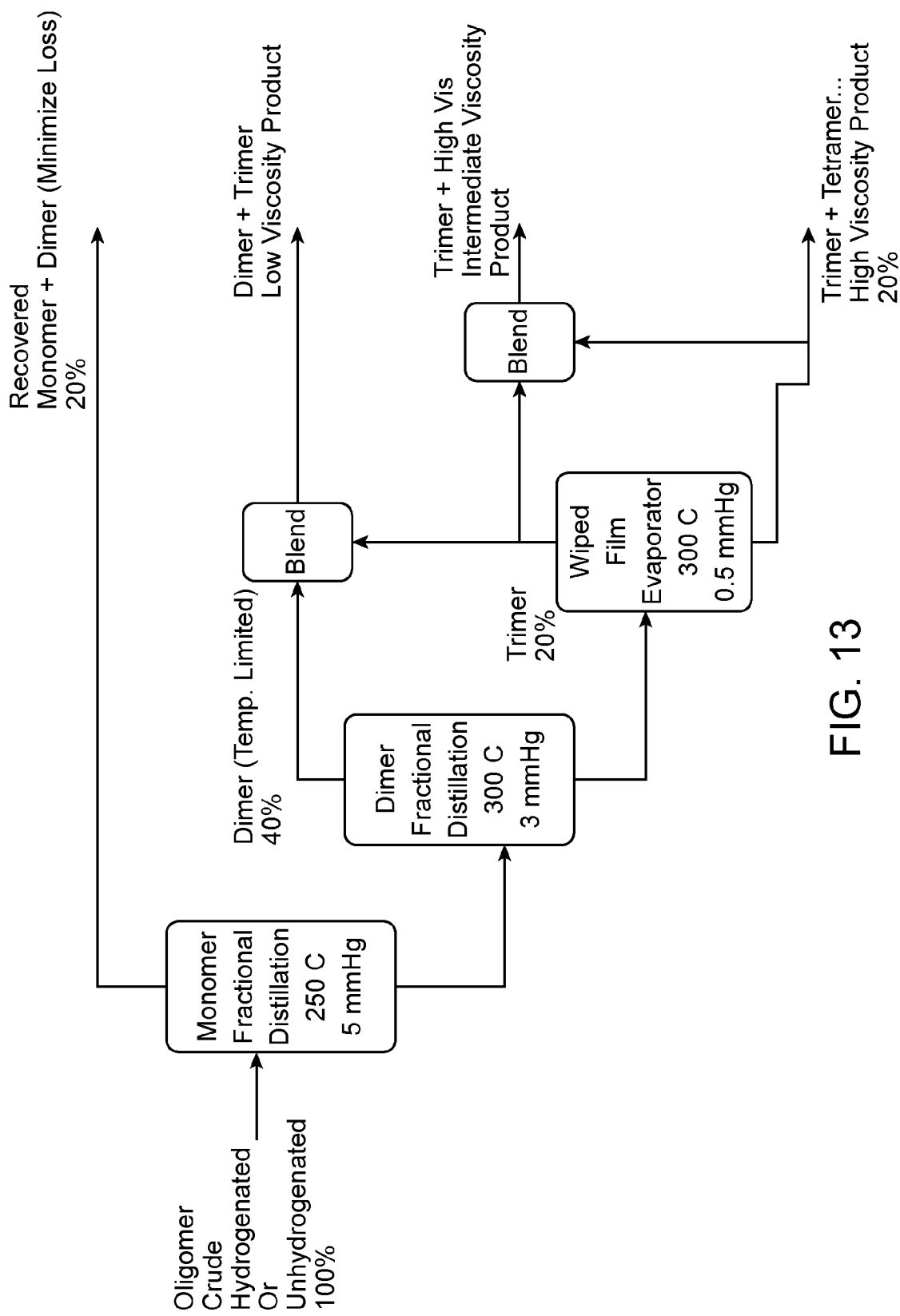
FIG. 13 provides an additional non-limiting example of a distillation scheme that can be used to produce distillation cuts useful for making base oils as described herein.

In some variations, a distillation scheme comprises two or more different types of distillation apparatus, in which an efficient apparatus (e.g., a fractionation distillation column) operated at moderately low pressures (e.g., about 2-100 torr) are used at lower temperatures to separate out lower boiling species that have well differentiated boiling points, and a lower residence time apparatus such as a wiped film evaporator or a short path distillation unit capable of achieving lower pressures (e.g., less than about 0.5 torr, less than about 0.1 torr, less than about 0.01 torr, or less than about 0.001 torr) are used to separate temperature sensitive species with low volatility (e.g., to separate trimers from higher oligomers) at a sufficiently low temperature so that undesired thermal breakdown such as cracking does not occur. A non-limiting example of such a distillation scheme is shown in FIG. 13. As shown, a first pass utilizes an efficient distillation apparatus such as a fractionation column operating at about 200° C.-250° C. and a pressure of about 3-10 mm Hg (e.g., about 5 mm Hg) to selectively remove monomeric species, a second pass utilizes another efficient distillation apparatus such as a fractionation column operating at about 250°-300° C. and a pressure of about 2-3 mm Hg) a to selectively remove dimeric species, and a third pass utilizes a distillation apparatus capable of achieving low pressure (e.g., about 0.5, 0.1, 0.05, 0.01, 0.005, or 0.001 mm Hg) at or near the maximum temperature to which the substance may be exposed (e.g., about 300° C.) with a shorter residence time (e.g., a WFE or short path distillation) to selectively remove trimeric species from the residue following the second pass, and leave as bottoms a trimer-enriched mixture comprising trimers, tetramers, pentamers and potentially higher order oligomers, where the concentration of trimers has decreased and the concentration of tetramers and higher oligomers has increased relative to the residue following the second stage. Note that in some cases, a light ends stripping step may take place prior to the first pass.

In certain embodiments, the compositions comprise one or more compounds according to the following formula:

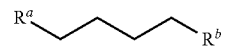

wherein $R^a$ and $R^b$ are selected from the table below:

| $R^a$ | $R^b$ |
|---|---|

-continued
| $R^a$ | $R^b$ |
|---|---|
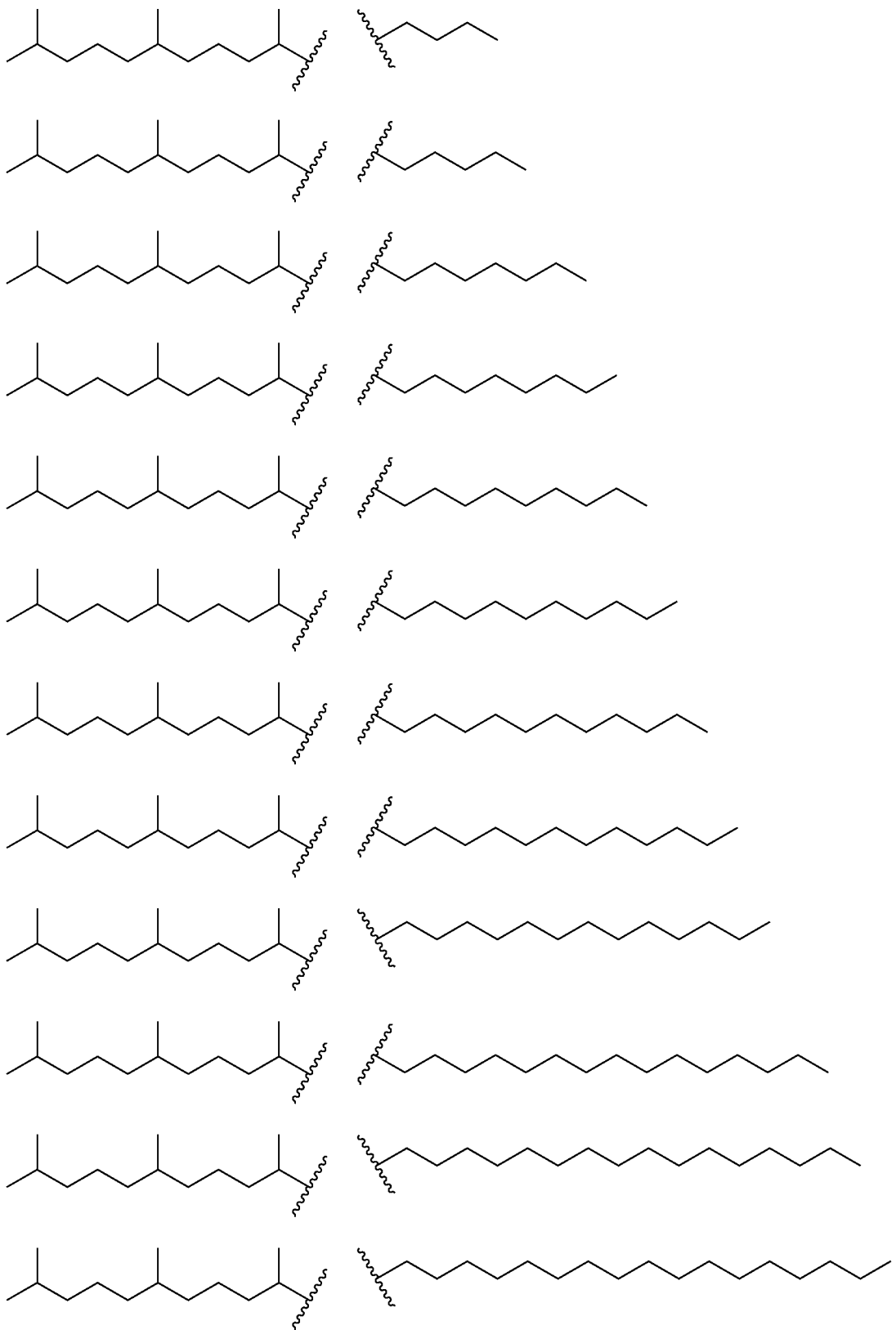

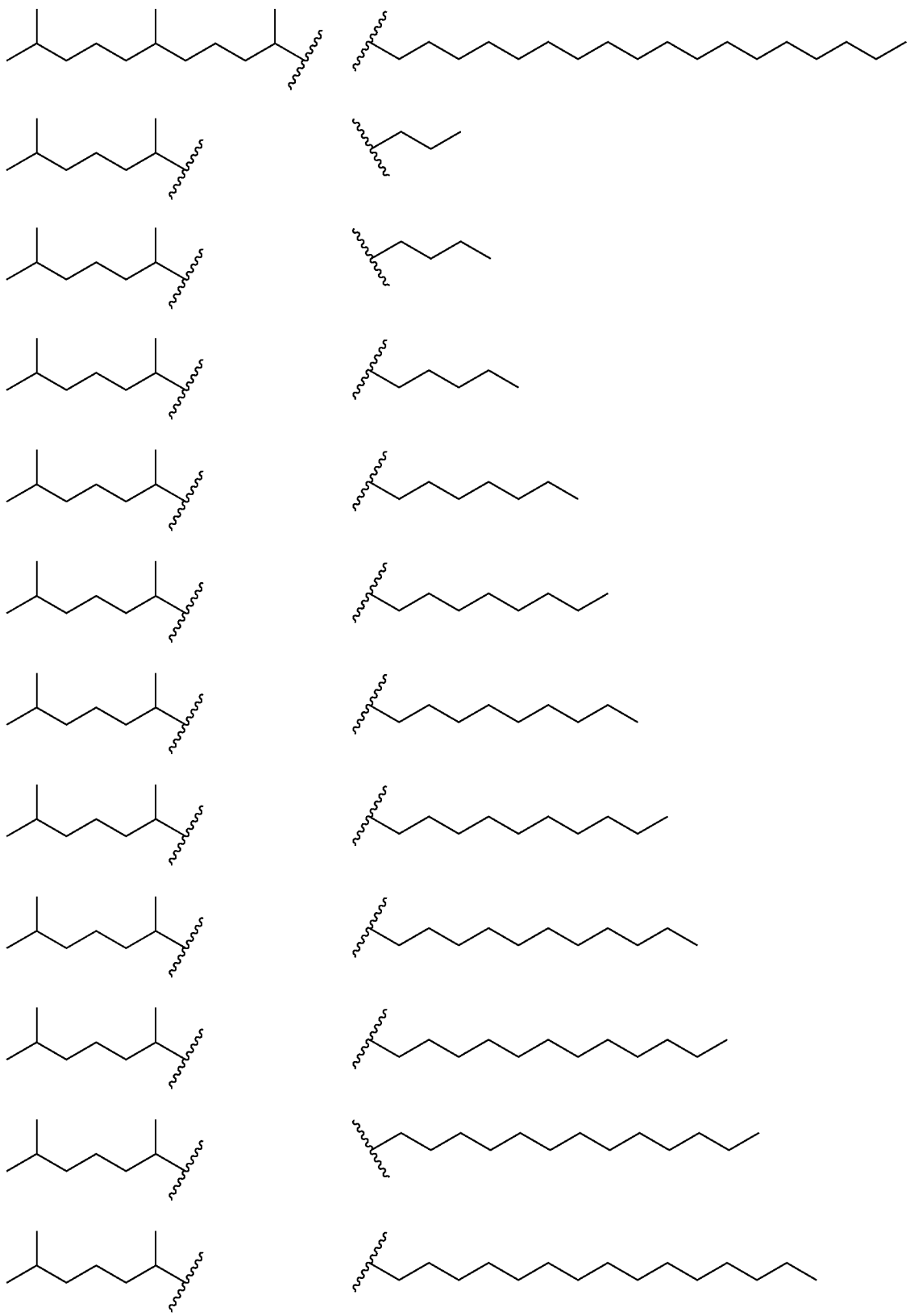

-continued
| $R^a$ | $R^b$ |
|---|---|
| 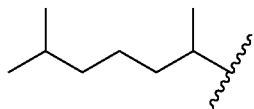 [SMILES: *C(C)CCCC(C)C] | 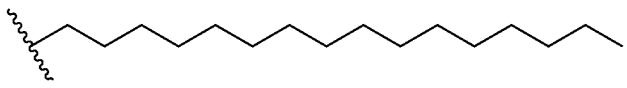 [SMILES: *CCCCCCCCCCCCCCCC] |
| 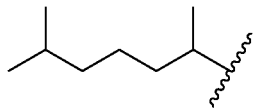 [SMILES: *C(C)CCCC(C)C] | 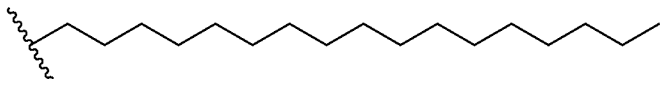 [SMILES: *CCCCCCCCCCCCCCCCC] |
| 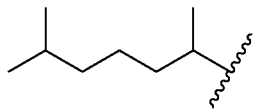 [SMILES: *C(C)CCCC(C)C] | 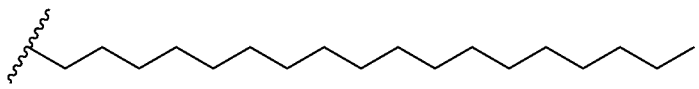 [SMILES: *CCCCCCCCCCCCCCCCCC] |
| 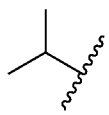 | 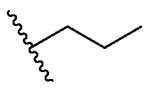 [SMILES: *CCC] |
| 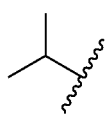 [SMILES: *C(C)C] | 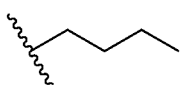 [SMILES: *CCCC] |
| 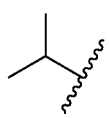 [SMILES: *C(C)C] | 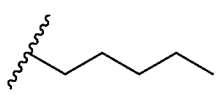 |
| 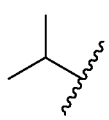 | 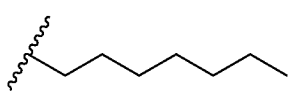 [SMILES: *CCCCCCC] |
| 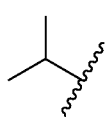 [SMILES: *C(C)C] | 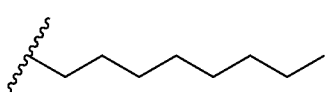 [SMILES: *CCCCCCCC] |
| 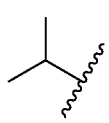 [SMILES: *C(C)C] | 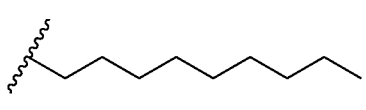 |
| 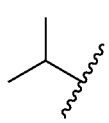 [SMILES: *C(C)C] | 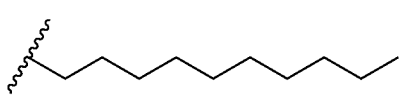 [SMILES: *CCCCCCCCCC] |
| 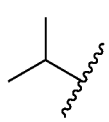 [SMILES: *C(C)C] | 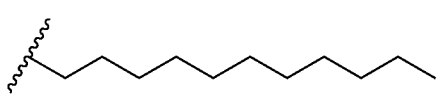 [SMILES: *CCCCCCCCCCC] |
| 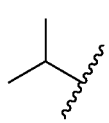 [SMILES: *C(C)C] | 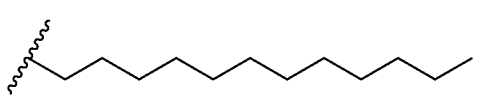 [SMILES: *CCCCCCCCCCCC] |

-continued
| $R^a$ | $R^b$ |
|---|---|
| 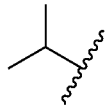 [SMILES: *C(C)C] | 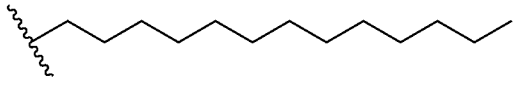 |
| 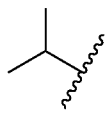 [SMILES: *C(C)C] | 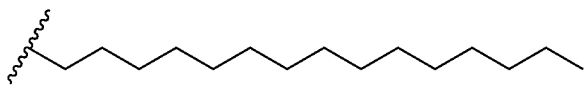 [SMILES: *CCCCCCCCCCCCCCC] |
| 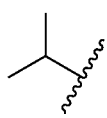 [SMILES: *C(C)C] | 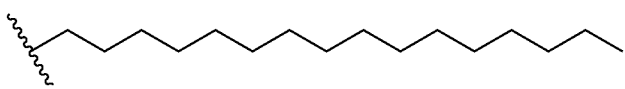 [SMILES: *CCCCCCCCCCCCCCCC] |
| 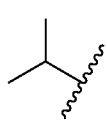 [SMILES: *C(C)C] | 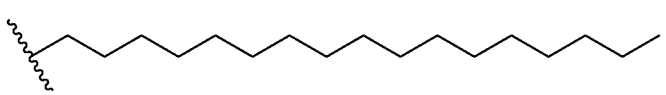 [SMILES: *CCCCCCCCCCCCCCCCC] |
| 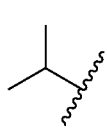 [SMILES: *C(C)C] | 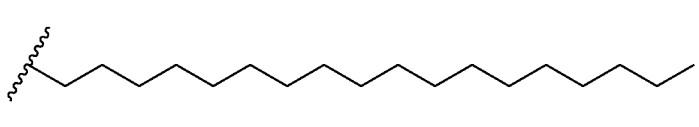 [SMILES: *CCCCCCCCCCCCCCCCCC] |
| 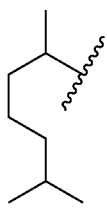 [SMILES: *C(C)CCCC(C)C] |  |
| 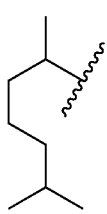 [SMILES: *C(C)CCCC(C)C] | 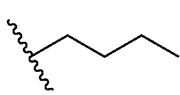 [SMILES: *CCCC] |
| 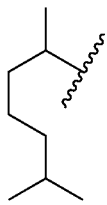 [SMILES: *C(C)CCCC(C)C] | 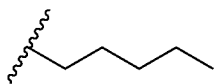 [SMILES: *CCCCC] |
| 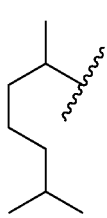 [SMILES: *C(C)CCCC(C)C] | 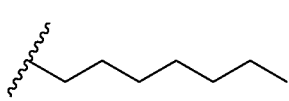 [SMILES: *CCCCCCC] |

| $R^a$ | $R^b$ |
|---|---|
| 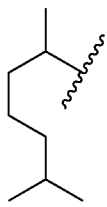 [SMILES: *C(C)CCCC(C)C] | 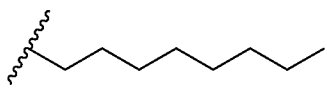 [SMILES: *CCCCCCCC] |
| 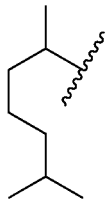 [SMILES: *C(C)CCCC(C)C] | 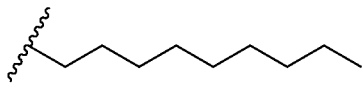 [SMILES: *CCCCCCCCC] |
| 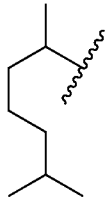 [SMILES: *C(C)CCCC(C)C] | 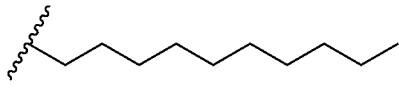 [SMILES: *CCCCCCCCCC] |
| 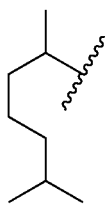 [SMILES: *C(C)CCCC(C)C] | 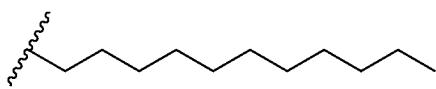 [SMILES: *CCCCCCCCCCC] |
| 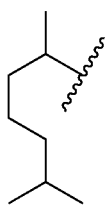 [SMILES: *C(C)CCCC(C)C] | 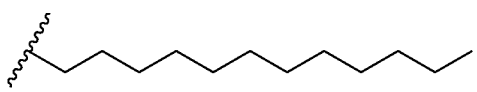 [SMILES: *CCCCCCCCCCCC] |
| 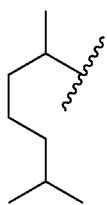 [SMILES: *C(C)CCCC(C)C] | 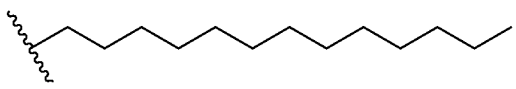 [SMILES: *CCCCCCCCCCCCC] |
| 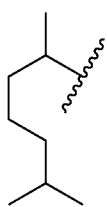 [SMILES: *C(C)CCCC(C)C] | 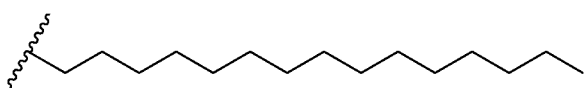 [SMILES: *CCCCCCCCCCCCCCC] |

-continued

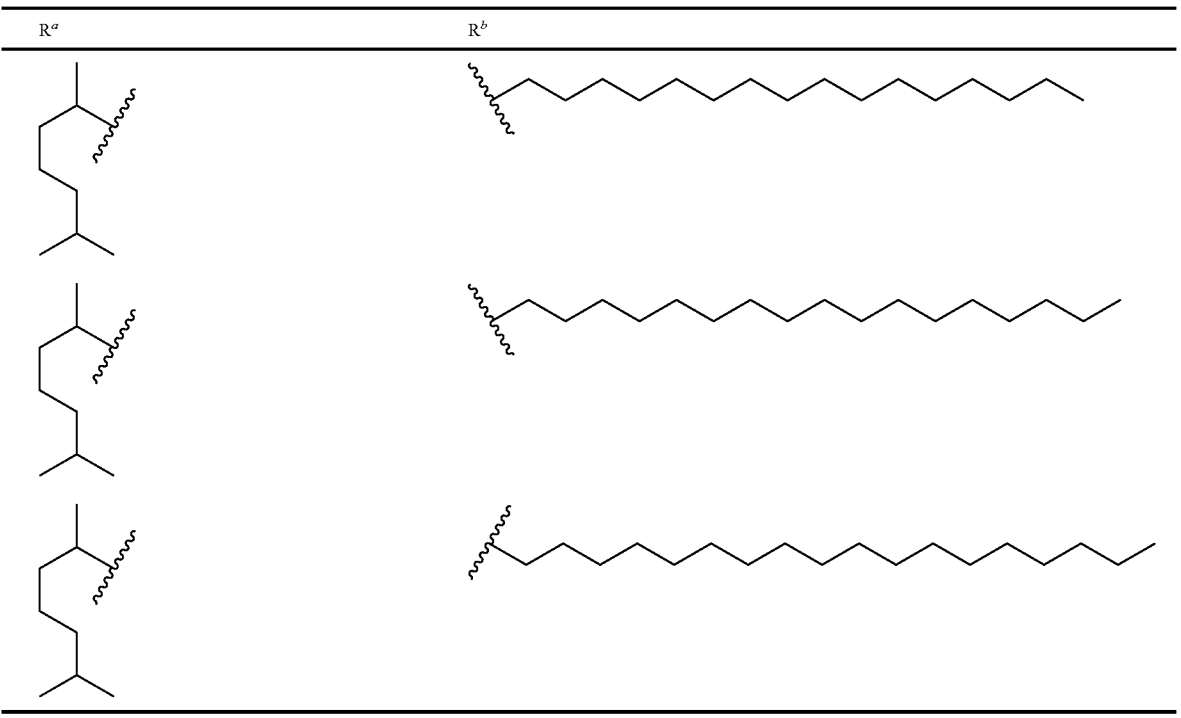

In certain embodiments, the compositions comprise one or more compounds according to the following formulas (X-1 through X-10):

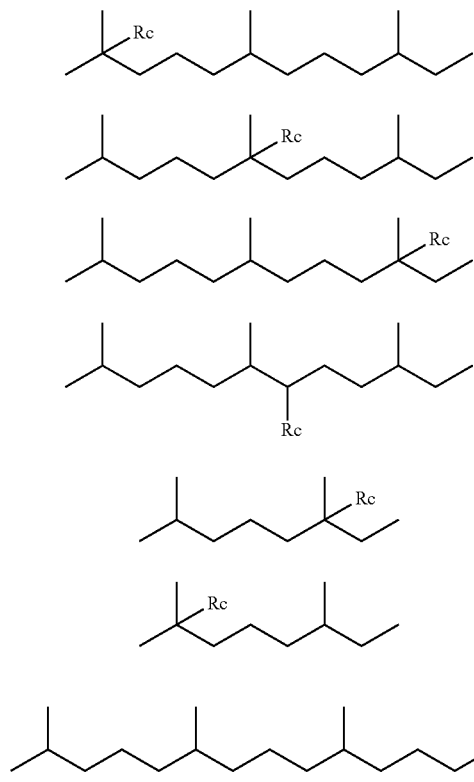

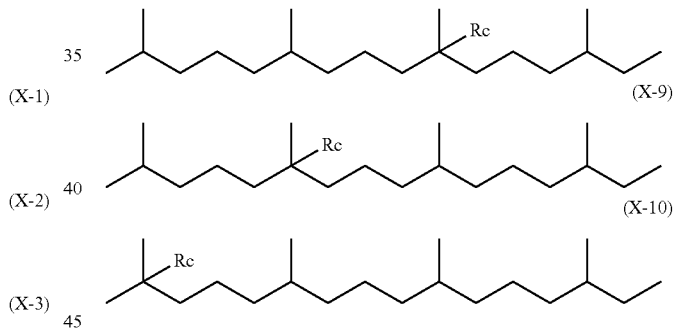

or isomers thereof, where Rc is a $C_3$-$C_{30}$ linear or branched alkyl group. It should be noted that the attachment point between the Rc group and the hydrocarbon terpene feedstock may be varied, depending on catalyst and mechanism. If an olefin co-monomer is used that comprises more than one component, Rc may vary. For example, if an olefin co-monomer is used that comprises a mixture of 1-hexadecene and 1-tetradecene, Rc may be a $C_{16}$ or a $C_{14}$ group.

It should be noted that trimer structures are envisioned in which two Rc groups are attached to a hydrocarbon terpene molecule, etc. Non-limiting examples of trimer structures that may be formed using β-farnesene as a hydrocarbon terpene are illustrated by formulae (X-11) through (X-13):

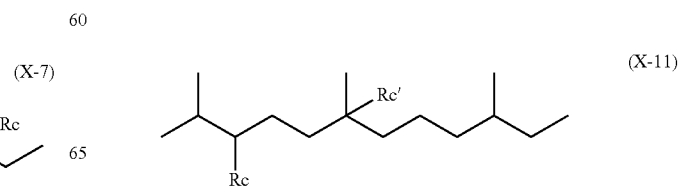

-continued

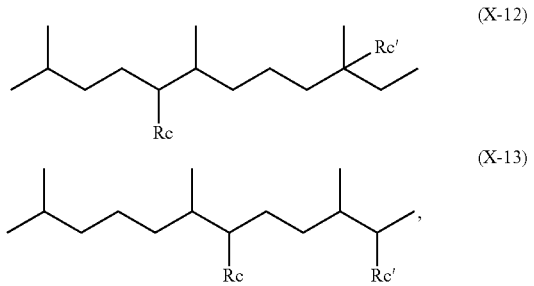

where Rc and Rc' are independently $C_3$-$C_{30}$ linear or branched alkyl group, and may be the same or different. It should be noted that the attachment point between the Rc and Rc' groups and the hydrocarbon terpene feedstock may vary, depending on catalyst, mechanism and reaction conditions. If an olefin co-monomer is used that comprises a mixture of 1-tetradecene and 1-hexadecene, Rc and Rc' may be $C_{14}$ and/or $C_{16}$ sidechains.

A non-limiting example of a pentamer structure that may be formed using β-farnesene as a hydrocarbon terpene are illustrated by formula (X-14), where R represents a C3-C30 linear or branched alkyl groups, and the two Rs shown may be the same or different, and n=1-10. It should be noted that the attachment point between the R groups and the hydrocarbon terpene feedstock may vary, depending on catalyst, mechanism, and reaction conditions. If the olefin comonomer is 1-tetradecene, n=1. If the olefin comonomer is 1-hexadecene, n=2. If the olefin comonomer is a mixture of 1-tetradecene and 1-hexadecene, a distribution of oligomers having n=1 and n=2 results.

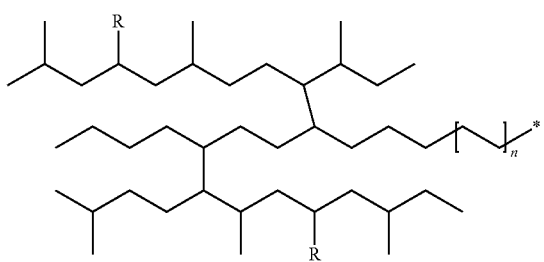

As described herein, at least a portion of an isoparaffinic mixture made by the methods described herein may be used as a base oil. In some variations, an isoparaffinic mixture is used as produced to make a base oil. In some variations, one or more distillation cuts of an isoparaffinic mixture is used to make a base stock, e.g., a distillation cut in a temperature range from about 350° C. to about 500° C. (AET), e.g., about 350° C. to about 380° C., about 380° C. to about 400° C., about 400° C. to about 420° C., or about 420° C. to about 435° C., about 435° C. to about 445° C., or about 445° C. to about 480° C. In some variations, a first distillation cut is collected for monomeric species having a boiling point at atmospheric pressure in a range between 200° C. and 370° c., the residue resulting from the first distillation pass is distilled in a second pass to collect dimeric species having a boiling point at atmospheric pressure in a range between about 370° C. to about 450° C., about 370° C. to about 455° C., about 370° C. to about 460° C., about 370° C. to about 465° C., about 370° C. to about 470° C., or about 370° C. to about 475° C. The residue remaining after the second distillation pass may comprise trimers, tetramers, and pentamers. In some variations, the residue remaining after the second distillation pass is further distilled, e.g., at a pot temperature of 300° C. and a pressure of about 0.5 torr or less, 0.1 torr or less, 0.05 torr or less, 0.01 torr or less, 0.005 torr or less, or about 0.001 torr to separate trimer species from higher oligomers. Additional distillation schemes that can be used with any of the isoparaffinic mixtures described herein are described in Section II below. In some variations, more than one distillation cut may be combined together to form a base stock. In certain variations, at least a portion of the residue left in the pot following distillation may be used as a base stock or as a component of a base stock. For example, at least a portion of a residue remaining after distillation up to about 380° C., 400° C., 420° C., 430° C., 440° C., 450° C., 455° C., 460° C., 465° C., 470° C., 475° C., or 480° C. (AET) may be used as or in a base stock. In some variations, one or more distillation cuts or a residue may be subsequently redistilled (polished) and one or more of such polished fractions may be used as or in a base stock.

In some variations, a distillation cut (or distillation residue) temperature range may be selected to correspond to a particular hydrocarbon molecular weight. In those variations, a distillation cut may preferentially select dimers, trimers, tetramers, etc. out of the isoparaffinic mixture. In some variations, it may be desirable to preferentially select $C_{25}$ hydrocarbons using a distillation cut (e.g., corresponding to β-farnesene:1-decene adducts). In some variations, $C_{27}$ hydrocarbons may be preferentially selected using a distillation cut (e.g., corresponding to 1:1 β-farnesene:1-dodecene adducts). In some variations, $C_{29}$ hydrocarbons may be preferentially selected using a distillation cut (e.g., corresponding to 1:1 β-farnesene:1-tetradecene adducts). In some variations, $C_{30}$ hydrocarbons may be preferentially selected using a distillation cut (e.g., corresponding to farnesene dimers). In some variations, $C_{31}$ hydrocarbons may be preferentially selected using a distillation cut (e.g., corresponding to 1:1 β-farnesene:1-hexadecene adducts). In some variations $C_{29}$-$C_{31}$ hydrocarbons may be preferentially selected using a distillation cut (e.g., corresponding to 1:1 farnesene:1-tetradecene adducts and 1:1 farnesene:1-hexadecene adducts). In some variation, $C_{33}$ hydrocarbons may be preferentially selected using a distillation cut (e.g., corresponding to 1:1 β-farnesene:1-octadecene adducts). In some variations, higher carbon number hydrocarbons are selected by distillation cut, e.g. $C_{35}$-$C_{50}$ hydrocarbons. For example, $C_{35}$, $C_{39}$, $C_{43}$, or $C_{47}$ hydrocarbons may be preferentially selected by distillation, corresponding to 2:1 olefin: β-farnesene adducts of 1-decene, 1-dodecene, 1-tetradecene, and 1-hexadecene, respectively. In some variations $C_{43}$-$C_{47}$ hydrocarbons may be preferentially selected by distillation, corresponding to 2:1 olefin:farnesene adducts of 1-tetradecene and 1-hexadecene. $C_{45}$ hydrocarbons may be preferentially selected by distillation, corresponding to farnesene trimers. In certain variations, even higher carbon number hydrocarbons are selected by distillation, e.g., >$C_{50}$ hydrocarbons, or >$C_{60}$ hydrocarbons which may comprise tetramers and higher oligomers. As stated above, in some cases, a residue left following a distillation may be selected. Such residue may for example contain primarily trimers and tetramers, or may contain trimers, tetramers and pentamers. In some variations, a residue may contain even higher oligomers than pentamers, e.g., hexamers and above.

In one variation, partially hydrogenated β-farnesene that is about 65-85% hydrogenated and comprises at least about 55% mono-olefin and at most about 5% di-olefin is reacted with 1-tetradecene or a mixture of 1-tetradecene and 1-hexadecene (e.g., about 50:50, about 60:40, about 70:30, about 80:20, about 90:10 1-tetradecene:1-hexadecene) using a $BF_3$ catalyst to form branched alkenes that are hydrogenated to form an isoparaffinic mixture. Reaction conditions may be tuned so that the non-monomeric content is predominantly dimeric species. The isoparaffinic mixture may be subjected to a distillation process to obtain a first distillation cut that comprises about 95% monomeric species and about 5% dimer may be obtained. The first distillation cut may be used as a fuel stream (e.g., diesel fuel). The bottoms remaining after the first distillation cut is removed may be subjected to a second distillation process to obtain a second distillation cut that comprises less than 0.4% monomer, about 97% dimer, and about 1-3% trimer. The second distillation cut may have a kinematic viscosity at 100° C. of about 4 cSt, a viscosity index in a range 120-125, a pour point of about −39° C., and a CCS at −30° C. of about 1000-1100 cP. One or more additional distillation and blending processes may be carried out to obtain conducted to obtain a product comprising <0.2% monomer, about 55% dimer, about 42-46% trimer, and about 1% tetramer to make a base oil having a kinematic viscosity at 100° C. of about 6 cSt, a viscosity index in a range 130-135, a pour point of about −30° C., and a CCS at −30° C. of <3000 cP. One nonlimiting example of a method to obtain the 6 cSt base oil is as follows. The bottoms remaining after the second distillation cut may be subjected to a third distillation process to select a trimer-rich cut. Blends made from the trimer-rich cut and any suitable amount of the bottoms remaining following the third distillation process (which may be 0 in some cases) and any suitable amount of the second distillation cut (which may be 0 in some cases) may be made to make an oil having a kinematic viscosity of about 5-10 cSt, e.g., about 6 cSt, 8 cSt, or 10 cSt. Another product that can be obtained comprises no detectable monomer, about 1% dimer, about 80-82% trimer (e.g., 82%), and about 17-19% tetramer (e.g., about 18% tetramer), and having a kinematic viscosity at 100° C. of about 12 cSt and a viscosity index of about 125-130 (e.g., 128). In one variation, the bottoms remaining after a third distillation cut used to select a trimer-rich cut may be used to make a 12 cSt base oil, which may or may not have a portion of a trimer-rich distillation cut blended therewith.

In some variations, the lower boiling portions of the dimeric population are removed by distillation, e.g., the lower boiling 5 area % of the dimeric species as detected by GC-MS. The lower boiling portions of the dimeric population may cause undesired reduction in viscosity index, increase pour point and/or degrade low temperature viscosity properties.

In some variations, the methods described herein form oligomers higher than tetramers or polymers. For example, the transition metal catalysts (e.g., early transition metal catalysts, late transition metal catalysts) or the lanthanide catalysts disclosed herein or known in the art to catalyze oligomerization of alpha-olefins may form oligomers higher than tetramers or polymers from hydrocarbon terpene feedstock and one or more alpha-olefin co-monomers. In some variations, homogeneous or heterogeneous Ziegler-Natta catalysts as described herein or known in the art may form higher olefins than tetramers or polymers from hydrocarbon terpene feedstock and one or more alpha-olefin co-monomers. In certain variations, at least a portion of the higher oligomers or polymers may be used prior to hydrogenation as a base oil, or as a component of a base oil. In other variations, higher oligomers or polymers may be hydrogenated, and at least a portion of the hydrogenated compounds may be used as a base oil, or as a component of a base oil. In some cases, a non-hydrogenated oligomer or polymer formed by the methods described herein may be useful as very viscosity index base oils. The very high viscosity index based oils may exhibit a kinematic viscosity at 100° C. in the range from 10-2000 cSt, and a viscosity index in a range from 150 to 300.

In certain variations, a base oil prepared according to the methods described herein is blended with one or more additional base oils, e.g., one or more commercially available PAOs, a Gas to Liquid (GTL) base stock, one or more mineral oils, a vegetable oil base oil, an algae-derived base oil, a second base oil as described herein, or any other type of renewable base oil. In certain variations, a base oil prepared according to the methods described herein is blended with farnesane. Any effective amount of additional base oil may be added to reach a blended base oil having desired properties. For example, a blended base oil that comprises a ratio of a first base oil as described herein to a second base oil (e.g., a commercially available base oil PAO, a GTL base stock, one or more mineral oils, a vegetable oil base oil, an algae-derived base oil, a second base oil as described herein, or farnesane) that is about 100:1, 50:1, 20:1, 10:1, 5:1, 4:1, 3:1, 2:1, or 1:1 may be made.

In certain variations, base oils prepared according to the methods described herein include a pour point depressant, e.g., a methacrylate-base pour point depressant as is known in the art. Any effective amount of pour point depressant may be added, e.g., about 0.1 wt %, 0.5 wt %, or 1 wt %. In some cases, it may be desirable to add a pour point depressant to isoparaffins prepared according to the methods herein that comprise long straight linear segments (e.g., the isoparaffins as prepared in Examples 1-5) to improve low temperature properties. If a pour point depressant is added, the amount added may be small enough so as to not substantially lower viscosity index.

Also disclosed herein are lubricant compositions comprising an isoparaffinic base stock described herein. In some variations, the lubricant compositions comprise a base stock comprising at least a portion of a mixture of isoparaffins produced by any of the methods described herein (e.g., one or more distillation cuts, or a distillation residue), and one or more additives selected from the group consisting of antioxidants, viscosity modifiers, pour point depressants, foam inhibitors, detergents, dispersants, dyes, markers, rust inhibitors or other corrosion inhibitors, emulsifiers, de-emulsifiers, flame retardants, antiwear agents, friction modifiers, thermal stability improvers, multifunctional additives (e.g., an additive that functions as both an antioxidant and a dispersant) and any combination thereof. In some variations, farnesane is an additive blended with an isoparaffinic base stock as described herein. Lubricant compositions may comprise isoparaffins described herein and any lubricant additive, combination of lubricant additives, or available additive package.

Any of the isoparaffinic compositions described herein that is used as a base stock may be present at greater than about 1% based on the total weight of a finished lubricant composition. In certain embodiments, the amount of the isoparaffinic base stock in the formulation is greater that about 2, 5, 15 or 20 wt % based on the total weight of the formulation. In some embodiments, the amount of the base oil in the composition is from about 1-90%, from about 1-80%, from about 1-70%, from about 1-60%, from about 1-50%, from about 1-40%, from about 1-30%, from about 1-20%, or from about 1-10% based on the total weight of the composition. In certain embodiments, the amount of base stock in formulations provided herein is about 1%, 5%, 7%, 10%, 13%, 15%, 20%, 30%, 40%, 50%, 60%, 70%, 80% or 90%, based on total weight of the formulation.

As is known in the art, types and amounts of lubricant additives are selected in combination with a base stock so that the finished lubricant composition meets certain industry standards or specifications for specific applications. In general, the concentration of each of the additives in the composition, when used, may range from about 0.001 wt. % to about 20 wt. %, from about 0.01 wt. % to about 10 wt. %, from about 0.1 wt. % to about 5 wt. % or from about 0.1 wt. % to about 2.5 wt. %, based on the total weight of the composition. Further, the total amount of the additives in the composition may range from about 0.001 wt. % to about 50 wt. %, from about 0.01 wt % to about 40 wt %, from about 0.01 wt % to about 50 wt %, from about 0.01 wt. % to about 20 wt. %, from about 0.1 wt. % to about 10 wt. %, or from about 0.1 wt. % to about 5 wt. %, based on the total weight of the composition. In some variations, the base oils described herein are formulated as lubricant compositions for use in two cycle engines, in transmissions, as hydraulic fluids, in compressors, in turbines, as automotive engine oils, or as marine grade oils. In some variations, a base oil suitable for use as a hydraulic fluid is formulated using any suitable additive package or combination of additives to have the following properties:

| | |
|---|---|
| Viscosity, ASTM D 445 cSt @ 40° C. | 40-60 |
| Viscosity, ASTM D 445 cSt @ 100° C. | 8-10 |
| Brookfield Viscosity @ 40° C. | 12,000-14,000 cP |
| Viscosity Index, ASTM D 2270 | 140-195 |
| Pour Point, ° C., ASTM D 97 | −40 to −50 |
| Flash Point, ° C., ASTM D 93 | >180 |
| Sulfated Ash, wt %, ASTM D 874 | 0 |
| Color | light amber |

In some variations, any one of the isoparaffinic compositions described herein or farnesane may function as a lubricant additive, e.g., as a pour point depressant, or as a viscosity modifier.

Any of the base oils described herein, including 1:1 hydrocarbon terpene feedstock:olefin comonomer adducts and 1:1 hydrocarbon terpene:hydrocarbon terpene adducts may exhibit performance that is equal to or superior to Group III base oils. In some variations, fully hydrogenated 1:1 farnesene: farnesene adducts or fully hydrogenated 1:1 partially hydrogenated farnesene:partially hydrogenated farnesene adducts made by any method described herein or known in the art and having a chemical formula $C_{30}H_{62}$ may exhibit properties equal to or superior than Group III base oils. In some variations, fully hydrogenated fully hydrogenated 1:1 farnesene: farnesene adducts or fully hydrogenated 1:1 partially hydrogenated farnesene:partially hydrogenated farnesene adducts made by any method described herein or known in the art and having a chemical formula $C_{30}H_{62}$ may be used as a base oil or as an additive in a variety of industrial applications (e.g., in formulations useful for metal working fluids, transformer oils, silicone sealants, demolding formulations, or crop protection).

It is noted that the processes and compositions provided herein have been described with respect to a limited number of embodiments and variations thereof. In certain embodiments, the processes may include one or more steps not specifically mentioned herein. In certain embodiments, steps may be performed in any sequence. In certain embodiments, one or more steps may be omitted or combined with another step but still achieve substantially the same results. Additional variations and modifications from the described embodiments are contemplated.

Each publication, patent, and patent application mentioned in this specification is incorporated herein by reference in its entirety, as if put forth fully below.

Although the claimed subject matter has been described in some detail by way of illustration and example for purposes of clarity of understanding, it will be readily apparent to those of ordinary skill in the art in light of the teachings herein that certain changes and modifications may be made thereto without departing from the spirit or scope of the appended claims.

The following examples are intended for illustrative purposes only and do not limit in any way the scope of the present invention.

EXAMPLES

Examples 1-5: Co(I)-Catalyzed Hydrovinylation of Trans-β-Farnesene and $C_{10}$-$C_{18}$ Alpha-Olefins to Form a Family of Base Oils Examples 1-5 illustrate how methods described herein may be used to build a family of base oils by systematic coupling of a hydrocarbon terpene feedstock with selected olefin co-monomers. The properties of the resulting base oils are varied as the olefin co-monomer is varied. In these Examples 1-5, the hydrocarbon terpene feedstock is β-farnesene, the olefin co-monomers are increasing chain length linear alpha-olefins, and the coupling reaction is a hydrovinylation reaction catalyzed by a Co(I) catalyst.

For Examples 1-5, all flasks used were three-necked round-bottomed flasks. They were equipped with a magnetic stir bar, were oven-dried at 120-150° C., and were subjected to three house vacuum/argon-fill cycles prior to use. After the flask was charged with all the reagents, the flask was equipped with a thermometer and condenser. The syringes used to deliver trans-beta-farnesene and 1-octadecene were weighed before and after addition, and the difference was reported. All reactions were heated to reflux (40° C.) under nitrogen while stirring. Hydrogenation of samples up to 50 g was carried out in a 100 mL Parr high pressure reactor; samples 50-500 g were hydrogenated in a 1 L Parr high pressure reactor. Distillations were done on a Kugelrohr still. Pour points were measured according to ASTM D97, bromine index measurements were performed according to ASTM D2710, kinematic viscosities at 40° C. and at 100° C. were measured according to ASTM D445, and viscosity index was measured according to ASTM D2270. ASTM D97, ASTM D2710, ASTM D445 and ASTM D2270 are each incorporated herein by reference in their entirety.

Figure 10A:
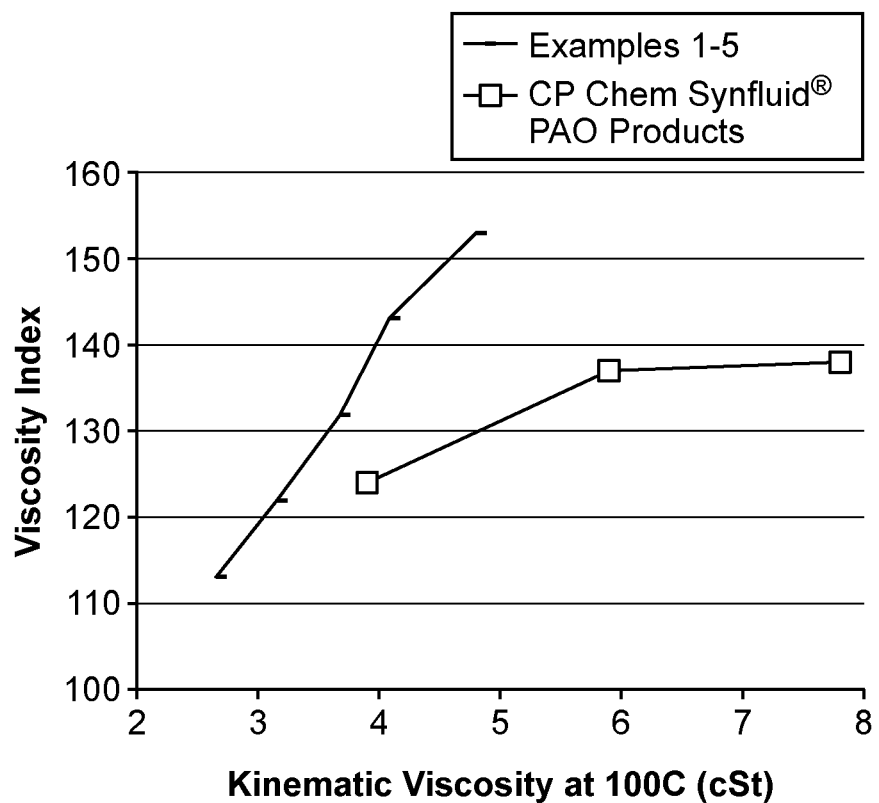
FIG. 10A provides a plot of viscosity index (measured by ASTM D2270) as a function of kinematic viscosity at 100° C. (measured by ASTM D445) for the base oils of Examples 1-5 (light line, dashes). For comparison purposes only, the plot in FIG. 10A also provides viscosity index vs kinematic viscosity at 100° C. for conventional C10-based commercially available highly branched isoparaffins SYNFLUID® PAO 4 cSt, SYNFLUID® PAO 6 cSt, and SYNFLUID® PAO 8 cSt (heavy line, filled squares).
Figure 10B:
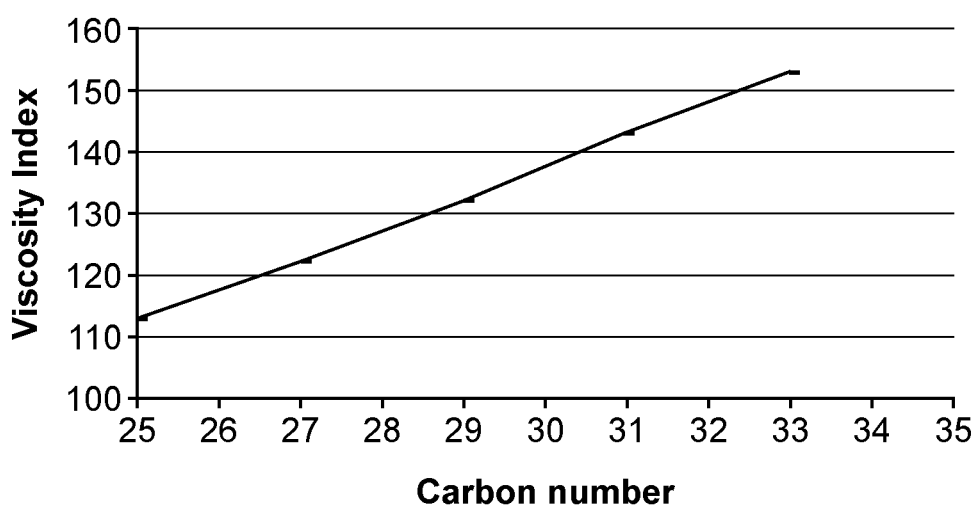
FIG. 10B provides a plot of viscosity index as measured by ASTM D2270 as a function of carbon number for the base oils of Examples 1-5.

FIGS. 10A and 10B show the viscosity index as a function of kinematic viscosity at 100° C., and carbon number, respectively, for the family of base oils made by hydrovinylation of β-farnesene with alpha-olefins of increasing molecular weight. As shown in FIGS. 10A-10B, the viscosity index increases monotonically as the carbon number of the olefin co-monomer is increased, and viscosity index also increases monotonically as the kinematic viscosity at 100° C. increases. For comparison purposes only, FIG. 10A also includes typical viscosity index vs. typical kinematic viscosity at 100° C. for conventional C10-based commercially available highly branched isoparaffins SYNFLUID® PAO 4 cSt, SYNFLUID® PAO 6 cSt, and SYNFLUID® PAO 8 cSt, as published in technical data sheets by Chevron Philips Chemical Company LP, The Woodlands, Tex., available at www.cpchem.com. The base oils made in Examples 1-5 demonstrate a steeper dependence on kinematic viscosity at 100° C. than the conventional C10-based PAOs.

Example 1: 2,6,10,13-tetramethylnonacosane and minor product 10-ethyl-2,6,12-trimethyloctacosane

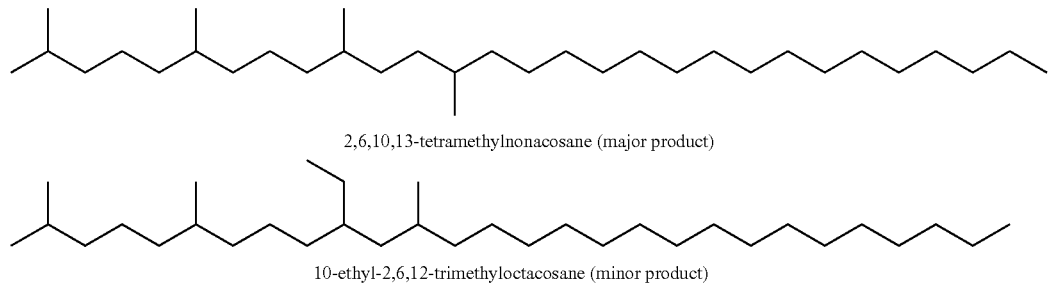

2,6,10,13-tetramethylnonacosane (major product)

10-ethyl-2,6,12-trimethyloctacosane (minor product)

A 250 mL flask was charged with zinc iodide (2.06 g, 6.45 mmol) then subjected to three cycles of vacuum/argon-fill. The flask was charged with dibromo(bis(diphenylphosphino)ethane)cobalt (II) (1.8076 g, 2.9289 mmol) followed by three vacuum/argon-fill cycles. To the reaction flask was added dichloromethane (100 mL), trans-beta-farnesene (20.09 g, 98.31 mmol) and 1-octadecene (24.90 g, 98.62 mmol) via syringe and the mixture was stirred. Finally, tetra-n-butylammonium borohydride (0.3180 g, 2.136 mmol) was added to the reaction flask resulting a dark brown mixture. The reaction was heated for 18 hours and analyzed by GCMS. The dark reaction mixture was vacuum filtered through a short silica column and the filtrate was concentrated in vacuo, resulting a slightly turbid yellow oil (45.07 g). The mixture was distilled at 240° C. and 0.05 mm Hg and the distillate (42.26 g) recovered, a clear colorless oil, was characterized by GCMS and $^1$H NMR. A portion of the distilled unsaturated intermediate (24.0553 g, 52.6547 mmol) was diluted in hexanes and hydrogenated over 10% Pd/C (0.4445 g) at 900 psi $H_2$, 800 rpm, and 150° C. overnight. GCMS analysis of the reaction showed hydrogenation was incomplete so the mixture was filtered through a short silica column to remove the catalyst. The filtrate was concentrated in vacuo affording a clear colorless oil (24.34 g) and subjected to hydrogenation under the same conditions as before except it was done over 5% Pd/C (0.3070 g) and it was continued for three days. The reaction mixture was filtered through a short silica column and concentrated under vacuum resulting a clear colorless oil (24.26 g). The C33 was isolated from the mixture by a two-step distillation: the first distillation was done at 165° C. and 0.02 mm Hg, while the second distillation was done at 225° C. and 0.05 mm Hg. 21.34 g (82.0% yield overall) of the C33 was obtained, while 2.70 g of a mixture of octadecane and farnesane was recovered. The purified product was a clear colorless oil that was characterized by GCMS, GC-FID, and $^1$H NMR.

Example 2: 2,6,10,13-tetramethylheptacosane and minor product 10-ethyl-2,6,12-trimethylhexacosane

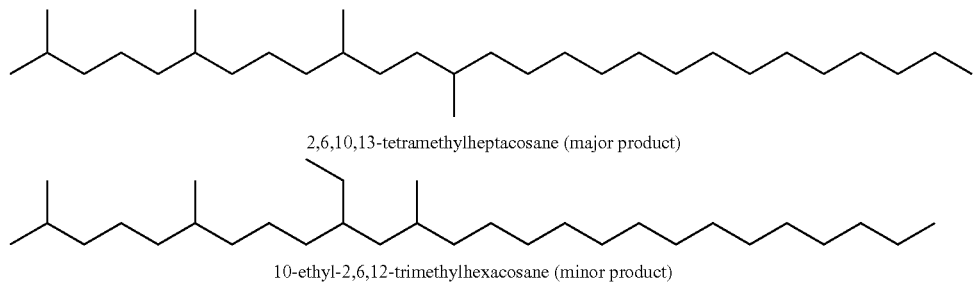

2,6,10,13-tetramethylheptacosane (major product)

10-ethyl-2,6,12-trimethylhexacosane (minor product)

A 2000 mL flask was charged with zinc iodide (21.7 g, 68.0 mmol) followed by 400 mL of dichloromethane. The flask was placed under house vacuum for a few seconds and filled with argon. Dibromo(bis(diphenylphosphino)ethane) cobalt (II) (7.9731 g, 12.919 mmol) was added to the reaction flask, followed by trans-beta-farnesene (106.56 g, 521.43 mmol), 1-hexadecene (97.46 g, 434.3 mmol), and the inside walls of the flask were rinsed with 100 mL dichloromethane. To the mixture was added tetra-n-butylammonium borohydride (4.1940 g, 16.299 mmol) resulting a dark brown mixture. The reaction was heated for 18 hours and the mixture was filtered through a 6.0 cm long by 6.5 cm diameter silica column. The column was rinsed with hexanes and the reddish-brown filtrate was concentrated under vacuum resulting a cloudy brown oil (203.1 g). Hydrogenation of the latter intermediate over 5% Pd/C (2.0762 g) at 1000 psi $H_2$, 75° C., and 800 rpm was unsuccessful, likely due to impurities. A portion of the latter intermediate (120.6 g) was distilled at 235° C. and 0.10 mm Hg. The distillate (107.2 g) recovered was a clear and colorless oil. The distillate was diluted in hexanes and hydrogenated at 900 psi $H_2$, 800 rpm, and 100° C. over 5% Pd/C (1.06 g) and after two days GCMS showed the reaction was incomplete. The catalyst was removed by filtration through celite; 108.5 g of clear colorless oil was obtained after concentration under vacuum. Hydrogenation of the latter material was continued under the same conditions as before except that 10% Pd/C (2.07 g) was used as the catalyst. Hydrogenation was determined to be complete by GCMS and the mixture was filtered through Celite and concentrated under vacuum, resulting 106.6 g of a clear colorless oil. The $C_{31}$ product was isolated from the mixture by a two-step distillation. The first step involved removal of farnesane and hexadecane at 165° C. and 0.20 mm Hg; 11.07 g distillate was recovered. The second step in the distillation involved removal of the C31 from the bottoms at 230° C. and 0.05 mm Hg; 94.6 g (84.0% yield overall) of the purified C31 was recovered. The product was characterized by GCMS, GC-FID, and $^1$H NMR. The bromine index of the product was determined to be 22.89 mg Br/100 g sample.

Example 3: 2,6,10,13-tetramethylpentacosane and minor product 10-ethyl-2,6,12-trimethyltetracosane

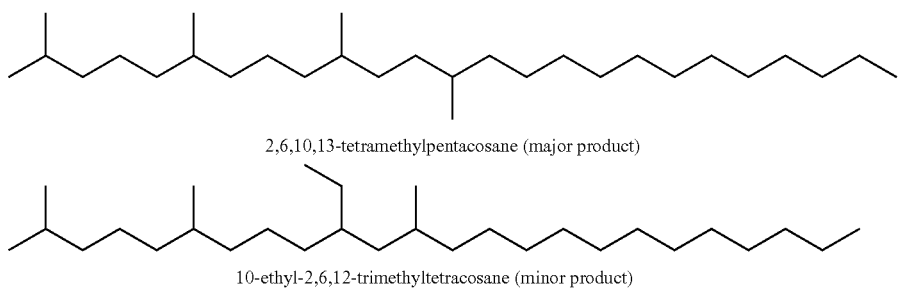

2,6,10,13-tetramethylpentacosane (major product)

10-ethyl-2,6,12-trimethyltetracosane (minor product)

A 100 mL flask was charged with (in the order mentioned) farnesene (9.1818 g, 44.930 mmol), 1-tetradecene (8.0123 g, 40.800 mmol), dibromo(bis(diphenylphosphino)ethane)cobalt (II) (0.4993 g, 0.8090 mmol), dichloromethane (25 mL), zinc iodide (1.3565 g, 4.2494 mmol), and finally tetra-n-butylammonium borohydride (0.2549 g, 0.9906 mmol) resulting a dark brown mixture. The reaction was heated for 17 hours and once it had cooled to room temperature the mixture was filtered through a short silica column prepared on a glass frit. A clear colorless oil (16.6112 g) was obtained after the filtrate was concentrated under vacuum. The intermediate was diluted in hexanes and hydrogenated at 800 psi $H_2$, 85° C., and 800 rpm over 10% Pd/C (1.0052 g) and the reaction was allowed to proceed overnight. The mixture was filtered through a short celite column and a clear colorless oil (15.6146 g) was obtained after the filtrate was concentrated under vacuum. The C29 was isolated from the hydrocarbon mixture (15.51 g) via a two-step distillation: the first step was done at 155° C./0.20 mm Hg and the second step was done at 230° C./0.15 mm Hg. The following was the mass balance from the distillation: 6.83 g (40.9% yield overall) of the C29 and 8.39 g of C15s/tetradecane. The isolated product was characterized by GCMS, GC-FID, and $^1$H NMR. The bromine index was 55.571 mg Br/100 g sample.

Example 4: 2,6,10,13-tetramethyltricosane and minor product 10-ethyl-2,6,12-trimethyldocosane

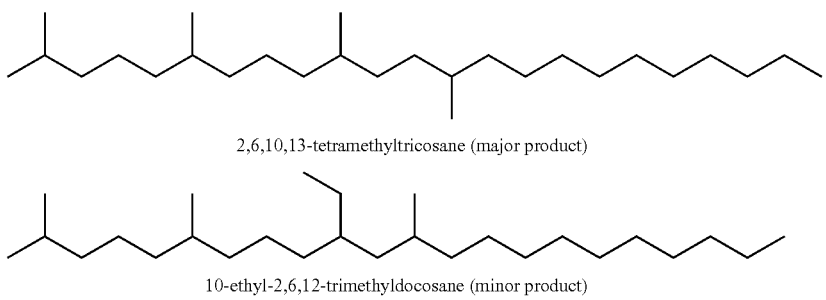

2,6,10,13-tetramethyltricosane (major product)

10-ethyl-2,6,12-trimethyldocosane (minor product)

A 250 mL flask was charged with zinc iodide (2.02 g, 6.33 mmol) and the flask was subjected to three cycles of vacuum/argon-fill. The flask was charged with dibromo(bis (diphenylphosphino)ethane)cobalt (II) (1.8232 g, 2.9542 mmol), placed under house vacuum and back-filled with argon a total of three times. To the flask was added dichloromethane (100 mL), followed by trans-beta-farnesene (20.13 g, 98.50 mmol) and 1-dodecene (16.45 g, 97.73 mmol) via syringe and the mixture was stirred. Finally, tetra-n-butylammonium borohydride (0.9337 g, 3.629 mmol) was added to the reaction mixture resulting a dark brown mixture. The reaction was heated for 19 hours and was analyzed by GCMS. The dark reaction mixture was vacuum filtered through a short silica column. The filtrate was concentrated in vacuo, resulting a clear yellowish-brown oil (45.07 g). A portion of the latter intermediate (35.6 g) was distilled at 230° C. and 0.05 mm Hg. The distillate recovered was a clear colorless oil (29.58 g) that was characterized by GCMS. The purified intermediate was hydrogenated at 900 psi $H_2$, 800 rpm, and 150° C., over 5% Pd/C (0.3197 g) and after two days GCMS showed incomplete conversion. The catalyst was removed from the mixture by filtration through a short silica column prepared on a glass frit. A clear colorless oil (29.31 g) was obtained after the filtrate was concentrated and it was subjected to hydrogenation overnight under the same condition as before except that 0.3070 g of 5% Pd/C was used. After the hydrogenation was determined to be complete by GCMS the $C_{27}$ was isolated from the hydrocarbon mixture by a two step distillation: first at 155° C./0.01 mm Hg then at 215° C./0.02 mm Hg. The following was the mass balance of the distillation: 22.77 g (61.2% yield overall) of the isolated $C_{27}$ was recovered and 5.79 g of farnesane/dodecane mixture. The product was characterized by GCMS, GPC and $^1H$ NMR. Partial proton NMR of the product prior to hydrogenation: 5.185 (bt, 1H), 5.106 (bs, 2H), 4.699 (d, 2H), 2.692 (d, 2H), 1.680 (s, 3H), 1.611 (s, 3H), 1.600 (s, 6H), 0.881 (t, 3H). The proton NMR demonstrates the major product prior to hydrogenation has the structure A 250 mL flask was charged with zinc iodide (1.40, 4.39 mmol) followed by three cycles of vacuum/argon back-fill. The flask was charged with dibromo(bis(diphenylphosphino)ethane)cobalt (II) (1.8275 g, 2.9612 mmol) placed under house vacuum and back-filled with argon a total of three times. Dichloromethane (100 mL), trans-beta-farnesene (20.16, 98.65 mmol) and 1-decene (13.28, 94.67 mmol) were delivered to the flask via syringe and the mixture was stirred. Finally, tetra-n-butylammonium borohydride (0.9150 g, 3.556 mmol) was added to the reaction mixture resulting in a dark brown mixture. The reaction was heated for 17 hours, analyzed by GCMS, and the dark mixture was vacuum filtered through a silica column. The filtrate was concentrated in vacuo, resulting a slightly turbid yellow oil (32.35 g) and purified by distillation at 225° C. and 0.15 mm Hg. The distillate, a light yellow oil (29.96 g) containing precipitate, was diluted in hexanes and filtered through a 3.1 cm diameter by 2.5 cm long column of neutral alumina. After concentration 28.77 g of the intermediate was recovered. A portion of the latter (24.90 g) was diluted in hexanes and hydrogenated at 900 psi $H_2$, 800 rpm, and 150° C., over 5% Pd/C (0.3182 g). After two days GCMS showed the reaction was incomplete so the catalyst was removed from the hydrocarbon phase by filtration through silica and the filtrate was concentrated in vacuo resulting a clear colorless oil (25.53 g). The reactor was charged with the latter and 0.3 g 10% Pd/C and the hydrogenation was done overnight at 150° C., 800 rpm, and 800 psi $H_2$. After the reaction was assessed complete by GCMS the mixture was filtered through silica and the filtrate was concentrated under vacuum affording 24.45 g of a clear colorless oil. The $C_{25}$ product was isolated from the hydrocarbon mixture by a two-step distillation. To remove the $C_{15}$ species and the decane, the distillation was done at 145° C./0.05 mm Hg, where 3.70 g was recovered as distillate. To isolate the $C_{25}$ product from any oligomers or polymers the distillation was done at 205° C./0.05 mm Hg, where 20.14 g (69.7% yield overall) of the isolated $C_{25}$ product was obtained.

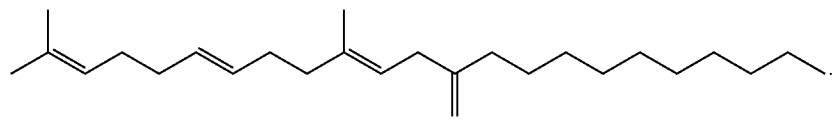 [SMILES: C=C(C/C=C(\C)CC/C=C/CCC=C(C)C)CCCCCCCCCC]

The signal at 4.699 corresponds the two vinylidene protons; the signal at 2.692 corresponds to the —$CH_2$— group between the olefins near the center of the molecule.

Example 5: 2,6,10,13-tetramethylhenicosane and minor product 10-ethyl-2,6,12-trimethylicosane

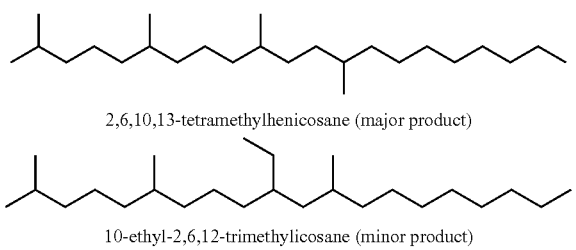

TABLE 5A

Properties of base oils made in Examples 1-5

| Example No. | Compound Formula | $Kv_{40°C.}$ cSt | $Kv_{100°C.}$ cSt | Viscosity Index | Pour Point ° C. | Bromine Index mg Br/ 100 g |
| --- | --- | --- | --- | --- | --- | --- |
| 1 | $C_{33}H_{68}$ | 21.46 | 4.81 | 153 | −9 | 0 |
| 2 | $C_{31}H_{64}$ | 17.42 | 4.12 | 143 | −18 | |
|   |   | 17.15 | 4.076 | 143 |   | 333 |
| 3 | $C_{29}H_{60}$ | 15.14 | 3.68 | 132 | −45 | 5 |
| 4 | $C_{22}H_{56}$ | 12.28 | 3.15 | 122 | <−70 | 6 |
| 5 | $C_{25}H_{52}$ | 9.637 | 2.657 | 113 | Not measured | Not measured |

Example 6: Protic Acid Catalyzed Coupling of a Mixture of $C_{14}$-$C_{20}$ Alpha-Olefins with a Hydrocarbon Terpene Feedstock Comprising Partially Hydrogenated β-Farnesene to Form a Base Oil The instant example provides an illustration of a base oil formed by using a cationic initiator (in this example, a protic acid) to couple a hydrocarbon terpene feedstock (in this example, partially hydrogenated β-farnesene) with olefin co-monomer (in this example, a mixture of alpha-olefins) to form a base oil.

To a 2 L round bottom flask was added 600 g of partially hydrogenated β-farnesene that had been hydrogenated using 3.5 molar equivalents of hydrogen gas in a batch slurry reactor, as in Examples 19-20 below, except that the hydrogenation catalyst was 2 g 10 wt % Pd/C, a total of 3.5 equivalents of hydrogen were added, the first two equivalents of hydrogen were added to the reactor without external heating, and the reaction was heated to 80° C. for the last 1.5 equivalents of hydrogen. The partially hydrogenated farnesene was approximately 82-85% hydrogenated, as measured by Br number. 600 g of a mixture of $C_{14}$-$C_{20}$ alphaolefins (Ineos $C_{16}C_{18}$ alphaolefins, CAS #68855-60-7, available from Ineos USA, LLC, League City, Tex.) was added to the flask. 60 g of sulfuric acid (96 wt % from Fisher Chemical) was added slowly to the flask containing the alphaolefins and partially hydrogenated β-farnesene. The reaction temperature was controlled to be below 20° C., and was stirred. After 2 hours, the reaction mixture turned red, and 80 g of dibutylamine was added while the temperature was maintained to a temperature less than 20° C., and the mixture was stirred. To the mixture was added 1200 g water, and mixing continued for about 30 min. The aqueous component of reaction mixture was separated out by centrifuge. The mass of the crude unsaturated hydrocarbon recovered was 1160 g. A 1 L filter funnel was packed with 500 ml silica gel. The crude unsaturated hydrocarbon was passed through the silica gel to remove sulfur and other impurities (e.g., polar impurities) in the sample. The silica gel was washed with 300 ml isopropyl alcohol, and the isopropyl alcohol was evaporated to yield 1075 g of the unsaturated hydrocarbon product. The unsaturated hydrocarbon product was hydrogenated in 3 batches in a batch slurry reactor using 2 g 10 wt % Pd/C as a catalyst at 1000 psig hydrogen for each batch, yielding approximately 1045 g hydrogenated product after filtration of the hydrogenation catalyst, washing of the filter with isopropyl alcohol as a solvent, and evaporation of the solvent. A first distillation using a Kugelrohr distillation apparatus at 1 torr and 200° C. was carried out, yielding 636 g.

A portion of the hydrogenated product was distilled at 1 torr and a reflux ratio of 10 using a spinning band distillation apparatus model 18-100, available from B/R Instrument Corp., Easton, Md. Results are shown in Table 6A.

TABLE 6A

| Cut | Initial Weight (g) | Final Weight (g) | Fraction Weight (g) | Fraction Weight (%) | Open Cut Temp (° C.) | Closed Cut Temp (° C.) |
|---|---|---|---|---|---|---|
| 1A | 59.90 | 151.83 | 91.93 | 21.18% | 225 | 380 |
| 1B | 121.82 | 169.02 | 47.20 | 10.88% | 225 | 380 |
| 2 | 60.03 | 73.07 | 13.04 | 3.00% | 380 | 400 |
| 3 | 60.93 | 79.45 | 18.52 | 4.27% | 400 | 420 |
| 4A | 60.58 | 151.75 | 91.17 | 21.01% | 420 | 462 |
| 4B | 61.58 | 105.75 | 44.17 | 10.18% | 420 | 462 |
| 4C | 60.40 | 123.49 | 63.09 | 14.54% | 420 | 462 |
| 4D | 61.97 | 65.09 | 3.12 | 0.72% | 420 | 462 |
| Pot Feed | 718.80 | 323.00 | 38.18 | 8.80% | | |
| | 433.98 | 38.18 | | | | |
| Accum. | | 410.42 | g | 94.57% | | |
| Missing | | 23.56 | g | | | |

Figure 8A:
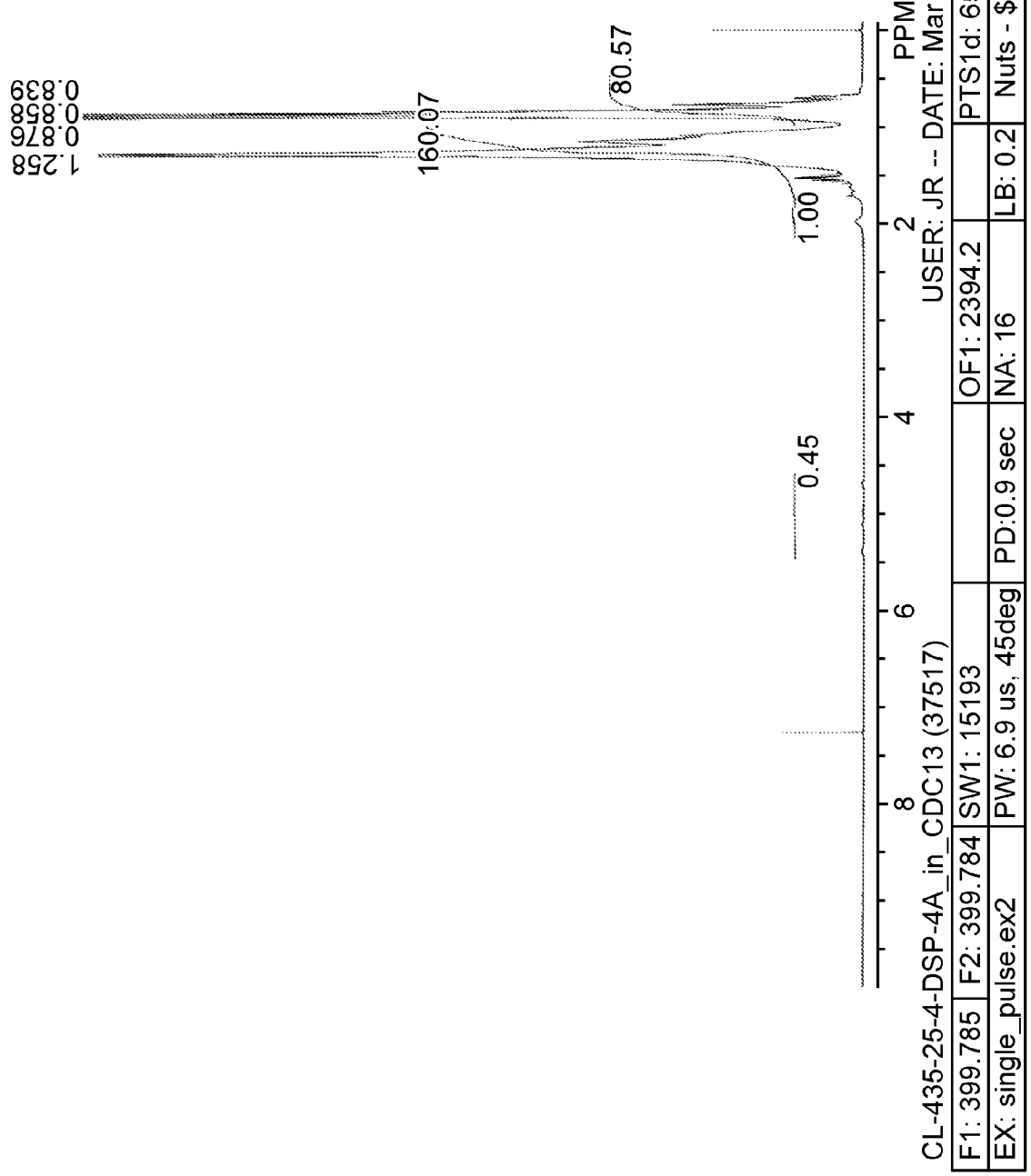
FIG. 8A provides a proton NMR spectrum (in $CDCl_3$) of a mixture of isoparaffins prepared by Example 6.
Figure 8C:
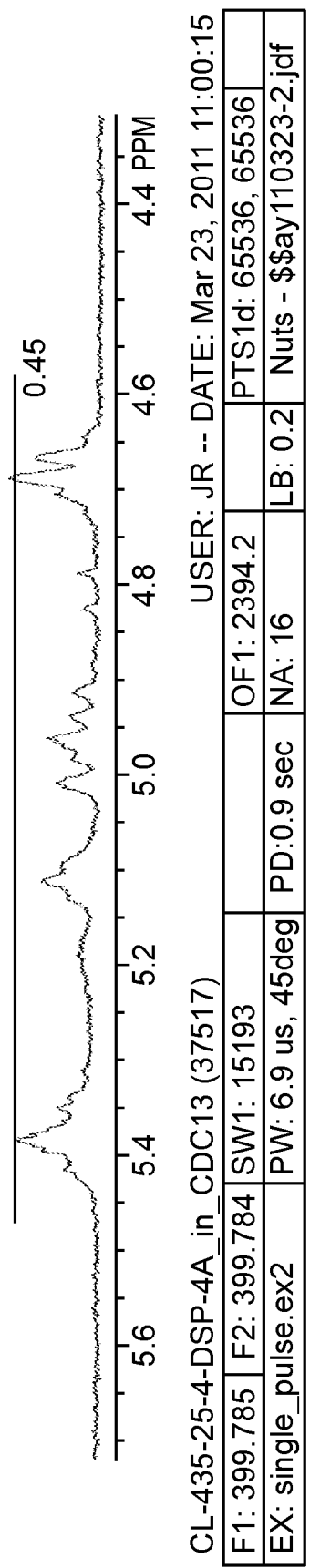
FIG. 8C provides a proton NMR spectrum of the mixture of isoparaffins as in FIG. 8A, on an expanded scale of about 4.3 ppm-5.7 ppm.
Figure 9A:
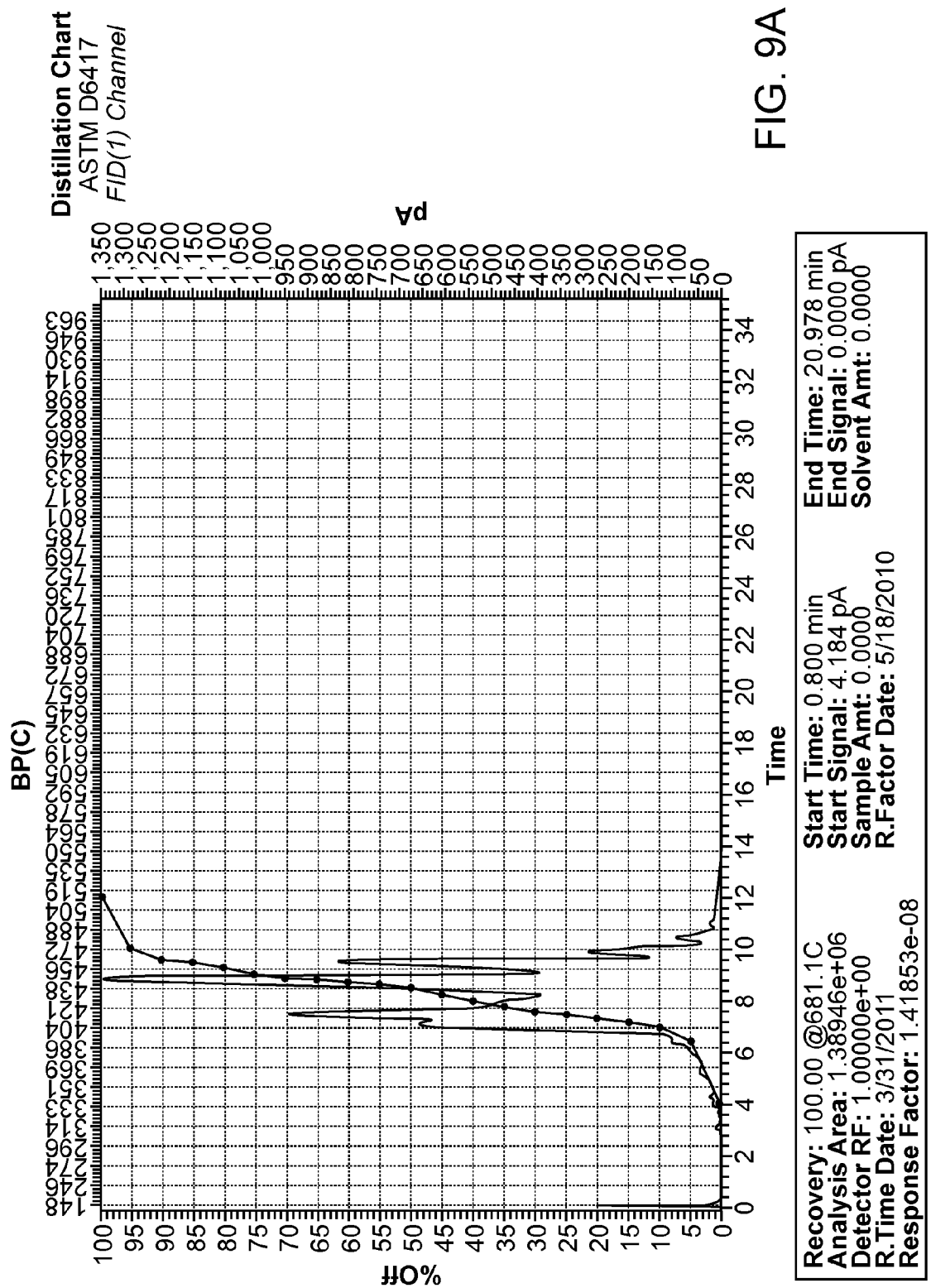
FIG. 9A provides a simulated distillation curve overlaid with cumulative distillation percentage for a mixture of isoparaffins prepared as in Example 6.
Figure 9B:
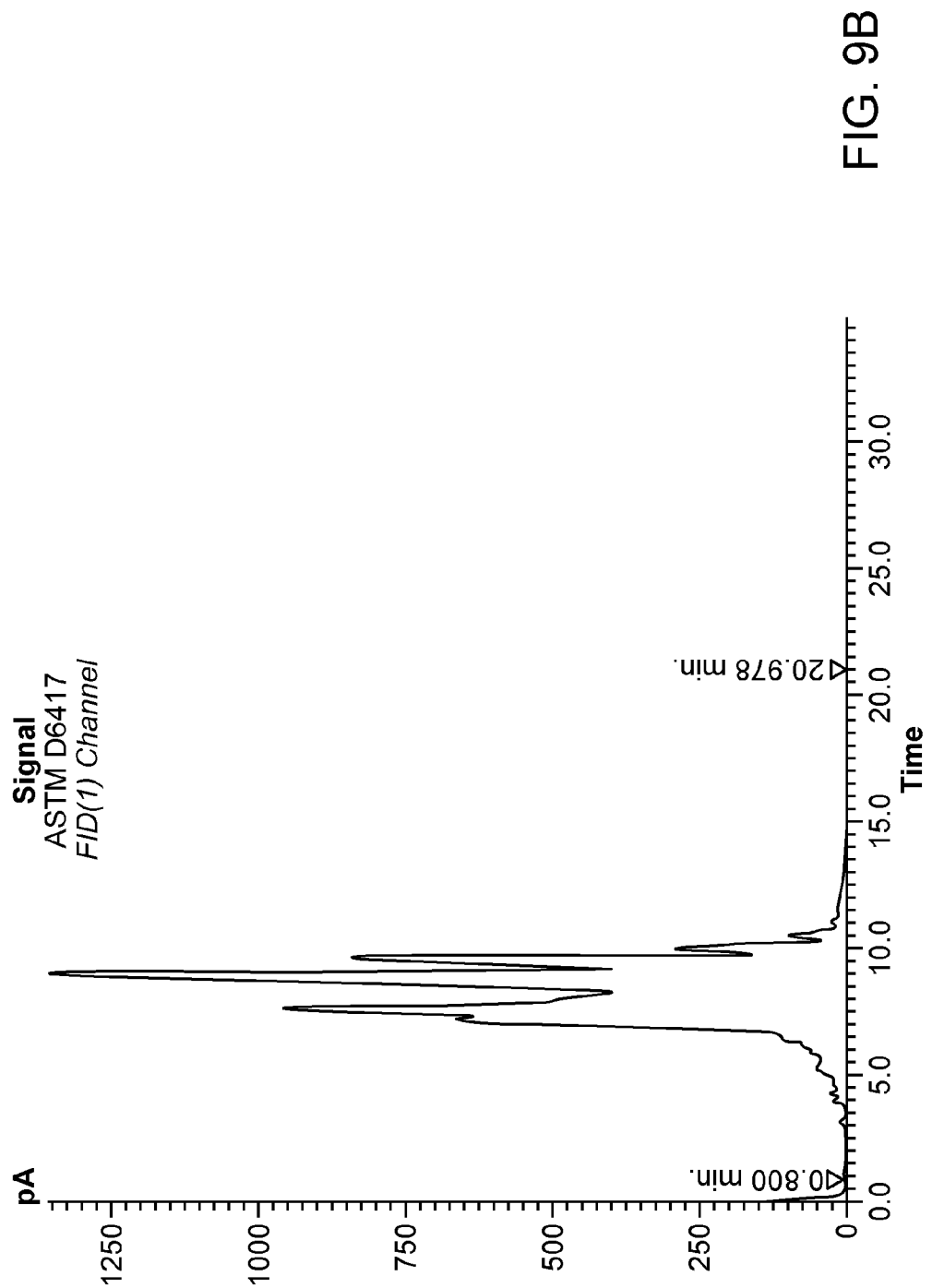
FIG. 9B provides an alternate view of the simulated distillation curve of FIG. 9A.
Figure 9C:
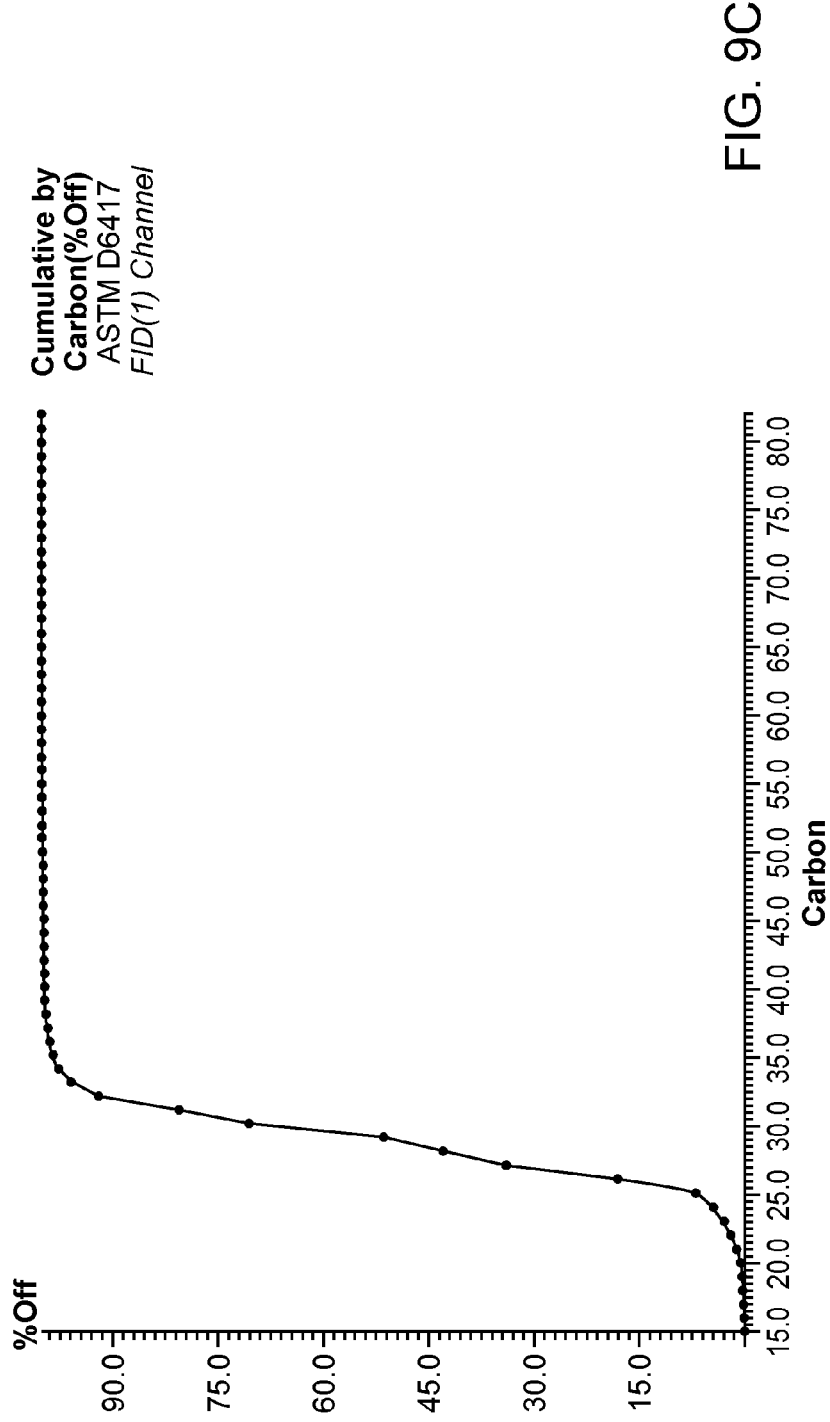
FIG. 9C provides a graph showing cumulative distillation percentage as a function of carbon number for the simulated distillation of FIG. 9A.
Figure 9D:
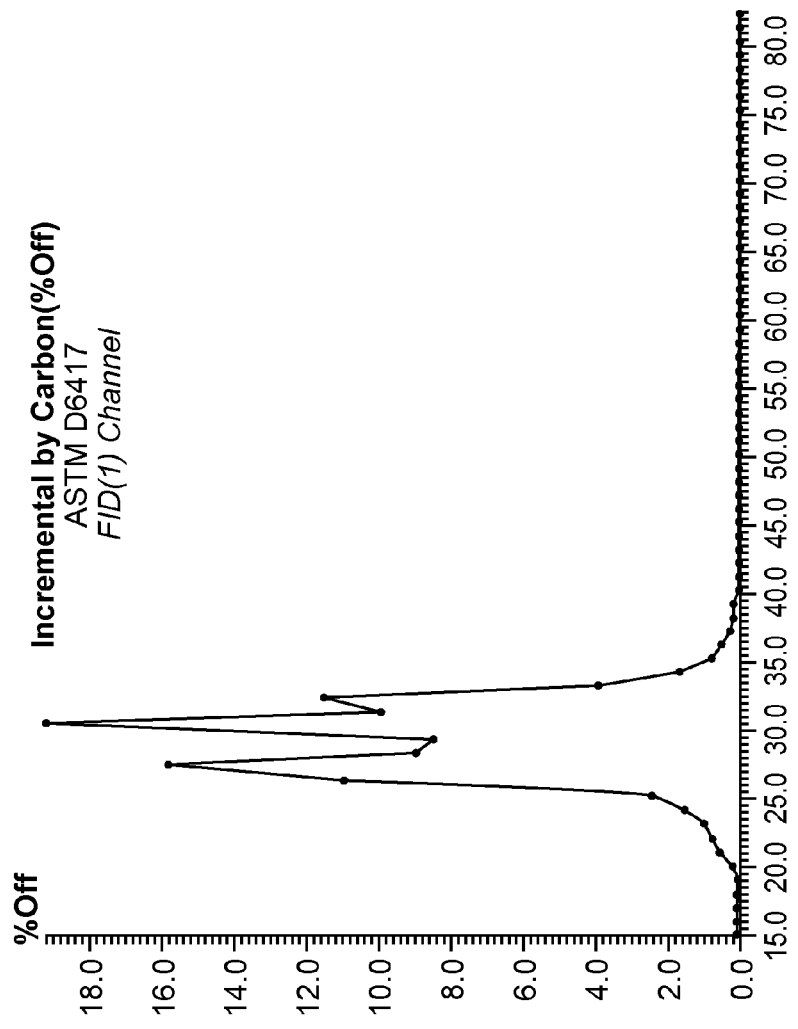
FIG. 9D provides a graph showing incremental distillation percentage as a function of carbon number for the simulated distillation of FIG. 9A.

$^{13}$C NMR spectra of distillation cut 4A are illustrated in FIGS. 7A-7D. Proton NMR spectra of distillation cut 4A are illustrated in FIGS. 8A-8C. Simulated distillation analysis using an Agilent 7890 Simulated Distillation Analyzer of distillation cut 4A is illustrated in FIGS. 9A-9E. The specific gravity of cut 4A was measured to be 0.824 according to ASTM D0452. The kinematic viscosity at 100° C. of cut 4A was measured to be 4.8 cSt according to ASTM D445. The kinematic viscosity of cut 4A at 40° C. was measured to be 23.42 cSt according to ASTM D445. The viscosity index of cut 4A was determined to be 129 according to ASTM D2270.

Examples 7-11: $BF_3$-Catalyzed Coupling of Partially Hydrogenated β-Farnesene and $C_{10}$-$C_{16}$ Alpha-Olefins to Form a Family of Base Oils Examples 7-11 provide further illustration of how methods described herein may be used to build a family of base oils by systematic coupling of a hydrocarbon terpene feedstock with selected olefin co-monomers. The properties of the resulting base oils are varied as the olefin co-monomer is varied. In these Examples 7-11, the hydrocarbon terpene feedstock is partially hydrogenated β-farnesene, the olefin co-monomers are increasing chain length linear alpha-olefins, and for Example 11, a mixture of linear alpha-olefins, and the coupling reaction is catalyzed using a cationic initiator ($BF_3$ and one or more co-catalysts).

Example 7: Preparation of Isoparaffinic Base Oil by Coupling Partially Hydrogenated Farnesene and 1-hexadecene Using $BF_3$ as a Cationic Initiator To a clean and dry 2 liter Parr reactor was added 200 ml isoparaffinic hydrocarbon fluid (ISOPAR™ L, available from ExxonMobil Chemical Company, Houston, Tex.). The reactor temperature was maintained at 20° C. to within +/−1° C. The reactor was evacuated to 50 torr, and held under vacuum for 10 minutes. The reactor was charged with $BF_3$ gas (99% pure, available from Airgas) to bring the reactor up to a reactor pressure of 3 psig. A co-feed was made by mixing 500 ml of 75% partially hydrogenated farnesene and 500 ml 1-hexadecene (NEODENE®16, available from Shell Chemicals, Houston, Tex.) in a graduated flask. The 75% hydrogenated farnesene was prepared according to Example 23 below, had the following composition: 69% mono-olefin, 15% di-olefin, <0.3% tri-olefin, <0.3% tetra-olefin, and 16% farnesane. The co-feed was delivered to the reactor at a rate of about 10 ml/min. To the reactor was added 2 ml liquid adduct that includes $BF_3$:butanol and $BF_3$:butyl acetate. The liquid adduct was made by adding 2 mol $BF_3$ to 1 mol butanol (reagent grade, <0.5 wt % $H_2O$, available from Sigma-Aldrich, St. Louis, Mo.) and 1 mol butyl acetate Instrument Corp., Easton, Md. The distillation cuts (as wt % of the 533.8 g of crude hydrogenated reaction product) are shown in Table 7A below (AET):

TABLE 7A

| Dsp_1 | Dsp_2 | Dsp_3 | Dsp_4 | Dsp_5 | Dsp_6 | Dsp_7 | Dsp_8 | Residual |
|---|---|---|---|---|---|---|---|---|
| 160° C. < T < 230° C. | 230° C. < T < 285° C. | 285° C. < T < 360° C. | 360° C. < T < 405° C. | 405° C. < T < 420° C. | 420° C. < T < 435° C. | 435° C. < T < 445° C. | 445° C. < T < 480° C. | >480° C. |
| 21.1% | 17.2% | 2% | 5.9% | 2% | 14.7% | 6.9% | 0.1% | 29.6% |

(reagent grade, <0.5 wt % $H_2O$, available from Sigma-Aldrich). A total volume of 15 ml of liquid adduct (corresponding to 15 mmol) was added to the reacted in 10 equal charges over a period of about two hours as the liquid co-feed was delivered at a rate of 10 ml/min. During the reaction, the $BF_3$ pressure in the reactor was maintained within +/−0.5 psig of the desired setpoint of 3 psig. The reactor was cooled using chilled water cooling, and the feed rate of the reactants was adjusted to help maintain temperature control. After the co-feed and liquid adduct deliveries were complete, the reactor was held at the temperature setpoint and at the pressure setpoint for three hours. A sample was taken from the reactor every hour to monitor the extent of conversion by GC-FID. At the end of the two hour hold period, $BF_3$ pressure was released, and the reactor was sparged with dry nitrogen gas to remove residual $BF_3$ from the crude reaction product. The crude reaction product was quenched with an equimolar or excess amount of 50% in water caustic solution (available from Sigma-Aldrich). The quenched crude reaction product was washed with water (50 pounds water per 100 pounds of co-feed), and the organic layer was allowed to separate from the water layer via gravity separation. The organic layer was collected, and a second wash of the oil was performed. Any solids remaining in the washed crude reaction product were removed by filtering through a 10-20 micron mesh silica gel filter. The washed, filtered crude reaction product was diluted to a 1:1 ratio with decane. The diluted reaction product was fed through a fixed bed hydrogenation reactor at a rate of 40 ml/min using 0.3 wt % $Pd/Al_2O_3$ trilobe extrudate 2.5 mm catalyst mixed with Selexsorb™ CD adsorbent as (70 wt % catalyst/30 wt % Selexsorb™ adsorbent) at a pressure of 500 psig $H_2$, a temperature of 150° C. Following hydrogenation, the diluted reaction producted was evaporated at 120° C.-130° C., 20 torr to remove decane. 533.88 g of crude hydrogenated reaction product was isolated.

Simulated distillation using an Agilent 7890 Simulated Distillation Analyzer in a manner similar to Example 6 on the hydrogenated crude reaction product showed the following composition: $C_{12}$ range (200° C.-240° C.): 0.60 area %; $C_{15}$ range (240° C.-320° C.): 29.20 area %; $C_{20}$ (320° C.-370° C.) range: 0.00 area %; $C_{25}$ range (370° C.-420° C.): 4.30 area %; $C_{30}$ range (420° C.-481° C.): 40.30 area %; $C_{35}$ range (481° C.-508° C.): 1.70 area %; $C_{40}$-$C_{50}$ range (508° C.-575° C.): 19.30 area %; $C_{51}$-$C_{60}$ (575° C.-615° C.): 3.60 area %; and $C_{61}$-$C_{72}$ range (615° C.-700° C.): 1.20 area % with all temperatures representing boiling points at atmospheric pressure. The hydrogenated crude reaction product was distilled into eight separate distillation cuts using a spinning band distillation apparatus, available from B/R Of these, Dsp_5 (collected over 405° C.-420° C.), Dsp_6 (collected over 420° C.-435° C.), Dsp_7 (435° C.-445° C.), and Dsp_R (residual with boiling point>480° C.) were characterized for their cold cranking simulator viscosity at −25° C., −30° C., −35° C. according to ASTM D5293 and for their viscometric properties (kinematic viscosity at 40° C. and at 100° C. according to ASTM D445, and viscosity index according to ASTM D2270). Results are shown in Table 7B.

TABLE 7B

| Temperature | Cold Cranking Simulator Viscosity (mPa-sec) | | | Kinematic viscosity (cSt) | | Viscosity index |
|---|---|---|---|---|---|---|
| | −25° C. | −30° C. | −35° C. | 40° C. | 100° C. | |
| Dsp_5 | 1025.9 | 1755.8 | 4201.8 | 22.85 | 4.55 | 113 |
| Dsp_6 | 958.1 | 2684.3 | 17294.0 | 23.2 | 4.82 | 133 |
| Dsp_7 | 936.7 | 2813.2 | 22658.3 | 22.68 | 4.73 | 130 |
| Dsp_R | NM | NM | NM | 67.16 | 10.0 | 133 |

NM = not measured

As shown, selection of the distillation cuts from the crude hydrogenated reaction product yields multiple base stocks having distinct physical properties. Dsp_5 corresponds to a 4-5 cSt base stock with viscosity index<120, whereas Dsp_6 and Dsp_7 each correspond to a 5 cSt base stock with viscosity index>120. As seen, Dsp_6 has a higher viscosity index than Dsp_5, and also exhibits superior cold cranking simulator performance. Dsp_R corresponds to a 10 cSt base stock with viscosity index=133.

Example 8: Preparation of Isoparaffinic Base Oil by Coupling Partially Hydrogenated Farnesene and 1-hexadecene Using $BF_3$ as a Cationic Initiator The oligomerization reaction was carried out as in Example 7, except the liquid adduct was made by adding 1 mol $BF_3$ to 1 mol butanol, and the reaction was conducted using 200 g partially hydrogenated β-farnesene prepared as in Example 20, 1-hexadecene (volume of 1-hexadecene was one third the volume of partially hydrogenated β-farnesene), and 15 mmol liquid adduct. Hydrogenation was carried out as in Example 7. 224 g crude hydrogenated product was recovered.

The hydrogenated crude reaction product was distilled using a spinning band distillation apparatus into several cuts over temperatures ranging from 165° C.-422° C., with a residual being those components with a boiling point greater than 422° C. (AET). The distillation cuts (as wt % of the 224 g) are shown in Table 8A below:

TABLE 8A

| Dsp_1 | Dsp_2 | Dsp_3 | Dsp_4 | Residual |
|---|---|---|---|---|
| 165° C. < T < 210° C. | 210° C. < T < 300° C. | 300° C. < T < 380° C. | 380° C. < T < 410° C. | T > 422° C. |
| 10.4% | 24.1% | 1.1% | 1.3% | 63.2% |

Simulated distillation results for the crude hydrogenated reaction product and the residual following distillation are shown in Table 8B, with areas given as area % of each distillation cut. Simulated distillation was conducted using an Agilent 7890 Simulated Distillation Analyzer in a manner similar to Example 6. For Table 8B, the following boiling point at atmospheric pressure correspond to the carbon number ranges provided in the column headings: $C_{12}$ range (200° C.-240° C.); $C_{15}$ range (240° C.-320° C.); $C_{20}$ range (320° C.-370° C.); $C_{25}$ range (370° C.-420° C.); $C_{30}$ range (420° C.-481° C.); $C_{35}$ range (481° C.-508° C.); $C_{40}$-$C_{50}$ range (508° C.-575° C.); $C_{51}$-$C_{60}$ (575° C.-615° C.); and $C_{61}$-$C_{72}$ range (615° C.-700° C.).

TABLE 8B

| | $C_{12}$ | $C_{15}$ | $C_{20}$ | $C_{25}$ | $C_{30}$ | $C_{35}$ | $C_{40}$-$C_{50}$ | $C_{51}$-$C_{60}$ | $C_{61}$-$C_{72}$ |
|---|---|---|---|---|---|---|---|---|---|
| crude | 0.6 | 28.4 | 0 | 24.7 | 19.3 | 6.3 | 15.6 | 3.8 | 1.6 |
| Dsp_R | 0 | 0.3 | 0.7 | 36.1 | 27.1 | 9.3 | 21.4 | 4 | 1.4 |

The residue from the distillation was characterized for viscometric properties (kinematic viscosity at 40° C. and at 100° C. according to ASTM D445, and viscosity index according to ASTM D2270). Results are shown in Table 8C.

TABLE 8C

| | Kinematic viscosity (cSt) | | Viscosity |
|---|---|---|---|
| | 40° C. | 100° C. | index |
| Dsp_R | 39.7 | 6.71 | 124 |

Example 9: Preparation of Isoparaffinic Base Oil by Coupling Partially Hydrogenated Farnesene and 1-dodecene Using $BF_3$ as a Cationic Initiator The oligomerization reaction was carried out as in Example 7, except that the co-feed was made from 600 ml of 75% hydrogenated farnesene (prepared as in Example 23) and 500 ml NEODENE® 12 1-dodecene (available from Shell Chemicals), and the reaction was allowed to stand for one hour instead of three hours. The hydrogenation reaction was carried out as in Example 7. 356.9 g crude hydrogenated product was isolated.

Simulated distillation on the hydrogenated crude reaction product showed the following composition: $C_{12}$ range (200° C.-240° C.): 0.5 area %; $C_{15}$ range (240° C.-320° C.): 19.6 area %; $C_{20}$ (320° C.-370° C.) range: 2 area %; $C_{25}$ range (370° C.-420° C.): 33.5 area %; $C_{30}$ range (420° C.-481° C.): 0.7 area %; $C_{35}$ range (481° C.-508° C.): 33.3 area %; $C_{40}$-$C_{50}$ range (508° C.-575° C.): 9.2 area %; $C_{51}$-$C_{60}$ (575° C.-615° C.): 1.2 area %; and $C_{61}$-$C_{72}$ range (615° C.-700° C.): 0 area %. Simulated distillation was conducted using an Agilent 7890 Simulated Distillation Analyzer in a manner similar to Example 6. The hydrogenated crude reaction product was distilled using a spinning band distillation apparatus into several cuts over temperatures ranging from 160° C.-420° C. (AET), with a residual being those components with a boiling point greater than 420° C. The distillation cuts (as wt % of the 356.9 g) are shown in Table 9A below:

TABLE 9A

| Dsp_1 | Dsp_2 | Dsp_3 | Dsp_4 | Dsp_5 | Dsp_6 | Dsp_7 | Residual |
|---|---|---|---|---|---|---|---|
| 160° C. < T < 210° C. | 210° C. < T < 260° C. | 260° C. < T < 345° C. | 345° C. < T < 375° C. | 375° C. < T < 395° C. | 395° C. < T < 402° C. | 402° C. < T < 420° C. | >420° C. |
| 5.5% | 16.7% | 1.2% | 3.3% | 4.8% | 22.6% | 6.4% | 38.9% |

Of these, Dsp_5 (collected over 375° C.-395° C.), Dsp_6 (collected over 395° C.-402° C.), Dsp_7 (402° C.-420° C.), and Dsp_R (residual with boiling point higher than 420° C.) (all temperatures AET) were characterized for their cold cranking simulator performance at −25° C., −30° C., −35° C. according to ASTM D5293 and for their viscometric properties (kinematic viscosity at 40° C. and at 100° C. according to ASTM D445, and viscosity index according to ASTM D2270). Results are shown in Table 9B.

TABLE 9B

| | Cold Cranking Simulator Viscosity (mPa-sec) | | | Kinematic viscosity (cSt) | | Viscosity |
|---|---|---|---|---|---|---|
| Temperature | −25° C. | −30° C. | −35° C. | 40° C. | 100° C. | index |
| Dsp_5 | 141.5 | 385.1 | 721.5 | 10.10 | 2.68 | 100 |
| Dsp_6 | 546.1 | 981.9 | 1703.3 | 16.71 | 3.67 | 103 |
| Dsp_7 | 2.2 | — | — | 10.70 | 2.81 | 106 |
| Dsp_R | NM | NM | NM | 61.58 | 8.96 | 122 |

Example 10: Preparation of Isoparaffinic Base Oil by Coupling Partially Hydrogenated Farnesene and 1-decene Using $BF_3$ as a Cationic Initiator The oligomerization reaction was carried out as in Example 7, 200 ml farnesane (97% pure, available from Amyris, Inc.) was added to the reactor instead of 200 ml ISOPAR™L isoparaffinic hydrocarbon fluid, and the co-feed was made from 600 ml of 75% hydrogenated farnesene (prepared as in Example 23) and 500 ml NEODENE® 10 1-decene (available from Shell Chemicals), and the reaction was allowed to stand for two hours instead of three hours. The hydrogenation reaction was carried out as in Example 7. 465.15 g crude hydrogenated product was isolated.

Simulated distillation on the hydrogenated crude reaction product showed the following composition: $C_{12}$ range (200° C.-240° C.): 2.1 area %; $C_{15}$ range (240° C.-320° C.): 35.7 area %; $C_{20}$ (320° C.-370° C.) range: 17.1 area %; $C_{25}$ range (370° C.-420° C.): 7.7 area %; $C_{30}$ range (420° C.-481° C.): 21.6 area %; $C_{35}$ range (481° C.-508° C.): 3.6 area %; $C_{40}$-$C_{50}$ range (508° C.-575° C.): 8.4 area %; $C_{51}$-$C_{60}$ (575° C.-615° C.): 1.2 area %; and $C_{61}$-$C_{72}$ range (615° C.-700° C.): 2.9 area % (all temperatures representing boiling point at atmospheric pressure). Simulated distillation was conducted using an Agilent 7890 Simulated Distillation Analyzer in a manner similar to Example 6. The hydrogenated crude reaction product was distilled using a spinning band distillation apparatus into several cuts over temperatures ranging from 160° C.-480° C., with a residual being those components with a boiling point greater than 480° C. The distillation cuts (as wt % of the 465 g crude hydrogenated product) are shown in Table 10A below:

TABLE 10A

| Dsp_1 | Dsp_2 | Dsp_3 | Dsp_4 | Dsp_5 | Dsp_6 | Dsp_7 | Dsp_8 | Residual |
|---|---|---|---|---|---|---|---|---|
| 160° C. < T < 240° C. | 240° C. < T < 320° C. | 320° C. < T < 360° C. | 360° C. < T < 385° C. | 385° C. < T < 405° C. | 405° C. < T < 420° C. | 420° C. < T < 435° C. | 435° C. < T < 480° C. | >480° C. |
| 23.2% | 17.3% | 2.8% | 7.6% | 0% | 15.6% | 4.4% | 14.3 | 13.9% |

Of these, Dsp_6 (collected over 405° C.-420° C.), Dsp_7 (collected over 420° C.-435° C.), and Dsp_8 (collected over 435° C.-480° C.) were characterized for their viscometric properties (kinematic viscosity at 40° C. and at 100° C. according to ASTM D445, and viscosity index according to ASTM D2270). Results are shown in Table 10B.

TABLE 10B

| | Kinematic viscosity (cSt) Temperature | | Viscosity index |
|---|---|---|---|
| | 40° C. | 100° C. | |
| Dsp_6 | 19.32 | 3.97 | 100 |
| Dsp_7 | 29.5 | 5.23 | 108 |
| Dsp_8 | 32.51 | 5.65 | 113 |

Example 11: Preparation of Isoparaffinic Base Oil by Coupling Partially Hydrogenated Farnesene and a Mixture of 1-tetradecene and 1-hexadecene Using $BF_3$ as a Cationic Initiator To a clean and dry 2 liter Parr reactor was added 200 ml farnesane (Amyris, Inc.). The reactor temperature was maintained at 30° C. to within +/−1° C. The reactor was cooled using chilled water cooling, and the feed rate of the reactants was adjusted to help maintain temperature control. The reactor was evacuated to about 50 torr, and held under vacuum for 10 minutes. The reactor was charged with $BF_3$ gas (99% pure, available from Airgas) to bring the reactor up to a reactor pressure of 3 psig. A co-feed was made by mixing 600 ml of 75% partially hydrogenated farnesene and 350 ml 1-tetradecane (NEODENE®14, available from Shell and 215 ml of 1-hexadecene (NEODENE®16, available from Shell Chemicals, Houston, Tex.) in a graduated flask. The 77% hydrogenated farnesene was prepared according to Example 24 below, had the following composition: 68.2% mono-olefin, 9.0% di-olefin, 0% tri-olefin, 0% tetra-olefin, and 22.8% farnesane. The partially hydrogenated farnesene was filtered through basic alumina, where the basic alumina was used at about 5% by weight. The co-feed was delivered to the reactor at a rate of about 10 ml/min. To the reactor was added 1.5 ml liquid that includes 1:1 molar ratio of butanol (reagent grade, <0.5 wt % $H_2O$, available from Sigma-Aldrich, St. Louis, Mo.) and butyl acetate (reagent grade, <0.5 wt % $H_2O$, available from Sigma-Aldrich). A volume of 15 ml of liquid mixture of butanol and butyl acetate in 10 equal charges over a period of about two hours as the liquid co-feed was delivered at a rate of 10 ml/min. During the reaction, the $BF_3$ pressure in the reactor was maintained within +/−0.5 psig of the desired setpoint of 3 psig by adding $BF_3$. Thus, a butanol/butyl acetate $BF_3$ adduct was formed in-situ during the reaction. After the co-feed and liquid butanol and butyl acetate deliveries were complete, the reactor was held at the temperature setpoint and at the pressure setpoint for two hours. A sample was taken from the reactor every hour to monitor the extent of conversion by GC-FID. At the end of the two hour hold period, $BF_3$ pressure was released, and the reactor was sparged with dry nitrogen gas to remove residual $BF_3$ from the crude reaction product. The crude reaction product was quenched with an equimolar or excess amount of 30% in water caustic solution (available from Sigma-Aldrich). The quenched crude reaction product was washed with water (50 pounds water per 100 pounds of co-feed), and the organic layer was allowed to separate from the water layer via gravity separation. The organic layer was collected, and a second wash of the oil was performed. Any solids remaining in the washed crude reaction product were removed by filtering through a 10-20 micron mesh silica gel filter. The washed, filtered crude reaction product was hydrogenated in a batch slurry reactor using 5-10 wt % Pd/C at a catalyst loading of 0.2 to 0.4% by weight at a pressure of 1000-1500 psig, a temperature of 180° C.-250° C. for 12 hours, stirring at a rate of 1000-1500 rpm.

Simulated distillation on the hydrogenated crude reaction product showed the following composition: C12 range area %: 0.80; C15 range area %: 40.60; C20 range area %: 0.00; C25 range area %: 13.3; C30 range area %: 8.6; C35 range area %: 1.70; C40-050 range area %: 30.1; C51-C60 range area %: 4.2; and C61-C72 range area %: 0.8. Simulated distillation was conducted using an Agilent 7890 Simulated Distillation Analyzer in a manner similar to Example 6. The hydrogenated crude reaction product was distilled into three separate distillation cuts (including residue) using a spinning band distillation apparatus, available from B/R Instrument Corp., Easton, Md. The cuts (as wt % of crude hydrogenated reaction product) are shown in Table 11A below:

TABLE 11A

| Dsp_1 | Dsp_2 | Residual |
|---|---|---|
| 180° C. < T < 375° C., 2 mm Hg, Reflux ratio 3:1 | 375° C. < T < 480° C., 0.1 mm Hg | >480° C. |
| 113.18 g (37.90%) | 61.57 g (20.62%) | 123.37 g (41.31%) |

Of these, Dsp_2 (collected over 375° C.-480° C. at 0.1 mm Hg) and the Residual (remaining after distillation) were characterized for their cold cranking simulator performance at −30° C. according to ASTM D5293 and for their viscometric properties (kinematic viscosity at 40° C. and at 100° C. according to ASTM D445, and viscosity index according to ASTM D2270). Results are shown in Table 11B.

TABLE 11B

| | Cold Cranking Simulator Viscosity (mPa-sec) | Kinematic viscosity (cSt) | | Viscosity index |
|---|---|---|---|---|
| | Temperature | | | |
| | −30° C. | 40° C. | 100° C. | |
| Dsp_2 | 1209.7 | 18.82 | 4.13 | 123 |
| Residual | NM | 73.58 | 10.66 | 132 |

As shown, selection of the distillation cuts from the crude hydrogenated reaction product yields multiple base stocks having distinct physical properties. Dsp_2 corresponds to a 4 cSt base oil with viscosity index<120 (specifically 123) and Cold Cranking Simulator Viscosity of 1200 at −30° C., and the Residual corresponds to a 10 cSt base oil with viscosity index>120 (specifically 132).

Examples 12-13: BF$_3$-Catalyzed Oligomerization of Partially Hydrogenated β-Farnesene to Make a Base Oil Examples 12-13 provide a non-limiting illustration of how methods described herein may be used to make a base oil by oligomerizing a hydrocarbon terpene feedstock using no additional olefin co-monomer. In these Examples 12-13, the hydrocarbon terpene feedstock is partially hydrogenated β-farnesene and the coupling reaction is catalyzed using a cationic initiator (BF$_3$ and one or more co-catalysts).

Example 12: Preparation of Isoparaffinic Base Oil by Oligomerizing Partially Hydrogenated Farnesene Using BF$_3$ as a Cationic Initiator The oligomerization reaction was carried out as in Example 7, except that no co-monomer was used, and the BF$_3$ pressure in the reactor was initially 1 psig and then raised to 3 psig. The feed was 1000 ml of 75% hydrogenated farnesene (prepared as in Example 23). The hydrogenation of the unsaturated reaction product was carried out as in Example 7.

Simulated distillation on the hydrogenated crude reaction product showed the following composition: $C_{12}$ range (200° C.-240° C.): 0.7 area %; $C_{15}$ range (240° C.-320° C.): 42.5 area %; $C_{20}$ (320° C.-370° C.) range: 0.9 area %; $C_{25}$ range (370° C.-420° C.): 29.1 area %; $C_{30}$ range (420° C.-481° C.): 3.7 area %; $C_{35}$ range (481° C.-508° C.): 9.5 area %; $C_{40}$-$C_{50}$ range (508° C.-575° C.): 4.9 area %; $C_{51}$-$C_{60}$ (575° C.-615° C.): 0 area %; and $C_{61}$-$C_{72}$ range (615° C.-700° C.): 0 area %. Simulated distillation was conducted using an Agilent 7890 Simulated Distillation Analyzer in a manner similar to Example 6. The hydrogenated crude reaction product was distilled using a spinning band distillation apparatus into several cuts, with a residual being those components with a boiling point greater than 435° C. The distillation cuts are shown in Table 12A below:

TABLE 12A

| Dsp_1 | Dsp_2 | Dsp_3 | Dsp_4 | Dsp_5 | Dsp_6 | Dsp_7 | Dsp_8 | Residual |
|---|---|---|---|---|---|---|---|---|
| 160° C. < T < 205° C. | 205° C. < T < 285° C. | 285° C. < T < 305° C. | 160° C. < T < 300° C.* | 300° C. < T < 360° C. | 360° C. < T < 380° C. | 380° C. < T < 410° C. | 410° C. < T < 435° C. | >435° C. |
| 9.7% | 33.2% | 1.8% | 1.7% | 1.1% | 6.9% | 23.4% | 15.8% | 6% |

Of these, Dsp_4 (collected over 160° C.-300° C.), Dsp_5 (collected over 300° C.-360° C.), Dsp_6 (collected over 360° C.-380° C.), Dsp_7 (collected over 380° C.-410° C.) and Dsp_R (residual with boiling point greater than 435° C.) were characterized for their viscometric properties (kinematic viscosity at 40° C. and at 100° C. according to ASTM D445, and viscosity index according to ASTM D2270). Results are shown in Table 12B.

TABLE 12B

| | Kinematic viscosity (cSt) | | Viscosity index |
|---|---|---|---|
| | Temperature | | |
| | 40° C. | 100° C. | |
| Dsp_4 | 20.49 | 3.88 | 65 |
| Dsp_5 | 24.5 | 4.26 | 59 |
| Dsp_6 | 54.12 | 6.96 | 79 |
| Dsp_7 | 42.94 | 6.02 | 77 |
| Dsp_R | 429.05 | 25.14 | 75 |

Example 13: Preparation of Isoparaffinic Base Oil by Oligomerizing Partially Hydrogenated Farnesene Using BF$_3$ as a Cationic Initiator The oligomerization reaction was carried out as in Example 12, except that the pressure of BF$_3$ in the reactor was 12 psia (approximately 10 psig).

Simulated distillation on the hydrogenated crude reaction product showed the following composition: $C_{12}$ range (200°

C.-240° C.): 1.1 area %; $C_{15}$ range (240° C.-320° C.): 42.5 area %; $C_{20}$ (320° C.-370° C.) range: 0 area %; $C_{25}$ range (370° C.-420° C.): 44.3 area %; $C_{30}$ range (420° C.-481° C.): 5 area %; $C_{35}$ range (481° C.-508° C.): 4.5 area %; $C_{40}$-$C_{50}$ range (508° C.-575° C.): 2.4 area %; $C_{51}$-$C_{60}$ (575° C.-615° C.): 0.2 area %; and $C_{61}$-$C_{72}$ range (615° C.-700° C.): 0 area %. Simulated distillation was conducted using an Agilent 7890 Simulated Distillation Analyzer in a manner similar to Example 6. The hydrogenated crude reaction product was distilled using a spinning band distillation apparatus into several cuts, with a residual being those components with a boiling point greater than 385° C. (AET). The distillation cuts are shown in Table 13A below:

that had been ground from pellets. The slurry so formed was stirred at about 1000 rpm. The reactor was heated to about 100° C. The reactor was pressurized to about 100 psig, and approximately 3 molar equivalents of hydrogen were delivered to the reactor (including auxiliary plumbing). The reaction was allowed to proceed for several hours. Analysis of the composition of the product by GC-MS (as described for Example 15 below) showed the sample had been 60% hydrogenated with the following distribution of species: 0 area % farnesene, 0 area % farnesane, 41.2 area % mono-olefin, 49.2 area % di-olefin, and 6.4 area % tri-olefin.

TABLE 13A

| Dsp_1 | Dsp_2 | Dsp_3 | Dsp_4 | Dsp_5 | Dsp_6 | Dsp_7 | Dsp_8 | Residual |
|---|---|---|---|---|---|---|---|---|
| 160° C. < T < 190° C. | 190° C. < T < 210° C. | 210° C. < T < 230° C. | 230° C. < T < 250° C.* | 250° C. < T < 280° C. | 280° C. < T < 320° C. | 320° C. < T < 350° C. | 350° C. < T < 385° C. | >385° C. |
| 0.2% | 2.9% | 4.9% | 9.4% | 14.4% | 15.3% | 1.1% | 3.2% | 48.5% |

Of these, Dsp_6 (collected over 280° C.-320° C.), Dsp_7 (collected over 320° C.-350° C.), Dsp_8 (collected over 350° C.-385° C.), and Dsp_R (residual with boiling point greater than 385° C.) were characterized for their viscometric properties (kinematic viscosity at 40° C. and at 100° C. according to ASTM D445, and viscosity index according to ASTM D2270). Results are shown in Table 13B.

TABLE 13B

| | Kinematic viscosity (cSt) Temperature | | Viscosity |
|---|---|---|---|
| | 40° C. | 100° C. | index |
| Dsp_6 | 2.82 | 1.16 | ** |
| Dsp_7 | 4.23 | 1.59 | ** |
| Dsp_7 | 11.4 | 2.83 | 89 |
| Dsp_R | 50.38 | 6.92 | 91 |

** could not be calculated.

Examples 14-28: Partially Hydrogenated Hydrocarbon Terpene Feedstocks

Examples 14-28 provide non-limiting illustrations of partially hydrogenated hydrocarbon terpene feedstocks that may be used in the methods described herein for making base oils. Examples 14-26 provide non-limiting examples of partially hydrogenated hydrocarbon terpene feedstocks that contain a distribution of partially hydrogenated species. Examples 27-28 provide non-limiting examples of particular species of partially hydrogenated hydrocarbon terpene feedstocks.

Example 14: Preparation of 60% Hydrogenated β-Farnesene Containing No Detectable Amount of β-Farnesene and No Detectable Amount of Farnesane β-farnesene was filtered through activated alumina. 20 mL of the alumina filtered β-farnesene was put into a reactor with 25 mg of 0.3 wt % Pd/$Al_2O_3$ (available from Johnson Matthey, PRICAT 309/7 (0.3% Pd/Alumina Trilobe 2.5 mm)

Examples 15-18: Preparation of Partially Hydrogenated Mono-Olefinic Feedstock from β-Farnesene Using Two Stage Hydrogenation For each of Examples 15-18, β-farnesene was hydrogenated to about 60% as described in Example 14 in a first stage, except that the β-farnesene was not treated with alumina prior to use, 100 mg of 0.3 wt % Pd/$Al_2O_3$ was used per 20 mL farnesene, and the reaction temperature was 160° C. In a second stage, the reactor was heated to a higher temperature (200° C. for Example 15, 220° C. for Example 16, 240° C. for Example 17, and 260° C. for Example 18), and the hydrogen pressure was decreased to about 20 psig in reactor pressure.

The composition of each of the partially hydrogenated products was analyzed by GC-MS and by GC/FID. Conditions for the GC-MS were as follows: Agilent 6890 GC, Column Agilent HP-1, 50 m×0.2 mm, 0.110 micron film, P/N 19091Z-005, Agilent 5973 Mass Selective Detector, oven ramp from 50° C. to 320° C., inlet in split mode (50:1 split ratio), helium as carrier gas, hexane as diluent, trans-β-farnesene or farnesane used as reference. Analysis of the composition of each of the products by GC/FID is as follows. An Agilent model 7890 GC having a flame ionization detector is used. A sample of partially hydrogenated farnesene is dissolved in n-heptane (at about 1 mg/mL) containing 100 μg/mL n-hexadecane that serves as a retention time reference. An Agilent model DB-17 ms GC column (60 m, 0.25 mm, 0.25 micron) is used that is made from 50% phenyl- and 50% methyl-polysiloxane. The parameters are as follows: inlet type is multi-mode or split-splitless, a split ratio 1:20 is used, a constant pressure of about 10.64 psi is used, inlet temperature is 250° C., flow rate is about 0.597 mL/min, carrier gas is hydrogen, injection volume is 1 microliter, the oven is set to have an initial temperature of 150° C., a run time of 20 minutes is used. The phenyl component in the column gives the stationary phase the ability to interact with the pi-electrons of the various double-bonds of the partially hydrogenated farnesene species. A variety of hydrogenated farnesene samples were analyzed on a GC-MS using the same column type, informing assignments as to molecular weight for each peak. β-farnesene and farnesane (at 0.5 mg/mL each) were used as assay calibration standards, and peak assignments as to molecular weight. A calibration table is created most easily from a chromatogram of 75% hydrogenated farnesene using the retention times and identifications suggested in Table 15A. Systems will differ in the exact retention times, but the order remains the same. The integration parameters and compound identification windows were adjusted to identify each peak of the sample, to not split overlapping peaks except where appropriate (overlapping peaks having similar amplitudes are split), and to exclude the solvent peak. The GC-FID is used to quantify the weight contribution of each molecular weight constituent peak, proportional to the peak's area percent. Using a manual setup, each peak is given a unique name, an area of 1.0, and an amount corresponding to the molecular mass of the peak shown in Table 15A. The n-hexadecane is given an amount of 1.0, an area of 1.0 and a multiplier of a very small number, e.g., $1\times10^{-10}$, and n-hexadecane is set as the only time reference peak. The calculation proceeds as follows. The sample is injected, separated by the column and detected. Peak areas are integrated and identified with the appropriate mass. The calibration report is set-up to multiply each peak's area percent times the calibration factor (amt/area) (the molecular mass). The resulting sum of amounts is reported as a number between 204 and 212, which represents the average molecular mass. The values for each mass level (204 to 212) are summed and divided by the overall sum to obtain and report the fraction for each mass level: Farnesane has a mass level of 212, hexahydrofarnesene has a mass level of 210, tetrahydrofarnesene has a mass level of 208, dihydrofarnesene has a mass level of 206, and farnesene (and its isomers) has a mass level of 204. The n-hexadecane is identified, but its amount contribution is very small and negligible. The peak area percent contributions for each molecular weight are summed and the average molecular weight of the entire sample is calculated to provide degree of hydrogenation. Results for Examples 15-18 are provided in Table 15B, with compositional results measured by GC-MS and GC-FID both shown (GC-FID results in parentheses).

TABLE 15A

Peak assignments as to molecular weight according to GC-MS

| Mass | Retention Time (approx.) | |
|---|---|---|
| 210a | 9.32 | |
| 210b | 9.45 | |
| 210c | 9.53 | |
| 212 | 9.67 | Farnesane |
| 210i | 10.09 | |
| 210d | 10.22 | |
| 210e | 10.32 | |
| 208a | 10.44 | |
| 210f | 10.56 | |
| 208b | 10.64 | |
| 210g | 10.91 | |
| 208c | 11.03 | |
| 208d | 11.14 | |
| 210h | 11.29 | |
| 208e | 11.49 | |
| 208f | 11.58 | |
| 208q | 11.73 | |
| 208g | 11.99 | |
| 208s | 12.05 | |
| 208h | 12.15 | |
| 208i | 12.28 | |
| 208j | 12.36 | |
| 206a | 12.48 | |
| 208u | 12.54 | |
| 208k | 12.59 | |
| 208l | 12.84 | |
| 208m | 12.94 | |
| 208n | 13.05 | |
| 208o | 13.16 | |
| 208t | 13.41 | |
| 208p | 13.55 | |
| 208r | 13.64 | |
| 206b | 13.94 | |
| 206n | 14.02 | |
| 206m | 14.09 | |
| 206c | 14.38 | |
| 206d | 14.60 | |
| 206e | 14.87 | |
| 206l | 15.12 | |
| 206f | 15.20 | |
| 206g | 15.38 | |

TABLE 15B

| Example | Catalyst | First stage pressure (psig) | First stage T (° C.) | Second stage pressure (psig) | Second stage T (° C.) | % hydrogenation | area % farnesane | area % hexahydrofarnesene | area % tetrahydrofarnesene | Area % dihydrofarnesene | Area % farnesene |
|---|---|---|---|---|---|---|---|---|---|---|---|
| 15 | 0.3 wt % Pd/Al$_2$O$_3$ | 100 | 160 | 20 | 200 | 78 (77)[c] | 17.2 (19.1) | 74.8 (69.5) | 8.0 (11.3) | 0 (0.1) | 0 (0) |
| 16 | 0.3 wt % Pd/Al$_2$O$_3$ | 100 | 160 | 20 | 220 | 75 (75)[c] | 11.5 (13.6) | 79.0 (73.8) | 9.4 (12.6) | 0 (0.1) | 0 (0) |
| 17 | 0.3 wt % Pd/Al$_2$O$_3$ | 100 | 160 | 20 | 240 | 75 (75)[c] | 8.4 (10.7) | 82.9 (77.6) | 8.7 (11.6) | 0 (0) | 0 (0) |
| 18 | 0.3 wt % Pd/Al$_2$O$_3$ | 100 | 160 | 20 | 260 | 73 (72)[c] | 6.3 (7.8) | 80.5 (74.1) | 13.2 (18.0) | 0 (0.1) | 0 (0) |
| 19 | 5 wt % Pd/C | 0-970 | 40-50 | 0-970 | 140 | 71[a,b] | 5 | 74** | 21** | 0* | 0* |
| 20 | 5 wt % Pd/C | 0-970 | 40-50 | 0-970 | 140 | 78[a,b] | 8 | 76** | 16** | 0* | 0* |

*Assumed to be zero, based on GC-MS
**calculated from GC-MS area % measured for farnesane and Bromine index as described in Examples 19 and 20.
[a]% hydrogenation measured by Bromine index of total sample.
[b]sample characterized by GC-MS using a 50 m column as described.
[c]% hydrogenation measured by GC-MS and GC-FID. Area % numbers in parentheses refer to GC FID area %; area % numbers not in parentheses refer to GC-MS area %.

Example 19: Preparation of 71% Hydrogenated Olefinic Feedstock from β-Farnesene The instant example provides a partially hydrogenated mono-olefinic farnesene feedstock prepared according to the staged hydrogenation methods described above.

To a one liter reactor (Parr Instrument Co., Moline, Ill.) was added 499.4 g microbial-derived β-farnesene (97% pure, Amyris, Emeryville Calif.) which had been distilled with a wiped film distillation apparatus and to which 100 ppmw 4-tert-butylcatechol was added. To the β-farnesene was added 1.5 g Pd/C (5 wt %) catalyst (Pd on activated carbon, surface area 1050 m²/g, pore volume 0.61 cc/g, Strem Chemicals, Newburyport, Mass.) to make a slurry. The slurry was stirred at about 250-300 rpm. The reactor was pressurized to 970 psig with hydrogen gas. The 970 psig hydrogen gas corresponded to about 0.5 molar equivalents of hydrogen. After the pressure in the reactor decreased to 0 psig, indicating the hydrogen had been substantially consumed, another pulse of hydrogen was added to pressurize the reactor to 970 psig. A total of 6 pulses of hydrogen were added to the reactor in this manner, with the first two pulses auto-heating the reactor to about 40° C.-50° C. Towards the end of consumption of the third pulse, the reactor was heated to about 140° c. to complete the consumption of the hydrogen. for the 4$^{th}$, 5$^{th}$, and 6$^{th}$ pulses, the reactor was heated to about 140° C. Following completion of the 6$^{th}$ pulse, the slurry was removed from the reactor. The catalyst was removed from the slurry by filtration through silica gel, yielding 453.4 of partially hydrogenated farnesene characterized by GC-MS as described for Example 15, except that the samples were diluted in ethyl acetate. The bromine index of the partially hydrogenated farnesene was measured according to ASTM D2710 using a titrant strength of 0.02 M bromide-bromate, and indicated the sample was 71% hydrogenated. The farnesane content in the hydrogenated sample was measured to be 5% by GC-MS, based on the total hydrogenated sample. The GC-MS spectrum showed no detectable amount of farnesene or dihydrofarnesene. The area percents of hexahydrofarnesene and tetrahydrofarnesene in the hydrogenated sample were calculated algebraically using the % hydrogenation in the total sample determined from the measured bromine index and the measured area % for the saturated component. Results are summarized in Table 15B. The area % farnesane is measured to within +/−2%, and the area % of hexahydrofarnesene and tetrahyrofarnesene are measured to within +/−4% accuracy.

Example 20: Preparation of a 78% Hydrogenated Olefinic Feedstock from β-Farnesene The instant example provides another example of a mono-olefinic farnesene feedstock prepared according to the methods described herein.

Example 20 was prepared and analyzed as in Example 19. Results are summarized in Table 15B.

Example 21: Preparation of a 25% Hydrogenated Olefinic Feedstock from β-Farnesene The instant example provides a dihydrofarnesene feedstock prepared according to the methods described herein.

Example 21 was carried out as in Example 19, except that only two pulses of hydrogen gas (corresponding to a total of one molar equivalent) were delivered to the reactor. The results were analyzed by GC-MS and NMR. A $^1$H NMR spectrum of the product is shown in FIG. 11. By NMR and GC-MS, the reaction product included the following species in the indicated molar percents:

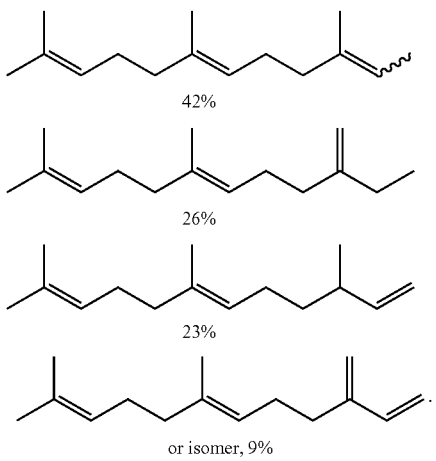

42%

26%

23% or isomer, 9%

Example 22: Alternate Preparation of a 25% Hydrogenated Olefinic Feedstock from β-Farnesene The instant example provides another example of a dihydrofarnesene feedstock prepared according to the methods described herein.

β-farnesene (26.0 g, 0.127 mol) and 0.26 g of Lindlar's catalyst (5% Pd/Pb on CaCO$_3$, available from Sigma Aldrich) were placed in a 100 mL autoclave. The apparatus was evacuated/flushed with N$_2$ three times and then charged with one equivalent of hydrogen (690 psig). The mixture was stirred (500 rpm) at 19° C. for 18 hours. The catalyst was removed by filtration to afford 25.8 g (98.5%) of a mixture of the following five compounds, with their corresponding molecular ion weights.

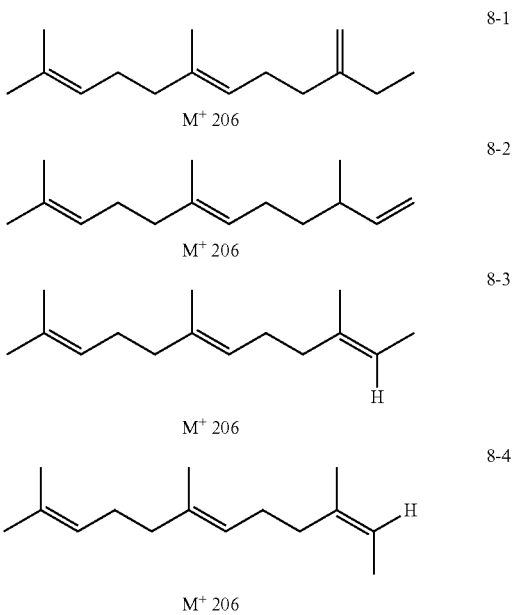

8-1
M$^+$ 206

8-2
M$^+$ 206

8-3
M$^+$ 206

8-4
M$^+$ 206

-continued

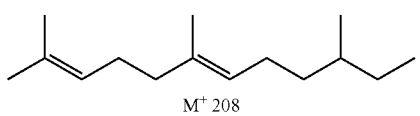

8-5

M⁺ 208

The mixture was analyzed using GC/MS as described for Example 15, and showed the following distribution of species:

| R$_T$ (Min.)* | M⁺ | % Run #1 | % Run #2 |
| --- | --- | --- | --- |
| 9.63 | 206 | 21.4 | 21.6 |
| 9.76 | 208 | 13.5 | 11.9 |
| 9.84 | 206 | 25.1 | 26.6 |
| 9.89 | 206 | 28.7 | 28.5 |
| 9.93 | 206 | 10.3 | 9.8 |

Example 23: Preparation of 75% Hydrogenated Olefinic Feedstock from β-Farnesene Using Single Stage Controlled Hydrogenation The instant example provides an additional example of a mono-olefinic farnesene feedstock prepared according to the methods described herein.

A catalyst (5 wt % Pd/C, available from Strem Chemicals, as described in Example 19 above) was immersed into β-farnesene (Amyris, as described in Example 19) to form a slurry in a closed reactor at a loading of 3.1 g/kg liquid. The slurry was agitated. The reactor was purged with nitrogen using 3 pressure/vacuum cycles, pressuring to 100 psig with nitrogen and evacuating to 3 or less psia in each cycle. After the third cycle, the reactor was left under 3 or less psia nitrogen, and agitation was stopped. The reactor was pressurized to 50 psig with hydrogen and allowed to stabilize. After stabilization, hydrogen was delivered to the reactor at 50 psig while the slurry was agitated. The reactor was heated to 100° C. The cumulative uptake of hydrogen was monitored using a flow totalizer. As the exothermic reaction proceeded the reactor was heated or cooled as appropriate to maintain the reaction temperature at 100° C. After 3.0 molar equivalent of hydrogen was consumed (as measured by the flow totalizer), the hydrogen flow and agitation were stopped. The reactor was purged with nitrogen as described above, leaving about 15 psig overpressure of nitrogen in the reactor headspace. The reactor was cooled to less than about 30° C., and the catalyst was filtered from the liquid by filtration. The partially hydrogenated farnesene was analyzed using GC-FID and GC-MS using an Agilent DB-17 ms 60 m column as described above for Examples 15-18, and was also characterized by GC-MS using an HP-1 50 m long×200 micron ID×110 nm film thickness column and using hexane as a solvent as described for Example 15. GC-FID results are shown in parentheses. Poorer resolution of peaks was achieved using the 50 m column, leading to increased need for splitting overlapping areas. Peak areas corresponding to each of farnesene, farnesane, dihydrofarnesene, tetrahydrofarnesene, and hexahydrofarnesene were determined to result in the species distribution as shown in Table 23A. The sample was calculated to have an average molecular weight of 210.0 by GC-FID, corresponding to 75% hydrogenated. The Bromine number of the sample was measured according to ASTM D1159 to be 80.6, and is estimated to be 76 if the substance responds to bromine as a triunsaturate.

Example 24: Preparation of 78% Hydrogenated Olefinic Feedstock from β-Farnesene Using Single Stage Controlled Partial Hydrogenation The instant example provides an additional example of a mono-olefinic farnesene feedstock prepared according to the methods described herein.

Example 24 was carried out as in Example 23, except that 3.1 molar equivalents of hydrogen were consumed during the reaction, and a catalyst loading of 2.1 g/kg was used. The partially hydrogenated farnesene was analyzed using GC-FID and GC-MS as described for Example 23. Results are shown in Table 23A. The sample was calculated to have an average molecular weight of 210.3 by GC-FID, corresponding to 78% hydrogenated. The Bromine number of the sample was measured according to ASTM D1159 to be 71.9, and is estimated to be 65.9 if the substance responds to bromine as a triunsaturate.

Example 25: Preparation of 67% Hydrogenated Hydrocarbon Terpene Feedstock from β-Farnesene Using Single Stage Controlled Partial Hydrogenation The instant example provides an additional example of a farnesene feedstock comprising predominantly di-olefins and mono-olefins prepared according to the methods described herein.

Example 25 was carried out as in Example 23, except that 2.5 molar equivalents of hydrogen were consumed during the reaction, and a catalyst loading of 2.1 g/kg was used. The partially hydrogenated farnesene was analyzed using GC-MS as described for Example 23. Results are shown in Table 23A. The sample was calculated to have an average molecular weight of 209.3 by GC-FID, corresponding to 67% hydrogenated. The Bromine number of the sample was measured according to ASTM D1159 to be 112.9, and is estimated to be 109.2 if the substance responds to bromine as a tri-unsaturate.

Example 26: Preparation of 85% Hydrogenated Hydrocarbon Terpene Feedstock from β-Farnesene Using Single Stage Partial Hydrogenation The instant example provides an additional example of a mono-olefinic farnesene feedstock prepared according to the methods described herein.

Example 26 was carried out as in Example 23, except that 3.35 molar equivalents of hydrogen were consumed during the reaction, a catalyst loading of 2.1 g/kg was used. The partially hydrogenated farnesene was analyzed using GC-MS as described for Example 23. Results are shown in Table 23A. The sample was calculated to have an average molecular weight of 210.8 by GC-FID, corresponding to 85% hydrogenated. The Bromine number of the sample was measured according to ASTM D1159 to be 52.7, and is estimated to be 49.2 if the substance responds to bromine as a tri-unsaturate.

TABLE 23A

| Example | % hydrogenation | % farnesane | % hexahydrofarnesene | % tetrahydrofarnesene | % dihydrofarnesene | % farnesene |
| --- | --- | --- | --- | --- | --- | --- |
| 23[a] | 75 (75)** | (18.3%) 16.0% | (65.3%) 68.6% | (16.4%) 15.2% | (0) <0.3% | (0) <0.3% |
| 24[a] | 78 (78)** | (24.9%) 23.3% | (64.6%) 66.6% | (10.4%) 10.1% | (0) <0.3% | (0) <0.3% |
| 25[a] | 63 (67)** | (8.5%) 7.8% | (50.5%) 49.8% | (40.5%) 34.1% | (0.5%) 2% | (0) 6% |
| 26[a] | 85 (84)** | (40.9%) 37.7% | (58.3%) 58.8% | (0.8%) 3.0% | (0) <0.3% | (0) <0.3% |

[a]% Samples characterized by GC-MS using 50 m column and GC-FID using 60 m column as described in Example 15. Area % numbers in parentheses refer to those measured by GC-FID; area % numbers not in parentheses refer to those measured by GC-MS.

Example 27: Preparation of 3,7,11-trimethyldodec-1-ene (Method A)

The instant example provides an example of an alphaolefin prepared according to the methods described herein.

The compound 3,7,11-trimethyldodec-1-ene was synthesized according to the following reaction: a) Commercially available farnesol (Compound 1 below) is hydrogenated in the presence of a palladium catalyst to produce 3,7,11-trimethyl-1-dedecanol (Compound 2 below). b) Stearoyl chloride (Compound 4 below) is prepared from stearic acid (Compound 3 below) and thionyl chloride. c) Compound 4 is reacted with Compound 2 and pyridine to form Compound 5 below. d) Compound 5 is distilled under heat to produce stearic acid and 3,7,11-trimethyldodec-1-ene (Compound 6 below).

Schematic Reaction for Method A for Preparation of 3,7,11-trimethyl-1-dodec-1-ene from farnesol a. Preparation of 3,7,11-trimethyl-1-dodecanol (Compound 2) from Commercially Available Farnesol Farnesol (95% pure, St. Louis, Mo., 202 g, 0.81 mol, ca. 3:1 mixture of 2E/2Z isomers, available from Sigma-Aldrich as catalog No. F203), 0.5 g of 5% Pd/C (matrix activated carbon support, available from Sigma-Aldrich as catalog No. 205680) and 200 mL of hexane were placed in a 1 L autoclave. After three evacuate/$N_2$ flush cycles the reactor was charged with 400 psig of $H_2$, stirred at 500 rpm. The reaction began to take up $H_2$ and liberate heat but stalled at approximately 50% completion. An additional 0.5 g of Pd/C was added to the cooled reactor under $N_2$. The reaction was heated to 75° C. under 600 psig of $H_2$. After 48 hr the reactor was cooled, the catalyst removed by vacuum filtration and the hexane under reduced pressure. A small amount of 2,6,10-trimethyldodecane was removed by vacuum distillation to afford 151 g (82.0%) of 3,7,11-trimethyl-1-decanol (Compound 2) as a colorless oil.

b. Preparation of Stearoyl Chloride (Compound 4)

A 2 L three-necked round-bottomed flask equipped with a mechanical stirrer, reflux condenser, heating mantle and pressure equalizing addition funnel was charged with stearic acid (97.6 g, 0.343 mol) and 750 mL of toluene. The mixture was stirred, heated to refluxing. Thionyl chloride (26.3 mL, 42.8 g, 0.360 mol) was added over a period of 30 minutes. The mixture was refluxed for an additional three hours and at ambient temperature over night. A small amount (12.0 g) of unreacted stearic acid was removed by vacuum filtration and the toluene removed under reduced pressure to afford 90.3 g (99.0% based on recovered starting material) of stearoyl chloride (Compound 4) as a light yellow oil.

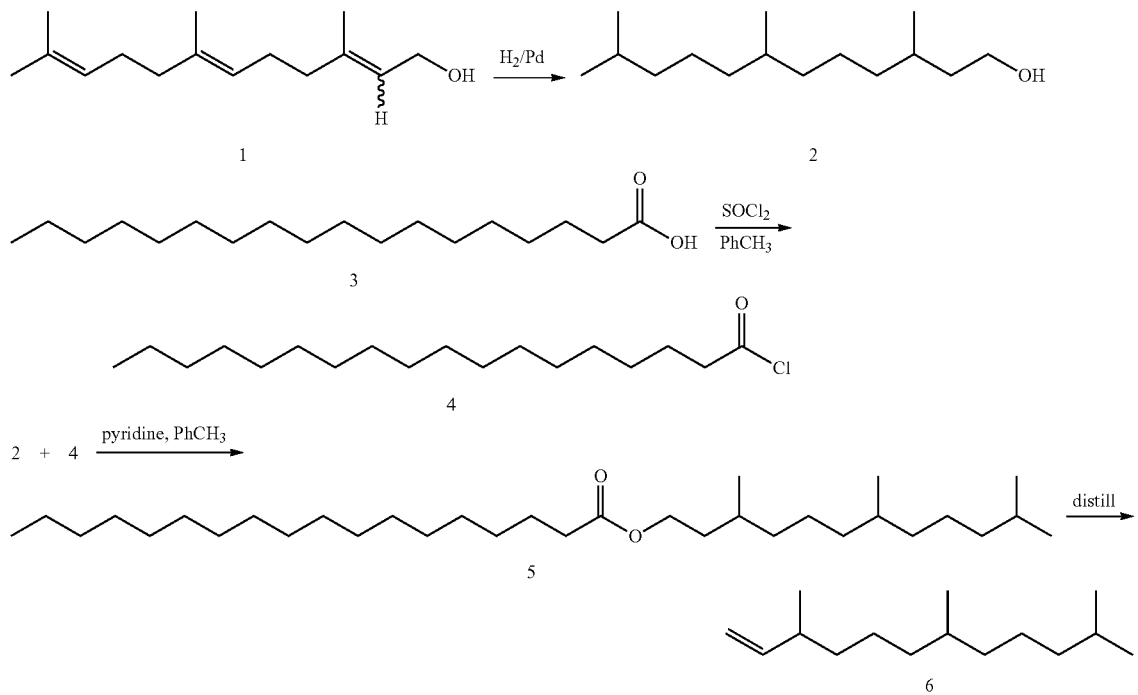

c. Preparation of (3,7,11-trimethyl-1-dodecyl) stearate (Compound 5)

A 2 L three-necked round-bottomed flask equipped with a mechanical stirrer, thermometer and pressure equalizing addition funnel was charged with 68.8 g (0.301 mol) of Compound 2, pyridine (29.2 g, 0.361 mol) and 300 mL of toluene. A solution of steroyl chloride (Compound 4) in 400 mL of toluene was added dropwise over 20 minutes with rapid stirring and occasional warming of the addition funnel with a heat gun to prevent the acid chloride from precipitating. As the addition progressed a granular precipitate of pyridine hydrochloride formed that became quite thick by the end of the reaction. The mixture was stirred for an additional three hours at which time the pyridine hydrochloride was removed by vacuum filtration. Removal of the solvent by rotary evaporation afforded an oil that was dissolved in 250 mL of hexane and cooled to 4° C. to precipitate unreacted stearic acid. After filtration the hexane was removed under reduced pressure to afford 128 g of crude Compound 5 containing unreacted Compound 2. The oil was passed down a 7×23 cm column of silica gel with hexane to afford 87.7 g (58.9%) of Compound 5 as colorless oil.

d. Preparation of 3,7,11-trimethyldodec-1-ene (6)

(3,7,11-Trimethyl-1-dodecyl) stearate (Compound 5, 87.7 g, 0.177 mol) was placed in a 200 mL round-bottomed flask equipped with a distillation head, magnetic stirrer and heating mantle and pyrolyzed at ambient pressure to afford crude Compound 6 (bp 230° C.) contaminated with a small amount of stearic acid. The crude product was slurried with 200 mL of pentane and vacuum filtered. The last traces of stearic acid were removed by passing the filtrate through a 40×35 mm pad of silica gel which resulted in the isolation of 31.9 g (85.5%) of Compound 6 as a colorless oil after removal of the pentane under reduced pressure.

Example 28: Preparation of 3,7,11-trimethyldodec-1-ene (Method B)

Example 28 provides an alternate synthesis (Method B) of 3,7,11-trimethyldodec-1-ene from farnesol. In step a) of Method B, 3,7,11-trimethyl-1-decanol (Compound 2, as prepared in Example 27 above) is reacted with diphenylcarbamoyl chloride (Compound 7 below, available from Sigma Aldrich) to form 3,7,11-trimethyl-1-dodecyl-N,N-diphenylcarbamate (Compound 8 below). In step b) of Method B, Compound 6 is prepared from Compound 8.

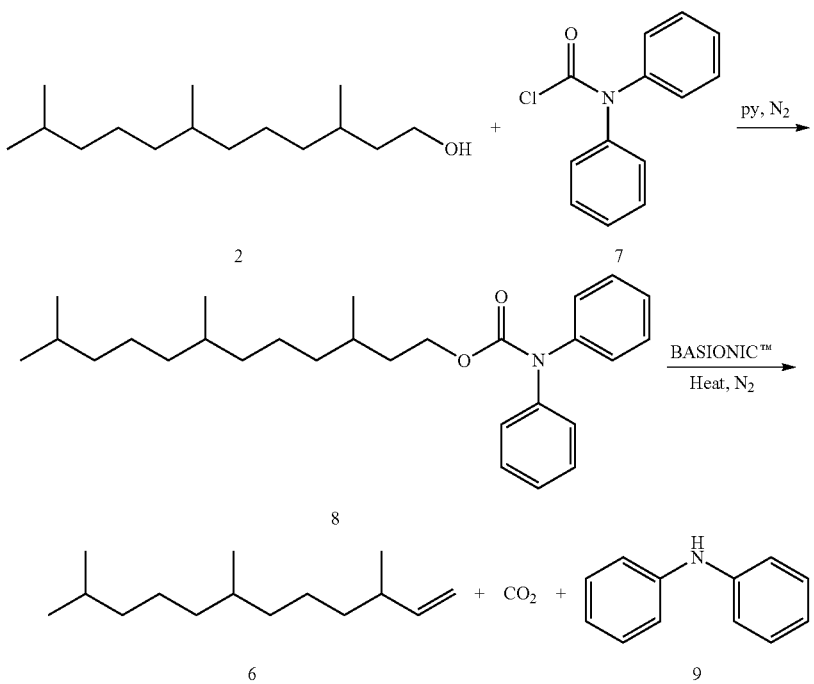

Method B for preparation of 3,7,11-trimethyl-1-dodec-1-ene from Farnesol a. Preparation of 3,7,11-trimethyl-1-dodecyl-N,N-diphenylcarbamate (Compound 8)

A 50 mL round-bottomed flask equipped with a magnetic stirrer and reflux condenser attached to a nitrogen inlet was charged with Compound 2, as prepared above in Example 27 (4.93 g, 21.6 mmol), diphenylcarbamoyl chloride (Compound 7, available from Sigma Aldrich, 5.50 g, 23.8 mmol) and 6.5 mL of freshly distilled (NaOH) pyridine. The flask was immersed in an oil bath maintained at 115° C. for 15 hours. The mixture was allowed to cool and partitioned between ether (20 mL) and water (100 mL). The layers were separated and the aqueous phase washed with 4×15 mL portions of ether. The extracts were combined, dried (MgSO$_4$) and the solvent removed under reduced pressure to afford 9.17 g (100%) of crude 8 as an orange oil that was subsequently passed through a 1×4.5 cm pad of silica gel with 10% ethyl acetate/hexane to remove some unreacted Compound 7.

b. Preparation of 3,7,11-trimethyldodec-1-ene (Compound 6)

A 50 mL round-bottomed flask equipped with a magnetic stirrer, heating mantle and short path distillation head was charged with 5.0 g (11.8 mmol) of Compound 8 and 5.0 g of BASIONIC™ (available from BASF Corporation) ionic liquid. The mixture was strongly heated which resulted in the isolation of 2.6 g of a mixture of Compound 6 and Compound 9 (by $^1$H NMR) which was not separated.

Example 29: Blending Distillation Cuts to Make a Family of Base Oils

Partially hydrogenated farnesene was reacted with a mixture of 1-tetradecene and 1-hexadecene using $BF_3$ as a cationic initiator as described in Example 11, except that 1-hexadecene from Ineos was used, and the reaction is conducted at a larger scale, with the amounts scaled for a reaction with 1720 lbs 75% partially hydrogenated β-farnesene, 891 lbs 1-tetradecene (Shell NEODENE® 14), and 594 lbs 1-hexadecene (INEOS™). The partially hydrogenated β-farnesene was filtered using 100 lbs basic alumina (SELEXORB™ CDX). The oligomerization reaction was carried out as described for Example 11. The crude olefinic mixture was hydrogenated using a nickel catalyst to form a crude saturate. The crude saturate was distilled according to the following procedure using three distillation passes. Two wiped film evaporators (WFE 1 and WFE 2) each having a heat transfer area per unit of 1.25 m$^2$ were operated in series for each distillation pass. In all cases, the wiper motor speed was 1800 rpm. Characterization of relative amounts of monomer, dimer, and trimer and higher oligomer content was conducted by simulated distillation.

First Distillation Pass 6050 lbs of crude saturate was fed into WFE 1 at a feed rate of 60 kg/hr, with WFE 1 operating at 200° C. and 110 torr, to selectively remove acetates, alcohols, and unreacted hydrogenated monomers. The residue from WFE 1 was fed into WFE 2 at a feed rate of 60 kg/hr, which was operated at 200° C. and 1.07 torr to selectively remove unreacted hydrogenated monomers.

2539 lbs of combined distillate from WFE 1 and WFE 2 were produced by the first distillation pass. 3367 lbs of residue was recovered from WFE 2, and characterized by simulated distillation to contain 4.2 lbs monomer, 1580 lbs dimeric species, and 1782 lbs trimeric and higher oligomers.

Second Distillation Pass 3367 lbs of residue from the WFE 2 was fed back into WFE 1 at a feed rate of 72 kg/hr. For the second pass, WFE 1 was operated at 228° C. and 10 torr. The residue from WFE 1 was fed into WFE 2 at a feed rate of 72 kg/hr. WFE 2 was operated at 220° C. and 0.023 torr.

77 lbs distillate (2D1) was recovered from WFE 1, consisting of 13.17 monomers, 58.06 lbs dimeric species and 5.78 lbs trimers and higher oligomers. 307 lbs distillate (2D2) was recovered from WFE 2, consisting of 0.31 lbs monomers, 249 lbs dimeric species and 57.1 lbs trimers and higher oligomers (0.1% monomer, 81.1% dimers, 18.6% trimers and higher oligomers). 1505 lbs of residue (2R2) was collected from WFE 2, which consisted of no detectable monomer, 16.25 lbs dimers, and 1488 lbs trimers and higher oligomers (1% dimers, 99% trimers and higher oligomers). The distillate (2D2) from WFE 2 in the second distillation pass was distilled in a third pass to obtain a distillation cut having a reduced amount trimers and higher oligomers.

Third Distillation Pass

2D2 was fed into WFE 1 at a feed rate of 65 kg/hr. WFE 1 was operated at 200° C. and 40 torr. No distillate was collected, but was instead fed into WFE 2. Residue and distillate from WFE 1 were fed into WFE 2 at a feed rate of 65 kg/hr. WFE 2 was operated at 200° C. and 0.35 torr. 1033 lbs distillate (3D2) was collected from WFE 2, which consisted of 0.77 lbs monomer, 1021 lbs dimer, and 10.59 lbs trimer and higher oligomers (0.07% monomer, 98.8% dimer, 1% trimer and higher oligomers). 444 lbs residue (3R2) was collected from WFE 2, which consisted of no detectable monomer, 185 lbs dimer, and 258 lbs trimer and higher oligomers (42% dimers and 58% trimers and higher oligomers).

Distillation progress for each of the three distillation passes was monitored by GC analysis. The distillation cuts are characterized using simulated distillation using an Agilent 7890 Simulated Distillation Analyzer in a manner similar to Example 6, with the following distillation cuts identified: Monomer cut (initial boiling point 200° C., final boiling point 370° C.), Dimer cut (initial boiling point 370° C., final boiling point 473° C.), Trimer and higher oligomers (initial boiling point 473° C., final boiling point 700° C.), using the following table to correlate carbon number binning with boiling point:

| Carbon Number Boiling Point Ranges Carbon Number Binning (Area %) | Initial Boiling Point (° C.) | Final Boiling Point (° C.) |
|---|---|---|
| C12 Range | 200 | 240 |
| C15 Range | 240 | 320 |
| C20 Range | 320 | 380 |
| C25 Range | 380 | 420 |
| C30 Range | 420 | 470 |
| C35 Range | 470 | 500 |
| C40-50 | 500 | 575 |
| C51-60 | 575 | 615 |
| C60-72 | 615 | 700 |

Blending to Make a Family of Base Oils

Blends of 3D2 (0.07% monomer, 98.8% dimer, 1% trimer and higher oligomers) and 2R2 (1% dimers, 99% trimers and higher oligomers) were made using standard methods. Table 29A below shows viscometric, cold cranking simulator, and TGA-Noack weight loss results. KV at 40° C. and at 100° C. were measured according ASTM D445, viscosity index was measured according to ASTM D2270, and CCS at −30° C. and at −25° C. were measured according to ASTM D5293. Evaporative weight loss (%) was measured using a TGA-Noack method.

TABLE 29A

|  | wt % 2R2 | KV @ 40° C. (cSt) | KV@100° C. (cSt) | VI | CCS@−30° C. (cP) | CCS@−25° C. (cP) | TGA-Noack (%) |
|---|---|---|---|---|---|---|---|
| 3D2 | 1 | 19.27 | 4.19 | 122 | 1011.9 | 541.9 | 13.83 |
| 3D2/2R2 5% R | 5.07 | 20.67 | 4.42 | 126 | 1177.0 |  | 13.21 |

TABLE 29A-continued

|  | wt % 2R2 | KV @ 40° C. (cSt) | KV@100° C. (cSt) | VI | CCS@−30° C. (cP) | CCS@−25° C. (cP) | TGA-Noack (%) |
|---|---|---|---|---|---|---|---|
| 3D2/2R2 10% R | 10.07 | 22.21 | 4.66 | 130 | 1334.2 |  | 12.40 |
| 3D2/2R2 15% R | 14.98 | 23.81 | 4.92 | 134 | 1517.5 | 862.9 | 12.50 |
| 3D2/2R2 20% R | 19.98 | 25.56 | 5.12 | 133 | 1752.3 | 999.3 | 11.77 |
| 3D2/2R2 30% R | 30.18 | 29.71 | 5.69 | 135 | 2303.7 | 1331.7 | 10.82 |
| 3D2/2R2 40% R | 39.99 | 34.35 | 6.29 | 135 | 2996.8 | 1737.9 |  |
| 3D2/2R2 50% R | 49.99 | 40.01 | 7.06 | 138 | 4462.8 | 2304.8 |  |
| 3D2/2R2 60% R | 60.04 | 46.85 | 7.75 | 134 | 6998.5 | 3033.3 |  |
| 3D2/2R2 70% R | 70.14 | 54.09 | 8.65 | 136 | 12887.9 | 3987.6 |  |
| 3D2/2R2 80% R | 79.95 | 63.42 | 9.64 | 135 | 26329.7 | 5425.3 |  |
| 3D2/2R2 90% R | 89.95 | 74.80 | 10.74 | 131 |  | 8802.3 |  |
| 2R2 | 100 | 88.71 | 12.06 | 129 |  | 15700.9 | 1.50 |

Blends of 3D2 (0.07% monomer, 98.8% dimer, 1% trimer and higher oligomers) and 3R2 (0% monomer, 42% dimers, 58% trimers and higher oligomers) were made using standard methods. % 3R2 refers to the actual mass percentage of 3R2 in the mixture; % trimer+refers to a calculated amount of trimers and higher oligomers that were in the 3R2 component of the mixture (0.58× mass 3R2). Table 29B below shows viscometric, cold cranking simulator, and TGA-Noack weight loss results. KV at 40° C. and at 100° C. were measured according ASTM D445, viscosity index was measured according to ASTM D2270, and CCS at −30° C. and at −25° C. were measured according to ASTM D5293. Evaporative weight loss (%) was measured using a TGA-Noack method.

100° C. of 4 cSt, viscosity index of 124 and CCS at −30° C. of about 1000 cP have been made. Base oils having renewable carbon content in a range from about 30-40%, KV at 100° C. of 6 cSt, viscosity index of 132 and CCS at −30° C. of about 3000 cP, and CCS at −25° C. of about 1740 cP have been made. A variety of base oils having renewable carbon content of at least about 30%, KV at 100° C. of 7-12 cSt and viscosity index>128 have been made.

Examples 30-45: Preparation of 75-78% hydrogenated β-Farnesene

For each of Examples 30-45, a 1-Liter reactor with an $H_2$ reservoir was charged with 660 mL β-farnesene as described

TABLE 29B

|  | % 3R2 | % trimer+ | KV @ 40° C. | KV@ 100° C. | VI | CCS −30° C. | CCS −25° C. | TGA-Noack (wt %) |
|---|---|---|---|---|---|---|---|---|
| 3D2 | 0 | 1 | 19.27 | 4.19 | 122 | 1011.9 | 541.9 | 13.83 |
| 3D2/3R2 5% T | 8.67 | 5.03 | 20.36 | 4.36 | 124 | 1190.3 |  | 12.13 |
| 3D2/3R2 10% T | 17.12 | 9.93 | 21.47 | 4.53 | 127 | 1262.0 |  | 11.72 |
| 3D2/3R2 15% T | 25.7 | 14.91 | 22.67 | 4.7 | 128 | 1410.7 |  | 11.25 |
| 3D2/3R2 20% T | 34.25 | 19.87 | 23.93 | 4.86 | 128 | 1577.6 | 894.1 | 10.78 |
| 3D2/3R2 30% T | 51.37 | 29.79 | 26.75 | 5.26 | 132 | 1943.2 | 1121.2 | 9.18 |
| 3D2/3R2 40% T | 68.48 | 39.72 | 29.95 | 5.68 | 133 | 2425.8 | 1413.5 | 7.82 |
| 3D2/3R2 50% T | 85.62 | 49.66 | 33.59 | 6.15 | 132 | 3018.3 | 1738.6 | 6.45 |
| 3R2 | 100 | 58 | 37.03 | 6.56 | 132 | 4134.8 | 2078.8 | 5.34 |

Figure 14A:
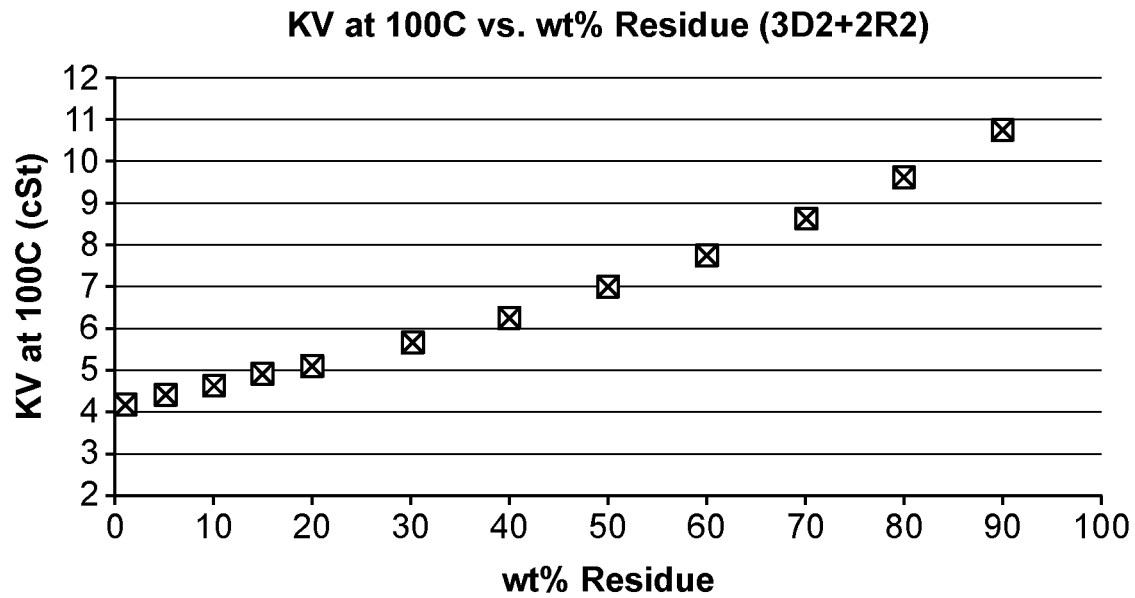
FIGS. 14A, 14B, 14C, and 14D provide plots of KV at 100° C. as a function of wt % residue for the data shown in Table 29A, KV at 100° C. as a function of wt % trimers and higher oligomers for the data shown in Table 29B, viscosity index as a function of KV at 100° C. for the data shown in Tables 29A and 29B, and CCS as a function of KV 100° C. for the data shown in Tables 29A and 29B, respectively.
Figure 14B:
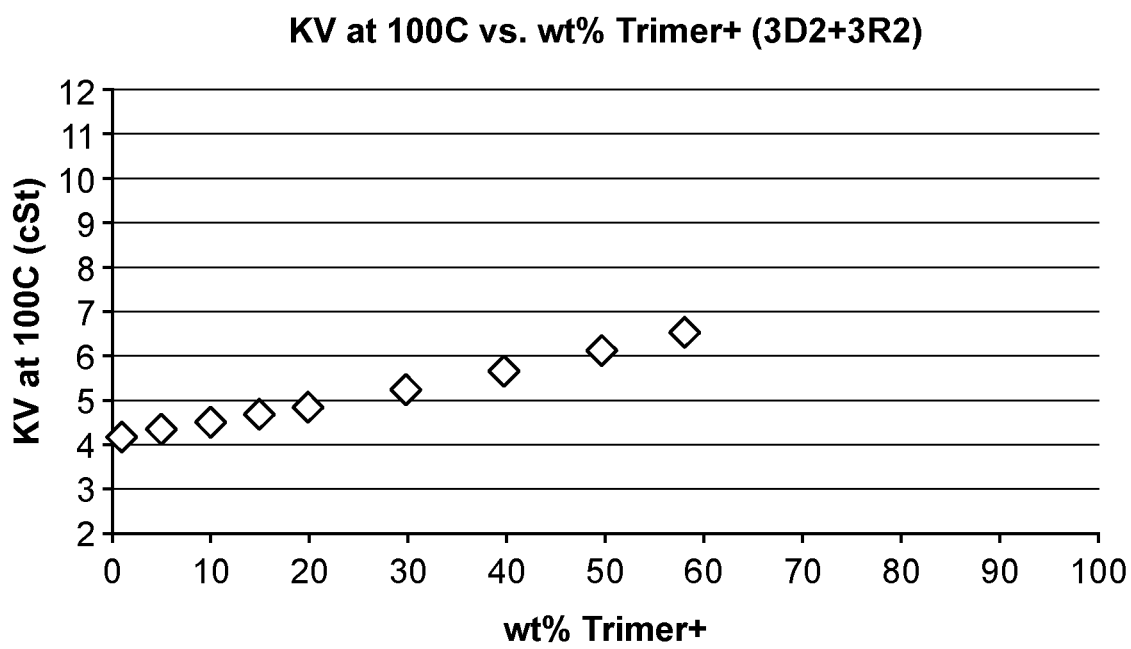
Figure 14C:
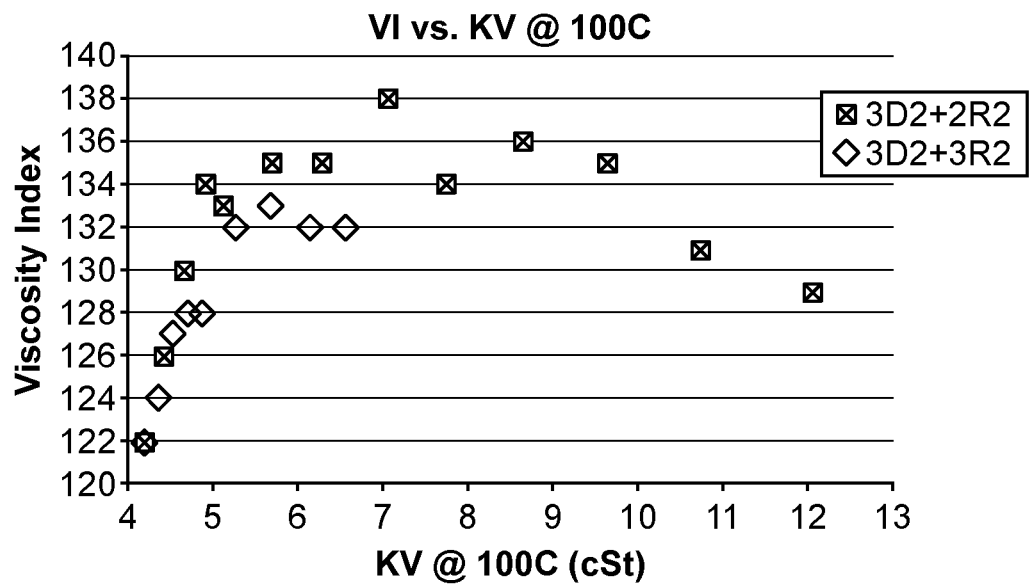
Figure 14D:
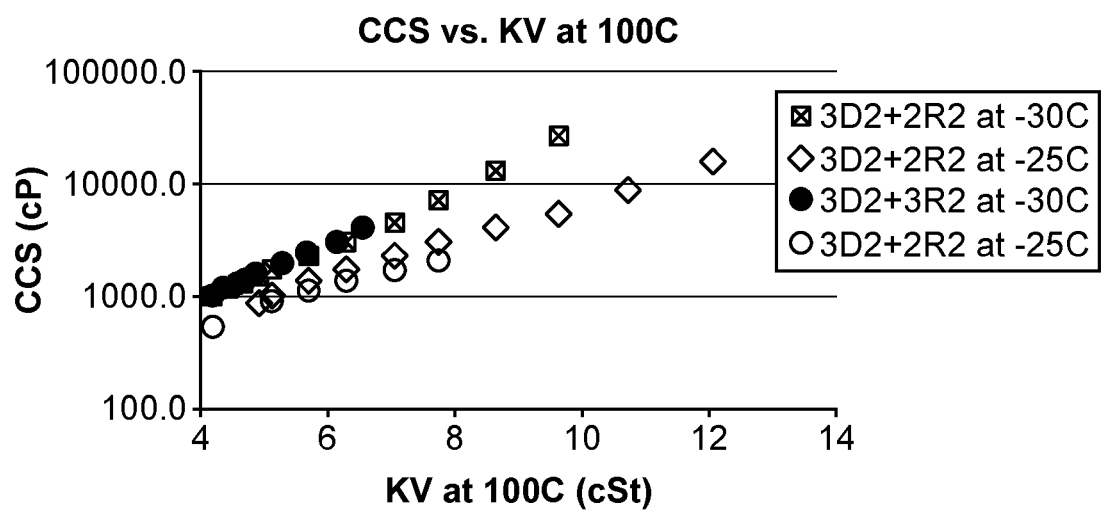

FIG. 14A shows a graph of kinematic viscosity at 100° C. as a function of wt % residue for the blends shown in Table 29A. FIG. 14B shows a graph of kinematic viscosity at 100° C. as a function of wt % trimer and higher oligomers for the blends shown in Table 29B. FIGS. 14A and 14B illustrate some of the possible base oils that can be made using specific distillation cuts (e.g., dimer cuts or trimer and higher oligomer residues) or blends of specific distillation cuts. It should be noted that the distillation cuts and blends illustrated in this Example 29 are not limiting—any desired distillation cut and any desired blend may be used to obtain a base oil with desired properties. In some variations, it may be desired to obtain a mixture comprising dimers and trimers by a direct distillation scheme, without requiring a blending step. FIG. 14C shows a graph of viscosity index as a function of kinematic viscosity at 100° C. for the blends of Table 29A and Table 29B. As shown in FIG. 14C, a peak or plateau in the viscosity index is observed for KV at 100° C. of about 5.5-7.5. FIG. 14D shows a graph of CCS as a function of KV at 100° C. for the blends of Table 29A and Table 29B. As shown, the methods described herein provide a family of base oils that have high viscosity index for base oils having KV at 100° C. ranging from 4 cSt to 12 cSt. Base oils having renewable carbon content of about 50%, KV at in Example 6. Catalyst as specified in Table 5 was mixed into the farnesene and the reactor was stirred at 1000 rpm, except Example 30, which was stirred at 500 rpm. After purging as described in Example 6, the reactor was pressurized with hydrogen to 100 psig (external). The reactor was allowed to self-heat as provided in Table 30, and then heated using an external heater to a first stage reaction temperature of 100° C. After a decline in hydrogenation rate to near zero indicated the 1.5 equivalents of hydrogen had been consumed, the temperature was increased in a second stage as shown in Table 30. For Examples 30-37, 41-42 and 44, hydrogen pressure in the second stage was the same as in the first stage (100 psig). For Examples 38-40, 43 and 45, hydrogen pressure in the second stage was lowered relative to the first stage, as shown in Table 30. For Example 45, the hydrogen pressure was initially reduced to 10 psig in the second stage after 1.5 equivalents hydrogen were consumed, then increased to 20 psig after 2.3 equivalents hydrogen were consumed, and increased again to 30 psig after 2.9 equivalents hydrogen were consumed.

In Examples 30-40, 42-43, and 45, 0.3 wt % Pd/A1203 was supplied by Johnson Matthey (Type 335, powder, size D50:45). In Example 41, 5 wt % Pd/C as in Example 6 is used. In Example 44, 0.5 wt % Pd/titanium silicate (powder, D50=25 µm, available from Strem Chemicals) is used. In Examples, 37-41, and 43-45, a catalyst loading of 18 ppm Pd in farnesene was used. In Example 42, a catalyst of 14 ppm Pd in farnesene was used.

Figure 15A:
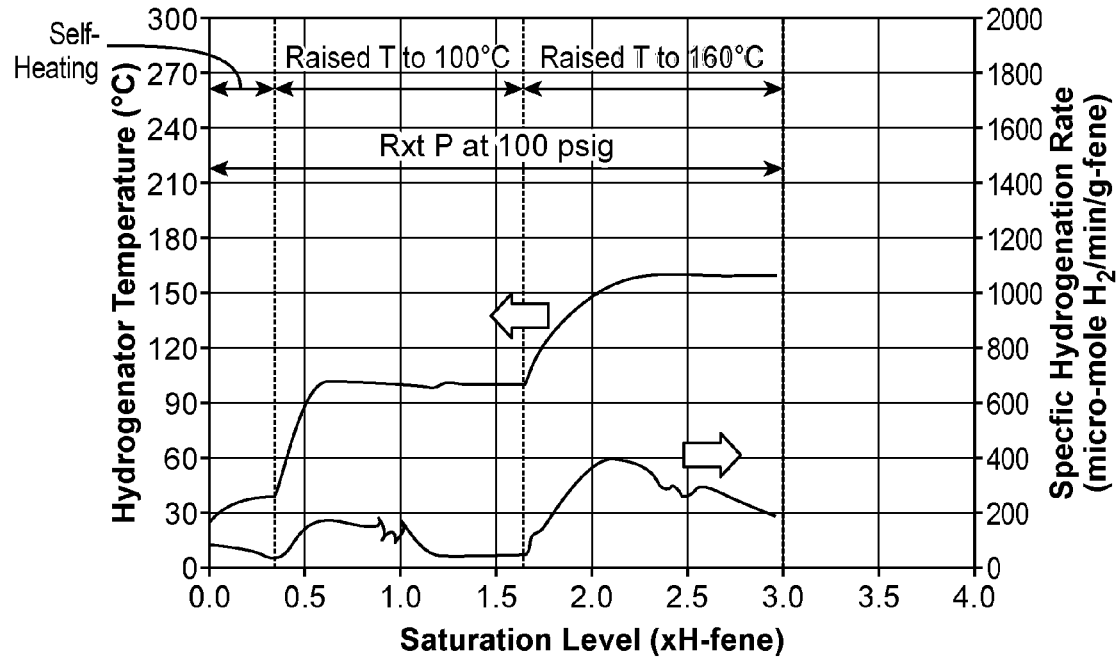
FIG. 15A provides a reaction profile for the selectively hydrogenated β-farnesene preparation method of Example 37.
Figure 15B:
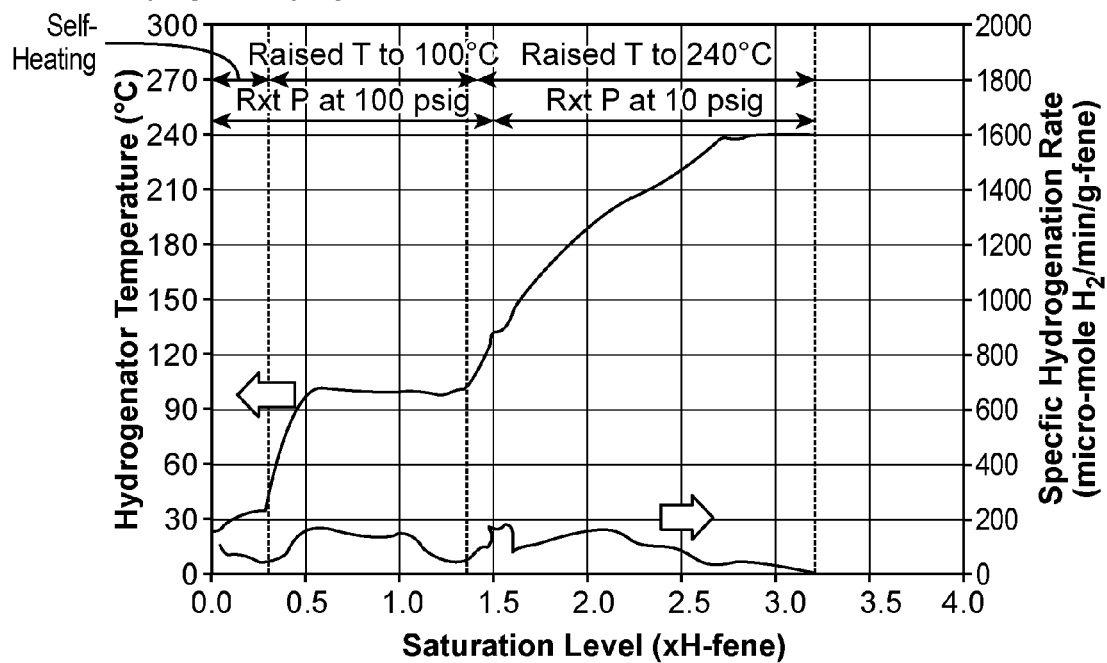
FIG. 15B provides a reaction profile for the selective hydrogenation process of Example 39.
Figure 16A:
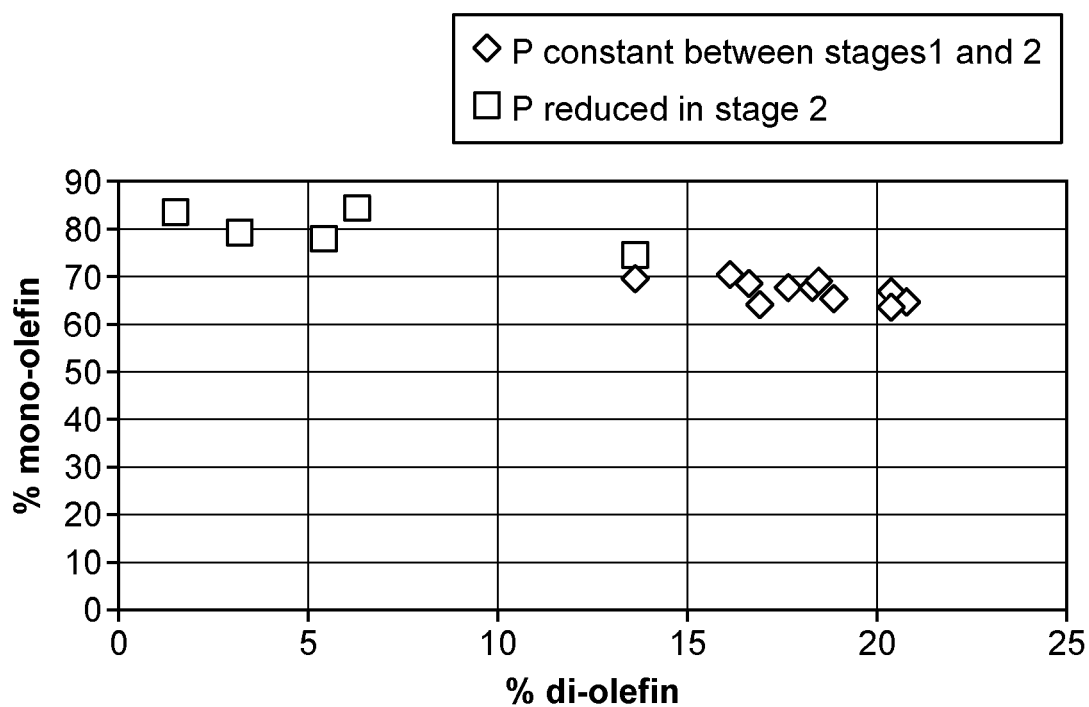
FIGS. 16A-16F provide plots of experimental results for Examples 30-45.
Figure 16B:
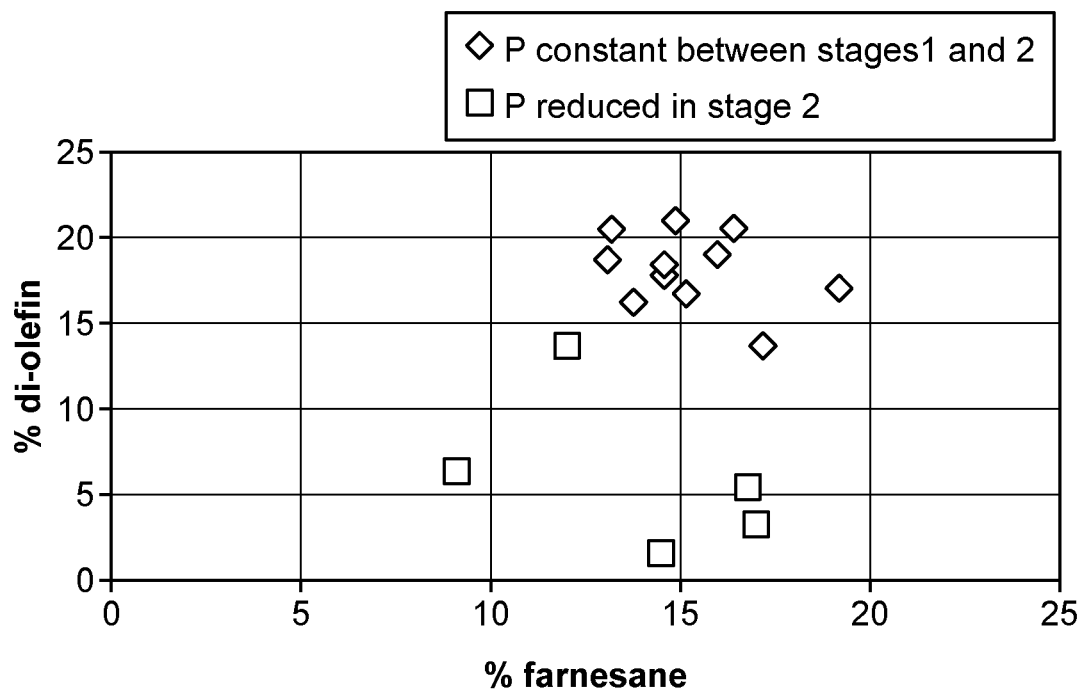
Figure 16C:
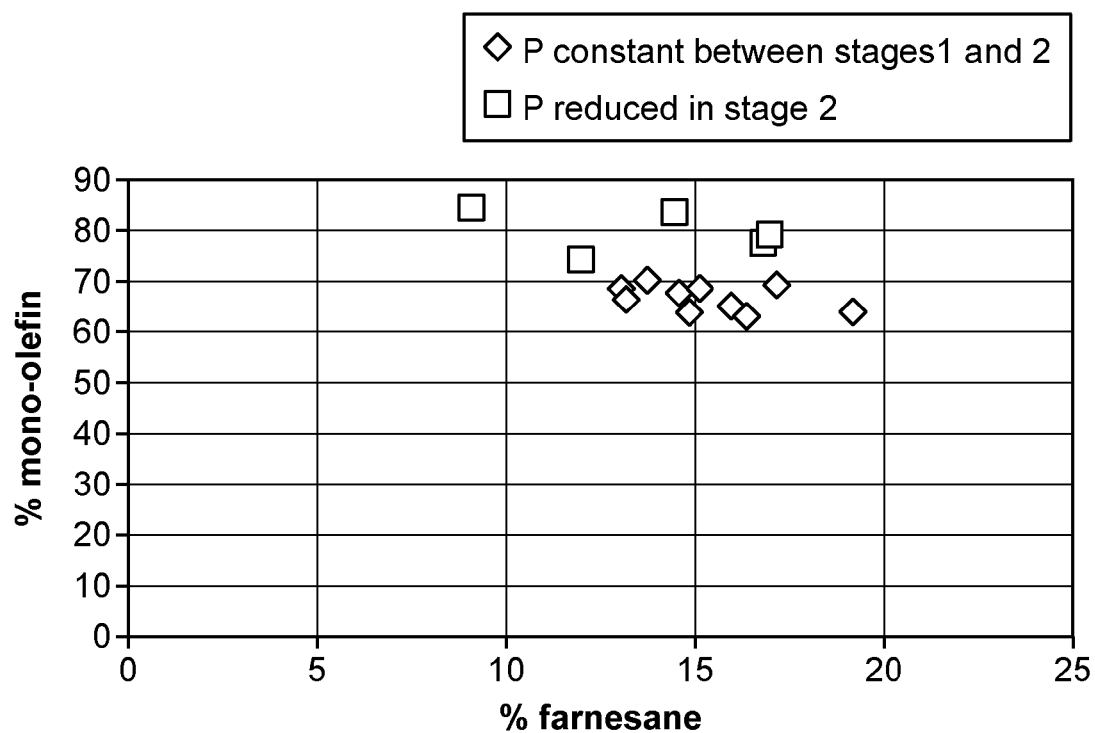
Figure 16D:
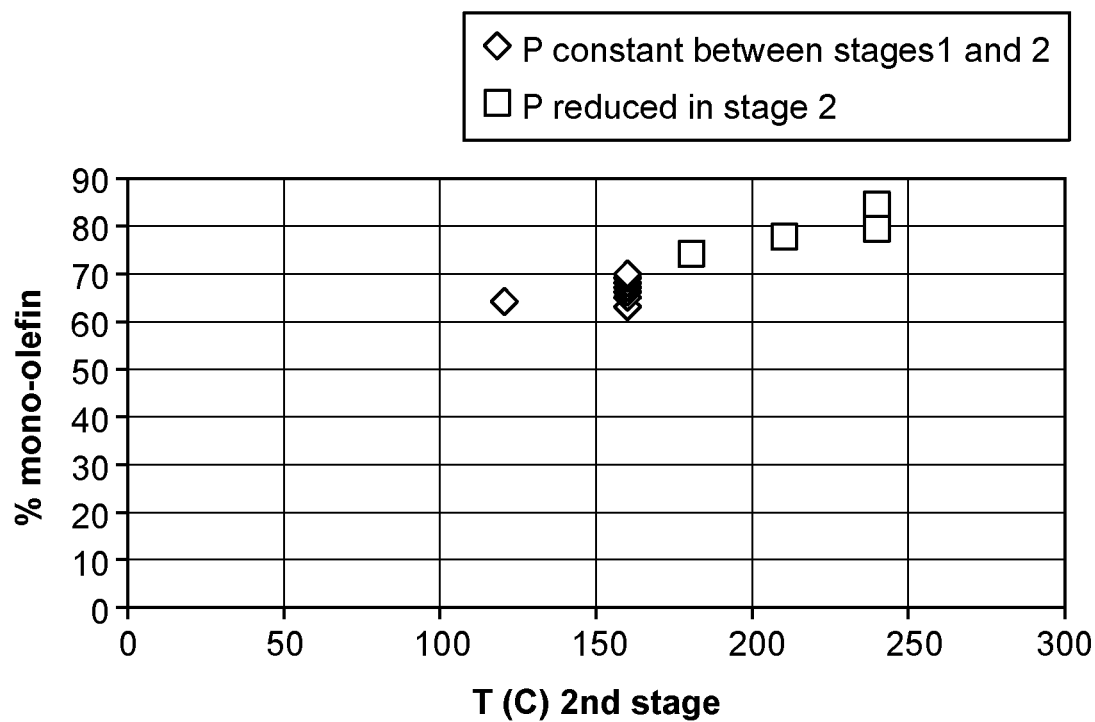
Figure 16E:
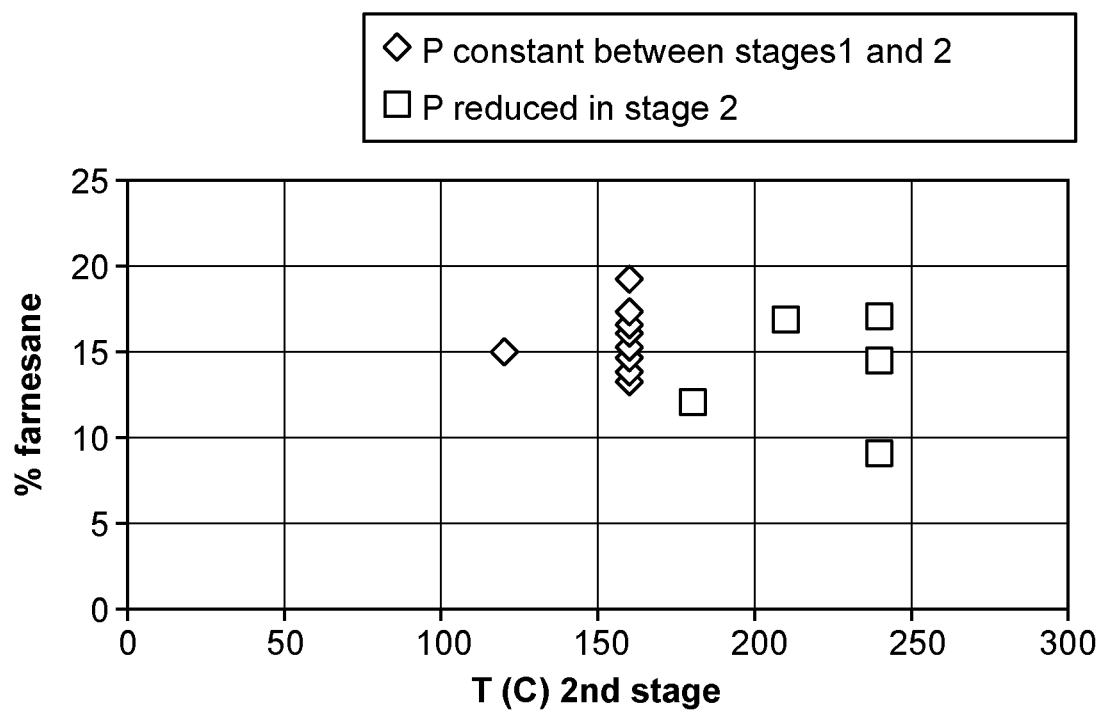
Figure 16F:
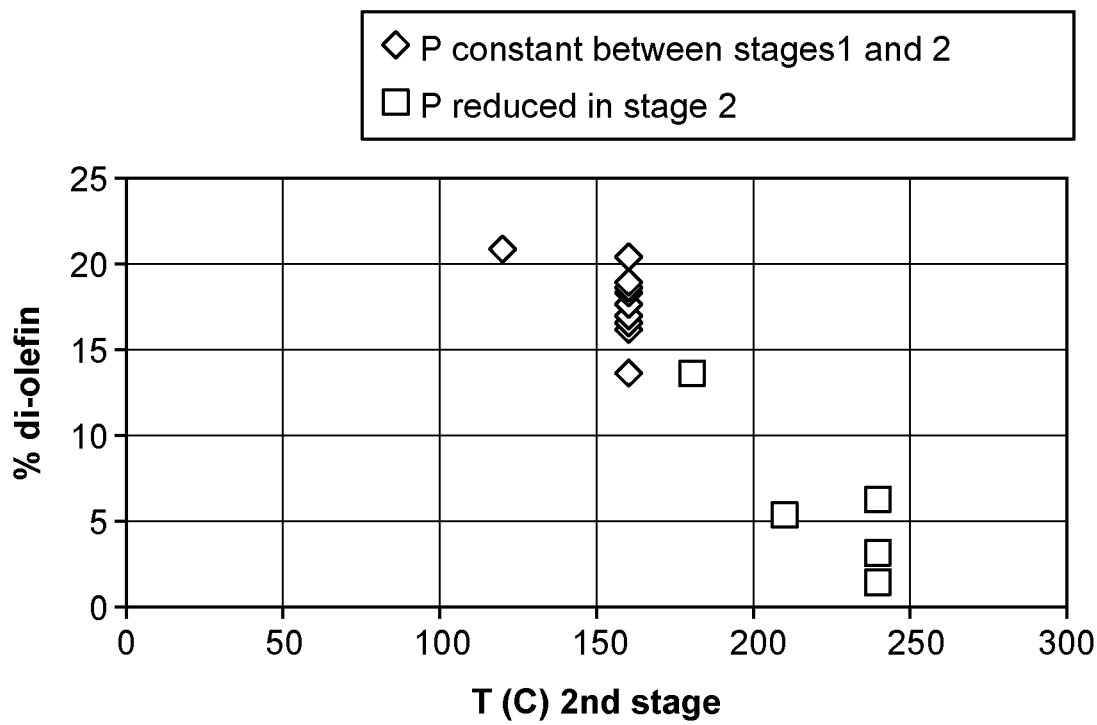

FIG. 15A illustrates the temperature and specific hydrogenation rate (µmole $H_2$/min/g-farnesene) for the hydrogenation process of Example 37. In Example 37, hydrogen pressure is 100 psig in the first and second stages. FIG. 15B illustrates the temperature and specific hydrogenation rate for the hydrogenation process of Example 39. In Example 39, hydrogen pressure is 100 psig in the first stage, and is reduced to 10 psig in the second stage.

Table 30 provides total equivalents of hydrogen consumed, run time, % mono-olefin, % di-olefin, % tri-olefin, and % farnesane for each of Examples 30-45. The relative quantities of the species is measured by GC-FID as described above for Example 15. For each of Examples 16-31, the amount of tetra-olefin present was negligible. Results are plotted in FIGS. 16A-16F. As shown in FIGS. 16A-16F, % mono-olefin is increased while % di-olefin is reduced by increasing temperature in the second stage and reducing pressure in the second stage. A composition comprising 75% or greater (in some cases 80% or greater) mono-olefin and 5% or less di-olefin is achieved using a second stage temperature of 210-240° C. and a second stage pressure of 10 psig.

The effect of pretreatment of β-farnesene to remove oxygenates and other polar substances was investigated. For Example 30, the β-farnesene was filtered with silica gel (1.1 L farnesene/400 ml silica gel). For Examples 31-32, the β-farnesene was filtered with basic alumina (0.9 kg farnesene/0.45 kg alumina basic, standard activity 1). For Example 33, the β-farnesene was treated by mixing with 0.45 kg Selexorb™ CDX ⅛" and stirred 1 hour. For Example 34, the β-farnesene was treated with caustic, washed with water, and treated with Celite. For Example 35, the β-farnesene was treated with 1 wt % NaOH beads. For Example 36, the β-farnesene was treated with 0.2 wt % NaOH. For Examples 37-44, the β-farnesene had been redistilled and filtered through basic alumina prior to use. For Example 45, the β-farnesene was not pretreated. The untreated farnesene exhibited very slow hydrogenation rates. Specific hydrogenation rates were measured after 2 equivalents of hydrogen had been consumed: Example 30 (silica gel treatment), specific hydrogenation rate of 400 µmole $H_2$/min/g-farnesene; Example 31 (basic alumina treatment), specific hydrogenation rate of 1200 µmole $H_2$/min/g-farnesene; Example 33 (Selexorb™ treatment), specific hydrogenation rate of 600 µmole $H_2$/min/g-farnesene; Example 34 (caustic-water treatment), specific hydrogenation rate of 210 µmole $H_2$/min/g-farnesene; Example 35 (1 wt % NaOH bead treatment), specific hydrogenation rate of 400 µmole $H_2$/min/g-farnesene; Example 36 (0.2 wt % NaOH bead treatment), specific hydrogenation rate of 400 µmole $H_2$/min/g-farnesene.

TABLE 30

Examples 30-45

| Ex. | Self-heat | T (° C.) stage 1 | T (° C.) stage 2 | P $H_2$ (psig) stage 1 | P $H_2$ (psig) stage 2 | Catalyst | Run time | Mol. $H_2$ | % mono-olefin | % di-olefine | % tri-olefin | % farnesane |
|---|---|---|---|---|---|---|---|---|---|---|---|---|
| 30 | To 39° C. | 100 | 160 | 100 | 100 | 3300 mg 0.3 wt % Pd/$Al_2O_3$ | 2 h 22 min | 2.97 | 69.9 | 16.1 | 0.25 | 13.75 |
| 31 | To 71° C. | 100 | 160 | 100 | 100 | 3300 mg 0.3 wt % Pd/$Al_2O_3$ | 1 h 35 min | 2.94 | 68.23 | 18.51 | 0.19 | 13.07 |
| 32 | To 56° C. | 100 | 120 | 100 | 100 | 3300 mg 0.3 wt % Pd/$Al_2O_3$ | 1 h 9 min | 2.91 | 63.76 | 20.79 | 0.5 | 14.88 |
| 33 | To 92° C. | 100 | 160 | 100 | 100 | 3300 mg 0.3 wt % Pd/$Al_2O_3$ | 1 h 7 min | 2.92 | 66.19 | 20.37 | 0.25 | 13.19 |
| 34 | To 65° C. | 100 | 160 | 100 | 100 | 3300 mg 0.3 wt % Pd/$Al_2O_3$ | 1 h 59 min | 2.97 | 64.89 | 18.89 | 0.24 | 15.97 |
| 35 | To 84° C. | 100 | 160 | 100 | 100 | 3300 mg 0.3 wt % Pd/$Al_2O_3$ | 1 h 31 min | 2.96 | 67.56 | 17.67 | 0.21 | 14.56 |
| 36 | To 88° C. | 100 | 160 | 100 | 100 | 3300 mg 0.3 wt % Pd/$Al_2O_3$ | 1 h 30 min | 2.98 | 68.08 | 16.61 | 0.16 | 15.15 |
| 37 | To 38° C. | 100 | 160 | 100 | 100 | 3300 mg 0.3 wt % Pd/$Al_2O_3$ | 2 h 36 min | 3.05 | 69.06 | 13.61 | 0.16 | 17.18 |
| 38 | To 36° C. | 100 | 210 | 100 | 20 | 3300 mg 0.3 wt % Pd/$Al_2O_3$ | 2 h 25 min | 3.11 | 77.58 | 5.45 | 0.16 | 16.81 |
| 39 | To 34° C. | 100 | 240 | 100 | 10 | 3300 mg 0.3 wt % Pd/$Al_2O_3$ | 5 h 4 min | 3.12 | 83.55 | 1.52 | 0.49 | 14.44 |
| 40 | To 40° C. | 100 | 240 | 100 | 10 | 3300 mg 0.3 wt % Pd/$Al_2O_3$ | 3 h 28 min | 3.02 | 84.3 | 6.3 | 0.3 | 9.1 |
| 41 | To 28° C. | 100 | 160 | 100 | 100 | 198 mg 5 wt % Pd/C | 2 h 25 min | 2.95 | 62.9 | 20.4 | 0.3 | 16.4 |

TABLE 30-continued

Examples 30-45

| Ex. | Self-heat | T (° C.) stage 1 | T (° C.) stage 2 | P H$_2$ (psig) stage 1 | P H$_2$ (psig) stage 2 | Catalyst | Run time | Mol. H$_2$ | % mono-olefin | % di-olefine | % tri-olefin | % farnesane |
|---|---|---|---|---|---|---|---|---|---|---|---|---|
| 42 | To 35° C. | 100 | 160 | 100 | 100 | 2567 mg 0.3 wt % Pd/Al$_2$O$_3$ | 4 h 25 min | 2.96 | 67.0 | 18.3 | 0.1 | 14.6 |
| 43 | To 37° C. | 100 | 160 | 100 | 10 | 3300 mg 0.3 wt % Pd/Al$_2$O$_3$ | 3 h 17 min | 2.98 | 74.2 | 13.6 | 0.2 | 12.0 |
| 44 | To 27° C. | 100 | 160 | 100 | 100 | 1980 mg 0.5 wt % Pd/titanium silicate | 4 h 45 min | 2.9 | 63.6 | 16.9 | 0.1 | 19.2 |
| 45 | none | 100 | 240 | 100 | 10, 20, 30 | 3300 mg 0.3 wt % Pd/Al$_2$O$_3$ | 10 h 30 min | 3.14 | 79.0 | 3.2 | 0.1 | 17.0 |

Example 46: Staged Hydrogenation in a Fixed Bed Reactor

Sixteen fixed bed reactors operating in parallel (Flowrence® fixed bed reactors, available from Avantium), each having a length of 48 cm and an inner diameter (id) of 2.0 mm, were configured to have two catalyst zones and two heated zones to accomplish a two stage hydrogenation reaction of β-farnesene. Each reactor was oriented vertically and fluid was directed into an inlet at the top of the reactor to flow downwards through the reactor. The catalyst was 0.3 wt % Pd/Al$_2$O$_3$ Pricat™ 309/7 extrudates, available from Johnson Matthey. The extrudates were crushed and sieved to a particle size of 212-425 μm. The feed was 25 vol/vol % β-farnesene in Durasyn® 164 PAO fluid. β-farnesene was supplied by Amyris (>97% pur) and received no further pretreatment before use. Pure hydrogen (no nitrogen diluent) was used. Each reactor was operated in trickle flow mode and configured to have two hydrogenation zones. A first (top) hydrogenation zone begins at the inlet and extends for the top to a maximum distance of 6 cm, depending on quantity of catalyst in the first zone. Each reactor is packed with catalyst in the first zone and is heated to maintain a temperature of 120° C. Below the first zone is an unheated intermediate section packed with inert Zirblast® ceramic beads, containing no catalyst, and extending for 26-43 cm below the top zone, with the length of the unheated intermediate section depending on quantity of catalyst used in the top and bottom zones. The second (bottom) hydrogenation zone begins below the unheated intermediate zone and extends downward for 2-14 cm (depending on quantity of catalyst in second zone), is packed with catalyst and heated to maintain a temperature of 225° C. The bottom two centimeters of the reactor are heated to 225° C. and are packed with inert Zirblast® ceramic beads with no catalyst. A diagram of the reactors is shown in FIG. 17. A factorial design was set up to result in 16 different combinations of top and bottom catalyst loadings as shown in Table 46A.

TABLE 46A

| Reactor | Bottom inert Zirblast® ceramic 225° C. [mass (mg), length (cm)] | Bottom catalyst 225° C. [mass (mg), length (cm)] | Inert Zirblast® ceramic [mass (mg), length (cm)] | Top catalyst 120° C. [mass (mg), length (cm)] |
|---|---|---|---|---|
| 1 | 591, 2.1 | 53, 2.6 | 3115, 41.8 | 0, 0 |
| 2 | 587, 2 | 52, 2.4 | 2956, 39.7 | 25, 1 |
| 3 | 580, 1.9 | 54, 2.2 | 2834, 35.2 | 48, 2.5 |
| 4 | 569, 1.8 | 56, 23.5 | 2611, 35.4 | 103, 4.9 |
| 5 | 576, 1.9 | 130, 6.5 | 2715, 36.4 | 0, 0 |
| 6 | 577, 1.8 | 138, 6.7 | 2616, 35.1 | 25, 1.3 |
| 7 | 583, 1.9 | 132, 6.4 | 2465, 33.2 | 52, 2.5 |
| 8 | 568, 1.5 | 131, 6 | 2252, 28.1 | 126, 5.3 |
| 9 | 586, 2 | 259, 13 | 2144, 28.4 | 0, 0 |
| 10 | 586, 1.9 | 266, 14.1 | 2013, 27.2 | 29, 1.1 |
| 11 | 577, 1.7 | 266, 13.6 | 1916, 25.6 | 64, 2.9 |
| 12 | 581, 1.5 | 259, 11.9 | 1684, 20.8 | 126, 5.3 |
| 13 | 576, 1.5 | 0, 0 | 3270, 43.6 | 0, 0 |
| 14 | 588, 1.9 | 0, 0 | 3145, 42.1 | 30, 1.3 |
| 15 | 581, 1.7 | 0, 0 | 3030, 40.5 | 63, 2.9 |
| 16 | 582, 1.7 | 0, 0 | 2819, 38.3 | 124, 5.8 |

The reaction was operated with a liquid hourly space velocity (LHSV) of 5-55 g-feed/g-catalyst/hour (x ¼ for farnesene LHSV) and gas hourly space velocity (GHSV) of 330-3000 Nml/g-catalyst/hour. Hydrogen was supplied in excess at 20-30%. Outlet pressure was 1 atmosphere. Liquid and gas flow rates are adjusted to limit hydrogenation at about 75% if possible. When the top loading of the catalyst is set to zero (reactors 1, 5, 9 and 13), the residence time in the heated zone induces thermal dimerization or polymerization of the farnesene and leads to blocked reactors after about 70 h. Catalyst reactivation at 250° C. did not reopen blocked reactors. Reactors neighboring blocked reactors (2, 4, 10, and 12) were impacted by the blocked reactors. When the bottom loading of the catalyst is set to zero (reactors 13-16), the degree of hydrogenation was less than 40%. Reactors having both top and bottom catalysts can achieve mono-olefin greater than 80% as long as activity is controlled to inhibit excess formation of farnesane. Reactors 3, 6, 7, 8, 11, 14, 15, 16 were running at 24 mg/min 25 vol % farnesene in Durasyn® 164, 45 Nml/min H$_2$, 40 and 35 Nml/min H$_2$, and a pressure drop less than 5 barg. Reactor 11 experienced pressure oscillations. Reactors 8 and 11 resulted in a degree of hydrogenation that was greater than 80%.

Reactors 3, 6, and 7 are measured under optimized conditions, and detailed experimental conditions and results are provided in Table 46B. Stable operation for these reactors was observed over 500 h. The catalyst could be reactivated at 250° C. under hydrogen. For samples, having degree of hydrogenation ranging from 72%-78%, mono-olefin content (as measured by GC) ranged from about 79-81%, di-olefin content ranged from 11%-2%, and farnesane ranged from 8-18%. Parameters for the GC-MS measurement are as follows. A Thermo Trace-GC with FID detection and DSQ II mass spectroscopy with electric ionization is used. The column type is VF-WaxMS 0.25 mm×0.25 micron×30 m. The start temperature is 60° C. and the hold time is 0 minute. The temperature is ramped to 150° C. at a rate of 6° C./min. and held for 6 minutes, and then ramped to 250° C. at 30° C./min and held for 2 minutes. The injection temperature is 250° C. Split flow at 200 mL/min is used. FID temperature is 275° C. The injection volume is 0.5 microliters. Mono-olefins (molecular weight of 210) are observed with retention times at 5.95-6.15, 6.25-7.03, and 7.15 minutes. Di-olefins (molecular weight of 208) are observed with retention times at 7.06 and 7.2-8.35 minutes. Tri-olefins (molecular weight of 206) are observed with retention times at 8.35-9.3 minutes. Tetra-olefins (molecular weight of 204) are observed with retention times of 9.4-9.6 minutes. Farnesane (MW 212) is observed with a retention time of 6.2 minutes. Parameters for GC-FID are as follows. A Thermo Trace-GC with FID detection is used. The column type is VF-WaxMS 0.25 mm×0.25 micron×30 m. The start temperature is 80° C., with a hold time of 0 minutes. The temperature is ramped to 140° C. with a hold time of 0 minutes. Split flow at 80 mL/min is used. The injection temperature is 250° C. The carrier flow rate is 2 mL/min. The FID temperature is 270° C. The injection volume is 0.2 microliters. Mono-olefins are observed with retention times of 5.62-7.02 minutes, di-olefins are observed with retention times of 7.02-9.18 minutes, tri-olefins are observed with retention times of 9.18-11.45 minutes, farnesane is observed at 5.04 minutes with a window of 0.15, tetra-olefins are observed at a retention time of 11.92 minutes with a window of 0.5, and farnesol is observed with a retention time of 13.5 minutes with a window of 0.2.

TABLE 46B

| | Reactor 3 | Reactor 6 | Reactor 7 |
|---|---|---|---|
| Zone 1 catalyst top loading (mg), 125° C. | 48 | 25 | 52 |
| Zone 2 catalyst bottom loading (mg), 225° C. | 54 | 138 | 132 |
| Total catalyst loading (mg) | 102 | 163 | 187 |
| Average H$_2$ feed flow (Nml/min) | 2.2 | 2.2 | 2.2 |
| LHSV (g-feed/g-cat/h) based on total catalyst loading (×0.25 for farnesene LHSV) | 14-17 | 8-9 | 7.5-8.5 |
| GHSV (Nml/g-cat/h) | 1290 | 810 | 700 |
| Reactor pressure drop (bar) | 2.5 | 1.2 | 1.2 |
| Total catalyst activity (mol farnesene/g-cat/h) | 0.018 (approx.) | 0.011 (approx.) | 0.011 (approx.) |
| Degree of hydrogenation (%) | 71-77 | 77-79 | 78-79 |
| Farnesane (%) | 8.5 | 15.8 | 17.6 |
| Mono-olefin (%) | 79.0 | 81.0 | 79.8 |
| di-olefin (%) | 11.4 | 2.4 | 2.1 |
| Tri-olefin (%) | 0.8 | 0.3 | 0.2 |
| Farnesene (%) | 0.2 | 0.3 | 0.3 |

Example 47: Effect of Hydrogen Pressure on Selectivity

In a first hydrogenation stage, 23.5% hydrogenated β-farnesene is prepared as follows. A reactor (10 L flask) was charged with farnesene (6.9 liter, 5540 g, 27.1 mol) and palladium 5% on alumina (Acros Organics Lot A0217435) (10 g) was added. The mixture was evacuated and flushed with hydrogen 2 times. To the well stirred mixture (with a stirring bar and stirring blade), hydrogen was applied via a balloon (max 1 mol (22 liter) each balloon). Initial the temperature rose to 23° C. and was steady for a long period of time. In order enhance the reaction rate it was decided after 2 days to increase the temperature of the mixture: first to 30° C. and later to 48° C. (internally measured). Overnight the mixture was also stirred in hydrogenen atmosphere at room temperature. The reaction progress was monitored by determination of the refraction index. In total the reaction took 10 days. The mixture was filtered through a layer (approximately 2 cm with a diameter of 18 cm) silica (40 mesh) covered by a paper filter with vacuum. The resulting mixture was still blackish turbid and was filtered again through a 3 cm layer silicagel with a diameter of 12 cm with vacuum. Obtained was a clear liquid 5405 g (26.23 mol, 97% yield) with a refractive index of 1.4708. The refractive index of farnesene is approximately 1.4880 and a sample having a degree of hydrogenation of 30% has a refractive index of approximately 1.4700. The composition of the 23.5% hydrogenated β-farnesene is 0.1% farnesane, 0.7% mono-olefin, 2.8% di-olefin, 86.3% tri-olefin, and 10.1% farnesene by GC-FID.

The 23.5% hydrogenated farnesene was distilled and treated with 10 wt % Al$_2$O$_3$ and 10 wt % silica. 20 g of the pretreated 25% hydrogenated farnesene is loaded into a reactor with 400 mg 0.3 wt % Pd/Al$_2$O$_3$ (Johnson Matthey 309/7). The reactor is stirred at 1200 rpm. The temperature of the reactor was set to 200° C. The hydrogen pressure was set to about 30 psig. The reaction was allowed to proceed until a total of about 3 equivalents hydrogen were consumed, including the 0.94 equivalents from the first stage. The experiment was repeated for hydrogen pressures of 50, 70, 90 and 110 psig. Results are shown in Table 8, where % of each species is determined by GC-FID as described in Example 2. Using a degree of hydrogenation of slightly less than 75%, a second stage hydrogen pressure of 50 psig and a second stage temperature of 200° C., a composition comprising 85% mono-olefin, <1% di-olefin, and <15% farnesane is achieved.

TABLE 8

| Stage 2 Hydrogen pressure (psig) | % hydrogenation | Reaction time | % mono-olefin | % di-olefin | % tri-olefin | % farnesane | Mono-olefin: di-olefin |
|---|---|---|---|---|---|---|---|
| 30 | 78.0 | 1.40 | 69.448 | 0.202 | 0.093 | 30.257 | 342.974 |
| 50 | 73.9 | 0.87 | 85.052 | 0.538 | 0.074 | 14.336 | 158.169 |
| 70 | 77.5 | 0.50 | 71.635 | 0.204 | 0.045 | 28.116 | 351.199 |
| 90 | 69.5 | 0.32 | 81.964 | 10.201 | 0.566 | 7.269 | 8.035 |
| 110 | 76.3 | 0.32 | 75.680 | 0.536 | 0.071 | 23.713 | 141.257 |

Example 48: Monitoring Population of Species During Hydrogenation

A first hydrogenation stage is carried out as in Example 47, except that about 30-40% hydrogenation is accomplished in the first stage. Three different second stage hydrogenations are carried out with the temperature being 200° C., with the hydrogen pressure being 2 bar, 1 bar, or 0.5 bar. Samples are taken as the hydrogenation proceeds and species are analyzed as described in Example 32. Results are shown in FIGS. 18A-18C. Second stage hydrogenation conditions for the data shown in FIG. 18A are 200° C., 2 bar hydrogen pressure; second stage hydrogenation conditions for the data shown in FIG. 18B are 200° C., 1 bar hydrogen pressure; second stage hydrogenation conditions for the data shown in FIG. 18C are 200° C., 0.5 bar hydrogen pressure. "X" represents farnesene content, solid squares represent mono-olefin content, solid triangles represent di-olefin content, and solid diamonds represent farnesane content. As shown in FIGS. 18B and 18C, it is possible to stop hydrogenation at less than 75% hydrogenated (e.g., about 74% hydrogenated) and at which mono-olefin content is maximized, di-olefin content has decreased to about 2% or less, and alkane content is about 10%.

Example 49: Coupling of Alpha-Olefin Co-Monomer with Partially Hydrogenated Hydrocarbon Feedstock Having Very Low Diene Content Example 49 was carried out as in Example 29, with the following conditions: the reaction was carried out in a continuously stirred tank reactor, the hydrocarbon terpene feedstock was 83.75% hydrogenated and comprised 58.8% mono-olefin, 3.0% di-olefin, no detectable amount of tri-olefin, no detectable tetra-olefin, 37.7% farnesane, and 0.5% unknown; no farnesane heel was used in the reactor; 936 g partially hydrogenated farnesene was used, 524 g 1-tetradecene (available from Ineos), 56 g 1-hexadecene (available from Ineos); 6.7 g n-butanol and 10.5 g n-butyl acetate were individually added to the reactor; feed time was 2 hours; hold time was 60 minutes; reaction temperature was 30° C.; and BF$_3$ pressure was 3 psig. The yield was 1404 g washed oil. By GC-MS, the composition of the product was 0.8% residual 1-hexadecene, 44.3% residual monomeric species, 41.7% dimeric species, 11.3% trimeric species, and 2.5% tetramer and higher oligomers. The unsaturated oil is hydrogenated as in Example 29. 1340 g hydrogenated product was distilled into 11 distillation cuts (including residue) using a short path distillation apparatus comprised of a 5 L round bottom flask equipped with an overhead stirrer, vertical condenser and containing 1-2 inches steel wool packing. The pot temperature, overhead temperature, pressure and relative weights of each cut are shown below in Table 48A.

TABLE 48A

| Cut | Mass (g) | Pressure (mmHg) | Pot temperature range (° C.) | Overhead temperature range (° C.) |
|---|---|---|---|---|
| 1A | 380 | 0.2 | 21-148 | 19-67 |
| 1B | 68 | 0.2 | 148-200 | 67-116 |
| 2 | 37 | 0.2 | 200-209 | 116-170 |
| 3A | 78 | 0.2 | 209-205 | 170-169 |
| 3B | 327 | 0.15 | 205-228 | 169-179 |
| 3C | 76 | 0.2 | 228-247 | 179-180 |
| 4 | 58 | 0.2 | 247-279 | 180-219 |
| 5 | 56 | 0.2 | 279-283 | 219-243 |
| 6 | 57 | 0.25 | 283-294 | 243-254 |
| 7 | 59 | 0.25 | 294-301 | 254-263 |
| Res. | 134 | n/a | n/a | n/a |

Distillation cuts are analyzed using Simulated Distillation using GC-FID. Although there is significant overlap to the peaks, Peaks are identified that correspond most likely to farnesene:farnesene dimers (C15:C15 dimers), farnesene:1-tetradecene dimers (C14:C15 dimers), farnesene:1-hexadecene dimers (C15:C16 dimers), 1-hexadecene:1-hexadecene dimers (C16:C16 dimers), farnesene:1-tetradecene:1-tetradecene trimers, unidentified trimers, tetramers and pentamers. Those peaks identified that are likely due to farnesene-farnesene coupling occur the lowest retention times, forming a low boiling shoulder. In some variations, it is desired to reduce the amount of farnesene:farnesene adducts that form a low boiling shoulder. Reduction of farnesene:farnesene adducts may improve low temperature properties (e.g., reduce CCS at −30° C. and/or reduce pour point to about −39° C. or lower) and/or improve viscosity index.

For each of cuts 3A, 3B, 3C, 4, 5, 6, 7 and the residue, Table 48B shows kinematic viscosity at 40° C. and 100° C. (measured according to ASTM D445), viscosity index (measured according to ASTM D2270), cold cranking simulator viscosity at −30° C. and −35° C. (measured according to ASTM D5293), pour point (measured according to ASTM D97), and TGA-wt loss (%).

TABLE 48B

| Cut | KV at 40° C. | KV at 100° C. | VI | CCS at −30° C. | CCS at −35° C. | Pour point (° C.) | TGA wt. loss |
|---|---|---|---|---|---|---|---|
| 3A | 16.92 | 3.769 | 112 | 987 | 1803 | <−45 | 21.6 |
| 3B | 16.88 | 3.828 | 119 | 879 | 1632 | <−45 | 17.8 |
| 3C | 17.82 | 4.023 | 126 | 942 | 1715 | <−45 | 13.97 |
| 4 | 23.73 | 4.8545 | 130 | 1844 | 3120 | −39 | 10.04 |
| 5 | 51.95 | 7.937 | 121 | 4789 | 8529 | −39 | |
| 6 | 58.54 | 8.6405 | 122 | 5933 | 22314 | −36 | |
| 7 | 55.66 | 8.55 | 128 | 9006 | 22292 | −36 | |
| Res. | 126.75 | 14.62 | 116 | | | | |

Blend 4B is made by blending together 16.2 wt % cut 3A, 68 wt % cut 3B and 15.8 wt % cut 3C. Blend 8B is made by blending together 25.2 wt % cut 4, 24.3 wt % cut 5, 24.8 wt % cut 6, and 25.7 wt % cut 7. A blend 6B having about 6 cSt kinematic viscosity at 100° C. is made by blending together 25 wt % Blend 4B and 75 wt % Blend 8B. The blend 6B exhibits a kinematic viscosity at 40° C. of 34.3 cSt, kinematic viscosity at 100° C. of 6.1 cSt, viscosity index of 127, CCS at −30° C. of 3791 cP, CCS at −35° C. of 6547 cP, pour point of −39° C., and TGA weight loss=7.680% (CV 0.270%); ref weight loss=14.500%, ref time=8.0800 sec.

What is claimed is:

1. A method for making a base oil, the method comprising:
coupling a hydrocarbon terpene feedstock obtained from a renewable carbon source with one or more non-terpene olefin co-monomers in the presence of a catalyst to form one or more branched alkenes comprising one or more hydrocarbon terpene:olefin adducts;
hydrogenating the branched alkenes to form one or more isoparaffins; and
making a base oil from at least a portion of the isoparaffins, wherein the base oil has at least 25% renewable carbon content.

2. The method of claim 1, wherein the one or more non-terpene olefin co-monomers comprise one or more alpha-olefins.

3. The method of claim 1, wherein the one or more non-terpene olefin co-monomers are a linear alkene or a branched alkene containing at most two branches.

4. The method of claim 1, adapted for making a base oil with a kinematic viscosity at 100° C. of about 2-3 cSt, about 4-5 cSt, about 6-8 cSt, or about 9-10 cSt.

5. The method of claim 1, adapted for making a base oil with a viscosity index of at least about 120, about 130, or about 140.

6. The method of claim 1, comprising one of the following:
selecting the one or more non-terpene olefin co-monomers and/or a coupling mechanism to modulate a degree of branching in the base oil;
tuning coupling conditions to form predominantly 1:1 hydrocarbon terpene:olefin adducts;
tuning coupling conditions to form a mixture of 1:1 hydrocarbon terpene:olefin adducts and 1:2 hydrocarbon terpene:olefin adducts;
distilling the isoparaffins to form one or more distillation cuts, and making the base oil from at least one of the distillation cuts;
adding a pour point depressant to the at least a portion of the isoparaffins to make the base oil; and
adding a viscosity modifier to the at least a portion of the isoparaffins to make the base oil.

7. The method of claim 2, comprising increasing a carbon chain length of the one or more alpha-olefins to increase a viscosity index of the base oil.

8. The method of claim 2, wherein the hydrocarbon terpene feedstock comprises a conjugated diene moiety, and the coupling comprises a hydrovinylation reaction between the conjugated diene moiety and the alpha-olefin.

9. The method of claim 8, wherein the catalyst comprises a Co(I) catalyst.

10. The method of claim 1, wherein the hydrocarbon terpene feedstock comprises a partially hydrogenated terpene, and the catalyst comprises a cationic initiator.

11. The method of claim 10, wherein the cationic initiator comprises a protic acid preferrably sulfuric acid.

12. The method of claim 10, wherein the catalyst comprises a Lewis acid, a first co-catalyst and a second co-catalyst.

13. The method of claim 12, wherein the Lewis acid comprises $BF_3$, the first co-catalyst comprises an alcohol having the formula $R^1OH$, and the second co-catalyst comprises an ester having the formula $R^2CO_2R^1$, with $R^1$ being a $C_1$-$C_{10}$ linear or branched alkyl group and $R^2$ being a $C_1$-$C_4$ linear or branched alkyl group; preferably the first co-catalyst comprises n-butanol; or the first co-catalyst comprises n-butanol and the second co-catalyst comprises n-butyl acetate.

14. The method of claim 13, capable of forming isoparaffins in which branching originates predominantly from the hydrocarbon terpene feedstock, or branching comprises predominantly methyl groups.

15. The method of claim 1, wherein the hydrocarbon terpene feedstock comprises β-farnesene.

16. The method of claim 1, wherein the hydrocarbon terpene feedstock comprises partially hydrogenated hydrocarbon terpene, preferably partially hydrogenated β-farnesene.

17. The method of claim 2, wherein the one or more alpha-olefins are selected from the group consisting of 1-hexene, 1-octene, 1-decene, 1-dodecene, 1-tetradecene, 1-hexadecene, 1-octadecene, 1-eicosene, and any combination of two or more thereof.

18. The method of claim 2, wherein the hydrocarbon terpene feedstock comprises β-farnesene or partially hydrogenated β-farnesene; and the one or more alpha-olefins are selected from the group consisting of 1-decene, 1-dodecene, 1-tetradecene, 1-hexadecene, 1-octadecene, and any combination of two or more thereof, preferably selected from the group consisting of 1-tetradecene, 1-hexadecene, or a mixture of 1-tetradecene and 1-hexadecene, more preferably a mixture of 1-tetradecene and 1-hexadecene.

19. The method of claim 1, comprising distilling the isoparaffins to form one or more distillation cuts, and making the base oil from at least one of the distillation cuts; wherein a first lighter distillation cut of the isoparaffins is used to make a first base oil and a second heavier distillation cut of the isoparaffins is to make a second base oil.

20. A base oil comprising hydrocarbon terpene feedstock:non-terpene olefin adducts, hydrogenated, wherein the hydrocarbon terpene feedstock is obtained from a renewable carbon source, and wherein the base oil has at least 25% renewable carbon content.

21. The base oil of claim 20, comprising 1:1 hydrocarbon terpene feedstock:non-terpene olefin adducts, hydrogenated; 1:2 hydrocarbon terpene feedstock:non-terpene olefin adducts, hydrogenated; or 2:1 hydrocarbon terpene feedstock:non-terpene olefin adducts, hydrogenated.

22. The base oil of claim 20, having a viscosity index of at least about 120, about 130, or about 140.

23. The base oil of claim 20, having a kinematic viscosity at 100° C. of about 4 cSt, about 5 cSt, or about 3 cSt and a viscosity index of about 120 or higher.

24. The base oil of claim 20, comprising β-farnesene:alpha-olefin adducts or partially hydrogenated β-farnesene:alpha-olefin adducts, hydrogenated.

25. The base oil of claim 24, comprising
β-farnesene:1-decene adducts or partially hydrogenated β-farnesene:1-decene adducts, hydrogenated;
β-farnesene:1-dodecene adducts or partially hydrogenated β-farnesene:1-dodecene adducts, hydrogenated;
β-farnesene:1-tetracene adducts or partially hydrogenated β-farnesene:1-tetracene adducts, hydrogenated;
β-farnesene:1-hexadecene adducts or partially hydrogenated β-farnesene:1-hexadecene adducts, hydrogenated;
β-farnesene:1-octadecene adducts or partially hydrogenated β-farnesene:1-octadecene adducts, hydrogenated;
β-farnesene:1-tetradecene adducts, hydrogenated and β-farnesene:1-hexadecene adducts, hydrogenated; or partially hydrogenated β-farnesene:1-tetradecene adducts and partially hydrogenated β-farnesene:1-hexadecene adducts, hydrogenated.

26. The base oil of claim 20, comprising a pour point depressant and/or a viscosity modifier.

27. The base oil of claim 20, wherein the hydrocarbon terpene feedstock comprises a partially hydrogenated hydrocarbon terpene.

28. The base oil of claim 27, wherein the hydrocarbon terpene feedstock comprises partially hydrogenated β-farnesene.

29. The base oil of claim 28, wherein the non-terpene olefin comprises 1-tetradecene, 1-hexadecene, or a mixture of 1-tetradecene and 1-hexadecene.

30. The base oil of claim 20, comprising at least about 85% 1:1 hydrocarbon terpene feedstock:non-terpene olefin adducts; or at least about 70% trimeric hydrocarbon terpene feedstock:non-terpene olefin adducts.

31. The base oil of claim 20, having at least about 50% renewable carbon content; or about 100% renewable carbon content.

32. A lubricant composition comprising the base oil of claim 20 and one or more additives selected from the group consisting of antioxidants, viscosity modifiers, pour point depressants, foam inhibitors, detergents, dispersants, dyes, markers, rust inhibitors or other corrosion inhibiors, emulsifiers, de-emulsifiers, flame retardants, antiwear agents, friction modifiers, thermal stability improvers, and multifunctional additives.

33. The lubricant composition of claim 32, formulated for use in two cycle engines; as a transmission fluid; as a hydraulic fluid; in compressors; in turbines; in an automotive engine oil; or as a marine grade lubricant.

* * * * *